(12) United States Patent
Allen et al.

(10) Patent No.: US 8,048,892 B2
(45) Date of Patent: Nov. 1, 2011

(54) AZAQUINOLONE BASED COMPOUNDS EXHIBITING PROLYL HYDROXYLASE INHIBITORY ACTIVITY, COMPOSITIONS, AND USES THEREOF

(75) Inventors: Jennifer R. Allen, Newbury Park, CA (US); Kaustav Biswas, Calabasas, CA (US); Guo-Qiang Cao, Thousand Oaks, CA (US); Jennifer E. Golden, Simi Valley, CA (US); Stephanie Mercede, Thousand Oaks, CA (US); Tanya Peterkin, Woodland Hills, CA (US); Anthony Reed, Oxnard, CA (US); Christopher M. Tegley, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 984 days.

(21) Appl. No.: 12/002,538

(22) Filed: Dec. 17, 2007

(65) Prior Publication Data
US 2009/0111806 A1    Apr. 30, 2009

Related U.S. Application Data

(60) Provisional application No. 60/875,706, filed on Dec. 18, 2006.

(51) Int. Cl.
A61K 31/4375 (2006.01)
C07D 471/04 (2006.01)
(52) U.S. Cl. .......................... 514/300; 546/123
(58) Field of Classification Search ............... 514/234.5, 514/300; 546/123; 544/127
See application file for complete search history.

(56) References Cited

U.S. PATENT DOCUMENTS

| | | |
|---|---|---|
| 3,954,733 A | 5/1976 | Tobiki et al. |
| 3,992,371 A | 11/1976 | Tobiki et al. |
| 4,215,123 A | 7/1980 | Scotese et al. |
| 4,374,138 A | 2/1983 | Haskell et al. |
| 4,382,089 A | 5/1983 | Haskell et al. |
| 4,404,201 A | 9/1983 | Haskell et al. |
| 4,468,394 A | 8/1984 | Machida et al. |
| 4,710,473 A | 12/1987 | Morris |
| 5,037,826 A | 8/1991 | Blythin et al. |
| 5,126,341 A | 6/1992 | Suzuki et al. |
| 5,378,679 A | 1/1995 | Nuebling et al. |
| 5,502,035 A | 3/1996 | Haviv et al. |
| 5,620,995 A | 4/1997 | Weidmann et al. |
| 5,719,164 A | 2/1998 | Weidmann et al. |
| 5,798,451 A | 8/1998 | von Deyn et al. |
| 5,972,841 A | 10/1999 | von Deyn et al. |
| 6,093,730 A | 7/2000 | Weidmann et al. |
| 6,593,343 B2 | 7/2003 | Björk et al. |
| 6,787,326 B1 | 9/2004 | Ratcliffe et al. |
| 2003/0153503 A1 | 8/2003 | Klaus et al. |
| 2004/0235082 A1 | 11/2004 | Fourney et al. |
| 2004/0254215 A1 | 12/2004 | Arend et al. |
| 2005/0020487 A1 | 1/2005 | Klaus et al. |
| 2005/0107364 A1 | 5/2005 | Hutchinson et al. |
| 2006/0216295 A1 | 9/2006 | Crabtree et al. |
| 2006/0251638 A1 | 11/2006 | Guenzler-Pukall et al. |
| 2006/0276477 A1 | 12/2006 | Klaus et al. |
| 2007/0004627 A1 | 1/2007 | Seeley et al. |
| 2007/0203174 A1 | 8/2007 | Klimko et al. |
| 2007/0249605 A1 | 10/2007 | Allen et al. |
| 2008/0171756 A1 | 7/2008 | Shaw et al. |
| 2009/0082357 A1* | 3/2009 | Fitch et al. ............ 514/249 |

FOREIGN PATENT DOCUMENTS

| | | |
|---|---|---|
| AT | 328085 | 3/1976 |
| EP | 0 500 297 A1 | 8/1992 |
| EP | 0 503 844 A1 | 9/1992 |
| EP | 0 937 459 A2 | 8/1999 |
| EP | 0 547 708 B1 | 2/2003 |
| EP | 1 541 558 A1 | 8/2003 |
| EP | 1 538 160 A1 | 6/2005 |
| GB | 1 449 256 | 9/1976 |
| JP | 493592 A | 4/1974 |
| JP | 7224040 A2 | 8/1995 |
| SU | 1735288 | 5/1992 |
| WO | WO 01/85732 A1 | 11/2001 |
| WO | WO 02/24679 A1 * | 3/2002 |
| WO | WO 02/076396 A2 | 10/2002 |
| WO | WO 03/053997 A2 | 7/2003 |
| WO | WO 2004/037853 A2 | 5/2004 |
| WO | WO 2004/103974 A1 | 12/2004 |
| WO | WO 2004/104000 A1 | 12/2004 |
| WO | WO 2004/108121 A1 | 12/2004 |
| WO | WO 2004/108681 A1 | 12/2004 |

(Continued)

OTHER PUBLICATIONS

Vippagunta et al., Crystalline solids, 2001, Advanced Drug Delivery Reviews, 48, pp. 3 and 18.*
Lala et al., Role of nitric oxide in tumor progression: Lessons from experimental tumors, Cancer and Metastasis Reviews (1998),17, 91-106.*
Golub et al., Molecular Classification of Cancer: Class Discovery and Class Prediction by Gene Expression Monitoring, Science (1999), vol. 286, 531-537.*
U.S. Appl. No. 12/002,537, filed Dec. 17, 2007, Allen et al.
U.S. Appl. No. 12/082,263, filed Apr. 9, 2008, Allen et al.
U.S. Appl. No. 12/148,179, filed Apr. 16, 2008, Allen et al.
U.S. Appl. No. 12/150,675, filed Apr. 29, 2008, Allen et al.
U.S. Appl. No. 12/150,998, filed May 2, 2008, Allen et al.

(Continued)

Primary Examiner — Kamal Saeed
Assistant Examiner — Kristin Bianchi
(74) Attorney, Agent, or Firm — Bernard P. Friedrichsen

(57) ABSTRACT

Compounds of Formula I

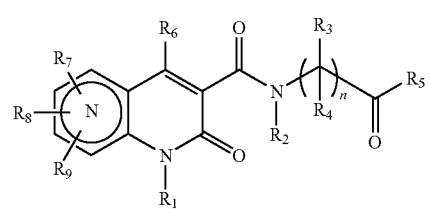

are useful as inhibitors of HIF prolyl hydroxylases where the definitions of the variables are provided herein.

50 Claims, 3 Drawing Sheets

FOREIGN PATENT DOCUMENTS

| | | |
|---|---|---|
| WO | WO 2005/011696 A1 | 2/2005 |
| WO | WO 2005/021546 A1 | 3/2005 |
| WO | WO 2005/047285 A1 | 5/2005 |
| WO | WO 2005/077050 A2 | 8/2005 |
| WO | WO 2005/111044 A1 | 11/2005 |
| WO | WO 2006/088246 A1 | 8/2006 |
| WO | WO 2006/094292 A2 | 9/2006 |
| WO | WO 2007/038571 A2 | 4/2007 |
| WO | WO 2007/070359 A2 | 6/2007 |
| WO | WO 2007/097929 A1 | 8/2007 |
| WO | WO 2007/103905 A2 | 9/2007 |
| WO | WO 2007/136990 A2 | 11/2007 |
| WO | WO 2007/150011 A2 | 12/2007 |
| WO | WO 2008/040002 A2 | 4/2008 |

OTHER PUBLICATIONS

International Search Report and Written Opinion from co-pending PCT Application No. PCT/US2007/025799 (WO 2008/076425) mailed on May 8, 2008.

He, L. et al., "Probabilistic Neural Network Multiple Classifier System for Predicting the Genotoxicity of Quinolones and Quinoline Derivatives," Chem. Res. Toxicol. 18, pp. 428-440 (2005).

Ukrainets, I.V. et al., "4-Hydroxy-2-Quinolines. XXI. 1H-2-Oxo-4-Hydroxyquinoline-3-Carboxylic Alkylamides as a Novel Group of Antithyroid Drugs," Farmatsevtichnii Zhurnal (Kiev) 6, pp. 54-55 (1995).

Bezuglyi, P.A., "Amides of 4-Hydroxyquinoline-2-oxo-3-carboxylic Acid: Synthesis and Anticoagulant Activity," Khimiko-Farmatsevticheskii Zhurnal, 24(4) pp. 31-32 (1990). This document is in the Russian language—an English language abstract is included.

Schofield, C.J. et al., "Oxygen Sensing by HIF Hydroxylases", Nature Reviews, Molecular Cell Biology, 5(5), pp. 243-254 (2004).

McDowell, R. S. et al., "From Peptide to Non-Peptide. 2. The De Novo Design of Potent, Non-peptidal Inhibitors of Platelet Aggregation Based on a Benzodiazepinedione Scaffold," J. Am. Chem. Soc. 116(12) pp. 5077-5083 (1994).

Bohnert et al., "Redox Reactions with Cyclopeptide-Like Quinoline Derivatives as Lipophilic, Masked NAD Model Compounds," Zeitschrift für Naturforschung, B.: Chemical Sciences, 42(9) pp. 1159-1166 (1987). This document is in the German language—an English language abstract is included.

Kath, J.C. et al., Potent Small Molecule CCR1 Antagonists, Bioorg & Med. Chem. Letters, 14(9), pp. 2169-2173 (2004).

Ukrainets, I.V. et al., "4-Hydroxy-2-Quinolones. 4. Selection of the Optimum Path for Synthesis of N-R-Substituted 4-Hydroxy-2-Quinolone-3-Carboxylic Acid Amides." Chemistry of Heterocyclic Compounds 28(5), pp. 538-540 (1992).

Warshakoon, N.C. et al., "Design and Synthesis of a Series of Novel Pyrazolopyridines as HIF 1-α Prolyl Hydroxylase Inhibitors," Bioorg & Med. Chem. Letters, 16, pp. 5687-5690 (2006).

Warshakoon, N.C. et al., "Structure-Based Design, Synthesis, and SAR Evaluation of a New Series of 8-Hydroxyquinolinse as HIF-1α Prolyl Hydroxylase Inhibitors," Bioorg & Med. Chem. Letters, 16, pp. 5517-5522 (2006).

Warshakoon, N.C. et al., "A Novel Series of Imidazo[1,2-a]pyridine Derivatives as HIF-1α Prolyl Hydroxylase Inhibitors," Bioorg & Med. Chem. Letters, 16, pp. 5598-5601 (2006).

McDonough, M.A. et al., "Cellular Oxygen Sensing: Crystal Structure of Hypoxia-Inducible Factor Prolyl Hydroxylase (PHD2)," Proc. Natl. Acad. Sci., 103(26) pp. 9814-9819 (2006).

Jönssen, S. et al., "Synthesis and Biological Evaluation of New 1,2-Dihydro-4-hydroxy-2-oxo-3-quinolinecarboxamides for Treatment of Autoimmune Diorders: Structure-Activity Relationship," J. Med. Chem. 47, pp. 2075-2088 (2004).

Buckle, D.R. et al., "Synthesis and Antiallergic Activity of 2-Hydroxy-3-nitro-1,4-naphthoquinones," J. Med. Chem. 20(8), pp. 1059-1064 (1977).

Franklin, T.J. et al., "Approaches to the Design of Anti-Fibrotic Drugs," Biochem. Soc. Trans. 19, pp. 812-815 (1991).

Prosecution History of U.S. Appl. No. 11/635,683 Without Cited References, From Dec. 8, 2006 to Aug. 2, 2010.

Prosecution History of U.S. Appl. No. 12/703,496 Without Cited References, From Feb. 10, 2010 to May 16, 2011.

Prosecution History of U.S. Appl. No. 12/703,716 Without Cited References, From Feb. 10, 2010 to May 17, 2011.

Prosecution History of U.S. Appl. No. 12/002,537 Without Cited References, From Dec. 17, 2007 to Dec. 22, 2009.

Prosecution History of U.S. Appl. No. 12/612,465 Without Cited References, From Nov. 4, 2009 to Apr. 19, 2011.

Prosecution History of U.S. Appl. No. 12/082,263 Without Cited References, From Apr. 9, 2008 to Aug. 4, 2009.

Prosecution History of U.S. Appl. No. 12/148,179 Without Cited References, From Apr. 16, 2008 to May 24, 2011.

Prosecution History of U.S. Appl. No. 13/109,877 Without Cited References, From May 17, 2011 to Jun. 9, 2011.

Prosecution History of U.S. Appl. No. 12/150,675 Without Cited References, From Apr. 29, 2008 to Jun. 16, 2011.

Prosecution History of U.S. Appl. No. 12/150,998 Without Cited References, From May 2, 2008 to May 5, 2011.

* cited by examiner

SEQUENCE LISTING

<160> NUMBER OF SEQ ID NOS: 7

<210> SEQ ID NO 1
<211> LENGTH: 166
<212> TYPE: PRT
<213> ORGANISM: Homo sapiens

<400> SEQUENCE: 1

Met His His His His His Glu Ala Gly Arg Pro Arg Pro Val Leu
1               5                   10                  15

Arg Ser Val Asn Ser Arg Glu Pro Ser Gln Val Ile Phe Cys Asn Arg
                20                  25                  30

Ser Pro Arg Val Val Leu Pro Val Trp Leu Asn Phe Asp Gly Glu Pro
            35                  40                  45

Gln Pro Tyr Pro Thr Leu Pro Pro Gly Thr Gly Arg Arg Ile His Ser
    50                  55                  60

Tyr Arg Gly His Leu Trp Leu Phe Arg Asp Ala Gly Thr His Asp Gly
65                  70                  75                  80

Leu Leu Val Asn Gln Thr Glu Leu Phe Val Pro Ser Leu Asn Val Asp
                85                  90                  95

Gly Gln Pro Ile Phe Ala Asn Ile Thr Leu Pro Val Tyr Thr Leu Lys
            100                 105                 110

Glu Arg Cys Leu Gln Val Val Arg Ser Leu Val Lys Pro Glu Asn Tyr
        115                 120                 125

Arg Arg Leu Asp Ile Val Arg Ser Leu Tyr Glu Asp Leu Glu Asp His
    130                 135                 140

Pro Asn Val Gln Lys Asp Leu Glu Arg Leu Thr Gln Glu Arg Ile Ala
145                 150                 155                 160

His Gln Arg Met Gly Asp
                165

<210> SEQ ID NO 2
<211> LENGTH: 118
<212> TYPE: PRT
<213> ORGANISM: Homo sapiens

<400> SEQUENCE: 2

Met Asp Val Phe Leu Met Ile Arg Arg His Lys Thr Thr Ile Phe Thr
1               5                   10                  15

Asp Ala Lys Glu Ser Ser Thr Val Phe Glu Leu Lys Arg Ile Val Glu
                20                  25                  30

Gly Ile Leu Lys Arg Pro Pro Asp Glu Gln Arg Leu Tyr Lys Asp Asp
            35                  40                  45

Gln Leu Leu Asp Asp Gly Lys Thr Leu Gly Glu Cys Gly Phe Thr Ser
    50                  55                  60

Gln Thr Ala Arg Pro Gln Ala Pro Ala Thr Val Gly Leu Ala Phe Arg
65                  70                  75                  80

Ala Asp Asp Thr Phe Glu Ala Leu Cys Ile Glu Pro Phe Ser Ser Pro
                85                  90                  95

Pro Glu Leu Pro Asp Val Met Lys Pro Gln Asp Ser Gly Ser Ser Ala
            100                 105                 110

Asn Glu Gln Ala Val Gln
        115

<210> SEQ ID NO 3
<211> LENGTH: 96

<212> TYPE: PRT
<213> ORGANISM: Homo sapiens

<400> SEQUENCE: 3

Met Tyr Val Lys Leu Ile Ser Ser Asp Gly His Glu Phe Ile Val Lys
1               5                   10                  15

Arg Glu His Ala Leu Thr Ser Gly Thr Ile Lys Ala Met Leu Ser Gly
            20                  25                  30

Pro Gly Gln Phe Ala Glu Asn Glu Thr Asn Glu Val Asn Phe Arg Glu
        35                  40                  45

Ile Pro Ser His Val Leu Ser Lys Val Cys Met Tyr Phe Thr Tyr Lys
    50                  55                  60

Val Arg Tyr Thr Asn Ser Ser Thr Glu Ile Pro Glu Phe Pro Ile Ala
65                  70                  75                  80

Pro Glu Ile Ala Leu Glu Leu Leu Met Ala Ala Asn Phe Leu Asp Cys
                85                  90                  95

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation
<220> FEATURE:
<221> NAME/KEY: MISC_FEATURE
<222> LOCATION: (20)..(20)
<223> OTHER INFORMATION: Carboxylation

<400> SEQUENCE: 4

Asp Leu Asp Leu Glu Ala Leu Ala Pro Tyr Ile Pro Ala Asp Asp Asp
1               5                   10                  15

Phe Gln Leu Arg
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation
<220> FEATURE:
<221> NAME/KEY: MISC_FEATURE
<222> LOCATION: (9)..(9)
<223> OTHER INFORMATION: Xaa at position 9 is hydroxyproline
<220> FEATURE:
<221> NAME/KEY: MISC_FEATURE
<222> LOCATION: (20)..(20)
<223> OTHER INFORMATION: Carboxyamidated

<400> SEQUENCE: 5

Asp Leu Asp Leu Glu Ala Leu Ala Xaa Tyr Ile Pro Ala Asp Asp Asp
1               5                   10                  15

Phe Gln Leu Arg
            20

<210> SEQ ID NO 6
<211> LENGTH: 17
<212> TYPE: PRT
<213> ORGANISM: Artificial Sequence

```
<220> FEATURE:
<223> OTHER INFORMATION: Synthetic peptide

<400> SEQUENCE: 6

Asp Leu Glu Met Leu Ala Pro Tyr Ile Pro Met Asp Asp Asp Phe Gln
1               5                   10                  15

Leu

<210> SEQ ID NO 7
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation

<400> SEQUENCE: 7

Asp Leu Glu Met Leu Ala Pro Tyr Ile Pro Met Asp Asp Asp Phe Gln
1               5                   10                  15

Leu
```

AZAQUINOLONE BASED COMPOUNDS EXHIBITING PROLYL HYDROXYLASE INHIBITORY ACTIVITY, COMPOSITIONS, AND USES THEREOF

CROSS REFERENCES TO RELATED APPLICATIONS

This application claims the benefit of U.S. Provisional Application No. 60/875,706, filed on Dec. 18, 2006, which is hereby incorporated by reference in its entirety and for all purposes as if fully set forth herein.

FIELD OF THE INVENTION

The present invention relates to compounds capable of inhibiting prolyl hydroxylases such as HIF prolyl hydroxylases, compounds that modulate HIF levels, compounds that stabilize HIF, compositions comprising the compounds, and methods for their use for controlling HIF levels. The compounds and compositions may be used to treat diseases or conditions modulated by HIF such as ischemia, anemia, wound healing, auto-transplantation, allo-transplantation, xeno-transplantation, systemic high blood pressure, thalassemia, diabetes, cancer, and inflammatory disorders.

BACKGROUND OF THE INVENTION

The cellular transcription factor HIF (Hypoxia Inducible Factor) occupies a central position in oxygen homeostasis in a wide range of organisms and is a key regulator of responses to hypoxia. The genes regulated by HIF transcriptional activity can play critical roles in angiogenesis, erythropoiesis, hemoglobin F production, energy metabolism, inflammation, vasomotor function, apoptosis and cellular proliferation. HIF can also play a role in cancer, in which it is commonly upregulated, and in the pathophysiological responses to ischemia and hypoxia.

The HIF transcriptional complex comprises an αβ heterodimer: HIF-β is a constitutive nuclear protein that dimerizes with oxygen-regulated HIF-α subunits. Oxygen regulation occurs through hydroxylation of the HIF-α subunits, which are then rapidly destroyed by the proteasome. In oxygenated cells, the von Hippel-Lindau tumor suppressor protein (pVHL) binds to hydroxylated HIF-α subunits, thereby promoting their ubiquitin dependent proteolysis. This process is suppressed under hypoxic conditions, stabilizing HIF-α and promoting transcriptional activation by the HIF αβ complex. See, e.g., U.S. Pat. No. 6,787,326.

Hydroxylation of HIF-α subunits can occur on proline and asparagine residues and can be mediated by a family of 2-oxoglutarate dependent enzymes. This family includes the HIF prolyl hydroxylase isozymes (PHDs), which hydroxylate Pro 402 and Pro 564 of human HIF1α, as well as Factor Inhibiting HIF (FIH), which hydroxylates Asn 803 of human HIF1α. Inhibition of FIH or the PHDs leads to HIF stabilization and transcriptional activation. See, e.g., Schofield and Ratcliffe, Nature Rev. Mol. Cell. Biol., Vol 5, pages 343-354 (2004).

SUMMARY OF THE INVENTION

Provided herein is at least one compound of the Formula I:

a pharmaceutically acceptable salt thereof, a solvate thereof, a chelate thereof, a non-covalent complex thereof, a prodrug thereof, and mixtures of any of the foregoing, wherein:

n is 1 to 6;

each $R_1$ is independently chosen from H, lower alkyl or substituted lower alkyl;

$R_2$ is chosen from H, lower alkyl and substituted lower alkyl;

$R_3$ and $R_4$ are independently chosen from H, lower alkyl, substituted lower alkyl, lower haloalkyl, or substituted lower haloalkyl, or $R_3$ and $R_4$ can join together to form a 3 to 6 membered ring or a substituted 3 to 6 membered ring;

$R_5$ is chosen from OH, SH, $NH_2$, lower alkyl, substituted lower alkyl, lower alkoxy, substituted lower alkoxy or sulfanyl;

$R_6$ is chosen from H, OH, SH $NH_2$, $NHSO_2R_1$ and sulfonyl;

each of $R_7$, $R_8$, and $R_9$ is independently chosen from H, alkyl, substituted alkyl, alkenyl, substituted alkenyl, alkynyl, substituted alkynyl, alkoxy, substituted alkoxy, $NR_{3a}R_{4a}$, C(O)OH, $OR_{12a}$, $SR_{12a}$, $SO_2R_{12}$, CN, $NO_2$, halo, aryl, substituted aryl, heteroaryl, substituted heteroaryl, heteroarylalkyl, substituted heteroarylalkyl, heterocyclo, substituted heterocyclo, heterocycloalkyl, substituted heterocycloalkyl, alkoxycarbonyl, substituted alkoxycarbonyl, or —X—$R_{11}$, wherein:

$R_{3a}$ and $R_{4a}$ are independently chosen from H, lower alkyl, substituted lower alkyl, lower haloalkyl, or substituted lower haloalkyl, or $R_{3a}$ and $R_{4a}$ can join together to form a 3 to 6 membered ring or a substituted 3 to 6 membered ring;

X is chosen from —N($R_{10}$)—Y— and —Y—N($R_{10}$)—;

Y is chosen from C(O), $SO_2$, alkylene, substituted alkylene, alkenylene, substituted alkenylene, alkynylene, and substituted alkynylene;

$R_{10}$ is chosen from H, lower alkyl, and substituted lower alkyl, $R_{11}$ is chosen from H, heterocyclo, substituted heterocyclo, aryl, substituted aryl, heteroaryl and substituted heteroaryl;

$R_{12}$ is chosen from H, alkyl, substituted alkyl, alkenyl, substituted alkenyl, alkynyl, substituted alkynyl or $NR_{3a}R_{4a}$; and $R_{12a}$ is chosen from H, alkyl, substituted alkyl, alkenyl, substituted alkenyl, alkynyl, or substituted alkynyl;

wherein optionally at least one of adjacent pairs $R_6$ and $R_7$, $R_7$ and $R_8$, $R_8$ and $R_9$, and $R_9$ and $R_1$, join together to form a 4 to 7 membered ring or a substituted 4 to 7 membered ring.

In some embodiments, if n is 1, $R_3$ and $R_4$ are not both H.

In some embodiments, n is 1 and $R_3$ and $R_4$ are both H.

In some embodiments, the compound of Formula I has the Formula II

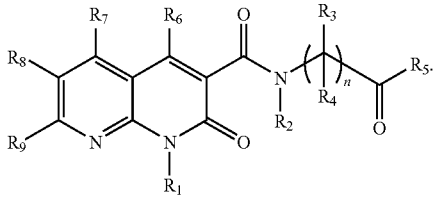

In some embodiments, the compound of Formula I has the Formula III

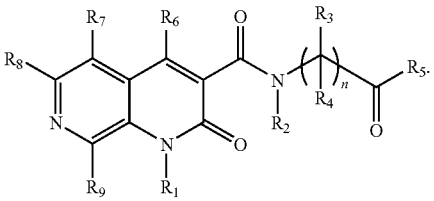

In some embodiments, the compound of Formula I has the Formula IV

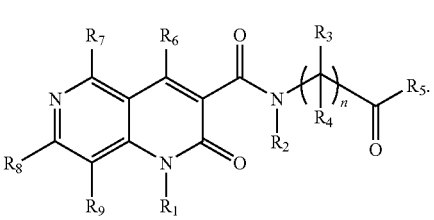

In some embodiments, the compound of Formula I has the Formula V

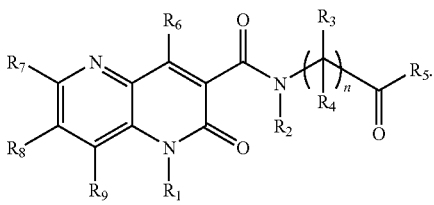

In some embodiments, $R_5$ is OH.

In some embodiments, $R_6$ is OH.

In some embodiments, at least one of $R_7$, $R_8$, and $R_9$ is H.

In some embodiments, at least one of $R_7$, $R_8$, and $R_9$ is a substituted or unsubstituted aryl, substituted or unsubstituted heteroaryl, substituted or unsubstituted cycloalkyl, or a substituted or unsubstituted heterocyclo group. In some such embodiments, at least one of $R_7$, $R_8$, and $R_9$ is a heterocyclo group. In other such embodiments, at least one of $R_7$, $R_8$, and $R_9$ is a heteroaryl group. In still other such embodiments, at least one of $R_7$, $R_8$, and $R_9$ is a phenyl or substituted phenyl group.

In some embodiments, at least one of $R_7$, $R_8$, and $R_9$ is independently chosen from halo or a moiety substituted with at least one halo. For example, in some such embodiments, at least one of $R_7$, $R_8$, and $R_9$ is trifluoromethyl.

In some embodiments, at least one of $R_7$, $R_8$, and $R_9$ is independently chosen from H, alkyl, substituted alkyl, alkenyl, substituted alkenyl, alkynyl, and substituted alkynyl.

In some embodiments, n is 1. In some such embodiments, $R_3$ is selected from H, lower alkyl, substituted lower alkyl, lower haloalkyl, or substituted lower haloalkyl and $R_4$ is selected from lower alkyl, substituted lower alkyl, lower haloalkyl, or substituted lower haloalkyl, or $R_3$ and $R_4$ can join together to form a 3 to 6 membered ring or a substituted 3 to 6 membered ring.

Also provided are pharmaceutical compositions that include at least one pharmaceutically acceptable carrier, and a therapeutically effective amount of at least one compound of any of the embodiments described herein. In such embodiments, the at least one compound is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

Further provided are pharmaceutical compositions that include at least one pharmaceutically acceptable carrier, and a therapeutically effective amount of at least one compound of any of the embodiments described herein in combination with at least one additional compound such as an erythropoiesis stimulating agent or chemotherapeutic agent.

In some embodiments, the at least one compound is a salt. Such salts may be anhydrous or associated with water as a hydrate.

In some embodiments, the compound is a prodrug. In some such embodiments, the compound is a $(C_1-C_6)$alkyl ester such as a methyl, ethyl, propyl, butyl, pentyl, or hexyl ester.

Additionally provided is a method of increasing HIF levels or activity in a subject by. Such methods include administering to the subject at least one compound of any of the embodiments described herein.

Further provided is a method of treating a condition where it is desired to modulate HIF activity. Such methods include administering to a subject at least one compound of any of the embodiments described herein. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder Also provided is a method of treating a hypoxic or ischemic related disorder in a subject. Such methods include administering to a subject at least one compound of any of the embodiments described herein.

Also provided is a method of treating anemia in a subject. Such methods include administering to a subject at least one compound of any of the embodiments described herein.

Further provided is a method of modulating the amount of HIF in a cell. Such methods include contacting the cell with at least one compound of any of the embodiments described herein.

Additionally provided is a method of increasing the amount of hemoglobin F in a subject. Such methods include administering to the subject at least one compound of any of the embodiments described herein.

Also provided is a method of modulating angiogenesis in a subject. Such methods include administering to the subject at least one compound of any of the embodiments described herein.

Additionally provided is a method of treating at least one disease in a patient in need of such treatment. Such methods include administering to the patient a therapeutically effective amount of at least one compound of any of the embodiments described herein. In some such embodiments, the at least one disease is selected from ischemia, anemia, wound healing, auto-transplantation, allo-transplantation, xeno-transplantation, systemic high blood pressure, thalassemia, diabetes, cancer, or an inflammatory disorder Also provided is a method of inhibiting HIF hydroxylation in a subject. Such methods include administering to the subject at least one compound of any of the embodiments described herein.

In some embodiments, the HIF PHD inhibitory activity $IC_{50}$ value of the compound is 40 μM or less. In other embodiments, the HIF PHD inhibitory activity $IC_{50}$ value of the compound is 10 μM or less.

In some embodiments, the at least one compound of any of the embodiments is used in the preparation of a medicament.

In some such embodiments, the at least one compound of any of the embodiments is used in the preparation of a medicament for increasing or stabilizing HIF levels or activity in a subject.

In some such embodiments, the at least one compound of any of the embodiments is used in the preparation of a medicament for treating a condition where it is desired to modulate HIF activity. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

In some embodiments, the at least one compound of any of the embodiments is used in the preparation of a medicament for treating a hypoxic or ischemic related disorder in a subject.

In some embodiments, the at least one compound of any of the embodiments is used in the preparation of a medicament for modulating the amount if HIF in a cell. In some embodiments, the at least one compound according to any of the embodiments is used to modulate the amount of HIF in a cell.

In some embodiments, the at least one compound of any of the embodiments is used in the preparation of a medicament for modulating angiogenesis in a subject.

In some embodiments, the at least one compound of any of the embodiments is used in the preparation of a medicament for inhibiting HIF hydroxylation in a subject.

In some embodiments, the at least one compound of any of the embodiments is used in the preparation of a medicament for treating anemia.

Other objects, features and advantages of the invention will become apparent to those skilled in the art from the following description and claims.

BRIEF DESCRIPTION OF THE DRAWINGS

FIG. 2A illustrates a 0-125 nM peptide range and FIG. 2B illustrates a 0-10 nM peptide range.

FIG. 3A illustrates a time course for the hydroxylation of the HIF1α peptide with increasing amounts of HIF PHD2 enzyme. FIG. 3B illustrates initial rates with increasing enzyme concentrations.

DETAILED DESCRIPTION OF THE INVENTION

Figure 1:
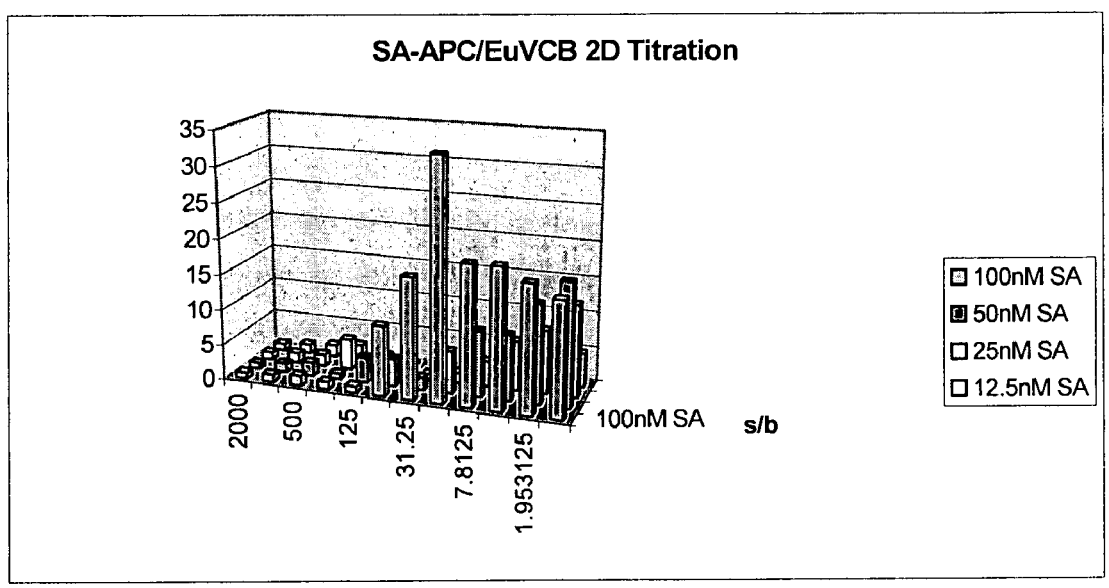
FIG. 1 is a graph illustrating the ratio of fluorescence signal to background generated by the interaction of Eu-VCB with streptavidin-APC-hydroxyprolyl HIF1α peptide.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. Should the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Compounds of Formula I include, but are not limited to optical isomers of compounds of Formula I, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I include Z- and E-forms (or cis- and trans-forms) of compounds with double bonds. Where compounds of Formula I exists in various tautomeric forms, chemical entities of the present invention include all tautomeric forms of the compound.

As noted above, compounds of the invention may exist in multiple tautomeric forms. These forms are illustrated below as "Tautomer A", "Tautomer B", and "Tautomer C":

Tautomer A

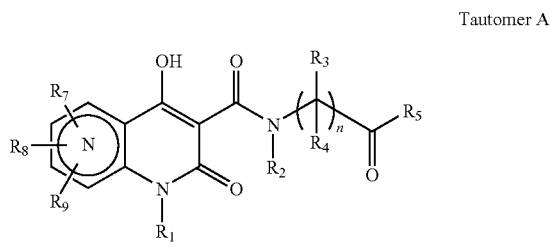

Tautomer B

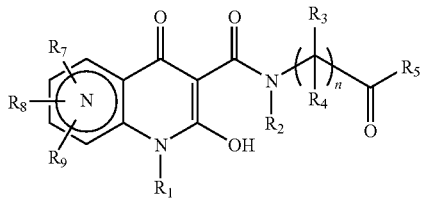

Tautomer C

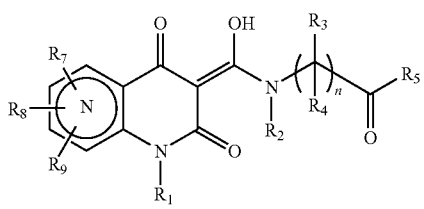

Compounds of the invention are depicted structurally and named as compounds in the "Tautomer A" form. However, it is specifically contemplated that the compounds may also exist in "Tautomer B" or "Tautomer C" form and compounds in "Tautomer B" form or "Tautomer C" form or another tautomeric form are expressly considered to be part of the invention.

Compounds of the present disclosure include, but are not limited to compounds of Formula I and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used henceforth, the term "compound" encompasses not only the compound itself, but also a pharmaceutically acceptable salt thereof, a solvate thereof, a chelate thereof, a non-covalent complex thereof, a prodrug thereof, and mixtures of any of the foregoing. In addition, the ring nitrogen that may be in the 5, 6, 7, or 8 position in the azaquinolone ring system is either unsubstituted or is present in its N-oxide form.

As noted above, prodrugs also fall within the scope of chemical entities, for example, ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, benzoate, carbomethoxy, carboethoxy, and like derivatives of functional groups (such as alcohol, carboxylic acid, ether, ester, or amine groups) in the compounds of Formula I. In some embodiments, the prodrugs of the compounds are esters such as methyl, ethyl, propyl, butyl, pentyl, and hexyl esters.

The term "solvate" refers to the compound formed by the interaction of a solvent and a compound. Suitable solvates are pharmaceutically acceptable solvates, such as hydrates, including monohydrates and hemi-hydrates.

"Alkenyl" refers to an unsaturated branched, straight-chain or cyclic hydrocarbon group having at least one carbon-carbon double bond derived by the removal of one hydrogen atom from a single carbon atom of a parent alkene. The group may be in either the Z- and E-forms (cis or trans) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms, i.e. "lower alkenyl."

"Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has from 2 to 20 carbon atoms and in other embodiments, from 2 to 6 carbon atoms, i.e. "lower alkynyl."

"Alkoxy" refers to a radical —OR where R represents an alkyl, substituted alkyl, alkenyl, substituted alkenyl, substituted cycloalkyl, substituted heterocyclyl, substituted aryl, or substituted heteroaryl group as defined herein. Representative examples include, but are not limited to, methoxy, ethoxy, propoxy, butoxy, cyclohexyloxy, and the like.

"Alkoxycarbonyl" refers to a radical —C(O)—OR where R is as defined above with respect to "Alkoxy".

"Alkyl" refers to a saturated, branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. In certain embodiments, an alkyl group comprises from 1 to 20 carbon atoms. As used herein the term "lower alkyl" refers to an alkyl group comprising from 1 to 6 carbon atoms.

"Alkylene" refers to a divalent saturated hydrocarbon group derived from a parent alkane by removal of two hydrogen atoms. Examples of alkylene group include, but are not limited to, —CH$_2$—, —CH$_2$CH$_2$—, —CH(CH$_3$)—, —CH$_2$CH$_2$CH$_2$—, —CH$_2$C(CH$_3$)(H)—, and the like.

"Alkenylene" refers to a divalent unsaturated hydrocarbon group having at least one carbon-carbon double bond derived by the removal of two hydrogen atoms from a parent alkene. The group may be in either the Z- or E-form (cis or trans) about the double bond(s). Examples of alkenylene groups, include, but are not limited to, —CH═CH—, —CH═C(H)CH$_2$—, —CH$_2$C(H)═C(H)CH$_2$—, and the like.

"Alkynylene" refers to a divalent unsaturated hydrocarbon group having at least one carbon-carbon triple bond derived by the removal of two hydrogen atoms from a parent alkyne. Example of alkynylene groups, include, but are not limited to, —C≡C—, —CH$_2$C≡C—, —CH$_2$C≡CCH$_2$—.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. For example, aryl includes 5- and 6-membered carbocyclic aromatic rings fused to a 5- to 7-membered heterocycloalkyl ring containing 1 or more heteroatoms chosen from N, O, and S. In certain embodiments, an aryl group can comprise from 6 to 10 carbon atoms. Aryl, however, does not encompass or overlap in any way with heteroaryl, separately defined below. Hence, if one or more carbocyclic aromatic rings is fused with a heterocyclic aromatic ring, the resulting ring system is heteroaryl, not aryl, as defined herein.

"Arylalkyl" or "aralkyl" refers to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkyl, arylalkenyl, and/or arylalkynyl is used. In certain embodiments, an arylalkyl group can be $(C_{6-30})$ arylalkyl, e.g., the alkyl group of the arylalkyl group can be $(C_{1-10})$ and the aryl moiety can be $(C_{5-20})$.

"Arylalkenyl" refers to an alkenyl group in which a bond to one of the hydrogen atoms of the alkenyl group is replaced with a bond to an aryl group.

"Arylalkynyl" refers to an alkynyl group in which a bond to one of the hydrogen atoms of the alkynyl group is replaced with a bond to an aryl group.

"Carbonyl" refers to the radical —C(O) group.

"Carboxy" refers to the radical —C(O)OH.

"Cyano" refers to the radical —CN.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In certain embodiments, the cycloalkyl group can be $C_{3-10}$ cycloalkyl, such as, for example, $C_{3-6}$ cycloalkyl.

"Heterocyclic", "heterocyclo", or "heterocyclyl" refers to a saturated or unsaturated, but non-aromatic, cyclic alkyl group in which one or more carbon atoms (and any associated hydrogen atoms) are independently replaced with the same or different heteroatom and its associated hydrogen atoms, where appropriate. Typical heteroatoms to replace the carbon atom(s) include, but are not limited to, N, O, and S. Where a specific level of saturation is intended, the nomenclature "heterocyclo" or "heterocyclyl" is used. Typical heterocyclo groups include, but are not limited to, groups derived from epoxides, imidazolidine, morpholine, piperazine, piperidine, pyrazolidine, pyrrolidine, quinuclidine, tetrahydrofuran, tetrahydropyran and the like. Substituted heterocyclo also includes ring systems substituted with one or more oxo (=O) or oxide (—O⁻) substituents, such as piperidinyl N-oxide, morpholinyl-N-oxide, 1-oxo-1-thiomorpholinyl, and 1,1-dioxo-1-thiomorpholinyl.

"Heterocyclyoalkyl" refers to an alkyl group in which one of the hydrogen atoms of the alkyl is replaced with a bond to a heterocyclyl group. Examples of heterocyclylalkyl groups, include, but are not limited to, morpholinylmethyl, morpholinylethyl, tetrahydrofuranylmethyl, piperidinylmethyl, and the like.

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl encompasses: 5- to 7-membered aromatic, monocyclic rings containing one or more, for example, from 1 to 4, or in certain embodiments, from 1 to 3, heteroatoms chosen from N, O, and S, with the remaining ring atoms being carbon; and polycyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heteroaromatic ring fused to a 5- to 7-membered cycloalkyl ring or a carbocyclic aromatic ring and a 5- to 7-membered heteroaromatic ring fused to a 5- to 7-membered heterocyclo ring. For fused, bicyclic heteroaryl ring systems wherein only one of the rings contains one or more heteroatoms, the point of attachment may be at the heteroaromatic ring or the carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Heteroarylalkyl" or "heteroaralkyl" refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, and/or heteroarylalkynyl is used. In certain embodiments, the heteroarylalkyl group can be a 6 to 30 membered heteroarylalkyl, e.g., the alkanyl, alkenyl or alkynyl moiety of the heteroarylalkyl can be 1 to 10 membered and the heteroaryl moiety can be a 5 to 20-membered heteroaryl.

"Sulfonyl" refers to a radical —S(O)₂R where R is an alkyl, substituted alkyl, substituted cycloalkyl, substituted heterocyclo, substituted aryl, or substituted heteroaryl group as defined herein. Representative examples include, but are not limited to methylsulfonyl, ethylsulfonyl, propylsulfonyl, butylsulfonyl, and the like.

"Sulfanyl" refers to a radical —SR where R is an alkyl, substituted alkyl, substituted cycloalkyl, substituted heterocyclo, substituted aryl, or substituted heteroaryl group as defined herein that may be optionally substituted as defined herein. Representative examples include, but are not limited to, methylthio, ethylthio, propylthio, butylthio, and the like.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Substituted" refers to a group in which one or more hydrogen atoms are each independently replaced with the same or different substituent(s). Typical substituents include, but are not limited to, —X, —$R_{33}$, —H, =O, —$OR_{33}$, —$SR_{33}$, —SH, =S, —$NR_{33}R_{34}$, =$NR_{33}$, —$CX_3$, —$CF_3$, —CN, —$NO_2$, —$S(O)_2R_{33}$, —$OS(O_2)OH$, —$OS(O)_2R_{33}$, —OP(O)($OR_{33}$)($OR_{34}$), —C(O)$R_{33}$, —C(S)$R_{33}$, —C(O)$OR_{33}$, —C(O)$NR_{33}R_{34}$, —C(O)OH, —C(S)$OR_{33}$, —$NR_{35}$C(O)$NR_{33}R_{34}$, —$NR_{35}$C(S)$NR_{33}R_{34}$, —$NR_{35}$C($NR_{33}$)$NR_{33}R_{34}$, —C($NR_{33}$)$NR_{33}R_{34}$, —S(O)$_2NR_{33}R_{34}$, —$NR_{35}$S(O)$_2R_{33}$, —$NR_{35}$C(O)$R_{33}$, and —S(O)$R_{33}$ where each X is independently a halo; each $R_{33}$ and $R_{34}$ are independently hydrogen, alkyl, substituted alkyl, alkyl interrupted by one or more —O— or —S— groups aryl, substituted aryl, arylalkyl, substituted arylalkyl, cycloalkyl, substituted cycloalkyl, heterocyclo, substituted heterocyclo, heteroaryl, substituted heteroaryl, heteroarylalkyl, substituted heteroarylalkyl, —$NR_{35}R_{36}$, C(O)$R_{35}$ or —S(O)$_2R_{35}$ or optionally $R_{33}$ and $R_{34}$ together with the atom to which $R_{33}$ and $R_{34}$ are attached form one or more heterocyclo, substituted heterocyclo, heteroaryl, or substituted heteroaryl rings; and $R_{35}$ and $R_{36}$ are independently hydrogen, alkyl, substituted alkyl, aryl, substituted aryl, arylalkyl, substituted arylalkyl, cycloalkyl, substituted cycloalkyl, heterocyclo, substituted heterocyclo, heteroaryl, substituted heteroaryl, heteroarylalkyl or substituted heteroarylalkyl, or optionally $R_{35}$ and $R_{36}$ together with the nitrogen atom to which $R_{35}$ and $R_{36}$ are attached form one or more heterocyclo, substituted heterocyclo, heteroaryl, or substituted heteroaryl rings. In certain embodiments, a tertiary amine or aromatic nitrogen may be substituted with on or more oxygen atoms to form the corresponding nitrogen oxide.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Embodiments of the present invention are directed to at least one compound of Formula I:

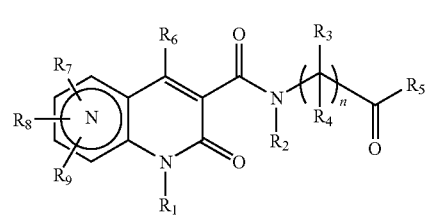

a pharmaceutically acceptable salt thereof, a solvate thereof, a chelate thereof, a non-covalent complex thereof, a prodrug thereof, or mixtures of any of the foregoing, wherein:

n is 1 to 6;

each $R_1$ is independently chosen from H, lower alkyl or substituted lower alkyl;

$R_2$ is chosen from H, lower alkyl and substituted lower alkyl;

$R_3$ and $R_4$ are independently chosen from H, lower alkyl, substituted lower alkyl, lower haloalkyl, or substituted lower haloalkyl, or $R_3$ and $R_4$ can join together to form a 3 to 6 membered ring or a substituted 3 to 6 membered ring;

$R_5$ is chosen from OH, SH, $NH_2$, lower alkyl, substituted lower alkyl, lower alkoxy, substituted lower alkoxy or sulfanyl;

$R_6$ is chosen from H, OH, SH $NH_2$, $NHSO_2R_1$ and sulfonyl;

each of $R_7$, $R_8$, and $R_9$ is independently chosen from H, alkyl, substituted alkyl, alkenyl, substituted alkenyl, alkynyl, substituted alkynyl, alkoxy, substituted alkoxy, $NR_{3a}R_{4a}$, C(O)OH, $OR_{12a}$, $SR_{12a}$, $SO_2R_{12}$, CN, $NO_2$, halo, aryl, substituted aryl, heteroaryl, substituted heteroaryl, heteroarylalkyl, substituted heteroarylalkyl, heterocyclo, substituted heterocyclo, heterocycloalkyl, substituted heterocycloalkyl, alkoxycarbonyl, substituted alkoxycarbonyl, or —X—$R_{11}$, wherein:

$R_{3a}$ and $R_{4a}$ are independently chosen from H, lower alkyl, substituted lower alkyl, lower haloalkyl, or substituted lower haloalkyl, or $R_{3a}$ and $R_{4a}$ can join together to form a 3 to 6 membered ring or a substituted 3 to 6 membered ring;

X is chosen from —N($R_{10}$)—Y— and —Y—N($R_{10}$)—;

Y is chosen from C(O), $SO_2$, alkylene, substituted alkylene, alkenylene, substituted alkenylene, alkynylene, and substituted alkynylene;

$R_{10}$ is chosen from H, lower alkyl, and substituted lower alkyl, $R_{11}$ is chosen from H, heterocyclo, substituted heterocyclo, aryl, substituted aryl, heteroaryl and substituted heteroaryl;

$R_{12}$ is chosen from H, alkyl, substituted alkyl, alkenyl, substituted alkenyl, alkynyl, substituted alkynyl or $NR_{3a}R_{4a}$; and $R_{12a}$ is chosen from H, alkyl, substituted alkyl, alkenyl, substituted alkenyl, alkynyl, or substituted alkynyl;

wherein optionally at least one of adjacent pairs $R_6$ and $R_7$, $R_7$ and $R_8$, $R_8$ and $R_9$, and $R_9$ and $R_1$, join together to form a 4 to 7 membered ring or a substituted 4 to 7 membered ring.

Some embodiments of the present invention are directed to at least one compound of the Formula II

II a pharmaceutically acceptable salt thereof, a solvate thereof, a chelate thereof, a non-covalent complex thereof, a prodrug thereof, or mixtures of any of the foregoing.

Some embodiments of the present invention are directed to at least one compound of the Formula III

III a pharmaceutically acceptable salt thereof, a solvate thereof, a chelate thereof, a non-covalent complex thereof, a prodrug thereof, or mixtures of any of the foregoing.

Some embodiments of the present invention are directed to at least one compound of the Formula IV

IV a pharmaceutically acceptable salt thereof, a solvate thereof, a chelate thereof, a non-covalent complex thereof, a prodrug thereof, or mixtures of any of the foregoing.

Some embodiments of the present invention are directed to at least one compound of the Formula V

V a pharmaceutically acceptable salt thereof, a solvate thereof, a chelate thereof, a non-covalent complex thereof, a prodrug thereof, or mixtures of any of the foregoing.

In certain embodiments of compounds of Formulas I, II, III, IV, and V, if n is 1, $R_3$ and $R_4$ are not both H. In certain embodiments of compounds of Formulas I, II, III, IV, and V, n is 1 and $R_3$ and $R_4$ are both H.

In certain embodiments of compounds of Formulas I, II, III, IV, and V, n is 1. In some such embodiments, $R_3$ is selected from H, lower alkyl, substituted lower alkyl, lower haloalkyl, or substituted lower haloalkyl and $R_4$ is selected from lower alkyl, substituted lower alkyl, lower haloalkyl, or substituted lower haloalkyl, or $R_3$ and $R_4$ can join together to form a 3 to 6 membered ring or a substituted 3 to 6 membered ring. In some embodiments, $R_4$ is a methyl group. In some such embodiments, $R_3$ is H.

In certain embodiments of compounds of Formulas I, II, III, IV, and V, $R_2$ is chosen from H.

In certain embodiments of compounds of Formulas I, II, III, IV, and V, $R_5$ is chosen from OH, a lower alkoxy such as methoxy, ethoxy and propoxy, a substituted lower alkoxy and a primary amide. In some such embodiments, $R_5$ is OH or a salt thereof.

In certain embodiments of compounds of Formulas I, II, III, IV, and V, $R_6$ is chosen from H, OH and alkoxy. In some embodiments, $R_6$ is chosen from OH, SH, $NH_2$, $NHSO_2R_1$, and sulfonyl. In some such embodiments, $R_6$ is OH.

In certain embodiments of compounds of Formulas I, II, III, IV, and V, $R_3$ and $R_4$ join together to form a 3 to 6 membered ring or a substituted 3 to 6 membered ring. The 3 to 6 membered rings can comprise at least one heteroatom, such as at least two heteroatoms.

In certain embodiments of compounds of Formulas I, II, III, IV, and V, $R_6$ and $R_7$ can join together to form a 4 to 7 membered ring or a substituted 4 to 7 membered ring. The 4 to 7 membered rings can comprise at least one heteroatom, such as at least two heteroatoms, and at least three heteroatoms.

In certain embodiments of compounds of Formulas I, II, III, IV, and V, at least one of $R_7$, $R_8$, and $R_9$ is independently chosen from halo or a moiety substituted with at least one halo, such as trifluoromethyl.

In certain embodiments of compounds of Formulas I, II, III, IV, and V, at least one of $R_7$, $R_8$, and $R_9$ is independently chosen from alkoxy or substituted alkoxy.

In certain embodiments of compounds of Formulas I, II, III, IV, and V, at least one of $R_7$, $R_8$, and $R_9$ is independently chosen from aryl, substituted aryl, heteroaryl, substituted heteroaryl, heterocycloalkyl, or substituted heterocycloalkyl, such as substituted pyridines, substituted pyrimidines, substituted pyrazines, substituted pyridazines, substituted tetrahydrofurans and substituted piperidines In certain embodiments of compounds of Formulas I, II, III, IV, and V, at least one of $R_7$, $R_8$, and $R_9$ is independently chosen from a substituted or unsubstituted aryl, substituted or unsubstituted heteroaryl, substituted or unsubstituted cycloalkyl, or a substituted or unsubstituted heterocyclo group. In some such embodiments, at least one of $R_7$, $R_8$, and $R_9$ is a heterocyclo group. In other such embodiments, at least one of $R_7$, $R_8$, and $R_9$ is a heteroaryl group. In still other such embodiments, at least one of $R_7$, $R_8$, and $R_9$ is a phenyl or substituted phenyl group.

In certain embodiments of compounds of Formulas I, II, III, IV, and V, at least one of $R_7$, $R_8$, and $R_9$ is independently chosen from H, alkyl, substituted alkyl, alkenyl, substituted alkenyl, alkynyl, and substituted alkynyl, such as isopropyl, cyclohexane, cyclopentane, cyclohexene and cyclopentene. In some such embodiments, at least one of $R_7$, $R_8$, and $R_9$ is H.

In certain embodiments, a compound of the invention can be
- 2-(4-Hydroxy-1-methyl-2-oxo-6-(4-(trifluoromethyl)pyrimidin-2-yl)-1,2-dihydro-1,8-naphthyridine-3-carboxamido)acetic acid
- 2-(6-(2-(Dimethylamino)phenyl)-4-hydroxy-1-methyl-2-oxo-1,2-dihydro-1,8-naphthyridine-3-carboxamido)acetic acid
- 2-(6-Cyclohexyl-4-hydroxy-1-methyl-2-oxo-1,2-dihydro-1,8-naphthyridine-3-carboxamido)acetic acid
- 2-(6-Cyclohexenyl-4-hydroxy-1-methyl-2-oxo-1,2-dihydro-1,8-naphthyridine-3-carboxamido)acetic acid
- (R)-2-(4-hydroxy-1-methyl-2-oxo-6-(tetrahydro-2 H-pyran-2-yl)-1,2-dihydro-1,8-naphthyridine-3-carboxamido)acetic acid
- (S)-2-(4-Hydroxy-1-methyl-2-oxo-6-(tetrahydro-2 H-pyran-2-yl)-1,2-dihydro-1,8-naphthyridine-3-carboxamido)acetic acid.
- 2-(6-(2-Cyclopropylethynyl)-4-hydroxy-1-methyl-2-oxo-7-(trifluoromethyl)-1,2-dihydro-1,8-naphthyridine-3-carboxamido)acetic acid(f) 2-(4-Hydroxy-1-methyl-2-oxo-7-(trifluoromethyl)-1,2-dihydro-1,8-naphthyridine-3-carboxamido)acetic acid
- 2-(6-cyclopropyl-4-hydroxy-1-methyl-2-oxo-7-(trifluoromethyl)-1,2-dihydro-1,8-naphthyridine-3-carboxamido)acetic acid
- 2-(6-Cyclohexyl-4-hydroxy-1-methyl-2-oxo-7-(trifluoromethyl)-1,2-dihydro-1,8-naphthyridine-3-carboxamido)acetic acid
- 2-(6-(2-Cyclopropylethynyl)-4-hydroxy-1-methyl-2-oxo-7-(trifluoromethyl)-1,2-dihydro-1,8-naphthyridine-3-carboxamido)acetic acid or a pharmaceutically acceptable salt thereof.

In some embodiments, the at least one compound is any Example compound set forth in the following Examples.

Compounds of the present disclosure can contain one or more chiral centers. Such compounds can be prepared or isolated as pure stereoisomers, i.e., as individual enantiomers or diastereomers, or as stereoisomer-enriched mixtures. All such stereoisomers, and enriched mixtures thereof, are included within the scope of the present disclosure. Pure stereoisomers, and enriched mixtures thereof, can be prepared using, for example, optically active starting materials or stereoselective reagents well-known in the art. Alternatively, racemic mixtures of such compounds can be separated using, for example, chiral column chromatography, chiral resolving agents and the like.

In some embodiments, the at least one compound is a salt. Such salts may be anhydrous or associated with one or more molecules of water as a hydrate.

In some embodiments, the compound is a prodrug. In some such embodiments, the compound is a $(C_1-C_6)$alkyl ester such as a methyl, ethyl, propyl, butyl, pentyl, or hexyl ester.

Also provided herein are pharmaceutical compositions that include at least one pharmaceutically acceptable carrier, excipient, or diluent, and a therapeutically effective amount of at least one compound of any of the embodiments described herein. The at least one compound can be present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

Further provided are pharmaceutical compositions that include at least one pharmaceutically acceptable carrier, and a therapeutically effective amount of at least one compound of any of the embodiments described herein in combination with at least one additional compound such as an erythropoiesis stimulating agent or a chemotherapeutic agent.

Additionally provided is a method of increasing or stabilizing HIF levels or activity in a subject by administering to the subject at least one compound of any of the embodiments described herein.

Further provided is a method of treating a condition where it is desired to modulate HIF activity comprising administering to a subject at least one compound of any of the embodiments described herein. The condition can be selected from at least one of ischemia, anemia, wound healing, auto-transplantation, allo-transplantation, xeno-transplantation, systemic high blood pressure, thalassemia, diabetes, cancer, or an inflammatory disorder. Also provided is a method of treating a hypoxic or ischemic related disorder in a subject comprising administering to a subject at least one compound of any of the embodiments described herein.

Also provided is a method of treating anemia in a subject comprising administering to a subject at least one compound of any of the embodiments described herein.

Further provided is a method of modulating the amount of HIF in a cell comprising contacting the cell with at least one compound of any of the embodiments described herein.

Additionally provided is a method of increasing the amount of hemoglobin F in a subject comprising administering to the subject at least one compound of any of the embodiments described herein.

Also provided is a method of modulating angiogenesis in a subject comprising administering to the subject at least one compound of any of the embodiments described herein.

Additionally provided is a method of treating at least one disease in a patient in need of such treatment comprising administering to the patient a therapeutically effective amount of at least one compound of any of the embodiments described herein. In some such embodiments, the at least one disease can be selected from ischemia, anemia, wound healing, auto-transplantation, allo-transplantation, xeno-transplantation, systemic high blood pressure, thalassemia, diabetes, cancer, or an inflammatory disorder.

Also provided is a method of inhibiting HIF hydroxylation in a subject comprising administering to the subject at least one compound of any of the embodiments described herein.

In some embodiments, the HIF PHD inhibitory activity $IC_{50}$ value of the compound is 40 μM or less. In other embodiments, the HIF PHD inhibitory activity $IC_{50}$ value of the compound is 10 μM or less. In still other embodiments, the HIF PHD inhibitory activity $IC_{50}$ value of the compound is 100 nM or less, whereas in others it is 10 nM or less.

In some embodiments, the at least one compound of any of the embodiments is used in the preparation of a medicament.

In some such embodiments, the at least one compound of any of the embodiments is used in the preparation of a medicament for increasing or stabilizing HIF levels or activity in a subject.

In some such embodiments, the at least one compound of any of the embodiments is used in the preparation of a medicament for treating a condition where it is desired to modulate HIF activity. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

In some embodiments, the at least one compound of any of the embodiments is used in the preparation of a medicament for treating a hypoxic or ischemic related disorder in a subject.

In some embodiments, the at least one compound of any of the embodiments is used in the preparation of a medicament for modulating the amount if HIF in a cell. In some embodiments, the at least one compound according to any of the embodiments is used to modulate the amount of HIF in a cell.

In some embodiments, the at least one compound of any of the embodiments is used in the preparation of a medicament for modulating angiogenesis in a subject.

In some embodiments, the at least one compound of any of the embodiments is used in the preparation of a medicament for inhibiting HIF hydroxylation in a subject.

In some embodiments, the at least one compound of any of the embodiments is used in the preparation of a medicament for treating anemia. The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier, excipient, or diluent is compatible with the other ingredients of the formulation and is not deleterious to the recipient thereof.

Composition formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

Embodiments of the invention are further described by the following examples. These examples are illustrative of the invention and are not intended to be limiting in any way.

EXAMPLES

Unless otherwise noted, all materials were obtained from commercial suppliers and used without further purification. All parts are by weight and temperatures are in degrees centigrade unless otherwise indicated. All microwave assisted reactions were conducted with a Smith Synthesizer from Personal Chemistry, Uppsala, Sweden. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography. Unless otherwise stated, reactions were run at room temperature. The following abbreviations are used to refer to various reagents and solvents:
DMSO Dimethyl sulfoxide
DMF N,N-Dimethylformamide
THF Tetrahydrofuran
$Et_2O$ Diethyl ether
EtOAc Ethyl acetate
MeOH Methyl alcohol
EtOH Ethyl alcohol
MeCN Acetonitrile
MeI Iodomethane
NMP 1-Methyl-2-pyrrolidinone
DCM Dichloromethane
TFA Trifluoroacetic acid
TR-FRET Time Resolved-Fluorescence Resonance Energy Transfer Example 1

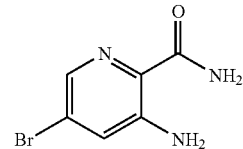

(a) 3-Amino-5-bromopicolinamide. A mixture of 5-bromo-3-nitropicolinonitrile (40 g, 0.17 mol) and Raney Ni (22 g) in EtOH (1500 mL) was stirred under 45 psi $H_2$ atmosphere at room temperature for 5 hours. The reaction mixture was filtered and the filtrate was evaporated under reduced pressure and dried in vacuo to give the title compound.

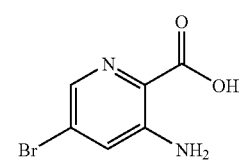

(b) 3-Amino-5-bromopicolinic acid. A mixture of 3-amino-5-bromopicolinamide (28.2 g, 0.13 mol) and concentrated HCl (361 mL) was heated at reflux for 12 hours. The reaction mixture was allowed to reach room temperature, and the solid which precipitated was filtered. The filter cake was dissolved in water, and the pH of the aqueous solution was adjusted to pH=4 with saturated NaOAc, and extracted with EtOAc (3×). The combined organic extracts were dried over anhydrous MgSO$_4$, and filtered. The filtrate was evaporated under reduced pressure, and the residue dried in vacuo to afford the title compound as a solid.

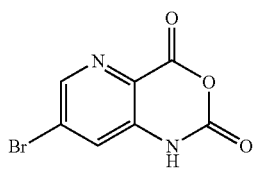

(c) 7-Bromo-1 H-pyrido[3,2-d][1,3]oxazine-2,4-dione. To a solution of 3-amino-5-bromopicolinic acid (18.5 g, 85.3 mmol) in dioxane (185 mL) was added 20% solution of phosgene in toluene (53.4 mL, 108 mmol) dropwise with stirring at room temperature. The reaction mixture was stirred at reflux for 3 hours, left to reach room temperature, and the solid precipitate was filtered, and dried in vacuo to give the title compound.

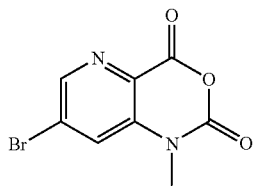

(d) 7-Bromo-1-methyl-1 H-pyrido[3,2-d][1,3]oxazine-2,4-dione. To a solution of 7-bromo-1 H-pyrido[3,2-d][1,3]oxazine-2,4-dione (12 g, 49.4 mmol) in dry N,N-dimethylacetamide (81 mL), was added NaH (60% dispersion in mineral oil, 2.4 g, 60 mmol) in small portions with stirring and cooling with an ice-bath. After the addition, the reaction mixture was treated with MeI (3.4 mL, 60 mmol) and stirred at room temperature overnight. The reaction mixture was poured into water, and the solid precipitate was filtered and dried in vacuo to afford the title compound as a solid.

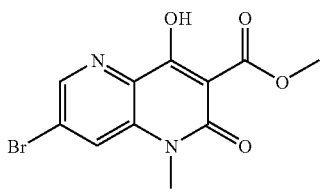

(e) Methyl 7-bromo-4-hydroxy-1-methyl-2-oxo-1,2-dihydro-1,5-naphthyridine-3-carboxylate. To a solution of methyl malonate (4.96 mL, 44.5 mmol) in dry N,N-dimethylacetamide (71.6 mL), was added NaH (60% dispersion in mineral oil, 1.78 g, 44.5 mmol) in small portions with stirring and cooling with an ice-bath. After the addition, the reaction mixture was stirred at room temperature for 30 minutes and then treated with 7-bromo-1-methyl-1 H-pyrido[3,2-d][1,3]oxazine-2,4-dione (7.4 g, 28.8 mmol). The resulting mixture was heated at 160° C. for 3 hours, left to reach room temperature, and poured into a large amount of ice-water. The pH of the aqueous solution was adjusted to pH=1 with concentrated HCl. The precipitate was filtered, washed with MeOH, and dried in vacuo to give the title compound as a solid.

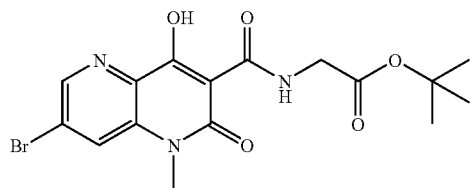

(f) tert-Butyl 2-(7-bromo-4-hydroxy-1-methyl-2-oxo-1,2-dihydro-1,5-naphthyridine-3-carboxamido)acetate. To a solution of methyl 7-bromo-4-hydroxy-1-methyl-2-oxo-1,2-dihydro-1,5-naphthyridine-3-carboxylate (1.0 g, 3.2 mmol) and tert-butyl 2-aminoacetate hydrochloride (0.54 g, 3.2 mmol) in 1,4-dioxane (30 mL) was added N,N-diisopropylethylamine (0.56 mL, 3.2 mmol), and the reaction mixture was heated to 120° C. for 18 hours under nitrogen in a sealed vessel. The reaction mixture was left to reach room temperature and was evaporated under reduced pressure. The residue was diluted with water (100 mL), and the precipitated solid was filtered. The filter cake was washed with water (100 mL) and dried under vacuum to provide the crude product, which was purified by silica gel chromatography (gradient: 0-3% MeOH/DCM) to give the title compound as a white solid. MS (ESI, pos. ion) m/z: 413 (M+1).

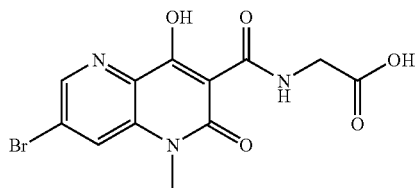

(g) N-((7-Bromo-4-hydroxy-1-methyl-2-oxo-1,2-dihydro-1,5-naphthyridin-3-yl)carbonyl)glycine. A mixture of tert-butyl 2-(7-bromo-4-hydroxy-1-methyl-2-oxo-1,2-dihydro-1,5-naphthyridine-3-carboxamido)acetate (0.200 g, 0.578 mmol) and TFA (5 mL) was stirred at room temperature for 15 minutes. The reaction mixture was evaporated under reduced pressure, and the oily residue was treated with Et$_2$O. The solid which precipitated was filtered, washed with water, Et$_2$O and MeOH, and dried in vacuo to provide the title compound as an off-white solid. MS (ESI, pos. ion) m/z: 357 (M+1). $^1$H NMR (300 MHz, DMSO-d$_6$) δ ppm: 12.98 (s, 1 H), 10.47 (t, J=5.3 Hz, 1 H), 8.74 (d, J=1.8 Hz, 1 H), 8.43 (d, J=1.8 Hz, 1 H), 4.14 (d, J=5.6 Hz, 2 H), 3.62 (s, 3 H).

Example 2

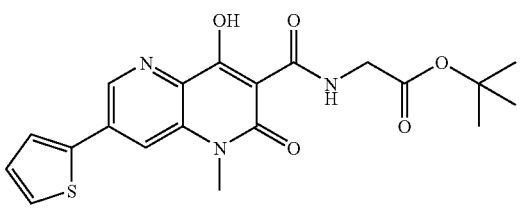

(a) tert-Butyl 2-(4-hydroxy-1-methyl-2-oxo-7-(thiophen-2-yl)-1,2-dihydro-1,5-naphthyridine-3-carboxamido)acetate. To a mixture of tert-butyl 2-(7-bromo-4-hydroxy-1-methyl-2-oxo-1,2-dihydro-1,5-naphthyridine-3-carboxamido)acetate (0.500 g, 1.2 mmol, Example 1(f)), Pd(PPh$_3$)$_4$ (0.14 g, 0.12 mmol) and 2-thienylboronic acid (0.307 g, 2.4 mmol) in 1,4-dioxane (15 mL) was added 2 M aqueous Na$_2$CO$_3$ (1.8 mL, 3.6 mmol), and the reaction mixture was heated to 120° C. for 4 hours under nitrogen in a sealed vessel. The reaction mixture was left to reach room temperature and was evaporated under reduced pressure. The residue was purified by silica gel column chromatography (gradient: 0-3% MeOH/DCM) to provide the title compound as an off-white solid. MS (ESI, pos. ion) m/z: 416 (M+1).

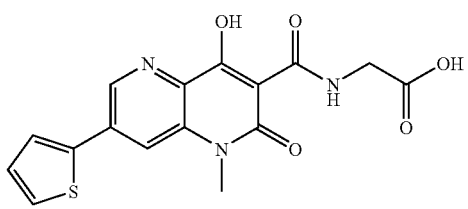

(b) 2-(4-Hydroxy-1-methyl-2-oxo-7-(thiophen-2-yl)-1,2-dihydro-1,5-naphthyridine-3-carboxamido)acetic acid. The title compound was prepared similarly to the procedure described for Example 1(g) by treatment of tert-butyl 2-(4-hydroxy-1-methyl-2-oxo-7-(thiophen-2-yl)-1,2-dihydro-1,5-naphthyridine-3-carboxamido)acetate with TFA. MS (ESI, pos. ion) m/z: 360 (M+1). $^1$H NMR (300 MHz, DMSO-d$_6$) δ ppm: 12.96 (s, 1 H), 10.52 (t, J=5.6 Hz, 1 H), 8.97 (d, J=1.8 Hz, 1 H), 8.15 (d, J=1.8 Hz, 1 H), 8.01 (d, J=2.8 Hz, 1 H,), 7.84 (dd, J=5.0, 0.9 Hz, 1 H), 7.30 (dd, J=5.0, 3.8 Hz, 1 H,), 4.15 (d, J=5.6 Hz, 2 H), 3.71 (s, 3 H).

Example 3

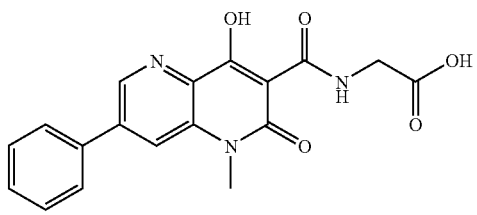

2-(4-Hydroxy-1-methyl-2-oxo-7-phenyl-1,2-dihydro-1,5-naphthyridine-3-carboxamido)acetic acid. The title compound was prepared similarly to the procedures described for Example 2 from tert-butyl 2-(7-bromo-4-hydroxy-1-methyl-2-oxo-1,2-dihydro-1,5-naphthyridine-3-carboxamido)acetate (Example 1 (f)) and phenylboronic acid. MS (ESI, pos. ion) m/z: 354 (M+1). $^1$H NMR (400 MHz, CD$_3$OD) δ ppm: 8.86 (s, 1 H), 8.20 (s, 1 H), 7.84 (d, J=7.4 Hz, 2 H), 7.44-7.63 (m, 3 H), 4.16 (s, 2 H), 3.78 (s, 3 H).

Example 4

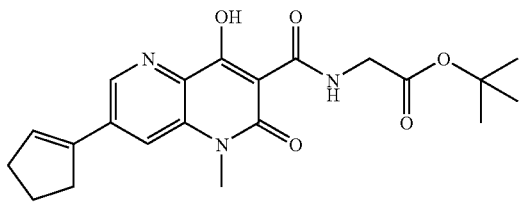

(a) tert-Butyl 2-(7-cyclopentenyl-4-hydroxy-1-methyl-2-oxo-1,2-dihydro-1,5-naphthyridine-3-carboxamido)acetate. The title compound was prepared similarly to the procedures described for Example 2 from tert-butyl 2-(7-bromo-4-hydroxy-1-methyl-2-oxo-1,2-dihydro-1,5-naphthyridine-3-carboxamido)acetate (Example 1 (f)) and cyclopenten-1-ylboronic acid.

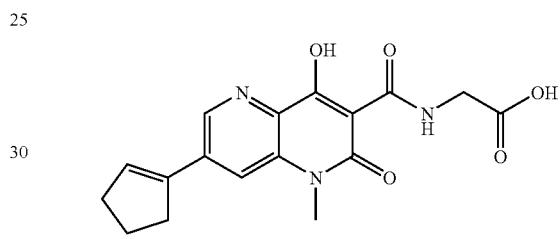

(b) 2-(7-Cyclopentenyl-4-hydroxy-1-methyl-2-oxo-1,2-dihydro-1,5-naphthyridine-3-carboxamido)acetic acid. The title compound was prepared similarly to the procedure described for Example 1 (g) by treatment of tert-butyl 2-(7-cyclopentenyl-4-hydroxy-1-methyl-2-oxo-1,2-dihydro-1,5-naphthyridine-3-carboxamido)acetate with TFA. MS (ESI, pos. ion) m/z: 344 (M+1). $^1$H NMR (300 MHz, DMSO-d$_6$) δ ppm: 10.54 (t, J=5.3 Hz, 1 H), 8.87 (s, 1 H), 7.84 (s, 1 H), 6.85 (s, 1 H), 4.14 (d, J=5.7 Hz, 2 H), 3.67 (s, 3 H), 2.82 (t, J=6.6 Hz, 2 H), 2.54-2.67 (m, 2 H), 1.95-2.10 (m, 2 H).

Example 5

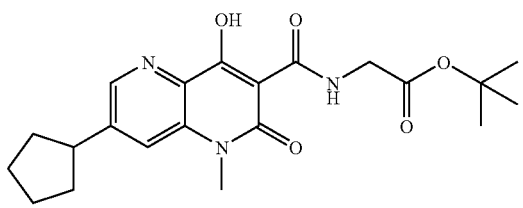

(a) tert-Butyl 2-(7-cyclopentyl-4-hydroxy-1-methyl-2-oxo-1,2-dihydro-1,5-naphthyridine-3-carboxamido)acetate. A solution of tert-butyl 2-(7-cyclopentenyl-4-hydroxy-1-methyl-2-oxo-1,2-dihydro-1,5-naphthyridine-3-carboxamido)acetate (0.399 g, 1 mmol, Example 4 (a)) in MeOH (25 mL) was flushed with nitrogen gas and 10% Pd/C (0.100 g) was added. The mixture was then stirred under hydrogen atmosphere for 18 hours at room temperature. The reaction mixture was filtered from the catalyst through a pad of Celite®, and the filter cake was washed with MeOH. The filtrate was evaporated under reduced pressure, and the residue dried in vacuo to provide the title compound as a light-yellow oil. MS (ESI, pos. ion) m/z: 402 [M+1].

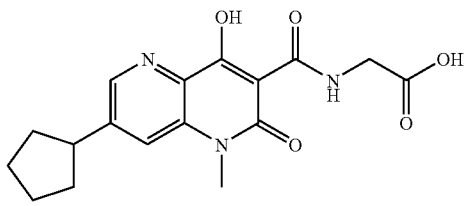

(b) 2-(7-Cyclopentyl-4-hydroxy-1-methyl-2-oxo-1,2-dihydro-1,5-naphthyridine-3-carboxamido)acetic acid. The title compound was prepared similarly to the procedure described for Example 1 (g) by treatment of tert-butyl 2-(7-cyclopentyl-4-hydroxy-1-methyl-2-oxo-1,2-dihydro-1,5-naphthyridine-3-carboxamido)acetate with TFA. MS (ESI, pos. ion) m/z: 346 (M+1). $^1$H NMR (300 MHz, DMSO-$d_6$) δ ppm: 12.94 (br. s, 1 H), 10.55 (t, J=5.6 Hz 1 H), 8.60 (s, 1 H), 7.88 (s, 1 H), 4.14 (d, J=5.5 Hz, 2 H), 3.65 (s, 3 H), 3.12-3.29 (m, 1 H), 2.03-2.19 (m, 2 H), 1.60-1.95 (m, 6H).

Example 6

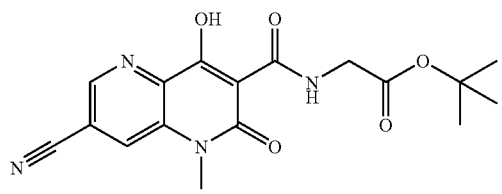

(a) tert-Butyl 2-(7-cyano-4-hydroxy-1-methyl-2-oxo-1,2-dihydro-1,5-naphthyridine-3-carboxamido)acetate. To a mixture of tert-butyl 2-(7-bromo-4-hydroxy-1-methyl-2-oxo-1,2-dihydro-1,5-naphthyridine-3-carboxamido)acetate (0.50 g, 1.2 mmol, Example 1(b)), $Pd_2(dba)_3$ (0.044 g, 0.049 mmol), copper(I) cyanide (0.43 g, 4.9 mmol) and 1',1'-bis(diphenyl-phosphino)ferrocene (0.105 g, 0.19 mmol) in 1,4-dioxane (15 mL), was added tetraethylammonium cyanide (0.19 g, 1.2 mmol), and the reaction mixture was stirred at 75° C. for 4 hours under nitrogen in a sealed vessel. The reaction mixture was left to reach room temperature and was evaporated under reduced pressure. The residue was purified by silica gel column chromatography (gradient: 0-3% MeOH/DCM) to provide the title compound as a light-yellow solid. MS (ESI, pos. ion) m/z: 359 (M+1).

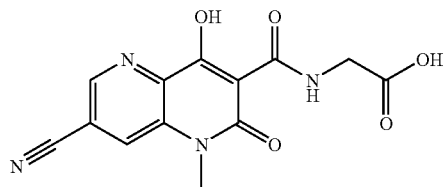

(b) 2-(7-Cyano-4-hydroxy-1-methyl-2-oxo-1,2-dihydro-1,5-naphthyridine-3-carboxamido)acetic acid. The title compound was prepared similarly to the procedure described for Example 1 (g) by treatment of tert-butyl 2-(7-cyano-4-hydroxy-1-methyl-2-oxo-1,2-dihydro-1,5-naphthyridine-3-carboxamido)acetate with TFA. MS (ESI, pos. ion) m/z: 303 (M+1). $^1$H NMR (300 MHz, DMSO-$d_6$) δ ppm: 12.92 (br. s, 1 H), 10.46 (t, J=4.7 Hz, 1 H), 8.99 (s, 1 H), 8.76 (s, 1 H), 4.16 (d, J=5.5 Hz, 2 H), 3.64 (s, 3 H).

Example 7

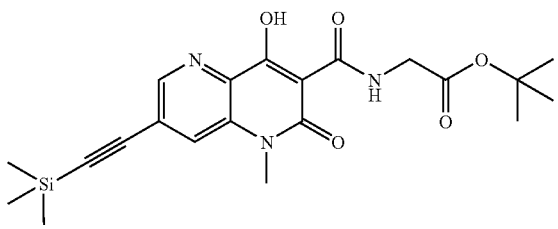

(a) tert-Butyl 2-(4-hydroxy-1-methyl-2-oxo-7-(2-(trimethylsilyl)ethynyl)-1,2-dihydro-1,5-naphthyridine-3-carboxamido)acetate. A pressure vial was charged with tert-butyl 2-(7-bromo-4-hydroxy-1-methyl-2-oxo-1,2-dihydro-1,5-naphthyridine-3-carboxamido)acetate (0.500 g, 1.21 mmol, Example 1(b)), copper(I) iodide (0.046 g, 0.24 mmol), $Pd(PPh_3)_2Cl_2$ (0.085 g, 0.121 mmol), $NEt_3$ (10 mL) and ethynyltrimethylsilane (0.119 g, 1.21 mmol) under nitrogen. The vial was sealed and heated at 100° C. for 18 hours. The reaction mixture was left to reach room temperature and was evaporated under reduced pressure. The residue was purified by silica gel column chromatography (DCM) to provide the product as an off-white solid. MS (ESI, pos. ion) m/z: 430 (M+1).

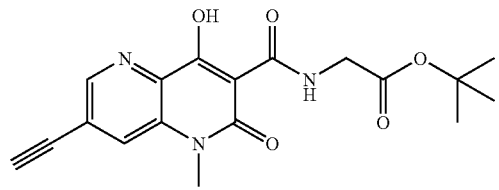

(b) tert-Butyl 2-(7-ethynyl-4-hydroxy-1-methyl-2-oxo-1,2-dihydro-1,5-naphthyridine-3-carboxamido)acetate. A mixture of tert-butyl 2-(4-hydroxy-1-methyl-2-oxo-7-(2-(trimethylsilyl)ethynyl)-1,2-dihydro-1,5-naphthyridine-3-carboxamido)acetate (0.134 g, 0.31 mmol) and CsF (0.047 g, 0.31 mmol) in DMF (15 mL) was stirred for 1 hour at 23° C. The reaction mixture was evaporated in vacuo to provide a light-yellow solid. The solid was suspended in $Et_2O$, filtered, and the filter cake was dried in vacuo to give the title compound which was used in the next step without additional purification in the next step. MS (ESI, pos. ion) m/z: 358 (M+1).

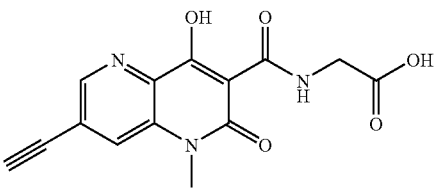

(c) 2-(7-Ethynyl-4-hydroxy-1-methyl-2-oxo-1,2-dihydro-1,5-naphthyridine-3-carboxamido)acetic acid. The title compound was prepared similarly to the procedure described for Example 1 (g) by treatment of tert-butyl 2-(7-ethynyl-4-hydroxy-1-methyl-2-oxo-1,2-dihydro-1,5-naphthyridine-3-carboxamido)acetate with TFA. MS (ESI, pos. ion) m/z: 302 (M+1). $^1$H NMR (300 MHz, DMSO-$d_6$) δ ppm: 12.96 (br. s, 1 H), 10.50 (t, J=5.4 Hz, 1 H), 8.68 (d, J=1.5 Hz, 1 H), 8.23 (d, J=1.3 Hz, 1 H), 4.83 (s, 1 H), 4.15 (d, J=5.6 Hz, 2 H,), 3.63 (s, 3 H).

Additional Examples

TABLE 1

The following examples were prepared from tert-butyl 2-(7-bromo-4-hydroxy-1-methyl-2-oxo-1,2-dihydro-1,5-naphthyridine-3-carboxamido)acetate (Example 1 (f)) and commercially available alkynes, analogously to the general procedures described in Example 7 (a) and Example 7 (c).

| Ex. | Structure | Name | MS (ESI) m/z | $^1$H NMR |
|---|---|---|---|---|
| 8 | 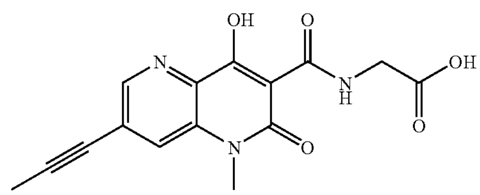 | 2-(4-Hydroxy-1-methyl-2-oxo-7-(prop-1-ynyl)-1,2-dihydro-1,5-naphthyridine-3-carboxamido)acetic acid | 316 (M + 1) | $^1$H NMR (300 MHz, DMSO-$d_6$) δ ppm: 12.96 (br. s, 1 H), 10.51 (t, J = 5.4 Hz, 1 H), 8.60 (s, 1 H), 8.11 (s, 1 H), 4.14 (d, J = 5.5 Hz, 2 H), 3.61 (s, 3 H), 2.18 (s, 3 H). |
| 9 | 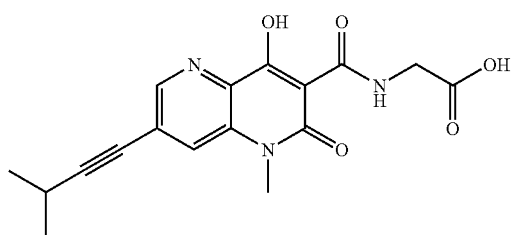 | 2-(4-Hydroxy-1-methyl-7-(3-methylbut-1-ynyl)-2-oxo-1,2-dihydro-1,5-naphthyridine-3-carboxamido)acetic acid | 344 (M + 1) | $^1$H NMR (300 MHz, DMSO-$d_6$) δ ppm: 12.97 (br. s, 1 H), 10.50 (t, J = 5.3 Hz, 1 H), 8.67 (d, J = 1.3 Hz, 1 H), 8.21 (d, J = 1.2 Hz, 1 H), 4.45 (s, 2 H), 4.15 (d, J = 5.6 Hz, 2 H), 3.63 (s, 3 H), 3.39 (s, 3 H). |
| 10 | 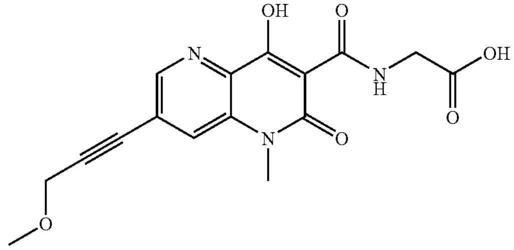 | 2-(4-Hydroxy-7-(3-methoxyprop-1-ynyl)-1-methyl-2-oxo-1,2-dihydro-1,5-naphthyridine-3-carboxamido)acetic acid | 346 (M + 1) | $^1$H NMR (300 MHz, DMSO-$d_6$) δ ppm: 12.97 (br. s, 1 H), 10.50 (t, J = 5.3 Hz, 1 H), 8.67 (d, J = 1.3 Hz, 1 H), 8.21 (d, J = 1.2 Hz, 1 H), 4.45 (s, 2 H), 4.15 (d, J = 5.6 Hz, 2 H), 3.63 (s, 3 H), 3.39 (s, 3 H). |

Example 11

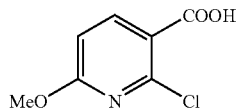

(a) 2-Chloro-6-methoxynicotinic acid. A mixture of 2,6-dichloronicotinic acid (50 g, 0.26 mol) and potassium tert-butoxide (87.7 g, 0.783 mol) in MeOH (2300 mL) was heated at reflux for 48 hours. After evaporation of the solvent, the residue was diluted with $H_2O$ and acidified with concentrated HCl. The solid precipitate was filtered, washed with water, and dried in vacuo to give the title compound as a white solid.

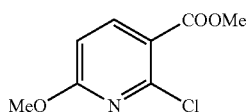

(b) Methyl 2-chloro-6-methoxynicotinate. A mixture of 2-chloro-6-methoxynicotinic acid (300 g, 1.34 mol) in $SOCl_2$ (1400 mL) was heated at reflux overnight. The reaction mixture was left to reach room temperature and was evaporated under reduced pressure. The residue was dissolved in toluene and the solution was concentrated. The residue was re-dissolved in toluene, the solution was evaporated, and the residue was diluted with MeOH (2000 mL), and heated at reflux for 3 hours. The reaction mixture was left to reach room temperature and evaporated under reduced pressure. The solid residue was re-crystallized from EtOH (400 mL) and dried in vacuo to give the title compound.

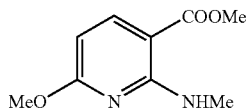

(c) Methyl 6-methoxy-2-(methylamino)nicotinate. A mixture of methyl 2-chloro-6-methoxynicotinate (60 g, 0.3 mol) and 30% solution of $MeNH_2$ in EtOH (256 mL, 2.48 mol) in EtOH (500 mL) was heated to 75° C. in a sealed tube overnight. The reaction mixture was left to reach room temperature and evaporated under reduced pressure. The residue was diluted with water and extracted with chloroform (3×). The combined extract was washed with water and brine, dried over anhydrous $Na_2SO_4$, and filtered. The filtrate was evaporated under reduced pressure, and the residue was purified by silica gel chromatography to give the title compound.

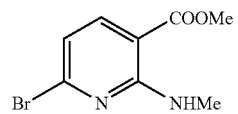

(d) Methyl 6-bromo-2-(methylamino)nicotinate. A mixture of methyl 6-methoxy-2-(methylamino)nicotinate (20 g, 100 mmol), $POBr_3$ (58.6 g, 204.4 mmol), $H_3PO_4$ (1.0 g, 10.2 mmol) and $C_5H_5N \cdot HBr$ (1.6 g, 10.0 mmol) in benzene (200 mL) was heated at reflux overnight. The reaction mixture was left to reach room temperature, poured into ice-water, basified to pH=7-8 with sodium carbonate, and extracted with DCM. The organic layer was washed with water and brine, dried over anhydrous $Na_2SO_4$, and filtered. The filtrate was evaporated under reduced pressure, and the residue purified by silica gel chromatography to give the title compound.

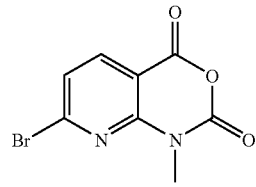

(e) 7-Bromo-1-methyl-1 H-pyrido[2,3-d][1,3]oxazine-2,4-dione. To a mixture of methyl 6-bromo-2-(methylamino)nicotinate (10.5 g, 42.9 mmol) and 1,4-dioxane (10 mL) in anhydrous 1,2-dichloroethane (1000 mL) was added trichloromethyl chloroformate (15.43 mL, 128.45 mmol) dropwise over 1 hour, with stirring and heating at 80° C. After the addition, the reaction mixture was stirred at 80° C. for 4 hours, and was left to reach room temperature. The solvent was evaporated, and the residue was washed with a 1:1 mixture of EtOAc/hexanes (100 mL) and dried in vacuo to give the title compound as an off-white solid.

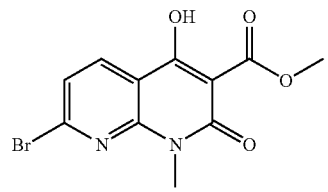

(f) Methyl 7-bromo-4-hydroxy-1-methyl-2-oxo-1,2-dihydro-1,8-naphthyridine-3-carboxylate. To a solution of dimethyl malonate (25.5 g, 196 mmol) in anhydrous N,N-dimethylacetamide (50 mL) was added NaH (60% suspension in mineral oil, 0.97 g, 23 mmol) in small portions over 1 hour, with stirring and cooling with an ice-bath. When the evolution of hydrogen ceased, 7-bromo-1-methyl-1 H-pyrido[2,3-d][1,3]oxazine-2,4-dione (5.0 g, 19.5 mmol) was added, and the temperature of the reaction mixture was raised slowly to 160° C. and kept at the same temperature for 3.5 hours (carbon dioxide evolved). The mixture was left to reach room temperature, poured into ice-water, and acidified to pH=2-3. The precipitated crystals were collected by filtration, washed with MeOH and dried in vacuo to give the title compound.

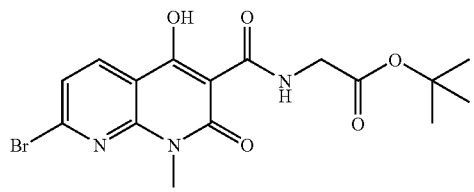

(g) tert-Butyl 2-(7-bromo-4-hydroxy-1-methyl-2-oxo-1,2-dihydro-1,8-naphthyridine-3-carboxamido)acetate. The title compound was prepared similarly to the procedure described for Example 1 (f) from methyl 7-bromo-4-hydroxy-1-methyl-2-oxo-1,2-dihydro-1,8-naphthyridine-3-carboxylate and glycine tert-butyl ester hydrochloride. MS (ESI, pos. ion) m/z: 410 (M−1). ¹H NMR (400 MHz, CDCl₃) δ ppm: 10.56 (br. s, 1 H), 8.25 (d, J=8.2 Hz, 1 H), 7.39 (d, J=8.2 Hz, 1 H), 4.12 (d, J=5.3 Hz, 2 H), 3.77 (s, 3 H), 1.51 (s, 9 H).

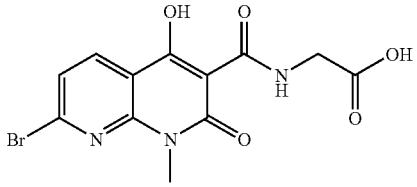

(h) 2-(7-Bromo-4-hydroxy-1-methyl-2-oxo-1,2-dihydro-1,8-naphthyridine-3-carboxamido)acetic acid. The title compound was prepared similarly to the procedure described for Example 1 (g) by treatment of tert-butyl 2-(7-bromo-4-hydroxy-1-methyl-2-oxo-1,2-dihydro-1,8-naphthyridine-3-carboxamido)acetate with TFA. MS (ESI, pos. ion) m/z: 354 (M−1). ¹H NMR (400 MHz, DMSO-d₆) δ ppm: 10.37 (br. s, 1 H), 8.32 (d, J=8.0 Hz, 1 H), 7.62 (d, J=8.0 Hz, 1 H), 4.13 (d, J=5.3 Hz, 2 H), 3.62 (s, 3 H).

Example 12

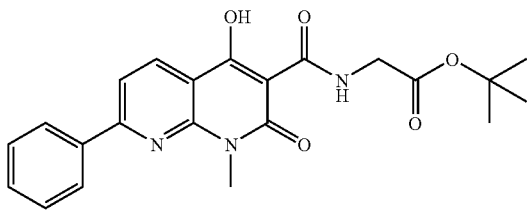

(a) tert-Butyl 2-(4-hydroxy-1-methyl-2-oxo-7-phenyl-1,2-dihydro-1,8-naphthyridine-3-carboxamido)acetate. A suspension of tert-butyl 2-(7-bromo-4-hydroxy-1-methyl-2-oxo-1,2-dihydro-1,8-naphthyridine-3-carboxamido)acetate (315 mg, 764 μmol, Example 11(g)), phenylboronic acid (186 mg, 1528 μmol) and sodium carbonate, 2 M aqueous solution (764 μL, 1528 μmol) in 1,4-dioxane (6 mL) was treated with Pd(PPh₃)₄ (88 mg, 76 μmol). The reaction mixture was degassed and backfilled with nitrogen, and heated to 150° C. in a microwave synthesizer for 25 minutes. The reaction mixture was evaporated in vacuo, and the residue was purified by silica gel column chromatography (15% EtOAc/hexanes) to give the title compound as a light-yellow solid. MS (ESI, pos. ion) m/z: 410 (M+1). ¹H NMR (400 MHz, CDCl₃) δ ppm: 10.70 (s, 1 H), 8.50 (d, J=8.4 Hz, 1 H), 8.17 (dd, J=7.6, 1.8 Hz, 2 H), 7.68-7.74 (m, 2 H), 7.49-7.56 (m, 2 H), 4.14 (d, J=5.3 Hz, 2 H), 3.92 (s, 3 H), 1.51 (s, 9 H).

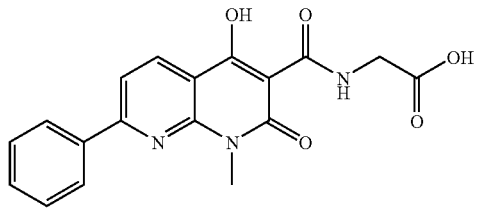

(b) 2-(4-Hydroxy-1-methyl-2-oxo-7-phenyl-1,2-dihydro-1,8-naphthyridine-3-carboxamido)acetic acid. The title compound was prepared similarly to the procedure described for Example 1 (g) by treatment of tert-butyl 2-(4-hydroxy-1-methyl-2-oxo-7-phenyl-1,2-dihydro-1,8-naphthyridine-3-carboxamido)acetate with TFA. MS (ESI, pos. ion) m/z: 354 (M+1). ¹H NMR (400 MHz, DMSO-d₆) δ ppm: 10.45 (s, 1 H), 8.48 (d, J=8.0 Hz, 1 H), 8.27 (d, J=5.7 Hz, 2 H), 8.02 (d, J=8.2 Hz, 1 H), 7.43-7.68 (m, 4H), 4.14 (d, J=4.9 Hz, 2H), 3.79 (s, 3 H).

Additional Examples

TABLE 2

The following examples were prepared from tert-butyl 2-(7-bromo-4-hydroxy-1-methyl-2-oxo-1,2-dihydro-1,8-naphthyridine-3-carboxamido)acetate (315 mg, 764 μmol, Example 11(g)) and commercially available boronic acids or boronic acid esters analogously to the procedure described for the preparation of Example 12.

| Ex. | Structure | Name | MS (ESI) m/z | ¹H NMR |
|---|---|---|---|---|
| 13 | 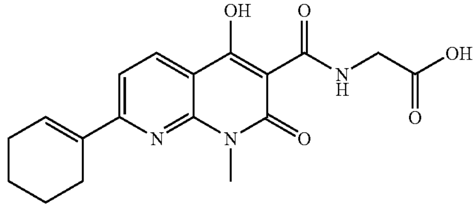 | 2-(7-Cyclohexenyl-4-hydroxy-1-methyl-2-oxo-1,2-dihydro-1,8-naphthyridine-3-carboxamido)acetic acid | 356 (M − 1) | ¹H NMR (400 MHz, DMSO-d₆) δ ppm: 10.46 (br. s, 1 H), 8.34 (d, J = 8.0 Hz, 1 H), 7.57 (d, J = 5.9 Hz, 1 H), 6.97-7.22 (m, 1 H), 4.06 (d, J = 4.7 Hz, 2 H), 3.69 (s, 3 H), 2.53-2.63 (m, 2 H), 2.20-2.36 (m, 2 H), 1.67-1.85 (m, 2 H), 1.65 (s, 2 H). |

TABLE 2-continued

The following examples were prepared from tert-butyl 2-(7-bromo-4-hydroxy-1-methyl-2-oxo-1,2-dihydro-1,8-naphthyridine-3-carboxamido)acetate (315 mg, 764 μmol, Example 11(g)) and commercially available boronic acids or boronic acid esters analogously to the procedure described for the preparation of Example 12.

| Ex. | Structure | Name | MS (ESI) m/z | $^1$H NMR |
|---|---|---|---|---|
| 14 | 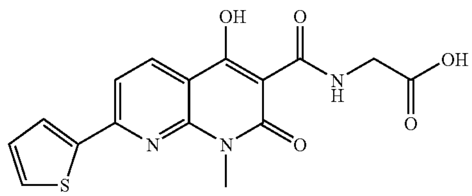 | N-((4-Hydroxy-1-methyl-2-oxo-7-(2-thienyl)-1,2-dihydro-1,8-naphthyridin-3-yl)carbonyl)glycine | 360 (M + 1) | $^1$H NMR (400 MHz, DMSO-d$_6$) δ ppm: 12.95 (s, 1 H), 10.41 (t, J = 5.3 Hz, 1 H), 8.40 (d, J = 8.4 Hz, 1 H), 8.07 (d, J = 3.3 Hz, 1 H), 7.91 (d, J = 8.4 Hz, 1 H), 7.84 (d, J = 4.7 Hz, 1 H), 7.26 (t, J = 4.1 Hz, 1 H), 4.13 (d, J = 5.5 Hz, 2 H), 3.70 (s, 3 H). |
| 15 | 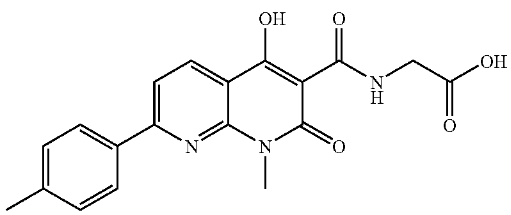 | N-((4-Hydroxy-1-methyl-7-(4-methylphenyl)-2-oxo-1,2-dihydro-1,8-naphthyridin-3-yl)carbonyl)glycine | 366 (M − 1) | $^1$H NMR (400 MHz, DMSO-d$_6$) δ ppm: 10.44 (t, J = 5.1 Hz, 1 H), 8.44 (d, J = 8.2 Hz, 1 H), 8.17 (d, J = 8.0 Hz, 2 H), 7.97 (d, J = 8.2 Hz, 1 H), 7.37 (d, J = 8.0 Hz, 1 H), 4.13 (d, J = 5.5 Hz, 2 H), 3.78 (s, 3 H), 2.40 (s, 3 H). |
| 16 | 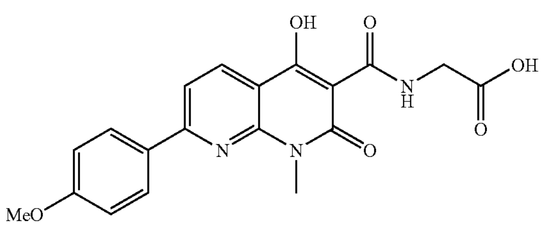 | N-((4-Hydroxy-1-methyl-7-(4-(methyloxy)phenyl)-2-oxo-1,2-dihydro-1,8-naphthyridin-3-yl)carbonyl)glycine | 384 (M + 1) | $^1$H NMR (400 MHz, DMSO-d$_6$) δ ppm: 10.45 (t, J = 4.9 Hz, 1 H), 8.41 (d, J = 8.2 Hz, 1 H), 8.25 (d, J = 8.6 Hz, 2 H), 7.95 (d, J = 8.2 Hz, 1 H), 7.11 (d, J = 8.4 Hz, 2 H), 4.13 (d, J = 4.9 Hz, 2 H), 3.85 (s, 3 H), 3.77 (s, 3 H). |
| 17 | 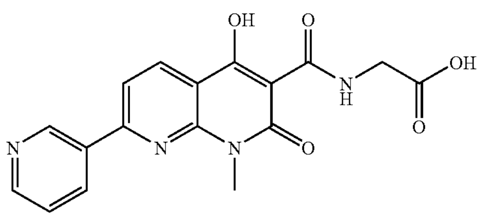 | N-((4-Hydroxy-1-methyl-2-oxo-7-(3-pyridinyl)-1,2-dihydro-1,8-naphthyridin-3-yl)carbonyl)glycine | 355 (M + 1) | $^1$H NMR (400 MHz, DMSO-d$_6$) δ ppm: 10.43 (t, J = 5.2 Hz, 1 H), 9.47 (s, 1 H), 8.76 (d, J = 4.1 Hz, 1 H), 8.69 (d, J = 7.8 Hz, 1 H), 8.53 (d, J = 8.2 Hz, 1 H), 8.10 (d, J = 8.2 Hz, 1 H), 7.66 (dd, J = 7.8, 4.9 Hz, 1 H), 4.14 (d, J = 5.5 Hz, 2 H), 3.79 (s, 3 H). |

Example 18

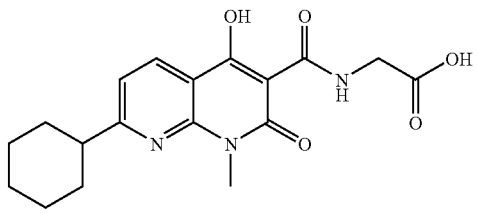

2-(7-Cyclohexyl-4-hydroxy-1-methyl-2-oxo-1,2-dihydro-1,8-naphthyridine-3-carboxamido)acetic acid. The title compound was prepared similarly to the procedure described for Example 5(a) by hydrogenation of tert-butyl 2-(7-cyclohexenyl-4-hydroxy-1-methyl-2-oxo-1,2-dihydro-1,8-naphthyridine-3-carboxamido)acetate, and was isolated as a white amorphous solid. MS (ESI, pos. ion) m/z: 360 (M+1). $^1$H NMR (400 MHz, CDCl$_3$) δ ppm: 10.73 (t, J=4.3 Hz, 1 H), 8.34 (d, J=8.2 Hz, 1 H), 7.11 (d, J=8.2 Hz, 1 H), 4.13 (d, J=5.5 Hz, 2 H), 3.83 (s, 3 H), 2.65-2.87 (m, 1 H), 1.95-2.06 (m, 2 H), 1.85-1.94 (m, 2 H), 1.79 (d, J=12.5 Hz, 1 H), 1.58-1.69 (m, 2 H), 1.51 (s, 9 H), 1.38-1.48 (m, 2 H), 1.24-1.38 (m, 1 H).

Example 19

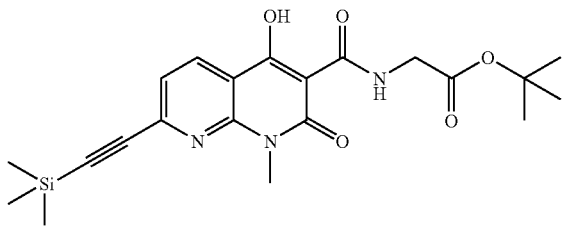

(a) tert-Butyl 2-(4-hydroxy-1-methyl-2-oxo-7-(2-(trimethylsilyl)ethynyl)-1,2-dihydro-1,8-naphthyridine-3-carboxamido)acetate. A pressure vial was charged with tert-butyl 2-(7-bromo-4-hydroxy-1-methyl-2-oxo-1,2-dihydro-1,8-naphthyridine-3-carboxamido)acetate (372 mg, 902 μmol, Example 11(g)), copper(I) iodide (17.2 mg, 90.2 μmol), Pd(PPh$_3$)$_4$ (104 mg, 90.2 μmol), triethylamine (4 mL) and (trimethylsilyl)acetylene (638 μL, 4512 μmol) under nitrogen. The vial was sealed and heated at 80° C. for 15 hours. The reaction mixture was left to reach room temperature and evaporated under reduced pressure. The residue was purified by silica gel column chromatography (12% EtOAc/hexanes) to give the title compound as a yellow solid. $^1$H NMR (400 MHz, CDCl$_3$) δ ppm: 10.62 (t, J=5.0 Hz, 1 H), 8.38 (d, J=8.2 Hz, 1 H), 7.36 (d, J=8.0 Hz, 1 H), 4.11 (d, J=5.3 Hz, 2 H), 3.79 (s, 3 H), 1.49 (s, 9 H), 0.30 (s, 9 H).

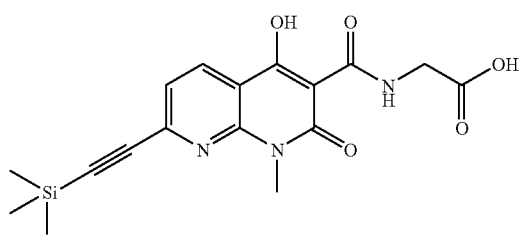

(b) 2-(4-Hydroxy-1-methyl-2-oxo-7-(2-(trimethylsilyl)ethynyl)-1,2-dihydro-1,8-naphthyridine-3-carboxamido)acetic acid. The title compound was prepared similarly to the procedure described for Example 1 (g) by treatment of tert-butyl 2-(4-hydroxy-1-methyl-2-oxo-7-(2-(trimethylsilyl)ethynyl)-1,2-dihydro-1,8-naphthyridine-3-carboxamido)acetate with TFA. MS (ESI, pos. ion) m/z: 374 (M+1). $^1$H NMR (400 MHz, DMSO-d$_6$) δ ppm: 10.38 (t, J=5.5 Hz, 1 H), 8.41 (d, J=8.0 Hz, 1 H), 7.51 (d, J=8.0 Hz, 1 H), 4.14 (d, J=5.7 Hz, 2 H), 3.64 (s, 3 H), 0.29 (s, 9 H).

Example 20

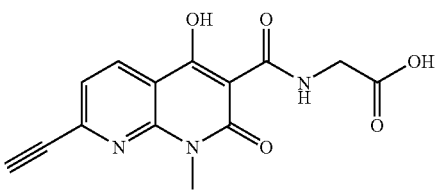

2-(7-Ethynyl-4-hydroxy-1-methyl-2-oxo-1,2-dihydro-1,8-naphthyridine-3-carboxamido)acetic acid. To a solution of 2-(4-hydroxy-1-methyl-2-oxo-7-(2-(trimethylsilyl)ethynyl)-1,2-dihydro-1,8-naphthyridine-3-carboxamido)acetic acid (183 mg, 490 μmol, Example 19 (b)) in MeOH (5 mL) and THF (5 mL) was added potassium carbonate (339 mg, 2450 mmol), and the reaction mixture was stirred at 23° C. for 23 hours. The mixture was acidified with concentrated HCl, and filtered. The filter cake was washed with water (10 mL), Et$_2$O (10 mL) and DCM (10 mL), and dried in vacuo to give the title compound as a brown solid. MS (ESI, pos. ion) m/z: 302 (M+1). $^1$H NMR (400 MHz, DMSO-d$_6$) δ ppm: 10.22-10.52 (m, 1 H), 8.43 (d, J=8.0 Hz, 1 H), 7.54 (d, J=8.2 Hz, 1 H), 4.74 (s, 1 H), 4.14 (d, J=5.5 Hz, 2 H), 3.64 (s, 3 H).

Example 21

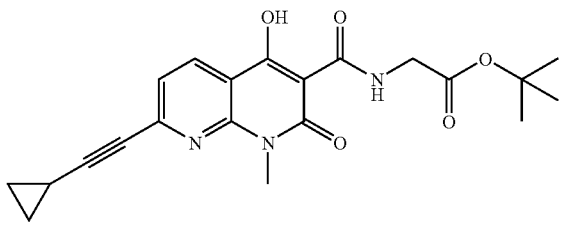

(a) tert-Butyl 2-(7-(2-cyclopropylethynyl)-4-hydroxy-1-methyl-2-oxo-1,2-dihydro-1,8-naphthyridine-3-carboxamido)acetate. The title compound was prepared similarly to the procedure described for Example 19 (a) from tert-butyl 2-(7-bromo-4-hydroxy-1-methyl-2-oxo-1,2-dihydro-1,8-naphthyridine-3-carboxamido)acetate (Example 11(g)) and cyclopropylacetylene.

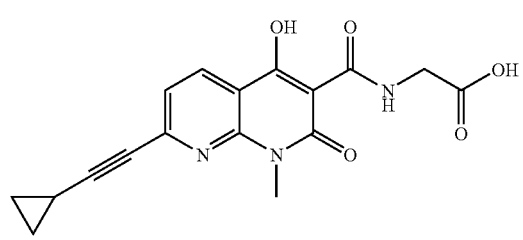

(b) 2-(7-(2-Cyclopropylethynyl)-4-hydroxy-1-methyl-2-oxo-1,2-dihydro-1,8-naphthyridine-3-carboxamido)acetic acid. To a suspension of tert-butyl 2-(7-(2-cyclopropylethynyl)-4-hydroxy-1-methyl-2-oxo-1,2-dihydro-1,8-naphthyridine-3-carboxamido)acetate (181 mg, 455 µmol) in toluene (10 mL) was added silica gel (274 mg, 4554 µmol), and the mixture was heated to 110° C. for 30 minutes. The reaction mixture was cooled to 23° C., diluted with DCM (25 mL), and filtered. The filter cake was separated, suspended in 10% MeOH/DCM (200 mL), and filtered. The filtrate was evaporated under reduced pressure, and the residue was washed with DCM (10 mL) and filtered. The filter cake was separated and dried in vacuo to give the title compound as a light-yellow solid. MS (ESI, pos. ion) m/z: 340 (M−1). $^1$H NMR (400 MHz, DMSO-$d_6$) δ ppm: 10.40 (s, 1 H), 8.36 (d, J=8.0 Hz, 1 H), 7.39 (d, J=8.0 Hz, 1 H), 4.11 (d, J=5.5 Hz, 2H), 3.62 (s, 3 H), 1.58-1.78 (m, 1 H), 0.93-1.06 (m, 2 H), 0.77-0.93 (m, 2 H).

Example 22

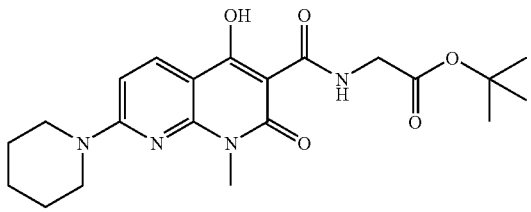

(a) tert-Butyl 2-(4-hydroxy-1-methyl-2-oxo-7-(piperidin-1-yl)-1,2-dihydro-1,8-naphthyridine-3-carboxamido)acetate. A pressure vial was charged with tert-butyl 2-(7-bromo-4-hydroxy-1-methyl-2-oxo-1,2-dihydro-1,8-naphthyridine-3-carboxamido)acetate (330 mg, 801 µmol, Example 11 (g)), NMP (4 mL) and piperidine (316 µl, 3202 µmol). The vial was sealed and heated at 80° C. for 3 hours. The reaction mixture was left to reach room temperature, diluted with EtOAc (75 mL), washed with saturated aqueous solution of sodium bicarbonate (50 mL) and brine (75 mL), dried over MgSO$_4$, and filtered. The filtrate was evaporated in vacuo and the residue purified by silica gel column chromatography (gradient: 5-10% MeOH/EtOAc) to give the title compound as a white solid. MS (ESI, pos. ion) m/z: 417 (M+1). $^1$H NMR (400 MHz, DMSO-$d_6$) δ ppm: 10.38 (t, J=5.8 Hz, 1 H), 8.00 (d, J=9.2 Hz, 1 H), 6.88 (d, J=9.0 Hz, 1H), 4.06 (d, J=5.7 Hz, 2 H), 3.66-3.88 (m, 4H), 3.57 (3 H, s), 1.64-1.72 (m, 2H), 1.54-1.62 (m, 4H), 1.44 (s, 9 H).

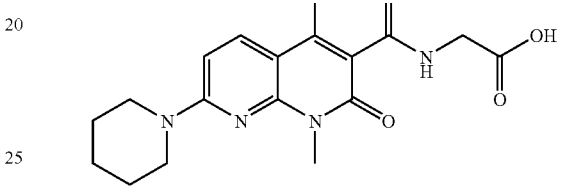

(b) 2-(4-Hydroxy-1-methyl-2-oxo-7-(piperidin-1-yl)-1,2-dihydro-1,8-naphthyridine-3-carboxamido)acetic acid. The title compound was prepared similarly to the procedure described for Example 1 (g) by treatment of tert-butyl 2-(4-hydroxy-1-methyl-2-oxo-7-(piperidin-1-yl)-1,2-dihydro-1,8-naphthyridine-3-carboxamido)acetate with TFA. MS (ESI, pos. ion) m/z: 361 (M+1). $^1$H NMR (400 MHz, DMSO-$d_6$) δ ppm: 12.84 (br. s, 1 H), 10.39 (t, J=5.6 Hz, 1 H), 7.99 (d, J=9.0 Hz, 1 H), 6.86 (d, J=9.0 Hz, 1 H), 4.09 (d, J=5.7 Hz, 2 H), 3.72-3.79 (m, 4H), 3.57 (s, 3 H), 1.63-1.73 (m, 2 H), 1.53-1.63 (m, 4H).

Additional Examples

TABLE 3

The following examples were prepared from tert-butyl 2-(7-bromo-4-hydroxy-1-methyl-2-oxo-1,2-dihydro-1,8-naphthyridine-3-carboxamido)acetate (Example 11 (g)) and commercially available amines analogously to the procedure described for the preparation of Example 22.

| Ex. | Structure | Name | MS (ESI) m/z | $^1$H NMR |
|---|---|---|---|---|
| 23 | 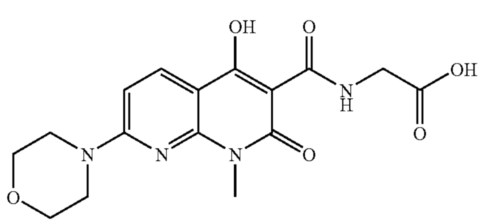 | 2-(4-Hydroxy-1-methyl-7-morpholino-2-oxo-1,2-dihydro-1,8-naphthyridine-3-carboxamido) acetic acid | 363 (M + 1) | $^1$H NMR (400 MHz, DMSO-$d_6$) δ ppm: 10.38 (s, 1 H), 8.05 (d, J = 8.0 Hz, 1 H), 6.87 (d, J = 8.6 Hz, 1 H), 4.09 (d, J = 2.7 Hz, 2 H), 3.70-3.78 (m, 7 H), 3.53-3.61 (m, 4 H). |

TABLE 3-continued

The following examples were prepared from tert-butyl 2-(7-bromo-4-hydroxy-1-methyl-2-oxo-1,2-dihydro-1,8-naphthyridine-3-carboxamido)acetate (Example 11 (g)) and commercially available amines analogously to the procedure described for the preparation of Example 22.

| Ex. | Structure | Name | MS (ESI) m/z | $^1$H NMR |
|---|---|---|---|---|
| 24 | 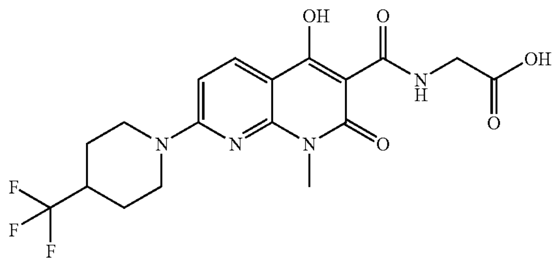 | 2-(4-Hydroxy-1-methyl-2-oxo-7-(4-(trifluoromethyl)piperidin-1-yl)-1,2-dihydro-1,8-naphthyridine-3-carboxamido)acetic acid | 429 (M + 1) | $^1$H NMR (400 MHz, DMSO-$d_6$) δ ppm: 10.39 (t, J = 5.5 Hz, 1 H), 8.03 (d, J = 9.0 Hz, 1 H), 6.91 (d, J = 9.0 Hz, 1 H), 4.65 (d, J = 11.9 Hz, 2 H), 4.10 (d, J = 5.5 Hz, 2 H), 3.57 (s, 3 H), 3.08 (t, J = 12.7 Hz, 2 H), 2.67-2.82 (m, 1 H), 1.95 (d, J = 11.5 Hz, 2 H), 1.39-1.52 (m, 2 H). |

Example 25

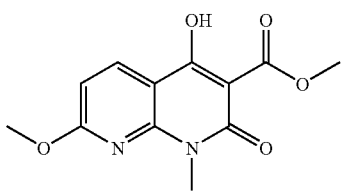

(a) Methyl 4-hydroxy-7-methoxy-1-methyl-2-oxo-1,2-dihydro-1,8-naphthyridine-3-carboxylate. To a suspension of methyl 7-bromo-4-hydroxy-1-methyl-2-oxo-1,2-dihydro-1,8-naphthyridine-3-carboxylate (520 mg, 1661 μmol, Example 11 (f)) in MeOH (8 mL) and DMSO (10 mL) in a pressure vial, was added 0.5 M sodium methoxide in MeOH (13.3 mL, 6.6 mmol). The vial was sealed and heated at 100° C. for 18 hours. The white suspension was cooled to 23° C., diluted with EtOAc (150 mL), and washed with 10% HCl (150 mL), water (150 mL) and brine (150 mL), dried over MgSO$_4$, and filtered. The filtrate was evaporated under reduced pressure, and the residue purified by silica gel chromatography (3% MeOH/DCM) to give the title compound as a white solid. MS (ESI, pos. ion) m/z: 265 (M+1). $^1$H NMR (400 MHz, CDCl$_3$) δ ppm: 8.26 (d, J=8.8 Hz, 1 H), 6.63 (d, J=8.6 Hz, 1 H), 4.07 (s, 3 H), 4.03 (s, 3 H), 3.74 (s, 3 H).

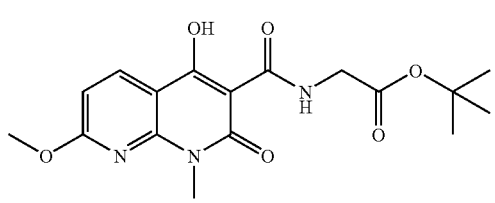

(b) tert-Butyl 2-(4-hydroxy-7-methoxy-1-methyl-2-oxo-1,2-dihydro-1,8-naphthyridine-3-carboxamido)acetate. The title compound was prepared similarly to the procedure described for Example 1(b) by treatment of methyl 4-hydroxy-7-methoxy-1-methyl-2-oxo-1,2-dihydro-1,8-naphthyridine-3-carboxylate with tert-butyl 2-aminoacetate, hydrochloride. MS (ESI, pos. ion) m/z: 364 (M+1).

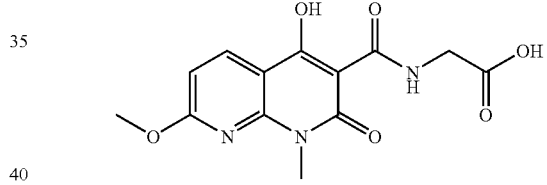

(c) 2-(4-Hydroxy-7-methoxy-1-methyl-2-oxo-1,2-dihydro-1,8-naphthyridine-3-carboxamido)acetic acid. The title compound was prepared similarly to the procedure described for Example 1 (g) by treatment of tert-butyl 2-(4-hydroxy-7-methoxy-1-methyl-2-oxo-1,2-dihydro-1,8-naphthyridine-3-carboxamido)acetate with TFA. MS (ESI, pos. ion) m/z: 308 (M+1). $^1$H NMR (400 MHz, DMSO-$d_6$) δ ppm: 10.38 (br. s, 1 H), 8.25 (d, J=8.6 Hz, 1 H), 6.79 (d, J=8.4 Hz, 1 H), 4.12 (d, J=4.7 Hz, 2 H), 4.02 (s, 3 H), 3.64 (s, 3 H).

Example 26

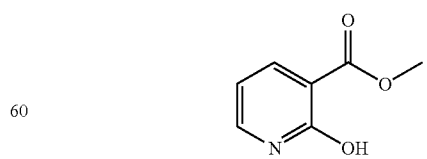

(a) Methyl 2-hydroxynicotinate. To a solution of 2-hydroxynicotinic acid (100 g, 0.72 mol) in MeOH (1000 mL) was added thionyl chloride (157 mL) dropwise with cooling at 0° C. with an ice-water bath. After the addition, the mixture was stirred at room temperature overnight. The reaction mixture was evaporated under reduced pressure, and the residue was diluted with water (500 mL). The pH of the aqueous solution was adjusted to pH=8-9 with saturated aqueous solution of NaHCO$_3$. The mixture was extracted with chloroform (5×300 mL). The combined organic layers were dried over Na$_2$SO$_4$, and filtered. The filtrate was evaporated under reduced pressure, and the residue was dried in vacuo to give the title compound as a white solid.

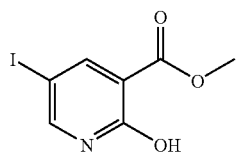

(b) Methyl 2-hydroxy-5-iodonicotinate. A solution of methyl 2-hydroxynicotinate (100 g, 0.65 mol) and N-iodosuccinimide (192 g, 0.85 mol) in dry DCM (2.5 L) was heated at reflux in the dark for 48 hours. The mixture was concentrated to 500 mL under reduced pressure. The solid which precipitated was collected by filtration, washed with small portions of cold CH$_2$Cl$_2$, and dried in vacuo to give the title compound as a pale-yellow solid.

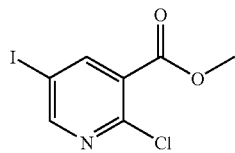

(c) Methyl 2-chloro-5-iodonicotinate. To a solution of anhydrous DMF (21.45 mL) and distilled POCl$_3$ (26.13 mL) in anhydrous DCM (900 mL), was added methyl 2-hydroxy-5-iodonicotinate (39 g, 0.14 mol) in one portion. The mixture was stirred at room temperature for 28 hours under a N$_2$ atmosphere. The solvent was removed under reduced pressure, and the residue was diluted with H$_2$O. The pH of the aqueous solution was adjusted to pH=8~9 with saturated aqueous solution of NaHCO$_3$. The mixture was extracted with DCM (5×). The combined organic layers were dried over Na$_2$SO$_4$, and filtered. The filtrate was evaporated under reduced pressure, and the oily residue was purified by silica gel column chromatography (1:10 EtOAc/hexanes) to give the title compound as a white solid.

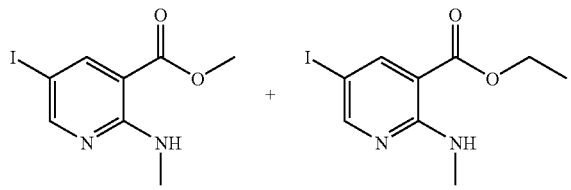

(d) Methyl 5-iodo-2-(methylamino)nicotinate and Ethyl 5-iodo-2-(methylamino)nicotinate. A mixture of methyl 2-chloro-5-iodonicotinate (10 g, 33.6 mmol) and a 30% solution of MeNH$_2$ in EtOH (14.3 mL, 460 mmol) in EtOH (100 mL) was heated at 65° C. for 4 hours. The reaction mixture was left to reach room temperature and evaporated under reduced pressure. The residue was purified by silica gel column chromatography (1:10 EtOAc/petroleum ether) to give the title compounds as a mixture.

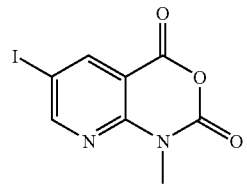

(e) 6-Iodo-1-methyl-1 H-pyrido[2,3-d][1,3]oxazine-2,4-dione. The title compound was prepared similarly to the procedure described for Example 11 (e) by treatment of the mixture of methyl 5-iodo-2-(methylamino)nicotinate and ethyl 5-iodo-2-(methylamino)nicotinate from step (d) above with trichloromethyl chloroformate.

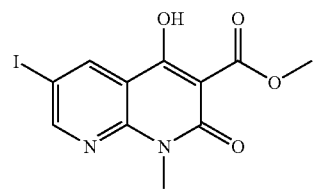

(f) Methyl 4-hydroxy-6-iodo-1-methyl-2-oxo-1,2-dihydro-1,8-naphthyridine-3-carboxylate. The title compound was prepared similarly to the procedure described for Example 11 (f) from 6-iodo-1-methyl-1 H-pyrido[2,3-d][1,3]oxazine-2,4-dione and dimethyl malonate.

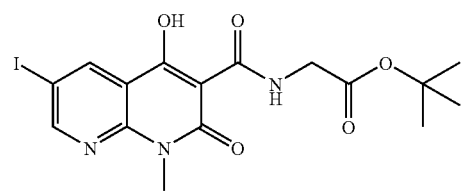

(g) tert-Butyl 2-(4-hydroxy-6-iodo-1-methyl-2-oxo-1,2-dihydro-1,8-naphthyridine-3-carboxamido)acetate. The title compound was prepared as a tan solid from methyl 4-hydroxy-6-iodo-1-methyl-2-oxo-1,2-dihydro-1,8-naphthyridine-3-carboxylate and tert-butyl 2-aminoacetate, hydrochloride, similarly to the procedure described for Example 1 (f). MS (ESI, pos. ion) m/z: 458 (M−1). $^1$H NMR (400 MHz, DMSO-d$_6$) δ ppm: 10.60 (t, J=4.7 Hz, 1 H), 8.84 (d, J=2.3 Hz, 1 H), 8.71 (d, J=2.2 Hz, 1 H), 4.12 (d, J=5.3 Hz, 2 H), 3.75 (s, 3 H), 1.50 (s, 9 H).

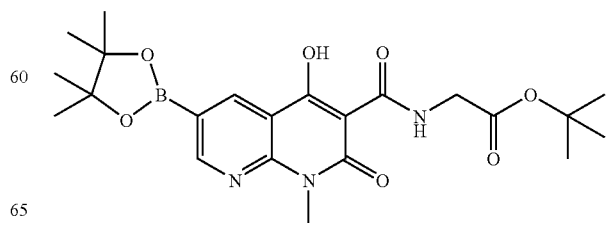

(h) tert-Butyl 2-(4-hydroxy-1-methyl-2-oxo-6-(4,4,5,5-tetramethyl-1,3,2-dioxaborolan-2-yl)-1,2-dihydro-1,8-naphthyridine-3-carboxamido)acetate. To a suspension of tert-butyl 2-(4-hydroxy-6-iodo-1-methyl-2-oxo-1,2-dihydro-1,8-naphthyridine-3-carboxamido)acetate (494 mg, 1076 μmol), bis(pinacolato)diboron (328 mg, 1291 μmol), potassium acetate (211 mg, 2151 μmol) and 1,4-dioxane (10 mL) in a pressure vial under argon atmosphere was added dichloro[1,1'-bis(diphenylphosphino)-ferrocene]palladium(II) DCM adduct (78.7 mg, 108 μmol). The vial was sealed and the mixture was heated at 100° C. for 21 hours. The reaction mixture was cooled to 23° C., diluted with EtOAc (50 mL), washed with water (50 mL) and brine (50 mL), dried over MgSO$_4$, and filtered. The filtrate was evaporated under reduced pressure, and the residue was washed with EtOH (30 mL), and dried in vacuo to give the title compound as a grey solid. MS (ESI, pos. ion) m/z: 460.2 (M+1). $^1$H NMR (400 MHz, CDCl$_3$) δ ppm: 10.64 (t, J=5.1 Hz, 1 H), 9.00 (s, 1 H), 8.85 (s, 1 H), 4.13 (d, J=5.3 Hz, 2 H), 3.82 (s, 3 H), 1.52 (s, 9 H), 1.37 (s, 12 H).

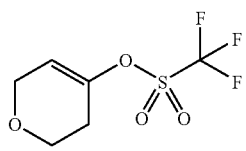

(i) 3,6-Dihydro-2 H-pyran-4-yl trifluoromethanesulfonate. A solution of di-isopropylamine (2663 μl, 18425 μmol) in THF (55 mL) in an oven-dried round bottomed flask was cooled to −10° C. under nitrogen and treated with butyllithium (2.5 M solution in hexanes, 7049 μL, 17624 μmol) in a dropwise fashion. The reaction mixture was stirred at −10° C. for 20 minutes, cooled to −78° C., and treated with a solution of 4-oxacyclohexanone (1480 μL, 16021 μmol) in THF (10 mL) in a dropwise fashion over 10 minutes. The stirring was continued at −78° C. for 2 hours and N-phenyl-trifluoromethanesulfonimide (6868 mg, 19226 μmol) was added in one portion. The reaction mixture was stirred at −78° C. for 30 minutes, and at 0° C. for 3 hours. The reaction mixture was warmed to 23° C., diluted with EtOAc (250 mL), washed with water (2×100 mL) and brine (100 mL), dried over MgSO$_4$, and filtered. The filtrate was evaporated under reduced pressure, and the residue was purified by silica gel column chromatography (gradient: 5-10% EtOAc/hexanes) to give the title compound as a light-yellow oil. $^1$H NMR (400 MHz, CDCl$_3$) δ ppm: 5.82 (dq, J=2.9, 1.4 Hz, 1 H), 4.27 (q, J=2.9 Hz, 2 H), 3.89 (t, J=5.5 Hz, 2 H), 2.44-2.49 (m, 2 H).

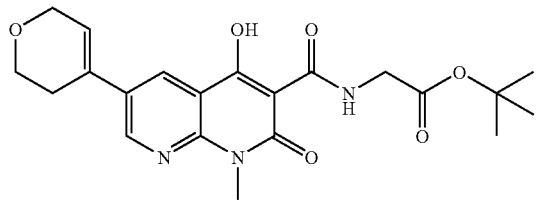

(j) tert-Butyl 2-(6-(3,6-dihydro-2 H-pyran-4-yl)-4-hydroxy-1-methyl-2-oxo-1,2-dihydro-1,8-naphthyridine-3-carboxamido)acetate. To a suspension of tert-butyl 2-(4-hydroxy-1-methyl-2-oxo-6-(4,4,5,5-tetramethyl-1,3,2-dioxaborolan-2-yl)-1,2-dihydro-1,8-naphthyridine-3-carboxamido)acetate (350 mg, 762 μmol), 3,6-dihydro-2 H-pyran-4-yl trifluoromethanesulfonate (239 mg, 1029 μmol), potassium carbonate (316 mg, 2286 μmol) and DMF (5 mL) in a pressure vial under argon atmosphere, was added dichloro[1,1'-bis(diphenyl-phosphino)ferrocene]palladium (II) DCM adduct (55.8 mg, 76.2 μmol). The vial was sealed, and the mixture was heated to 80° C. for 23 hours. The reaction mixture was cooled to 23° C., diluted with EtOAc (50 mL), washed with water (50 mL) and brine (50 mL), dried over MgSO$_4$, and filtered. The filtrate was evaporated under reduced pressure, and the residue was purified by silica gel chromatography (gradient: 24-36% EtOAc/hexanes) to give the title compound as a white solid. MS (ESI, pos. ion) m/z: 416 (M+1). $^1$H NMR (400 MHz, CDCl$_3$) δ ppm: 10.70 (t, J=5.2 Hz, 1 H), 8.79 (d, J=2.5 Hz, 1 H), 8.39 (d, J=2.5 Hz, 1 H), 6.20-6.37 (m, 1 H), 4.37 (d, J=2.9 Hz, 2 H), 4.13 (d, J=5.3 Hz, 2 H), 3.99 (t, J=5.4 Hz, 2 H), 3.81 (s, 3 H), 2.46-2.69 (m, 2 H), 1.51 (s, 9 H).

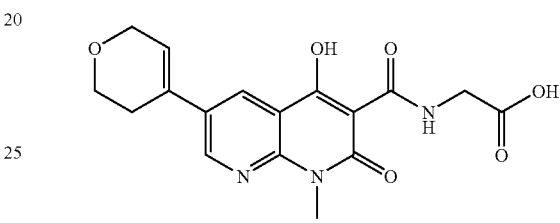

(k) 2-(6-(3,6-Dihydro-2 H-pyran-4-yl)-4-hydroxy-1-methyl-2-oxo-1,2-dihydro-1,8-naphthyridine-3-carboxamido)acetic acid. The title compound was prepared similarly to the procedure described for Example 21(b) by treatment of tert-butyl 2-(6-(3,6-dihydro-2 H-pyran-4-yl)-4-hydroxy-1-methyl-2-oxo-1,2-dihydro-1,8-naphthyridine-3-carboxamido)acetate with silica gel. MS (ESI, pos. ion) m/z: 302 (M+1). $^1$NMR (400 MHz, DMSO-d$_6$) δ ppm: 10.33-10.60 (m, 1 H), 8.99 (s, 1 H), 8.33 (s, 1 H), 6.47-6.58 (m, 1 H), 4.26 (d, J=1.6 Hz, 2 H), 4.14 (d, J=5.3 Hz, 2 H), 3.86 (t, J=5.3 Hz, 2 H), 3.69 (s, 3 H), 2.52-2.59 (m, 2 H).

Example 27

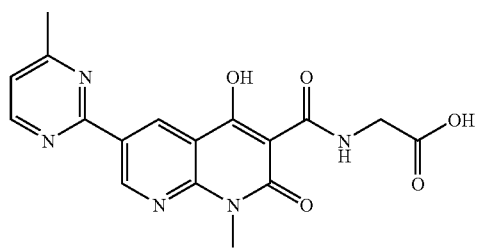

2-(4-Hydroxy-1-methyl-6-(4-methylpyrimidin-2-yl)-2-oxo-1,2-dihydro-1,8-naphthyridine-3-carboxamido)acetic acid. The title compound was prepared from tert-butyl 2-(4-hydroxy-1-methyl-2-oxo-6-(4,4,5,5-tetramethyl-1,3,2-dioxaborolan-2-yl)-1,2-dihydro-1,8-naphthyridine-3-carboxamido)acetate (Example 26 (h)) and 2-chloro-4-methylpyrimidine analogously to the procedures described for the preparation of Example 26 (i) and Example 26 (k), or Example 21 (b). MS (ESI, pos. ion) m/z: 370 (M+1). $^1$NMR (400 MHz, DMSO-d$_6$) δ ppm: 10.41 (s, 1 H), 9.65 (s, 1 H), 9.24 (s, 1 H), 8.80 (d, J=4.9 Hz, 1 H), 7.41 (d, J=4.9 Hz, 1 H), 4.13 (d, J=5.3 Hz, 2 H), 3.74 (s, 3 H), 2.59 (s, 3 H).

Additional Examples

TABLE 4

The following examples were prepared from tert-butyl 2-(4-hydroxy-1-methyl-2-oxo-6-(4,4,5,5-tetramethyl-1,3,2-dioxaborolan-2-yl)-1,2-dihydro-1,8-naphthyridine-3-carboxamido)acetate (Example 26 (h)) and commercially available chloropyrimidines analogously to the procedures described for the preparation of Example 26 (i) and Example 26 (k), or Example 21 (b).

| Ex. | Structure | Name | MS (ESI) m/z | $^1$H NMR |
|---|---|---|---|---|
| 28 | 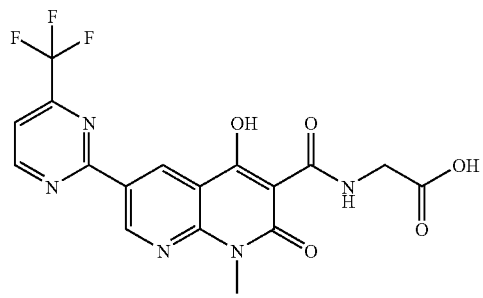 | 2-(4-Hydroxy-1-methyl-2-oxo-6-(4-(trifluoromethyl)pyrimidin-2-yl)-1,2-dihydro-1,8-naphthyridine-3-carboxamido)acetic acid | 422 (M − 1) | $^1$H NMR (400 MHz, DMSO-$d_6$) δ ppm: 10.22-10.49 (m, 1H), 9.62 (s, 1 H), 9.26-9.40 (m, 1 H), 9.19 (s, 1 H), 8.04 (d, J = 4.5 Hz, 1 H), 4.13 (d, J = 4.9 Hz, 2 H), 3.73 (s, 3 H). |
| 29 | 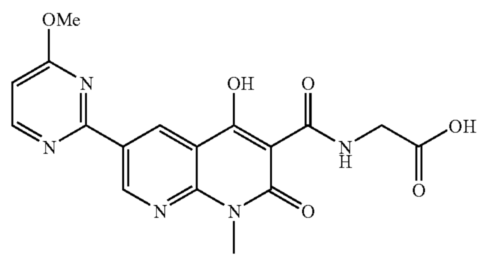 | 2-(4-Hydroxy-6-(4-methoxypyrimidin-2-yl)-1-methyl-2-oxo-1,2-dihydro-1,8-naphthyridine-3-carboxamido)acetic acid | 386 (M + 1) | $^1$H NMR (400 MHz, DMSO-$d_6$) δ ppm: 10.41 (s, 1 H), 9.64 (s, 1 H), 9.17 (s, 1 H), 8.65 (d, J = 5.5 Hz, 1 H), 6.94 (d, J = 5.7 Hz, 1 H), 4.10 (d, J = 5.1 Hz, 2 H), 4.07 (s, 3 H), 3.72 (s, 3 H). |
| 30 | 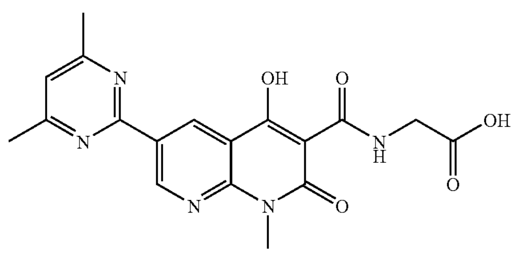 | 2-(6-(4,6-Dimethylpyrimidin-2-yl)-4-hydroxy-1-methyl-2-oxo-1,2-dihydro-1,8-naphthyridine-3-carboxamido)acetic acid | 384 (M + 1) | $^1$H NMR (400 MHz, DMSO-$d_6$) δ ppm: 10.25-10.51 (m, 1 H), 9.63 (s, 1 H), 9.23 (s, 1 H), 7.27 (s, 1 H), 4.10 (d, J = 5.3 Hz, 2 H), 3.73 (s, 3 H), 2.53 (s, 6 H). |
| 31 | 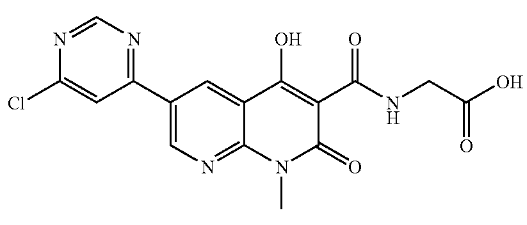 | 2-(6-(6-Chloropyrimidin-4-yl)-4-hydroxy-1-methyl-2-oxo-1,2-dihydro-1,8-naphthyridine-3-carboxamido)acetic acid | 390 (M + 1) | $^1$H NMR (400 MHz, DMSO-$d_6$) δ ppm: 10.37 (s, 1 H), 9.55 (s, 1 H), 9.14 (s, 2 H), 8.56 (s, 1 H), 4.12 (d, J = 3.4 Hz, 2 H), 3.71 (s, 3 H), 1.07 (s, 1 H). |
| 32 | 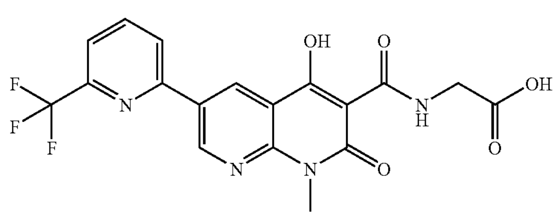 | N-((4-Hydroxy-1-methyl-2-oxo-6-(6-(trifluoromethyl)-2-pyridinyl)-1,2-dihydro-1,8-naphthyridin-3-yl)carbonyl)glycine | 423 (M + 1) | $^1$H NMR (400 MHz, DMSO-$d_6$) δ ppm: 10.43 (s, 1 H), 9.52 (s, 1 H), 9.05 (s, 1 H), 8.51 (d, J = 7.7 Hz, 1 H), 8.25 (t, J = 7.7 Hz, 1 H), 7.94 (d, J = 7.6 Hz, 1 H), 4.15 (d, J = 5.3 Hz, 2 H), 3.74 (s, 3 H). |

TABLE 4-continued

The following examples were prepared from tert-butyl 2-(4-hydroxy-1-methyl-2-oxo-6-(4,4,5,5-tetramethyl-1,3,2-dioxaborolan-2-yl)-1,2-dihydro-1,8-naphthyridine-3-carboxamido)acetate (Example 26 (h)) and commercially available chloropyrimidines analogously to the procedures described for the preparation of Example 26 (i) and Example 26 (k), or Example 21 (b).

| Ex. | Structure | Name | MS (ESI) m/z | $^1$H NMR |
|---|---|---|---|---|
| 33 | 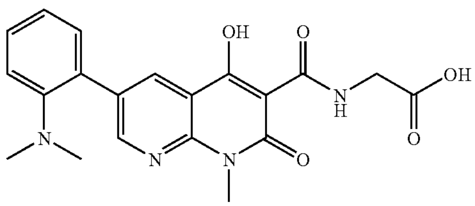 | 2-(6-(2-(Dimethylamino)phenyl)-4-hydroxy-1-methyl-2-oxo-1,2-dihydro-1,8-naphthyridine-3-carboxamido)acetic acid | 397 (M + 1) | $^1$H NMR (300 MHz, DMSO-$d_6$) δ ppm: 10.49 (t, J = 5.8, 5.3 Hz, 1 H), 9.00 (d, J = 2.2 Hz, 1 H), 8.56 (d, J = 2.2 Hz, 1 H), 7.09-7.45 (m, 4 H), 4.16 (d, J = 5.6 Hz, 2 H), 3.74 (s, 3 H), 2.53-2.62 (m, 6 H). |

Example 34

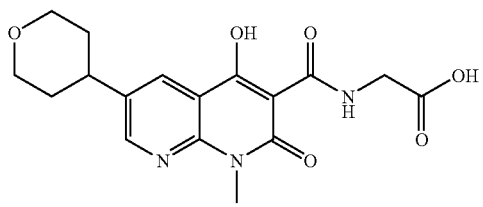

2-(4-Hydroxy-1-methyl-2-oxo-6-(tetrahydro-2 H-pyran-4-yl)-1,2-dihydro-1,8-naphthyridine-3-carboxamido)acetic acid. A mixture of 2-(6-(3,6-dihydro-2 H-pyran-4-yl)-4-hydroxy-1-methyl-2-oxo-1,2-dihydro-1,8-naphthyridine-3-carboxamido)acetic acid (71 mg, 198 μmol, Example 26 0)) and 1 N sodium hydroxide (988 μl, 988 μmol) in MeOH (5 mL) was treated with 10% Pd/C (5.3 mg, 49 μmol) under nitrogen atmosphere. The reaction vessel was degassed and backfilled with hydrogen (3×), and the mixture was stirred at 23° C. for 75 minutes under hydrogen atmosphere. The reaction mixture was filtered from the catalyst through a pad of Celite®, and the filter cake was washed with MeOH (50 mL). The combined filtrate was concentrated and acidified with concentrated HCl. The precipitated solid was collected by filtration, washed with water (10 mL), and dried in vacuo to give the title compound as a white solid. MS (ESI, pos. ion) m/z: 362 (M+1). $^1$NMR (400 MHz, DMSO-$d_6$) δ ppm: 10.49 (s, 1 H), 8.80 (d, J=2.0 Hz, 1 H), 8.26 (d, J=1.8 Hz, 1 H), 4.14 (d, J=5.3 Hz, 1 H), 3.98 (d, J=10.4 Hz, 2 H), 3.69 (s, 3 H), 3.42-3.52 (m, 2 H), 2.91-3.09 (m, 1 H), 1.65-1.88 (m, 4H).

Example 35

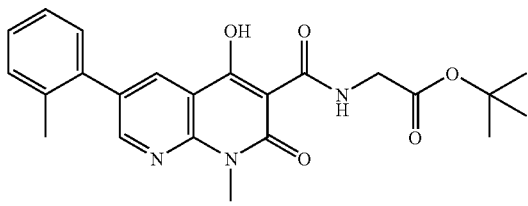

(a) tert-Butyl 2-(4-hydroxy-1-methyl-2-oxo-6-o-tolyl-1,2-dihydro-1,8-naphthyridine-3-carboxamido)acetate. The title compound was prepared similarly to the procedure described for Example 2 (a) by treatment of tert-butyl 2-(4-hydroxy-6-iodo-1-methyl-2-oxo-1,2-dihydro-1,8-naphthyridine-3-carboxamido)acetate (Example 26 (g)) with o-tolylboronic acid (111 mg, 817 μmol), and was isolated as an amber oil after purification by preparatory HPLC (gradient: 0% MeCN/water+0.1% TFA-90% MeCN/water+1% TFA). MS (ESI, pos. ion) m/z: 424 (M+1).

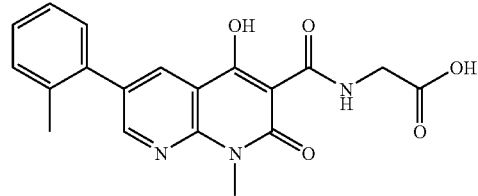

(b) N-((4-Hydroxy-1-methyl-6-(2-methylphenyl)-2-oxo-1,2-dihydro-1,8-naphthyridin-3-yl)carbonyl)glycine. The title compound was prepared similarly to the procedure described for Example 1 (g) by treatment of tert-butyl 2-(4-hydroxy-1-methyl-2-oxo-6-o-tolyl-1,2-dihydro-1,8-naphthyridine-3-carboxamido)acetate with TFA, and was isolated as a beige solid. MS (ESI, pos. ion) m/z: 368 (M+1). $^1$H NMR (300 MHz, DMSO-$d_6$) δ ppm: 10.49 (m, 1 H), 8.86 (d, J=1.8 Hz, 1 H), 8.35 (d, J=1.8 Hz, 1 H), 7.32-7.40 (m, 4H), 4.16 (d, J=5.5 Hz, 2 H), 3.75 (s, 3 H), 2.29 (s, 3 H).

Additional Examples

TABLE 5

The following examples were prepared from tert-butyl 2-(4-hydroxy-6-iodo-1-methyl-2-oxo-1,2-dihydro-1,8-naphthyridine-3-carboxamido)acetate (Example 26 (g)) and commercially available boronic acids or boronic acid esters analogously to the procedures described for the preparation of Example 35 (a, b) and 21(b).

| Ex. | Structure | Name | MS (ESI) m/z | $^1$H NMR |
|---|---|---|---|---|
| 36 | 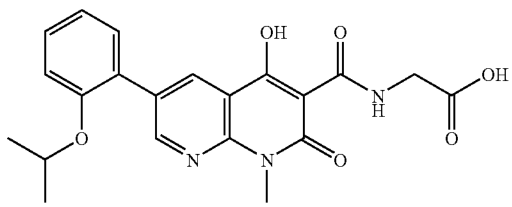 | N-((4-Hydroxy-1-methyl-6-(2-((1-methylethyl)oxy)phenyl)-2-oxo-1,2-dihydro-1,8-naphthyridin-3-yl)carbonyl)glycine | 412 (M + 1) | $^1$H NMR (400 MHz, DMSO-d$_6$) δ ppm: 12.96 (s, 1 H), 10.48 (t, J = 5.6 Hz, 1 H), 8.98 (d, J = 2.4 Hz, 1 H), 8.59 (d, J = 2.2 Hz, 1 H), 7.50 (m, 1 H), 7.37-7.43 (m, 1 H), 7.19 (d, J = 8.4 Hz, 1 H), 7.07 (t, J = 7.4 Hz, 1 H), 4.66-4.74 (m, 1 H), 4.15 (d, J = 5.7 Hz, 2 H), 3.73 (s, 3 H), 1.25 (d, J = 5.9 Hz, 6 H). |
| 37 | 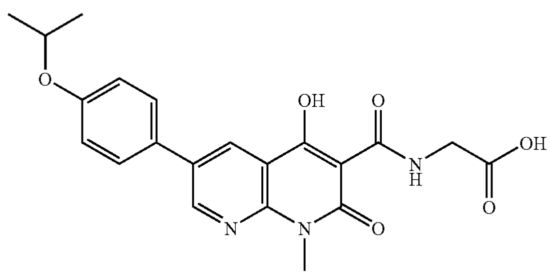 | N-((4-Hydroxy-1-methyl-6-(4-((1-methylethyl)oxy)phenyl)-2-oxo-1,2-dihydro-1,8-naphthyridin-3-yl)carbonyl)glycine | 412 (M + 1) | $^1$H NMR (400 MHz, DMSO-d$_6$) δ ppm: 10.49 (s, 1 H), 9.11 (d, J = 2.4 Hz, 1 H), 8.53 (d, J = 2.5 Hz, 1 H), 7.74 (d, J = 8.6 Hz, 2 H), 7.06 (d, J = 8.6 Hz, 2 H), 4.66-4.74 (m, 1 H), 4.13 (d, J = 5.5 Hz, 2 H), 3.72 (s, 3 H), 1.30 (d, J = 5.9 Hz, 6 H). |
| 38 | 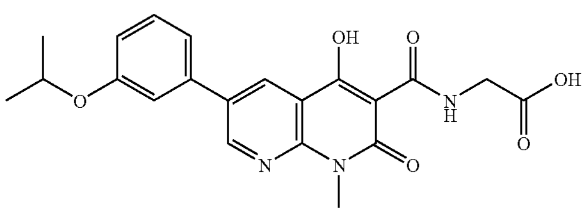 | N-((4-Hydroxy-1-methyl-6-(3-((1-methylethyl)oxy)phenyl)-2-oxo-1,2-dihydro-1,8-naphthyridin-3-yl)carbonyl)glycine | 412 (M + 1) | $^1$H NMR (400 MHz, DMSO-d$_6$) δ ppm: 12.98 (s, 1 H), 10.47 (t, J = 5.5 Hz, 1 H), 9.15 (d, J = 2.4 Hz, 1 H), 8.58 (d, J = 2.4 Hz, 1 H), 7.42 (t, J = 8.1 Hz, 1 H), 7.31-7.35 (m, 2 H), 7.00 (m, 1 H), 4.74-4.82 (m, 1 H), 4.16 (d, J = 5.5 Hz, 2 H), 3.73 (s, 3 H), 1.31 (d, J = 6.1 Hz, 6 H). |
| 39 | 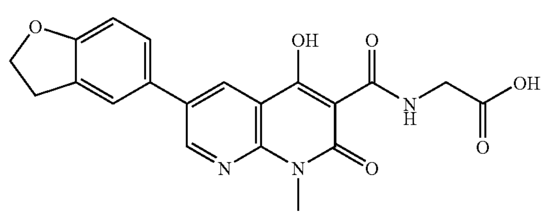 | N-((6-(2,3-Dihydro-1-benzofuran-5-yl)-4-hydroxy-1-methyl-2-oxo-1,2-dihydro-1,8-naphthyridin-3-yl)carbonyl)glycine | 396 (M + 1) | $^1$H NMR (400 MHz, DMSO-d$_6$) δ ppm: 12.98 (s, 1 H), 9.08 (d, J = 1.8 Hz, 1 H), 8.50 (d, J = 1.8 Hz, 1 H), 7.70 (s, 1 H), 7.53 (s, 1 H), 6.90 (d, J = 8.2 Hz, 1 H), 4.60 (t, J = 8.7 Hz, 2 H), 4.15 (d, J = 5.3 Hz, 2 H), 3.72 (s, 3 H), 3.26 (t, J = 8.8 Hz, 2 H). |

TABLE 5-continued

The following examples were prepared from tert-butyl 2-(4-hydroxy-6-iodo-1-methyl-2-oxo-1,2-dihydro-1,8-naphthyridine-3-carboxamido)acetate (Example 26 (g)) and commercially available boronic acids or boronic acid esters analogously to the procedures described for the preparation of Example 35 (a, b) and 21(b).

| Ex. | Structure | Name | MS (ESI) m/z | $^1$H NMR |
|---|---|---|---|---|
| 40 | 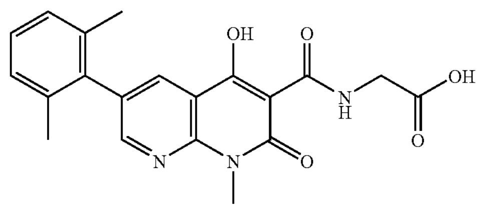 | N-((6-(2,6-Dimethylphenyl)-4-hydroxy-1-methyl-2-oxo-1,2-dihydro-1,8-naphthyridin-3-yl)carbonyl) glycine | 382 (M + 1) | $^1$H NMR (400 MHz, DMSO-d$_6$) δ ppm: 10.49 (m, 1 H), 8.68 (d, J = 2.4 Hz, 1 H), 8.21 (d, J = 2.2 Hz, 1 H), 7.18-7.27 (m, 3 H), 4.16 (d, J = 5.5 Hz, 2 H), 3.76 (s, 3 H), 2.02 (s, 12 H). |
| 41 | 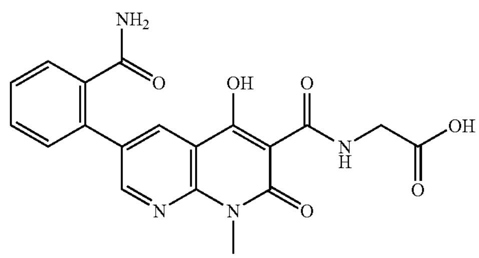 | N-((6-(2-(Aminocarbonyl)phenyl)-4-hydroxy-1-methyl-2-oxo-1,2-dihydro-1,8-naphthyridin-3-yl)carbonyl) glycine | 397 (M + 1) | $^1$H NMR (400 MHz, DMSO-d$_6$) δ ppm: 10.17-10.67 (m, 1 H), 8.82 (d, J = 2.4 Hz, 1 H), 8.42 (d, J = 2.4 Hz, 1 H), 7.86 (s, 1 H), 7.49-7.59 (m, 4 H), 7.39-7.48 (s, 1 H), 4.15 (d, J = 5.48 Hz, 2 H), 3.74 (s, 3 H). |
| 42 | 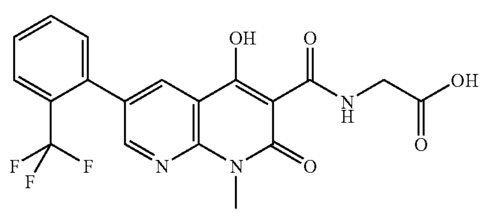 | N-((4-Hydroxy-1-methyl-2-oxo-6-(2-(trifluoromethyl)phenyl)-1,2-dihydro-1,8-naphthrydin-3-yl)carbonyl) glycine | 422 (M + 1) | $^1$H NMR (400 MHz, DMSO-d$_6$) δ ppm: 10.46 (t, J = 5.5 Hz, 1 H), 8.81 (d, J = 2.2 Hz, 1 H), 8.36 (d, J = 2.2 Hz, 1 H), 7.93 (d, J = 7.8 Hz, 1 H), 7.82 (t, J = 7.5 Hz, 1 H), 7.72 (t, J = 7.6 Hz, 1 H), 7.58 (d, J = 7.4 Hz, 1 H), 4.16 (d, J = 5.7 Hz, 2 H), 3.75 (s, 3 H). |
| 43 | 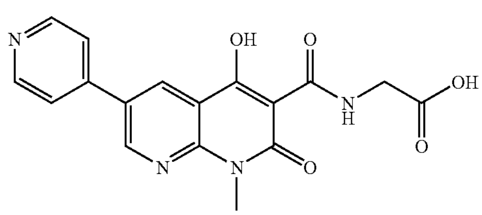 | 2-(4-Hydroxy-1-methyl-2-oxo-6-(pyridin-4-yl)-1,2-dihydro-1,8-naphthyridine-3-carboxamido) acetic acid | 355 (M + 1) | $^1$H NMR (300 MHz, DMSO-d$_6$) δ ppm: 10.42 (t, J = 4.8 Hz, 1 H), 9.37 (d, J = 2.0 Hz, 1 H), 8.80-8.90 (m, 3 H), 8.22 (d, J = 5.4 Hz, 2 H), 4.16 (d, J = 5.3 Hz, 2 H), 3.75 (s, 3 H). |
| 44 | 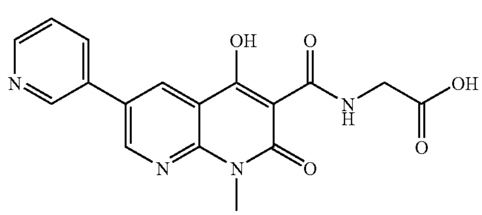 | 2-(4-Hydroxy-1-methyl-2-oxo-6-(pyridin-3-yl)-1,2-dihydro-1,8-naphthyridine-3-carboxamido) acetic acid | 355 (M + 1) | $^1$H NMR (300 MHz, DMSO-d$_6$) δ ppm: 10.45 (t, J = 5.6 Hz, 1 H), 9.26 (d, J = 2.3 Hz, 1 H), 9.21 (d, J = 1.6 Hz, 1 H), 8.79 (d, J = 2.5 Hz, 1 H), 8.77 (dd, J = 5.3, 1.2 Hz, 1 H), 8.57 (d, J = 7.9 Hz, 1 H), 7.76-7.83 (m, 1 H), 4.16 (d, J = 5.6 Hz, 2 H), 3.75 (s, 3 H). |

TABLE 5-continued

The following examples were prepared from tert-butyl 2-(4-hydroxy-6-iodo-1-methyl-2-oxo-1,2-dihydro-1,8-naphthyridine-3-carboxamido)acetate (Example 26 (g)) and commercially available boronic acids or boronic acid esters analogously to the procedures described for the preparation of Example 35 (a, b) and 21(b).

| Ex. | Structure | Name | MS (ESI) m/z | $^1$H NMR |
|---|---|---|---|---|
| 45 | 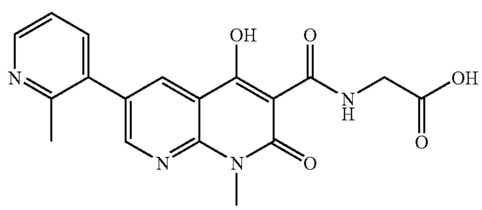 | 2-(4-Hydroxy-1-methyl-6-(2-methylpyridin-3-yl)-2-oxo-1,8-naphthyridine-3-carboxamido) acetic acid | 368 (M + 1) | $^1$H NMR (300 MHz, DMSO-d$_6$) δ ppm: 10.46 (t, J = 5.6 Hz, 1 H), 8.94 (d, J = 2.3 Hz, 1 H), 8.72 (d, J = 5.3 Hz, 1 H), 8.53 (d, J = 2.0 Hz, 1 H), 8.13-8.22 (m, 1 H), 7.64-7.75 (m, 1 H), 4.16 (d, J = 5.6 Hz, 2 H), 3.76 (s, 3 H), 2.59 (s, 3 H). |
| 46 | 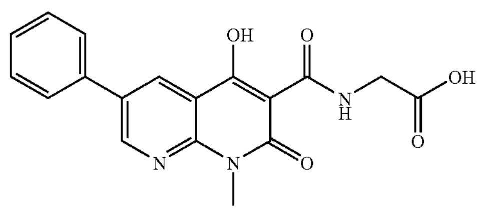 | 2-(4-Hydroxy-1-methyl-2-oxo-6-phenyl-1,2-dihydro-1,8-naphthyridine-3-carboxamido) acetic acid | 353 (M + 1) | $^1$H NMR (300 MHz, DMSO-d$_6$) δ ppm: 10.48 (t, J = 5.5 Hz, 1 H), 9.17 (d, J = 2.3 Hz, 1 H), 8.61 (d, J = 2.3 Hz, 1 H), 7.79-7.91 (m, 2 H), 7.33-7.65 (m, 3 H), 4.16 (d, J = 5.7 Hz, 2 H), 3.74 (s, 3 H). |
| 47 | 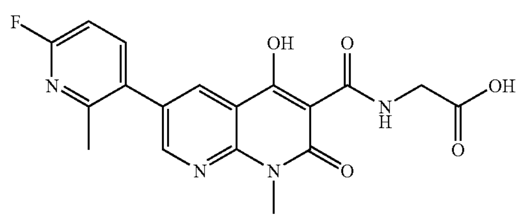 | 2-(6-(6-Fluoro-2-methylpyridin-3-yl)-4-hydroxy-1-methyl-2-oxo-1,2-dihydro-1,8-naphthyridine-3-carboxamido) acetic acid | 387 (M + 1) | $^1$H NMR (300 MHz, DMSO-d$_6$) δ ppm: 12.96 (s, 1 H), 10.47 (s, 1 H), 8.90 (s, 1 H), 8.45 (s, 1 H), 7.98 (t, J = 7.9 Hz, 1 H), 7.17 (d, J = 7.2 Hz, 1 H), 4.16 (d, J = 4.9 Hz, 2 H), 3.74 (s, 3 H), 2.43 (s, 3 H). |
| 48 | 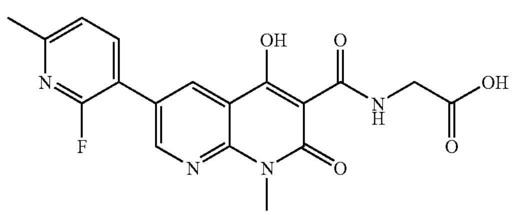 | N-((6-(2-Fluoro-6-methyl-3-pyridinyl)-4-hydroxy-1-methyl-2-oxo-1,2-dihydro-1,8-naphthyridin-3-yl)carbonyl) glycine | 387 (M + 1) | $^1$H NMR (300 MHz, DMSO-d$_6$) δ ppm: 12.88-13.13 (m, 1 H), 10.44 (t, J = 4.9 Hz, 1 H), 9.05 (s, 1 H), 8.60 (s, 1 H), 8.22 (dd, J = 10.5, 7.5 Hz, 1 H), 7.39 (dd, J = 7.7, 1.3 Hz, 1 H), 4.16 (d, J = 5.5 Hz, 2 H), 3.72 (s, 3 H), 3.17 (d, J = 3.0 Hz, 3 H). |
| 49 | 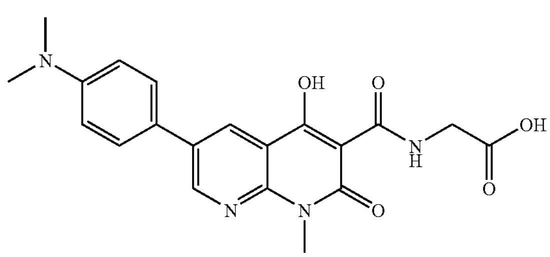 | N-((6-(4-(Dimethylamino) phenyl)-4-hydroxy-1-methyl-2-oxo-1,2-dihydro-1,8-naphthyridin-3-yl)carbonyl) glycine | 397 (M + 1) | $^1$H NMR (300 MHz, DMSO-d$_6$) δ ppm: 12.97 (s, 1 H), 10.46-10.57 (m, 1 H), 9.10 (s, J = 1.3 Hz, 1 H), 8.48 (s, 1 H), 7.65 (d, J = 8.5 Hz, 2 H), 6.86 (d, J = 8.7 Hz, 2 H), 4.15 (d, J = 4.9 Hz, 2 H), 3.72 (s, 3 H), 2.97 (s, 6 H). |

TABLE 5-continued

The following examples were prepared from tert-butyl 2-(4-hydroxy-6-iodo-1-methyl-2-oxo-1,2-dihydro-1,8-naphthyridine-3-carboxamido)acetate (Example 26 (g)) and commercially available boronic acids or boronic acid esters analogously to the procedures described for the preparation of Example 35 (a, b) and 21(b).

| Ex. | Structure | Name | MS (ESI) m/z | $^1$H NMR |
|---|---|---|---|---|
| 50 | 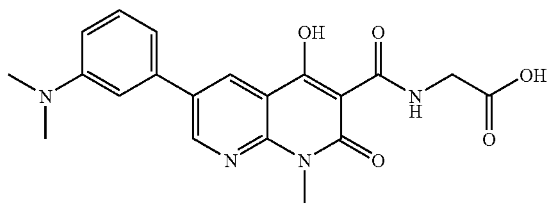 | N-((6-(3-(Dimethylamino)phenyl)-4-hydroxy-1-methyl-2-oxo-1,2-dihydro-1,8-naphthyridin-3-yl)carbonyl)glycine | 397 (M + 1) | $^1$H NMR (300 MHz, DMSO-d$_6$) δ ppm: 10.49 (t, J = 5.7 Hz, 1 H), 9.15 (d, J = 2.3 Hz, 1 H), 8.56 (d, J = 2.3 H, 1 H), 7.34 (t, J = 8.2 Hz, 1 H), 7.04-7.11 (m, 2 H), 6.85 (d, J = 8.5 Hz, 2 H), 4.16 (d, J = 5.6 Hz, 2 H), 3.17 (s, 3 H), 3.00 (s, 6 H). |
| 51 | 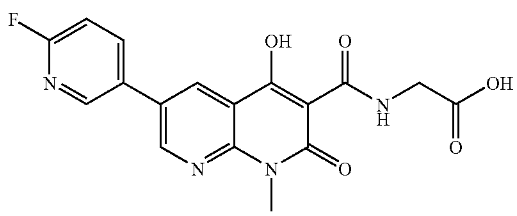 | N-((6-(6-Fluoro-3-pyridinyl)-4-hydroxy-1-methyl-2-oxo-1,2-dihydro-1,8-naphthyridin-3-yl)carbonyl)glycine | 373 (M + 1) | $^1$H NMR (300 MHz, DMSO-d$_6$) δ ppm: 10.48 (s, 1 H), 9.20 (s, 1 H), 8.73 (d, J = 7.0 Hz, 2 H), 8.49 (t, J = 8.5 Hz, 1 H), 7.32-7.42 (m, 1 H), 4.15 (s, 2 H), 3.73 (s, 3 H). |
| 52 | 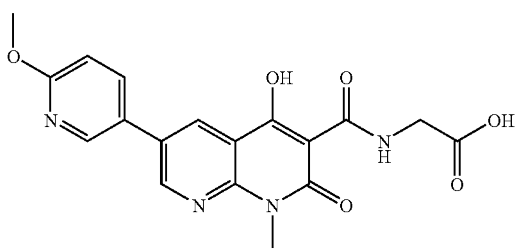 | N-((4-Hydroxy-1-methyl-6-(6-(methyloxy)-3-pyridinyl)-2-oxo-1,2-dihydro-1,8-naphthyridin-3-yl)carbonyl)glycine | 385 (M + 1) | $^1$H NMR (300 MHz, DMSO-d$_6$) δ ppm: 10.48 (s, 1 H), 9.16 (s, 1 H), 8.62 (d, J = 13.3 Hz, 2 H), 8.13-8.25 (m, 1 H), 7.03-7.39 (m, 1 H), 6.96 (d, J = 7.6 Hz, 1 H), 4.15 (d, J = 3.7 Hz, 2 H), 3.92 (s, 3 H), 3.73 (s, 3 H). |
| 53 | 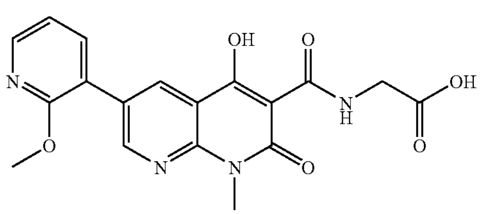 | N-((4-Hydroxy-1-methyl-6-(2-(methyloxy)-3-pyridinyl)-2-oxo-1,2-dihydro-1,8-naphthyridin-3-yl)carbonyl)glycine | 385 (m + 1) | $^1$H NMR (300 MHz, DMSO-d$_6$) δ ppm: 10.47 (1 H, s), 9.03 (s, 1 H), 8.60 (s, 1 H), 8.26 (t, J = 4.0 Hz, 1 H), 7.99 (t, J = 4.0 Hz, 1 H), 7.18 (t, J = 6.0 Hz, 1 H), 4.16 (d, J = 4.0 Hz, 2 H), 3.93 (s, 3 H), 3.73 (s, 3 H). |
| 54 | 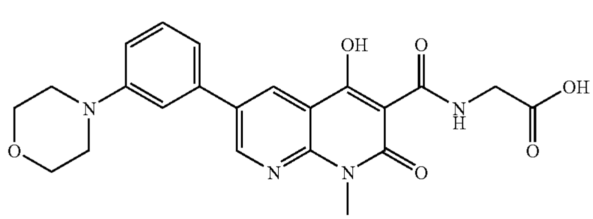 | N-((4-Hydroxy-1-methyl-6-(3-(4-morpholinyl)phenyl-2-oxo-1,2-dihydro-1,8-naphthyridin-3-yl)carbonyl)glycine | 439 (M + 1) | $^1$H NMR (300 MHz, DMSO-d$_6$) δ ppm: 10.48 (t, J = 5.4 Hz, 1 H), 9.16 (d, J = 2.3 Hz, 1 H), 8.60 (d, J = 2.3 Hz, 1 H), 7.32-7.42 (m, 2 H), 7.19-7.27 (m, 1 H), 7.00-7.08 (m, 1 H), 4.16 (d, J = 5.6 Hz, 2 H), 3.77 (t, J = 4.8 Hz, 4 H), 3.74 (s, 3 H), 3.24 (t, J = 4.8, 4.5 Hz, 4 H). |

TABLE 5-continued

The following examples were prepared from tert-butyl 2-(4-hydroxy-6-iodo-1-methyl-2-oxo-1,2-dihydro-1,8-naphthyridine-3-carboxamido)acetate (Example 26 (g)) and commercially available boronic acids or boronic acid esters analogously to the procedures described for the preparation of Example 35 (a, b) and 21(b).

| Ex. | Structure | Name | MS (ESI) m/z | $^1$H NMR |
|---|---|---|---|---|
| 55 | 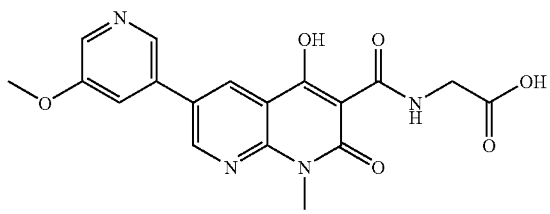 | N-((4-Hydroxy-1-methyl-6-(5-(methyloxy)-3-pyridinyl)-2-oxo-1,2-dihydro-1,8-naphthyridin-3-yl)carbonyl)glycine | 385 (M + 1) | $^1$H NMR (300 MHz, DMSO-d$_6$) δ ppm: 12.99 (br. s, 1 H) 10.46 (s, 1 H), 9.23 (s, 1 H), 8.72 (s, 1 H), 8.62 (s, 1 H), 8.36 (s, 1 H), 7.83 (s, 1 H), 4.16 (d, J = 4.0 Hz, 2 H), 3.94 (s, 3 H), 3.73 (s, 3 H). |
| 56 | 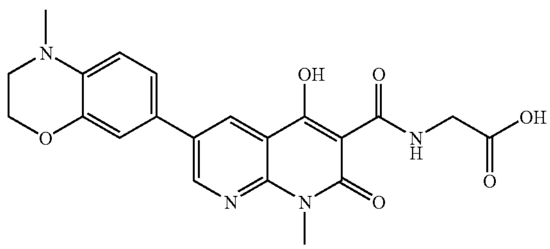 | N-((4-Hydroxy-1-methyl-6-(4-methyl-3,4-dihydro-2H-1,4-benzoxazin-7-yl)-2-oxo-1,2-dihydro-1,8-naphthyridin-3-yl)carbonyl)glycine | 425 (M + 1) | $^1$H NMR (300 MHz, DMSO-d$_6$) δ ppm: 12.99 (s, 1 H), 10.50 (s, 1 H), 9.06 (s, 1 H), 8.44 (s, 1 H), 7.18-7.34 (m, 1 H), 7.14 (s, 1 H), 6.72-6.90 (m, 1 H), 4.21 (d, J = 38.9 Hz, 4 H), 3.73 (s, 3 H), 3.03-3.56 (m, 3 H), 2.90 (s, 3 H). |
| 57 | 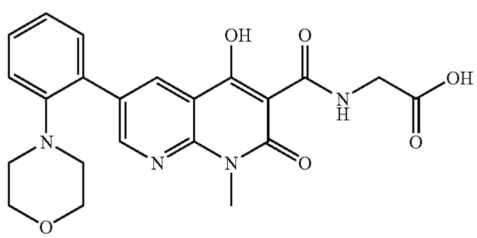 | N-((4-Hydroxy-1-methyl-6-(2-(4-morpholinyl)phenyl)-2-oxo-1,2-dihydro-1,8-naphthyridin-3-yl)carbonyl)glycine | 439 (M + 1) | $^1$H NMR (400 MHz, DMSO-d$_6$) δ ppm: 10.49 (s, 1 H), 9.05 (s, 1 H), 8.82 (s, 1 H), 7.41 (dd, J = 7.6, 7.0 Hz, 2 H), 7.16-7.23 (m, 2 H), 4.12 (d, J = 4.5 Hz, 2 H), 3.73 (s, 3 H), 3.49 (br. s, 4 H), 2.76 (br. s, 4 H). |
| 58 | 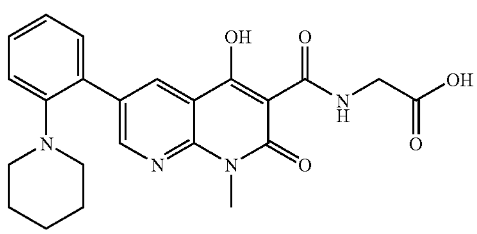 | N-((4-Hydroxy-1-methyl-2-oxo-6-(2-(1-piperidinyl)phenyl)-1,2-dihydro-1,8-naphthyridin-3-yl)carbonyl)glycine | 437 (M + 1) | $^1$H NMR (300 MHz, DMSO-d$_6$) δ ppm: 10.49 (s, 1 H), 9.03 (s, 1 H), 8.81 (s, 1 H), 7.37 (t, J = 8.0 Hz, 2 H), 7.07-7.24 (m, 2 H), 4.11 (d, J = 4.8 Hz, 2 H), 3.73 (s, 3 H), 2.73 (br. s, 4 H), 1.40 (br. s, 6 H). |
| 59 | 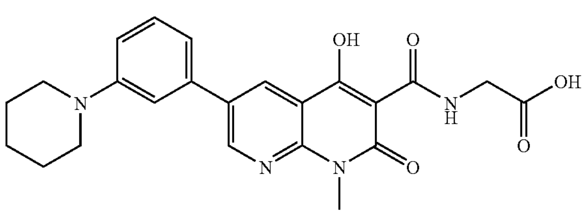 | N-((4-Hydroxy-1-methyl-2-oxo-6-(3-(1-piperidinyl)phenyl)-1,2-dihydro-1,8-naphthyridin-3-yl)carbonyl)glycine | 437 (M + 1) | $^1$H NMR (400 MHz, DMSO-d$_6$) δ ppm: 12.98 (s, 1 H), 10.47 (t, J = 5.3 Hz, 1 H), 9.13 (d, J = 1.8 Hz, 1 H), 8.56 (d, J = 1.8 Hz, 1 H), 7.34 (t, J = 7.9 Hz, 1 H), 7.28 (s, 1 H), 7.14 (d, J = 7.4 Hz, 1 H), 7.02 (d, J = 8.2 Hz, 1 H), 4.16 (d, J = 5.3 Hz, 2 H), 3.73 (s, 3 H), 3.17-3.29 (m, 4 H), 1.60-1.71 (m, 4 H), 1.49-1.60 (m, 2 H). |

TABLE 5-continued

The following examples were prepared from tert-butyl 2-(4-hydroxy-6-iodo-1-methyl-2-oxo-1,2-dihydro-1,8-naphthyridine-3-carboxamido)acetate (Example 26 (g)) and commercially available boronic acids or boronic acid esters analogously to the procedures described for the preparation of Example 35 (a, b) and 21(b).

| Ex. | Structure | Name | MS (ESI) m/z | $^1$H NMR |
|---|---|---|---|---|
| 60 | 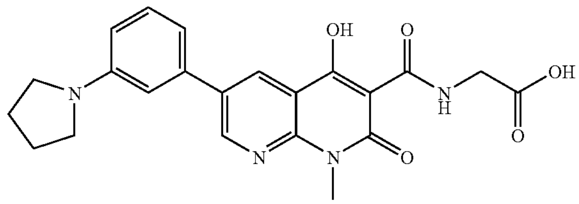 | N-((4-Hydroxy-1-methyl-2-oxo-6-(3-(1-pyrrolidinyl)phenyl)-1,2-dihydro-1,8-naphthyridin-3-yl)carbonyl)glycine | 423 (M + 1) | $^1$H NMR (300 MHz, DMSO-d$_6$) δ ppm: 10.39-10.57 (m, 1 H), 9.12 (s, 1 H), 8.45-8.62 (m, 1 H), 7.28 (s, 1 H), 6.88-7.06 (m, 1 H), 6.83 (s, 1 H), 6.52-6.67 (m, 1 H), 4.02-4.28 (m, 3 H), 3.72 (br. s, 6 H), 1.97 (br. s, 4 H). |
| 61 | 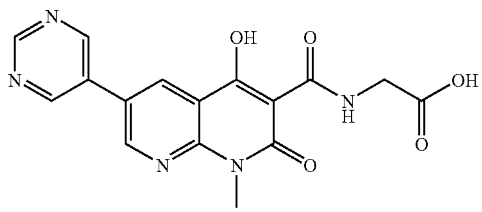 | N-((4-Hydroxy-1-methyl-2-oxo-6-(5-pyrimidinyl)-1,2-dihydro-1,8-naphthyridin-3-yl)carbonyl)glycine | 356 (M + 1) | $^1$H NMR (400 MHz, DMSO-d$_6$) δ ppm: 10.40-10.51 (m, 1 H), 9.21-9.39 (m, 4 H), 8.83 (s, 1 H), 4.15 (d, J = 5.3 Hz, 2 H), 3.74 (s, 3 H). |
| 62 | 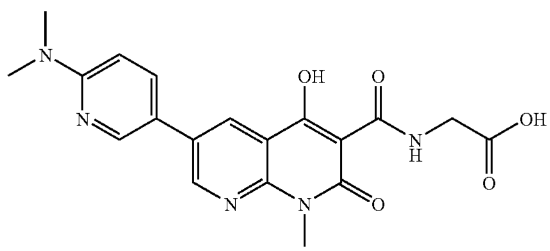 | N-((6-(6-(Dimethylamino)-3-pyridinyl)-4-hydroxy-1-methyl-2-oxo-1,2-dihydro-1,8-naphthyridin-3-yl)carbonyl)glycine | 398 (M + 1) | $^1$H NMR (300 MHz, DMSO-d$_6$) δ ppm: 10.50 (s, 1 H), 9.12 (s, 1 H), 8.56 (s, 1 H), 8.47-8.54 (m, 1 H), 7.97 (d, J = 9.8 Hz, 1 H), 6.78 (d, J = 9.2 Hz, 1 H), 4.15 (d, J = 4.2 Hz, 2 H), 3.72 (s, 3 H), 3.09 (s, 6 H). |
| 63 | 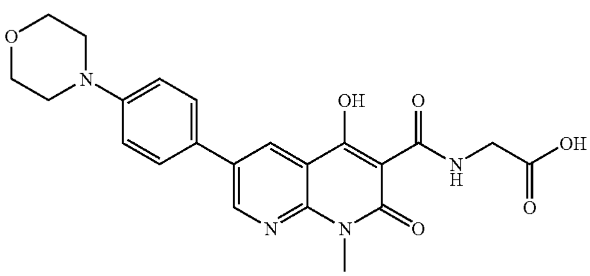 | N-((4-Hydroxy-1-methyl-6-(4-(4-morpholinyl)phenyl)-2-oxo-1,2-dihydro-1,8-naphthyridin-3-yl)carbonyl)glycine | 439 (M + 1) | $^1$H NMR (300 MHz, DMSO-d$_6$) δ ppm: 10.50 (s, 1 H), 9.11 (s, 1 H), 8.51 (s, 1 H), 7.72 (d, J = 7.3 Hz, 2 H), 7.08 (d, J = 8.2 Hz, 2 H), 4.14 (d, J = 5.4 Hz, 2 H), 3.77 (t, J = 4.8 Hz, 4 H), 3.72 (s, 3 H), 3.11-3.24 (m, 4 H). |

Example 64

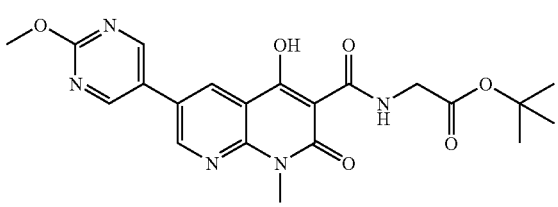

(a) tert-Butyl 2-(4-hydroxy-6-(2-methoxypyrimidin-5-yl)-1-methyl-2-oxo-1,2-dihydro-1,8-naphthyridine-3-carboxamido)acetate. A mixture of 2-methoxypyrimidine-5-boronic acid (0.34 g, 2.2 mmol), tert-butyl 2-(4-hydroxy-6-iodo-1-methyl-2-oxo-1,2-dihydro-1,8-naphthyridine-3-carboxamido)acetate (0.500 g, 1.1 mmol, Example 26 (g)), tri-tert-butylphosphonium tetrafluoroborate (0.063 g, 0.22 mmol), Pd$_2$(dba)$_3$ (0.100 g, 0.11 mmol) and potassium fluoride (0.076 mg, 3.3 mmol) in THF (8 mL) was stirred at 60° C. for 4 hours under an argon atmosphere. The reaction mixture was left to reach room temperature and was filtered. The filter cake was washed with EtOAc (3×100 mL). The combined filtrate was evaporated under reduced pressure, and the residue was diluted with DCM (100 mL), and was filtered. The filtrate was washed with deionized water (3×75 mL) and brine (75 mL), dried over MgSO$_4$, and filtered. The filtrate was evaporated under reduced pressure, and the residue was purified by silica gel column chromatography (gradient: 0-33% EtOAc/hexanes) to give the title compound.

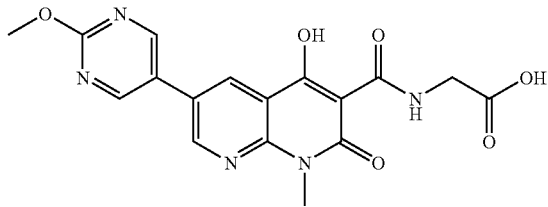

(b) 2-(4-Hydroxy-6-(2-methoxypyrimidin-5-yl)-1-methyl-2-oxo-1,2-dihydro-1,8-naphthyridine-3-carboxamido)acetic acid. The title compound was prepared similarly to the procedure described for Example 1 (g) by treatment of tert-butyl 2-(4-hydroxy-6-(2-methoxypyrimidin-5-yl)-1-methyl-2-oxo-1,2-dihydro-1,8-naphthyridine-3-carboxamido)acetate with TFA. MS (ESI, pos. ion) m/z: 386 (M+1). $^1$H NMR (300 MHz, DMSO-$d_6$) δ ppm: 13.00 (s, 1 H), 10.45 (t, J=4.8 Hz, 1 H), 9.15-9.23 (m, 1 H), 9.10 (s, 2 H), 8.72 (s, 1 H), 4.15 (d, J=5.3 Hz, 2 H), 3.98 (s, 3 H), 3.72 (s, 3 H).

Example 65

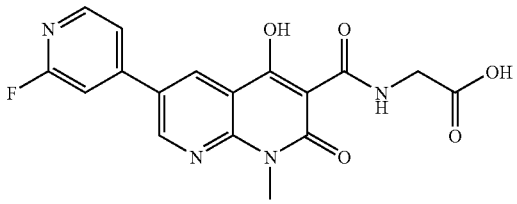

2-(6-(2-Fluoropyridin-4-yl)-4-hydroxy-1-methyl-2-oxo-1,2-dihydro-1,8-naphthyridine-3-carboxamido)acetic acid. The title compound was prepared similarly to the procedures described for Example 64 (a, b) from tert-butyl 2-(4-hydroxy-6-iodo-1-methyl-2-oxo-1,2-dihydro-1,8-naphthyridine-3-carboxamido)acetate (Example 26 (g)) and 2-fluoro-4-pyridinylboronic acid. MS (ESI, pos. ion) m/z: 373 (M+1). $^1$H NMR (300 MHz, DMSO-$d_6$) δ ppm: 12.99 (s, 1 H), 10.34-10.48 (m, 1 H), 9.31 (s, 1 H), 8.80 (s, 1 H), 8.30-8.41 (m, 1 H), 7.84-7.96 (m, 1 H), 7.78 (s, 1 H), 4.04-4.25 (m, 2 H), 3.72 (s, 3 H).

Example 66

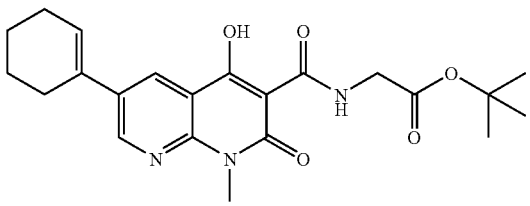

(a) tert-Butyl 2-(6-cyclohexenyl-4-hydroxy-1-methyl-2-oxo-1,2-dihydro-1,8-naphthyridine-3-carboxamido)acetate. The title compound was prepared similarly to the procedure described for Example 2 (a) by treatment of tert-butyl 2-(4-hydroxy-6-iodo-1-methyl-2-oxo-1,2-dihydro-1,8-naphthyridine-3-carboxamido)acetate (Example 26 (g)) with 2-cyclohexenyl-4,4,5,5-tetramethyl-1,3,2-dioxaborolane. MS (ESI, pos. ion) m/z: 414 (M+1).

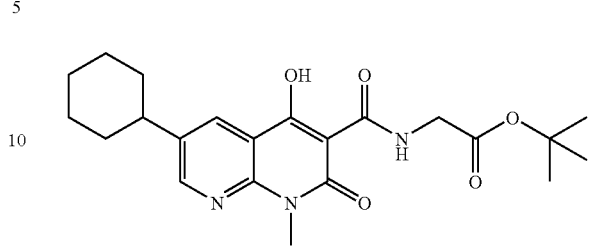

(b) tert-Butyl 2-(6-cyclohexyl-4-hydroxy-1-methyl-2-oxo-1,2-dihydro-1,8-naphthyridine-3-carboxamido)acetate. The title compound was prepared similarly to the procedure described for Example 5(a) by hydrogenation of tert-butyl 2-(6-cyclohexenyl-4-hydroxy-1-methyl-2-oxo-1,2-dihydro-1,8-naphthyridine-3-carboxamido)acetate. MS (ESI, pos. ion) m/z: 416 (M+1).

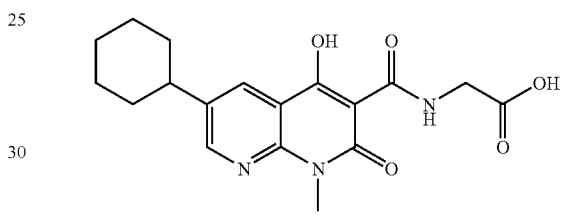

(c) 2-(6-Cyclohexyl-4-hydroxy-1-methyl-2-oxo-1,2-dihydro-1,8-naphthyridine-3-carboxamido)acetic acid. The title compound was prepared similarly to the procedure described for Example 1 (g) by treatment of tert-butyl 2-(6-cyclohexyl-4-hydroxy-1-methyl-2-oxo-1,2-dihydro-1,8-naphthyridine-3-carboxamido)acetate with TFA. MS (ESI, pos. ion) m/z: 360 (M+1). $^1$H NMR (300 MHz, DMSO-$d_6$) δ ppm: 10.50 (t, J=5.6 Hz, 1 H), 8.75 (d, J=2.3 Hz, 1 H), 8.24 (d, J=2.2 Hz, 1 H), 4.14 (d, J=5.6 Hz, 1 H), 3.68 (s, 3 H), 2.65-2.80 (m, 1 H), 1.64-1.94 (m, 5H), 1.12-1.63 (m, 5H).

Example 67

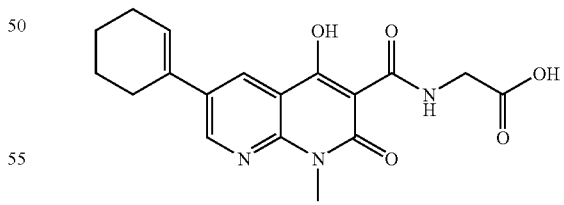

2-(6-Cyclohexenyl-4-hydroxy-1-methyl-2-oxo-1,2-dihydro-1,8-naphthyridine-3-carboxamido)acetic acid. The title compound was prepared similarly to the procedure described for Example 1 (g) by treatment of tert-butyl 2-(6-cyclohexenyl-4-hydroxy-1-methyl-2-oxo-1,2-dihydro-1,8-naphthyridine-3-carboxamido)acetate (Example 66 (a)) with TFA. MS (ESI, pos. ion) m/z: 357 (M+1). $^1$H NMR (300 MHz, DMSO-$d_6$) δ ppm: 10.48 (t, J=5.6 Hz, 1 H), 8.93 (d, J=2.3 Hz, 1 H), 8.28 (d, J=1.9 Hz, 1 H), 6.39 (br. s, 1 H), 4.13 (d, J=5.6 Hz, 2

H), 3.69 (s, 3 H), 2.39-2.46 (m, 2 H), 2.17-2.27 (m, 2 H), 1.70-1.84 (m, 2 H), 1.59-1.69 (m, 2 H).

Example 68

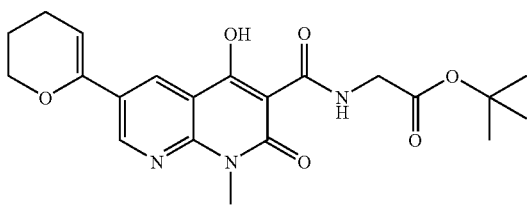

(a) tert-Butyl 2-(6-(5,6-dihydro-4H-pyran-2-yl)-4-hydroxy-1-methyl-2-oxo-1,2-dihydro-1,8-naphthyridine-3-carboxamido)acetate. The title compound was prepared similarly to the procedure described for Example 2 (a) by treatment of tert-butyl 2-(4-hydroxy-6-iodo-1-methyl-2-oxo-1,2-dihydro-1,8-naphthyridine-3-carboxamido)acetate (Example 26 (g)) with 2-(5,6-dihydro-4H-pyran-2-yl)-4,4,5,5-tetramethyl-1,3,2-dioxaborolane.

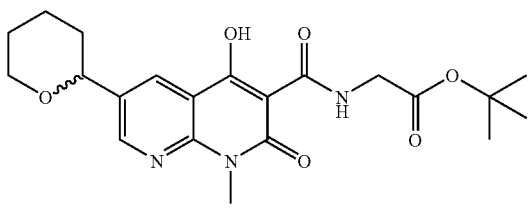

(b) (R,S)-tert-Butyl 2-(4-hydroxy-1-methyl-2-oxo-6-(tetrahydro-2 H-pyran-2-yl)-1,2-dihydro-1,8-naphthyridine-3-carboxamido)acetate. The title compound was prepared similarly to the procedure described for Example 5 (a) by hydrogenation of tert-butyl 2-(6-(5,6-dihydro-4H-pyran-2-yl)-4-hydroxy-1-methyl-2-oxo-1,2-dihydro-1,8-naphthyridine-3-carboxamido)acetate, and was isolated as a mixture of enantiomers.

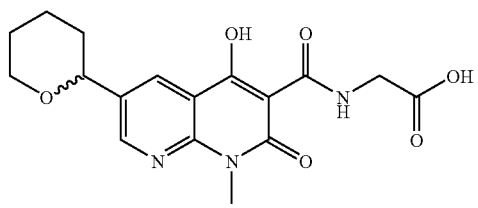

(c) (R,S)-2-(4-Hydroxy-1-methyl-2-oxo-6-(tetrahydro-2 H-pyran-2-yl)-1,2-dihydro-1,8-naphthyridine-3-carboxamido)acetic acid. The title compound was prepared similarly to the procedure described for Example 1 (g) by treatment of tert-butyl 2-(4-hydroxy-1-methyl-2-oxo-6-(tetrahydro-2 H-pyran-2-yl)-1,2-dihydro-1,8-naphthyridine-3-carboxamido)acetate with TFA. MS (ESI, pos. ion) m/z: 362 (M+1). $^1$H NMR (400 MHz, DMSO-$d_6$) δ ppm: 10.47 (t, J=5.5 Hz, 1 H), 8.79 (d, J=2.3 Hz, 1 H), 8.35 (d, J=2.2 Hz, 1 H), 4.55 (dd, J=11.2, 1.6 Hz, 1 H), 4.13 (d, J=5.7 Hz, 2 H), 4.04-4.11 (m, 1 H), 3.69 (s, 3 H), 3.55-3.62 (m, 1 H), 1.80-1.98 (m, 2 H), 1.41-1.75 (m, 4H).

Examples 69 and 70

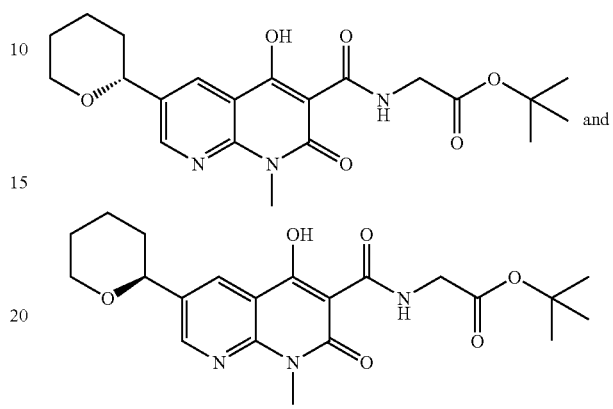

(a) (R)-tert-Butyl 2-(4-hydroxy-1-methyl-2-oxo-6-(tetrahydro-2H-pyran-2-yl)-1,2-dihydro-1,8-naphthyridine-3-carboxamido)acetate and (S)-tert-Butyl 2-(4-hydroxy-1-methyl-2-oxo-6-(tetrahydro-2 H-pyran-2-yl)-1,2-dihydro-1,8-naphthyridine-3-carboxamido)acetate. Separation of the racemic mixture (R,S)— tert-butyl 2-(4-hydroxy-1-methyl-2-oxo-6-(tetrahydro-2 H-pyran-2-yl)-1,2-dihydro-1,8-naphthyridine-3-carboxamido)acetate (Example 68 (b)) by preparative HPLC on a Chiralcel OD column (9:1 hexane/EtOH) afforded a fast running compound and its enantiomer.

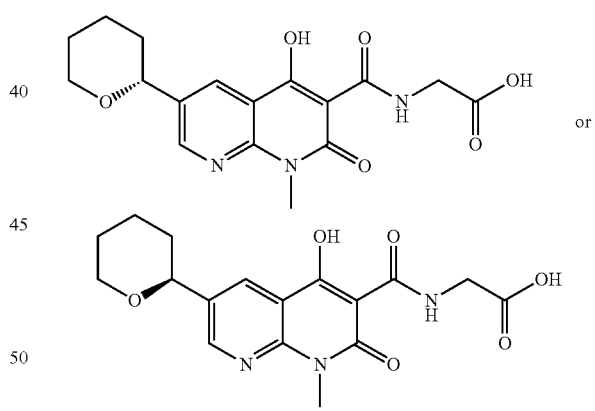

(b) (R)-2-(4-hydroxy-1-methyl-2-oxo-6-(tetrahydro-2 H-pyran-2-yl)-1,2-dihydro-1,8-naphthyridine-3-carboxamido)acetic acid or (S)-2-(4-hydroxy-1-methyl-2-oxo-6-(tetrahydro-2 H-pyran-2-yl)-1,2-dihydro-1,8-naphthyridine-3-carboxamido)acetic acid (Example 69). The title compound was prepared similarly to the procedure described for Example 1 (g) by treatment of the fast running compound from step (a) ((R)-tert-butyl 2-(4-hydroxy-1-methyl-2-oxo-6-(tetrahydro-2 H-pyran-2-yl)-1,2-dihydro-1,8-naphthyridine-3-carboxamido)acetate or (S)-tert-butyl 2-(4-hydroxy-1-methyl-2-oxo-6-(tetrahydro-2H-pyran-2-yl)-1,2-dihydro-1,8-naphthyridine-3-carboxamido)acetate) with TFA. MS (ESI, pos. ion) m/z: 362 (M+1). $^1$H NMR (300 MHz, DMSO-$d_6$) δ ppm: 10.47 (t, J=5.3 Hz, 1 H), 8.79 (d, J=2.3 Hz, 1 H), 8.35 (d, J=2.0 Hz, 1 H), 4.55 (dd, J=10.9, 1.8 Hz, 1 H), 4.14 (d, J=5.6 Hz, 2 H), 4.08 (d, J=12.0 Hz, 1 H), 3.69 (s, 3 H), 3.54-3.64 (m, 1 H), 1.78-2.00 (m, 2 H), 1.27-1.76 (m, 4H).

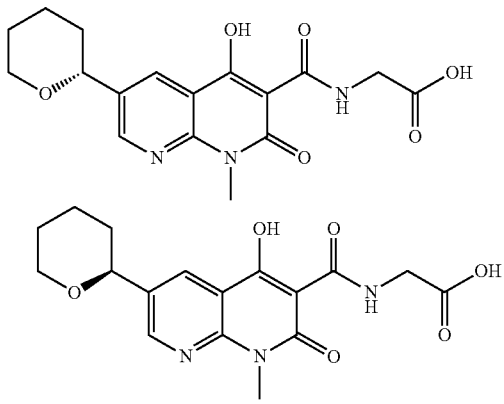

(c) (R)-2-(4-Hydroxy-1-methyl-2-oxo-6-(tetrahydro-2 H-pyran-2-yl)-1,2-dihydro-1,8-naphthyridine-3-carboxamido)acetic acid or (S)-2-(4-Hydroxy-1-methyl-2-oxo-6-(tetrahydro-2 H-pyran-2-yl)-1,2-dihydro-1,8-naphthyridine-3-carboxamido)acetic acid (Example 70). The title compound was prepared similarly to the procedure described for Example 1 (g) by treatment of the slower running enantiomer from step (a) ((R)-tert-butyl 2-(4-hydroxy-1-methyl-2-oxo-6-(tetrahydro-2 H-pyran-2-yl)-1,2-dihydro-1,8-naphthyridine-3-carboxamido)acetate or (S)-tert-butyl 2-(4-hydroxy-1-methyl-2-oxo-6-(tetrahydro-2H-pyran-2-yl)-1,2-dihydro-1,8-naphthyridine-3-carboxamido)acetate) with TFA. MS (ESI, pos. ion) m/z: 362 (M+1). $^1$H NMR (300 MHz, DMSO-$d_6$) δ ppm: 10.47 (t, J=5.3 Hz, 1 H), 8.79 (d, J=2.2 Hz, 1 H), 8.35 (d, J=2.2 Hz, 1 H), 4.55 (dd, J=11.3, 1.8 Hz, 1 H), 4.14 (d, J=5.6 Hz, 2 H), 4.08 (d, J=11.7 Hz, 1 H), 3.69 (s, 3 H), 3.53-3.65 (m, 1 H), 1.81-1.97 (m, 2 H), 1.43-1.71 (m, 4H).

Example 71

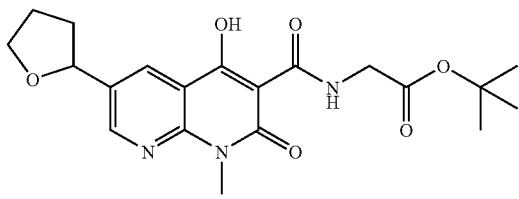

(a) tert-Butyl 2-(4-hydroxy-1-methyl-2-oxo-6-(tetrahydrofuran-2-yl)-1,2-dihydro-1,8-naphthyridine-3-carboxamido)acetate. A mixture of N,N-dicyclohexylmethylamine (0.5 mL, 2 mmol), 2,5-dihydrofuran (0.6 mL, 8 mmol), tris(dibenzylideneacetone)dipalladium(0) (0.183 g, 0.2 mmol), and tert-butyl 2-(4-hydroxy-6-iodo-1-methyl-2-oxo-1,2-dihydro-1,8-naphthyridine-3-carboxamido)acetate (0.700 g, 2 mmol, Example 26 (g)) in dioxane (20 mL) was flushed with argon and treated with tri-tert-butylphosphine (0.06 mL, 0.3 mmol). The reaction vessel was sealed and the mixture was heated at 120° C. for 18 hours. The reaction mixture was left to reach room temperature and filtered through a plug of Celite®. The filtrate was evaporated under reduced pressure, and the residue purified by silica gel column chromatography (gradient: 10-30% EtOAc/hexanes) to give an yellow oil. The oil was dissolved in EtOAc (20 mL) and was hydrogenated over palladium black (0.019 g) under 1 atmosphere hydrogen at room temperature for 16 hours. The reaction mixture was filtered through a plug of Celite®, and the filtrate was evaporated under reduced pressure, and dried in vacuo to give the title compound. MS (ESI, pos. ion) m/z: 404 (M+1).

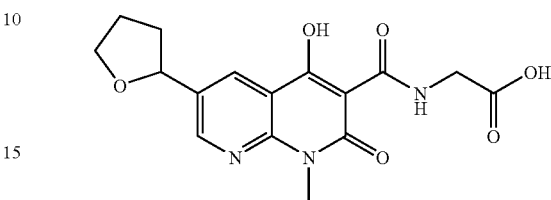

(b) 2-(4-Hydroxy-1-methyl-2-oxo-6-(tetrahydrofuran-2-yl)-1,2-dihydro-1,8-naphthyridine-3-carboxamido)acetic acid. The title compound was prepared similarly to the procedure described for Example 1 (g) by treatment of tert-butyl 2-(4-hydroxy-1-methyl-2-oxo-6-(tetrahydrofuran-2-yl)-1,2-dihydro-1,8-naphthyridine-3-carboxamido)acetate with TFA. MS (ESI, pos. ion) m/z: 348 (M+1). $^1$H NMR (300 MHz, DMSO-$d_6$) δ ppm: 10.48 (t, J=5.9 Hz, 1 H), 8.79 (d, J=2.2 Hz, 1 H), 8.34 (d, J=2.6 Hz, 1 H), 5.01 (t, J=7.3 Hz, 1 H), 4.14 (d, J=5.6 Hz, 2 H), 4.01-4.09 (m, 1 H), 3.80-3.90 (m, 1 H), 3.70 (s, 3 H), 2.32-2.44 (m, 1 H), 1.92-2.07 (m, 2 H), 1.68-1.82 (m, 1 H).

Example 72

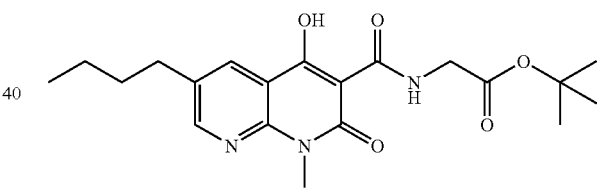

(a) tert-Butyl 2-(6-butyl-4-hydroxy-1-methyl-2-oxo-1,2-dihydro-1,8-naphthyridine-3-carboxamido)acetate. A mixture of tert-butyl 2-(4-hydroxy-6-iodo-1-methyl-2-oxo-1,2-dihydro-1,8-naphthyridine-3-carboxamido)acetate (0.500 g, 1.1 mmol, Example 26 (g)), palladium(II) acetate (0.049 g, 0.22 mmol), cesium fluoride (0.33 g, 2.2 mmol), copper(I) iodide (0.062 g, 0.33 mmol) and tri-tert-butylphosphine (0.088 g, 0.44 mmol) in DMF (5 mL) was flushed with argon and treated with tributyl(cyclopropyl)stannate (0.72 g, 2.2 mmol). The reaction vessel was sealed and the mixture was heated at 70° C. for 14 hours. The reaction mixture was left to reach room temperature, and was diluted with EtOAc (75 mL). The combined filtrate was evaporated under reduced pressure, and the residue was diluted with DCM (100 mL), and was filtered. The filtrate was washed with deionized water (3×50 mL) and brine (50 mL), dried over MgSO$_4$, and filtered. The filtrate was evaporated under reduced pressure, and the residue was purified by silica gel column chromatography (gradient: 25-50% Et$_2$O/hexanes) to give the title compound.

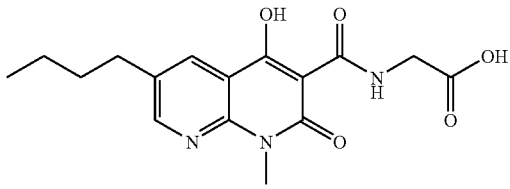

(b) 2-(6-Butyl-4-hydroxy-1-methyl-2-oxo-1,2-dihydro-1,8-naphthyridine-3-carboxamido)acetic acid. The title compound was prepared similarly to the procedure described for Example 1 (g) by treatment of tert-butyl 2-(6-(4-butylphenyl)-4-hydroxy-1-methyl-2-oxo-1,2-dihydro-1,8-naphthyridine-3-carboxamido)acetate with TFA. MS (ESI, pos. ion) m/z: 334 (M+1). $^1$H NMR (400 MHz, DMSO-d$_6$) δ ppm: 12.77-13.12 (m, 1 H), 10.50 (t, J=5.5, Hz, 1 H), 8.70 (d, J=2.0 Hz, 1 H), 8.25 (d, J=1.6 Hz, 1 H), 4.14 (d, J=5.5 Hz, 2 H), 3.68 (s, 3 H), 2.74 (t, J=7.6 Hz, 2 H), 1.55-1.66 (m, 2 H), 1.27-1.38 (m, 2 H), 0.91 (t, J=7.3 Hz, 3 H).

Example 73

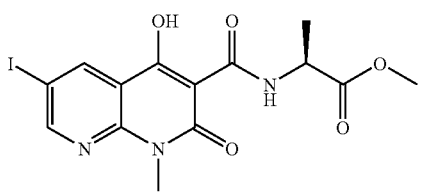

(a) (S)-Methyl 2-(4-hydroxy-6-iodo-1-methyl-2-oxo-1,2-dihydro-1,8-naphthyridine-3-carboxamido)propanoate. The title compound was prepared as a tan solid from methyl 4-hydroxy-6-iodo-1-methyl-2-oxo-1,2-dihydro-1,8-naphthyridine-3-carboxylate (Example 26 (f) and alanine methyl ester hydrochloride, similarly to the procedure described for Example 1 (f). MS (ESI, pos. ion) m/z: 432 (M+1).

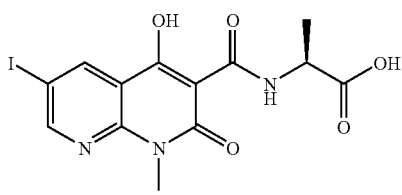

(b) (S)-2-(4-Hydroxy-6-iodo-1-methyl-2-oxo-1,2-dihydro-1,8-naphthyridine-3-carboxamido)propanoic acid. (S)-Methyl 2-(4-hydroxy-6-iodo-1-methyl-2-oxo-1,2-dihydro-1,8-naphthyridine-3-carboxamido)propanoate was stirred with a mixture of THF (10 mL) and 1N NaOH (10 mL) for 1 hour at room temperature. The organic solvent was removed under reduced pressure, and the aqueous residue was acidified with 1 N HCl. The solid precipitate was filtered, and the filter cake was washed with H$_2$O and Et$_2$O, and dried in vacuo to give the title compound. MS (ESI, pos. ion) m/z: 418 (M+1). $^1$H NMR (400 MHz, DMSO-d$_6$) δ ppm: 13.15 (s, 1 H), 10.58 (d, J=5.1 Hz, 1 H), 9.01 (s, 1 H), 8.65 (s, 1 H), 4.39-4.66 (m, 1 H), 3.64 (s, 3 H), 1.46 (d, J=7.0 Hz, 3 H).

Example 74

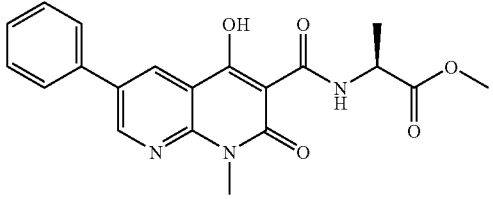

(a) (S)-Methyl 2-(4-hydroxy-1-methyl-2-oxo-6-phenyl-1,2-dihydro-1,8-naphthyridine-3-carboxamido)propanoate. The title compound was prepared from (S)-methyl 2-(4-hydroxy-6-iodo-1-methyl-2-oxo-1,2-dihydro-1,8-naphthyridine-3-carboxamido)propanoate (Example 73 (a) and phenylboronic acid, similarly to the procedure described for Example 2 (a).

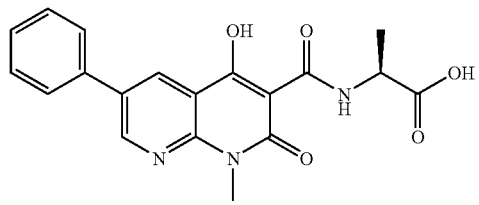

(b) (S)-2-(4-Hydroxy-1-methyl-2-oxo-6-phenyl-1,2-dihydro-1,8-naphthyridine-3-carboxamido)propanoic acid. The title compound was prepared by hydrolysis of (S)-methyl 2-(4-hydroxy-1-methyl-2-oxo-6-phenyl-1,2-dihydro-1,8-naphthyridine-3-carboxamido)propanoate, similarly to the procedure described for Example 73 (b). MS (ESI, pos. ion) m/z: 368 (M+1). $^1$H NMR (400 MHz, DMSO-d$_6$) δ ppm: 10.65 (d, J=6.7 Hz, 1 H), 9.17 (d, J=2.2 Hz, 1 H), 8.60 (d, J=2.0 Hz, 1 H), 7.83 (d, J=7.5 Hz, 2 H), 7.13-7.72 (m, 3 H), 4.31-4.72 (m, 1 H), 3.74 (s, 3 H), 1.48 (d, J=7.2 Hz, 3 H).

Example 75

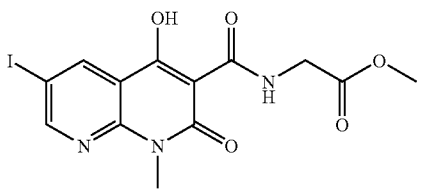

(a) Methyl 2-(4-hydroxy-6-iodo-1-methyl-2-oxo-1,2-dihydro-1,8-naphthyridine-3-carboxamido)acetate. The title compound was prepared from methyl 4-hydroxy-6-iodo-1- methyl-2-oxo-1,2-dihydro-1,8-naphthyridine-3-carboxylate (Example 26 (f)) and glycine methyl ester hydrochloride, similarly to the procedure described for Example 1 (f).

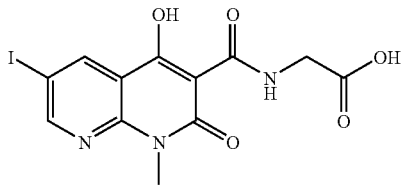

(b) 2-(4-Hydroxy-6-iodo-1-methyl-2-oxo-1,2-dihydro-1,8-naphthyridine-3-carboxamido)acetic acid. The title compound was prepared by hydrolysis of methyl 2-(4-hydroxy-6-iodo-1-methyl-2-oxo-1,2-dihydro-1,8-naphthyridine-3-carboxamido)acetate, similarly to the procedure described for Example 73 (b). MS (ESI, pos. ion) m/z: 404 (M+1). $^1$H NMR (300 MHz, DMSO-$d_6$) δ ppm: 10.41 (t, J=4.9 Hz, 1 H), 9.01 (d, J=2.2 Hz, 1 H), 8.66 (d, J=2.3 Hz, 1 H), 4.14 (d, J=5.4 Hz, 2 H), 3.65 (s, 3 H).

Example 76

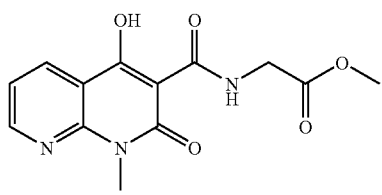

(a) Methyl 2-(4-hydroxy-1-methyl-2-oxo-1,2-dihydro-1,8-naphthyridine-3-carboxamido)acetate. The title compound was prepared by hydrogenation of methyl 2-(4-hydroxy-6-iodo-1-methyl-2-oxo-1,2-dihydro-1,8-naphthyridine-3-carboxamido)acetate (Example 75 (a)), similarly to the procedure described for Example 5 (a).

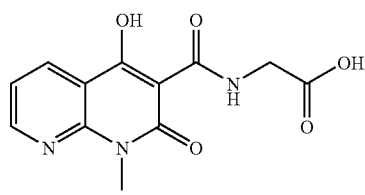

(b) 2-(4-Hydroxy-1-methyl-2-oxo-1,2-dihydro-1,8-naphthyridine-3-carboxamido)acetic acid. The title compound was prepared by hydrolysis of methyl 2-(4-hydroxy-1-methyl-2-oxo-1,2-dihydro-1,8-naphthyridine-3-carboxamido)acetate, similarly to the procedure described for Example 73 (b). MS (ESI, pos. ion) m/z: 278 (M+1). $^1$H NMR (300 MHz, DMSO-$d_6$) δ ppm: 10.46 (t, J=4.9 Hz, 1 H), 8.83 (dd, J=4.6, 1.8 Hz, 1 H), 8.47 (dd, J=7.9, 1.8 Hz, 1 H), 7.30-7.55 (m, 1 H), 4.15 (d, J=5.6 Hz, 2 H), 3.70 (s, 3H).

Example 77

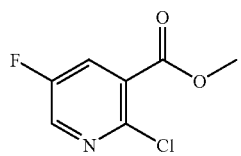

(a) Methyl 2-chloro-5-fluoronicotinate. To a mixture of 2-chloro-5-fluoronicotinic acid (6.66 g, 37.9 mmol) and K$_2$CO$_3$ (15.7 g, 114 mmol) in acetone (125 mL) was added iodomethane (2.60 mL, 41.7 mmol) dropwise with stirring at room temperature under nitrogen atmosphere. The reaction mixture was stirred at 35° C. for 18 hours and was filtered over a plug of Celite®. The filtrate was evaporated under reduced pressure to give the title compound. MS (ESI, pos. ion) m/z: 190 (M+1).

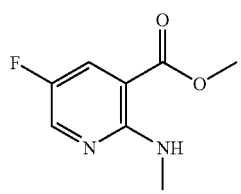

(b) Methyl 5-fluoro-2-(methylamino)nicotinate. A mixture of methyl 2-chloro-5-fluoronicotinate (3.82 g, 20 mmol) and K$_2$CO$_3$ (5.6 g, 40 mmol) in THF (25 mL) was stirred under nitrogen for 15 minutes. To the mixture was added a 2 M solution of methylamine in THF (10 mL, 20 mmol), and stirring was continued for 63 hours. The reaction mixture was filtered over Celite®, and the filtrate was evaporated under reduced pressure. The residue was purified by silica gel column chromatography (DCM) to give the title compound as an orange oil. MS (ESI, pos. ion) m/z: 185 (M+1).

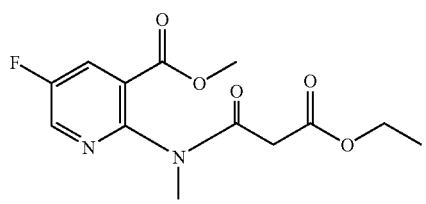

(c) Methyl 2-(3-ethoxy-N-methyl-3-oxopropanamido)-5-fluoronicotinate. A mixture of methyl 5-fluoro-2-(methylamino)nicotinate (0.300 g, 1.6 mmol) and ethyl malonoyl chloride (0.19 mL, 1.6 mmol) in 1,2-dichloroethane (50 mL) was heated to 80° C. for 63 hours. The reaction mixture was left to reach room temperature and was evaporated under reduced pressure. The residue was purified by silica gel column chromatography (gradient: 0-30% EtOAc/hexanes) to give the title compound. MS (ESI, pos. ion) m/z: 299 (M+1).

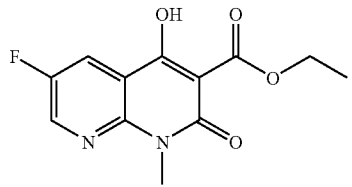

(d) Ethyl 6-fluoro-4-hydroxy-1-methyl-2-oxo-1,2-dihydro-1,8-naphthyridine-3-carboxylate. To a solution of methyl 2-(3-ethoxy-N-methyl-3-oxopropanamido)-5-fluoronicotinate (1.374 g, 4.6 mmol) in EtOH (25 mL) was added a 20% solution of EtONa in EtOH (3.2 mL, 9.2 mmol) dropwise with stirring at room temperature. The reaction mixture was stirred for 15 minutes, and the white solid which precipitated was filtered. The filter cake was separated and dried in vacuo to give the title compound. MS (ESI, pos. ion) m/z: 267 (M+1).

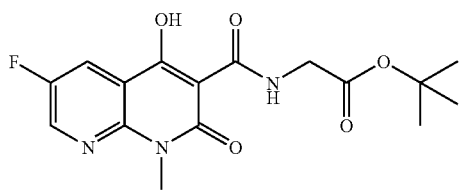

(e) tert-Butyl 2-(6-fluoro-4-hydroxy-1-methyl-2-oxo-1,2-dihydro-1,8-naphthyridine-3-carboxamido)acetate. The title compound was prepared from ethyl 6-fluoro-4-hydroxy-1-methyl-2-oxo-1,2-dihydro-1,8-naphthyridine-3-carboxylate and tert-butyl 2-aminoacetate hydrochloride analogously to the conditions described in Example 1 (f). MS (ESI, pos. ion) m/z: 351 (M+1).

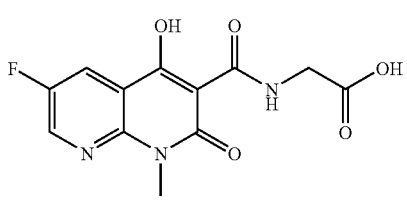

(f) 2-(6-Fluoro-4-hydroxy-1-methyl-2-oxo-1,2-dihydro-1,8-naphthyridine-3-carboxamido)acetic acid. The title compound was prepared similarly to the procedure described for Example 1 (g) by treatment of tert-butyl 2-(6-fluoro-4-hydroxy-1-methyl-2-oxo-1,2-dihydro-1,8-naphthyridine-3-carboxamido)acetate with TFA. MS (ESI, pos. ion) m/z: 296 (M+1). $^1$H NMR (400 MHz, DMSO-d$_6$) δ ppm: 10.46 (t, J=5.1 Hz, 1 H), 8.89 (d, J=2.9 Hz, 1 H), 8.31 (dd, J=8.1, 3.0 Hz, 1 H), 4.15 (d, J=5.6 Hz, 2 H), 3.68 (s, 3 H).

Example 78

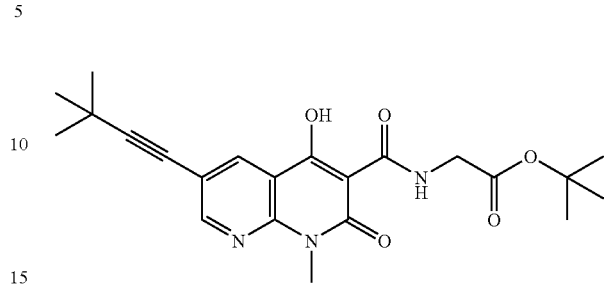

(a) tert-Butyl 2-(6-(3,3-dimethylbut-1-ynyl)-4-hydroxy-1-methyl-2-oxo-1,2-dihydro-1,8-naphthyridine-3-carboxamido)acetate. A pressure vial was charged with tert-butyl 2-(4-hydroxy-6-iodo-1-methyl-2-oxo-1,2-dihydro-1,8-naphthyridine-3-carboxamido)acetate (250 mg, 544 μmol, Example 26 (g)), Pd (PPh$_3$)$_2$Cl$_2$ (38.2 mg, 54.4 μmol), copper (I) iodide (20.7 mg, 109 μmol), THF (2.7 mL), N-ethyl-N-isopropylpropan-2-amine (0.284 mL, 1.633 mmol) and tert-butylacetylene (0.134 mL, 1.09 mmol) under nitrogen. The vial was sealed and heated to 110° C. for 1 hour. The reaction mixture was left to reach room temperature, diluted with EtOAc (100 mL), washed with saturated aqueous NaHCO$_3$ (3×50 mL), dried over Na$_2$SO$_4$, and filtered. The filtrate was evaporated under reduced pressure, and the solid residue was washed with Et$_2$O and dried in vacuo to give the title compound. MS (ESI, pos. ion) m/z: 414 (M+1).

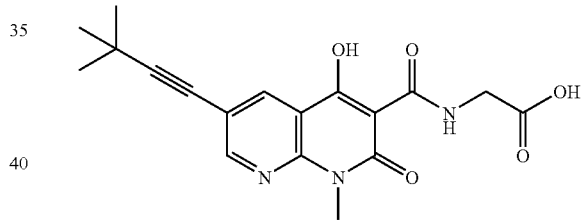

(b) N-((6-(3,3-Dimethyl-1-butyn-1-yl)-4-hydroxy-1-methyl-2-oxo-1,2-dihydro-1,8-naphthyridin-3-yl)carbonyl)glycine. The title compound was prepared similarly to the procedure described for Example 1 (g) by treatment of tert-butyl 2-(6-(3,3-dimethylbut-1-ynyl)-4-hydroxy-1-methyl-2-oxo-1,2-dihydro-1,8-naphthyridine-3-carboxamido)acetate with TFA. MS (ESI, pos. ion) m/z: 358 (M+1). $^1$H NMR (400 MHz, DMSO-d$_6$) δ ppm: 10.40 (m, 1 H), 8.69-8.86 (m, 1 H), 8.19-8.40 (m, 1 H), 4.15 (m, 2 H), 3.68 (s, 3 H), 1.33 (s, 9 H).

Example 79

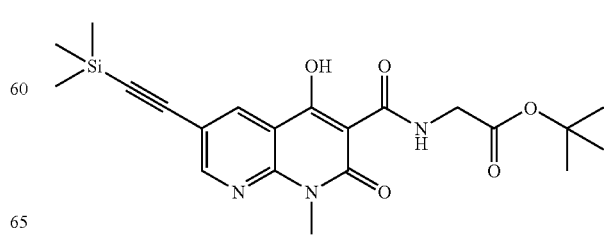

(a) tert-Butyl 2-(4-hydroxy-1-methyl-2-oxo-6-(2-(trimethylsilyl)ethynyl)-1,2-dihydro-1,8-naphthyridine-3-carboxamido)acetate. The title compound was prepared similarly to the procedure described for Example 78 (a) from tert-butyl 2-(4-hydroxy-6-iodo-1-methyl-2-oxo-1,2-dihydro-1,8-naphthyridine-3-carboxamido)acetate (Example 26 (g)) and (trimethylsilyl)acetylene. MS (ESI, pos. ion) m/z: 430 (M+1).

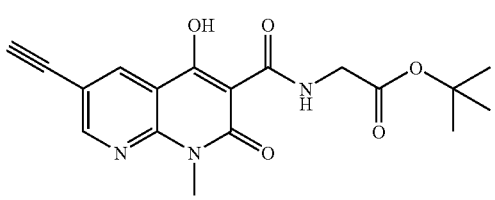

(b) tert-Butyl 2-(6-ethynyl-4-hydroxy-1-methyl-2-oxo-1,2-dihydro-1,8-naphthyridine-3-carboxamido)acetate. A mixture of tert-butyl 2-(4-hydroxy-1-methyl-2-oxo-6-(2-(trimethylsilyl)ethynyl)-1,2-dihydro-1,8-naphthyridine-3-carboxamido)acetate (0.450 g, 1.0 mmol), cesium fluoride (0.039 g, 1.0 mmol), DMF (0.25 mL, 3.2 mmol) and MeOH (10 mL) was stirred at room temperature under $N_2$ for 6 hours. The reaction mixture was evaporated under reduced pressure, and the residue was diluted with EtOAc (50 mL), washed with water (3×25 mL) and brine (25 mL), dried over $MgSO_4$, and filtered. The filtrate was evaporated under reduced pressure, and the residue dried in vacuo to give the title compound. MS (ESI, pos. ion) m/z: 358 (M+1).

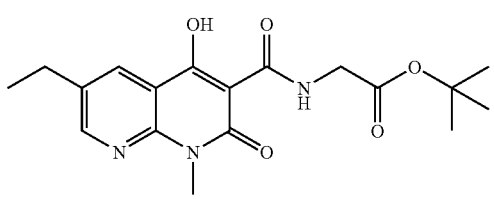

(c) tert-Butyl 2-(6-ethyl-4-hydroxy-1-methyl-2-oxo-1,2-dihydro-1,8-naphthyridine-3-carboxamido)acetate. The title compound was prepared similarly to the procedure described for Example 5(a) by hydrogenation of tert-butyl 2-(6-ethynyl-4-hydroxy-1-methyl-2-oxo-1,2-dihydro-1,8-naphthyridine-3-carboxamido)acetate. MS (ESI, pos. ion) m/z: 362 (M+1).

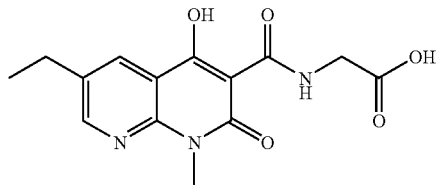

(d) 2-(6-Ethyl-4-hydroxy-1-methyl-2-oxo-1,2-dihydro-1,8-naphthyridine-3-carboxamido)acetic acid. The title compound was prepared similarly to the procedure described for Example 1 (g) by treatment of tert-butyl 2-(6-ethyl-4-hydroxy-1-methyl-2-oxo-1,2-dihydro-1,8-naphthyridine-3-carboxamido)acetate with TFA. MS (ESI, pos. ion) m/z: 306 (M+1). $^1$H NMR (300 MHz, DMSO-$d_6$) δ ppm: 10.50 (t, J=5.6 Hz, 1 H), 8.73 (d, J=2.3 Hz, 1 H), 8.29 (d, J=2.2 Hz, 1 H), 4.14 (d, J=5.7 Hz, 2 H), 3.69 (s, 3 H), 2.77 (q, J=7.5 Hz, 2 H), 1.25 (t, J=7.6 Hz, 3 H).

Example 80

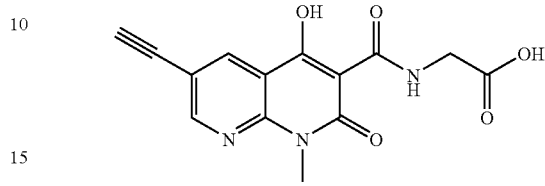

2-(6-Ethynyl-4-hydroxy-1-methyl-2-oxo-1,2-dihydro-1,8-naphthyridine-3-carboxamido)acetic acid. The title compound was prepared similarly to the procedure described for Example 1 (g) by treatment of tert-butyl 2-(6-ethynyl-4-hydroxy-1-methyl-2-oxo-1,2-dihydro-1,8-naphthyridine-3-carboxamido)acetate (Example 79 (b)) with TFA. MS (ESI, pos. ion) m/z: 302 (M+1). $^1$H NMR (300 MHz, DMSO-$d_6$) δ ppm: 10.39 (t, J=5.3 Hz, 1 H), 8.91 (d, J=2.2 Hz, 1 H), 8.44 (d, J=2.3 Hz, 1 H), 4.51 (s, 1 H), 4.15 (d, J=5.7 Hz, 2 H), 3.68 (s, 3 H).

Example 81

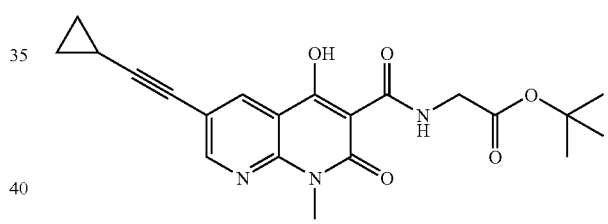

(a) tert-Butyl 2-(6-(2-cyclopropylethynyl)-4-hydroxy-1-methyl-2-oxo-1,2-dihydro-1,8-naphthyridine-3-carboxamido)acetate. The title compound was prepared from tert-butyl 2-(4-hydroxy-6-iodo-1-methyl-2-oxo-1,2-dihydro-1,8-naphthyridine-3-carboxamido)acetate (Example 26 (g)) and ethynylcyclopropane analogously to the procedure described for the preparation of Example 78 (a). MS (ESI, pos. ion) m/z: 398 (M+1).

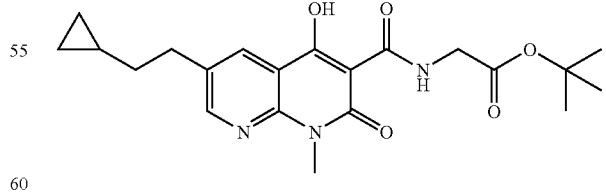

(b) tert-Butyl 2-(6-(2-cyclopropylethyl)-4-hydroxy-1-methyl-2-oxo-1,2-dihydro-1,8-naphthyridine-3-carboxamido)acetate. The title compound was prepared similarly to the procedure described for Example 5(a) by hydrogenation of tert-butyl 2-(6-(2-cyclopropylethynyl)-4-hydroxy-1-methyl--thyl--

2-oxo-1,2-dihydro-1,8-naphthyridine-3-carboxamido)ac-etate. MS (ESI, pos. ion) m/z: 402 (M+1).

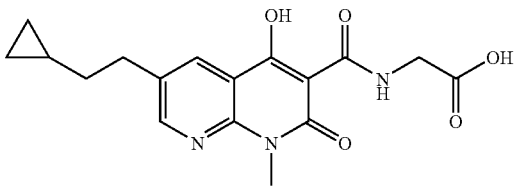

(c) 2-(6-(2-Cyclopropylethyl)-4-hydroxy-1-methyl-2-oxo-1,2-dihydro-1,8-naphthyridine-3-carboxamido)acetic acid. The title compound was prepared similarly to the procedure described for Example 1 (g) by treatment of tert-butyl 2-(6-(2-cyclopropylethyl)-4-hydroxy-1-methyl-2-oxo-1,2-dihydro-1,8-naphthyridine-3-carboxamido)acetate with TFA. MS (ESI, pos. ion) m/z: 346 (M+1). $^1$H NMR (300 MHz, DMSO-$d_6$) δ ppm: 10.50 (t, J=5.6 Hz, 1 H), 8.72 (d, J=2.2 Hz, 1 H), 8.28 (d, J=2.2 Hz, 1 H), 4.14 (d, J=5.6 Hz, 2 H), 3.68 (s, 3 H), 2.82 (t, 2 H), 1.40-1.63 (m, 2 H), 0.57-0.80 (m, 1 H), 0.29-0.44 (m, 2 H), 0.02-0.09 (m, 2 H).

Example 82

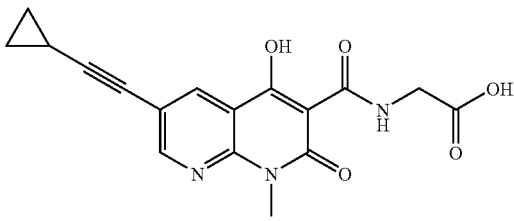

2-(6-(2-Cyclopropylethynyl)-4-hydroxy-1-methyl-2-oxo-1,2-dihydro-1,8-naphthyridine-3-carboxamido)acetic acid. The title compound was prepared similarly to the procedure described for Example 1 (g) by treatment of tert-butyl 2-(6-(2-cyclopropylethynyl)-4-hydroxy-1-methyl-2-oxo-1,2-dihydro-1,8-naphthyridine-3-carboxamido)acetate (Example 81 (a)) with TFA. MS (ESI, pos. ion) m/z: 342 (M+1). $^1$H NMR (300 MHz, DMSO-$d_6$) δ ppm: 10.40 (t, J=5.6 Hz, 1 H), 8.80 (d, J=2.2 Hz, 1 H), 8.31 (d, J=2.2 Hz, 1 H), 4.14 (d, J=5.6 Hz, 2 H), 3.67 (s, 3 H), 1.53-1.67 (m, 1 H), 0.86-0.99 (m, 2 H), 0.74-0.87 (m, 2 H).

Example 83

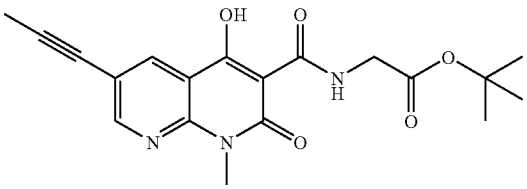

(a) tert-Butyl 2-(4-hydroxy-1-methyl-2-oxo-6-(prop-1-ynyl)-1,2-dihydro-1,8-naphthyridine-3-carboxamido)acetate. The title compound was prepared from tert-butyl 2-(4-hydroxy-6-iodo-1-methyl-2-oxo-1,2-dihydro-1,8-naphthyridine-3-carboxamido)acetate (Example 26 (g)) and prop-1-yne analogously to the procedure described for the preparation of Example 78 (a).

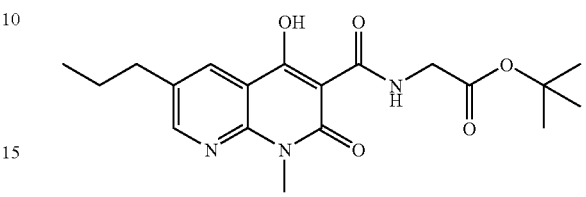

(b) tert-Butyl 2-(4-hydroxy-1-methyl-2-oxo-6-propyl-1,2-dihydro-1,8-naphthyridine-3-carboxamido)acetate. The title compound was prepared similarly to the procedure described for Example 5 (a) by hydrogenation of tert-butyl 2-(4-hydroxy-1-methyl-2-oxo-6-(prop-1-ynyl)-1,2-dihydro-1,8-naphthyridine-3-carboxamido)acetate.

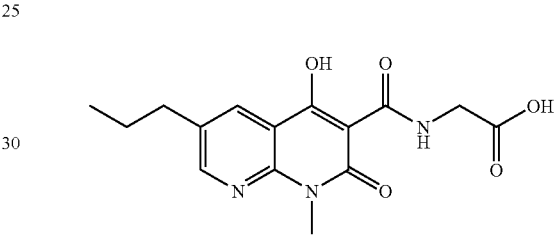

(c) 2-(4-Hydroxy-1-methyl-2-oxo-6-propyl-1,2-dihydro-1,8-naphthyridine-3-carboxamido)acetic acid. The title compound was prepared similarly to the procedure described for Example 1 (g) by treatment of tert-butyl 2-(4-hydroxy-1-methyl-2-oxo-6-propyl-1,2-dihydro-1,8-naphthyridine-3-carboxamido)acetate with TFA. MS (ESI, pos. ion) m/z: 320 (M+1). $^1$H NMR (300 MHz, DMSO-$d_6$) δ ppm: 10.50 (t, J=5.6 Hz, 1 H), 8.71 (d, J=2.3 Hz, 1 H), 8.27 (d, J=2.3 Hz, 1 H), 4.14 (d, J=5.6 Hz, 2 H), 3.69 (s, 3 H), 2.67-2.78 (m, 2 H), 1.56-1.77 (m, 2 H), 0.91 (t, J=7.3 Hz, 3 H).

Example 84

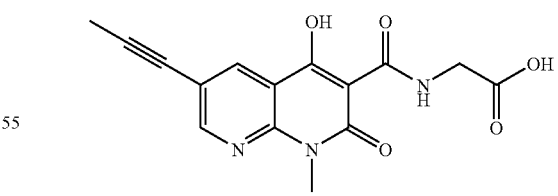

2-(4-Hydroxy-1-methyl-2-oxo-6-(prop-1-ynyl)-1,2-dihydro-1,8-naphthyridine-3-carboxamido)acetic acid. The title compound was prepared similarly to the procedure described for Example 1 (g) by treatment of tert-butyl 2-(4-hydroxy-1-methyl-2-oxo-6-(prop-1-ynyl)-1,2-dihydro-1,8-naphthyridine-3-carboxamido)acetate (Example 83 (a)) with TFA. MS (ESI, pos. ion) m/z: 315 (M+1). $^1$H NMR (300 MHz, DMSO-$d_6$) δ ppm: 12.98 (s, 1 H), 10.41 (t, J=5.4 Hz, 1 H), 8.83 (d, J=2.2 Hz, 1 H), 8.34 (d, J=2.0 Hz, 1 H), 4.14 (d, J=5.6 Hz, 2 H), 3.67 (s, 3 H), 2.12 (s, 3 H).

Example 85

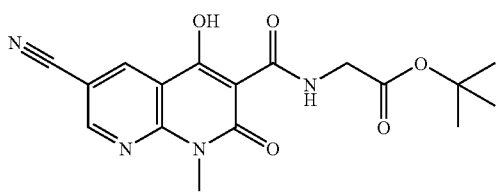

(a) tert-Butyl 2-(6-cyano-4-hydroxy-1-methyl-2-oxo-1,2-dihydro-1,8-naphthyridine-3-carboxamido)acetate. To a mixture of tert-butyl 2-(4-hydroxy-6-iodo-1-methyl-2-oxo-1,2-dihydro-1,8-naphthyridine-3-carboxamido)acetate (250 mg, 0.544 mmol, Example 26 (g)) and zinc cyanide (95.9 mg, 817 μmol) in DMF (2.7 mL) was added Pd$_2$(dba)$_3$ chloroform adduct (28.2 mg, 0.027 mmol) and dppf (15.1 mg, 0.027 mmol) under nitrogen atmosphere. The reaction mixture was heated at 110° C. for 2 hours and left to reach room temperature. The mixture was diluted with EtOAc (100 mL), washed with saturated aqueous NaHCO$_3$ (3×50 mL), dried over Na$_2$SO$_4$, and filtered. The filtrate was evaporated under reduced pressure and the residue purified by preparative HPLC (gradient: 0% MeCN/water+0.1% TFA-90% MeCN/water+1% TFA) to give the title compound. MS (ESI, pos. ion) m/z: 356 (M−1).

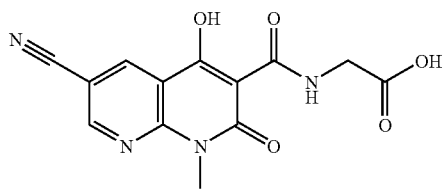

(b) N-((6-Cyano-4-hydroxy-1-methyl-2-oxo-1,2-dihydro-1,8-naphthyridin-3-yl)carbonyl)glycine. The title compound was prepared similarly to the procedure described for Example 1 (g) by treatment of tert-butyl 2-(6-cyano-4-hydroxy-1-methyl-2-oxo-1,2-dihydro-1,8-naphthyridine-3-carboxamido)acetate with TFA. MS (ESI, pos. ion) m/z: 303 (M+1). $^1$H NMR (400 MHz, DMSO-d$_6$) δ ppm: 10.30 (m, 1 H), 9.22 (d, J=2.2 Hz, 1 H), 8.92 (d, J=2.2 Hz, 1 H), 4.16 (d, J=5.5 Hz, 2 H), 3.69 (s, 3 H).

Example 86

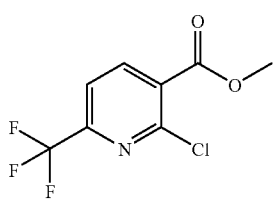

(a) Methyl 2-chloro-6-(trifluoromethyl)nicotinate. The title compound was prepared similarly to the procedure described for Example 77 (a) by treatment of 2-chloro-6-(trifluoromethyl)nicotinic acid with iodomethane. MS (ESI, pos. ion) m/z: 240 (M+1).

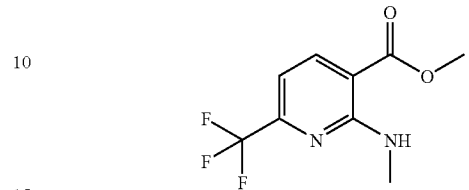

(b) Methyl 2-(methylamino)-6-(trifluoromethyl)nicotinate. The title compound was prepared similarly to the procedure described for Example 77 (b) by treatment of methyl 2-chloro-6-(trifluoromethyl)nicotinate with methylamine. MS (ESI, pos. ion) m/z: 235 (M+1).

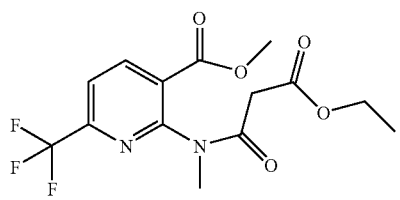

(c) Methyl 2-(3-ethoxy-N-methyl-3-oxopropanamido)-6-(trifluoromethyl)nicotinate. The title compound was prepared similarly to the procedure described for Example 77 (c) by treatment of methyl 2-(methylamino)-6-(trifluoromethyl)nicotinate with ethyl 3-chloro-3-oxopropanoate. MS (ESI, pos. ion) m/z: 349 (M+1).

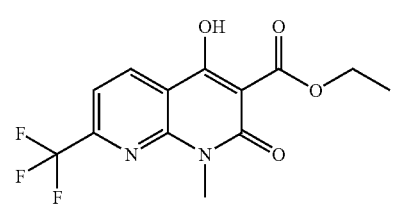

(d) Ethyl 4-hydroxy-1-methyl-2-oxo-7-(trifluoromethyl)-1,2-dihydro-1,8-naphthyridine-3-carboxylate. The title compound was prepared similarly to the procedure described for Example 77 (d) by treatment of methyl 2-(3-ethoxy-N-methyl-3-oxopropanamido)-6-(trifluoromethyl)nicotinate with NaOEt. MS (ESI, pos. ion) m/z: 317 (M+1).

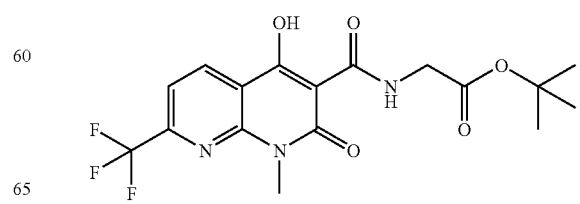

(e) tert-Butyl 2-(4-hydroxy-1-methyl-2-oxo-7-(trifluoromethyl)-1,2-dihydro-1,8-naphthyridine-3-carboxamido)acetate. The title compound was prepared from ethyl 4-hydroxy-1-methyl-2-oxo-7-(trifluoromethyl)-1,2-dihydro-1,8-naphthyridine-3-carboxylate and tert-butyl 2-aminoacetate hydrochloride analogously to the conditions described in Example 1 (f). MS (ESI, pos. ion) m/z: 346 (-tert-Bu) (M+1).

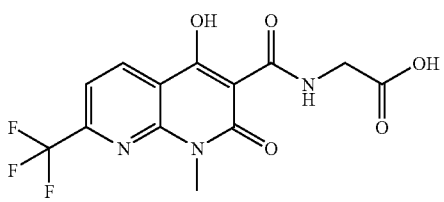

(f) 2-(4-Hydroxy-1-methyl-2-oxo-7-(trifluoromethyl)-1,2-dihydro-1,8-naphthyridine-3-carboxamido)acetic acid. The title compound was prepared similarly to the procedure described for Example 1 (g) by treatment of tert-butyl 2-(4-hydroxy-1-methyl-2-oxo-7-(trifluoromethyl)-1,2-dihydro-1,8-naphthyridine-3-carboxamido)acetate with TFA. MS (ESI, pos. ion) m/z: 346 (M+1). $^1$H NMR (400 MHz, DMSO-$d_6$) δ ppm: 12.99 (s, 1 H), 10.37 (s, 1 H), 8.71 (d, J=8.0 Hz, 1 H), 7.86 (d, J=8.0 Hz, 1 H), 4.16 (d, J=5.7 Hz, 2 H), 3.67 (s, 3 H).

Example 87

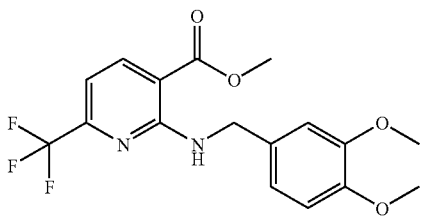

(a) Methyl 2-(3,4-dimethoxybenzylamino)-6-(trifluoromethyl)nicotinate. A mixture of methyl 2-chloro-6-(trifluoromethyl)nicotinate (0.122 g, 0.509 mmol, Example 86 (a)), $K_2CO_3$ (0.070 g, 0.509 mmol) and 3,4-dimethoxybenzylamine (0.077 mL, 0.509 mmol) in THF (10 mL) was stirred at room temperature for 24 hours. The reaction mixture was diluted with EtOAc (50 mL), washed with brine, dried over anhydrous $MgSO_4$, and filtered. The filtrate was evaporated under reduced pressure, and the residue was purified by silica gel column chromatography (10% EtOAc/hexanes) to give the title compound. MS (ESI, pos. ion) m/z: 371 (M+1).

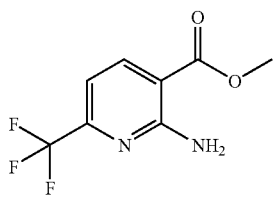

(b) Methyl 2-amino-6-(trifluoromethyl)nicotinate. The title compound was prepared similarly to the procedure described for Example 1 (g) by treatment of methyl 2-(3,4-dimethoxybenzylamino)-6-(trifluoromethyl)nicotinate with TFA. MS (ESI, pos. ion) m/z: 221 (M+1).

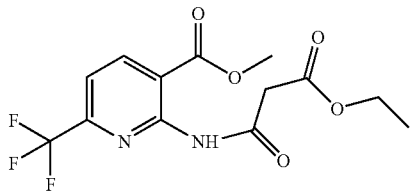

(c) Methyl 2-(3-ethoxy-3-oxopropanamido)-6-(trifluoromethyl)nicotinate. The title compound was prepared similarly to the procedure described for Example 77 (c) by treatment of methyl 2-amino-6-(trifluoromethyl)nicotinate with ethyl malonoyl chloride. MS (ESI, pos. ion) m/z: 335 (M+1).

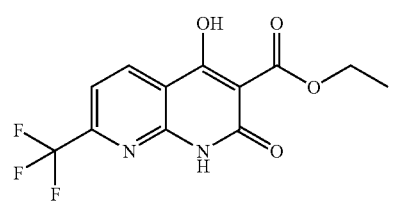

(d) Ethyl 4-hydroxy-2-oxo-7-(trifluoromethyl)-1,2-dihydro-1,8-naphthyridine-3-carboxylate. The title compound was prepared similarly to the procedure described for Example 77 (d) by treatment of methyl 2-(3-ethoxy-3-oxopropanamido)-6-(trifluoromethyl)nicotinate with EtONa. MS (ESI, pos. ion) m/z: 303 (M+1).

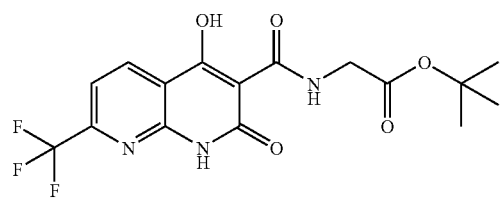

(e) tert-Butyl 2-(4-hydroxy-2-oxo-7-(trifluoromethyl)-1,2-dihydro-1,8-naphthyridine-3-carboxamido)acetate. The title compound was prepared from ethyl 4-hydroxy-2-oxo-7-(trifluoromethyl)-1,2-dihydro-1,8-naphthyridine-3-carboxylate and tert-butyl 2-aminoacetate hydrochloride analogously to the conditions described in Example 1 (f). MS (ESI, pos. ion) m/z: 388 (M+1).

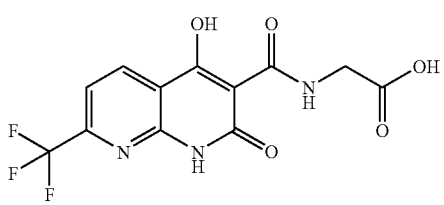

(f) 2-(4-Hydroxy-2-oxo-7-(trifluoromethyl)-1,2-dihydro-1,8-naphthyridine-3-carboxamido)acetic acid. The title compound was prepared similarly to the procedure described for Example 1 (g) by treatment of tert-butyl 2-(4-hydroxy-2-oxo- 7-(trifluoromethyl)-1,2-dihydro-1,8-naphthyridine-3-carboxamido)acetate with TFA. MS (ESI, pos. ion) m/z: 354 (M+1). ¹H NMR (300 MHz, DMSO-d₆) δ ppm: 2.67 (s, 1 H), 10.31 (t, J=5.3 Hz, 1 H), 8.63 (d, J=7.7 Hz, 1 H), 7.79 (d, J=8.2 Hz, 1 H), 4.15 (d, J=5.7 Hz, 2 H).

Example 88

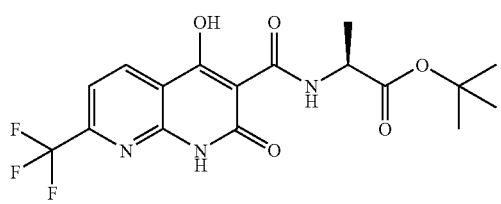

(a) (S)-tert-Butyl 2-(4-hydroxy-2-oxo-7-(trifluoromethyl)-1,2-dihydro-1,8-naphthyridine-3-carboxamido)propanoate. The title compound was prepared from ethyl 4-hydroxy-2-oxo-7-(trifluoromethyl)-1,2-dihydro-1,8-naphthyridine-3-carboxylate (Example 87 (d)) and alanine methyl ester hydrochloride, similarly to the procedure described for Example 1 (f).

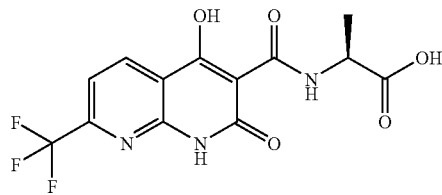

(b) (S)-2-(4-Hydroxy-2-oxo-7-(trifluoromethyl)-1,2-dihydro-1,8-naphthyridine-3-carboxamido)propanoic acid. The title compound was prepared similarly to the procedure described for Example 1 (g) by treatment of (s)-tert-butyl 2-(4-hydroxy-2-oxo-7-(trifluoromethyl)-1,2-dihydro-1,8-naphthyridine-3-carboxamido)propanoate with TFA. MS (ESI, pos. ion) m/z: 346 (M+1). ¹H NMR (300 MHz, DMSO-d₆) δ ppm: 13.17 (s, 1 H), 12.72 (s, 1 H), 10.48 (d, J=7.5 Hz, 1 H), 8.63 (d, J=8.2 Hz, 1 H), 7.79 (d, J=8.0 Hz, 1 H), 4.37-4.75 (m, 1 H), 1.46 (d, J=7.2 Hz, 3 H).

Example 89

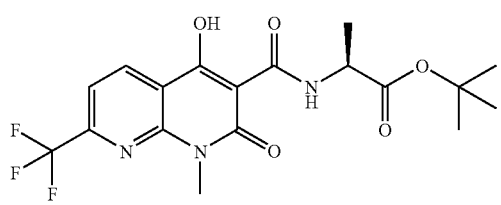

(a) (S)-tert-Butyl 2-(4-hydroxy-1-methyl-2-oxo-7-(trifluoromethyl)-1,2-dihydro-1,8-naphthyridine-3-carboxamido)propanoate. The title compound was prepared from ethyl 4-hydroxy-1-methyl-2-oxo-7-(trifluoromethyl)-1,2-dihydro-1,8-naphthyridine-3-carboxylate (Example 86 (d)) and alanine methyl ester hydrochloride, similarly to the procedure described for Example 1 (f).

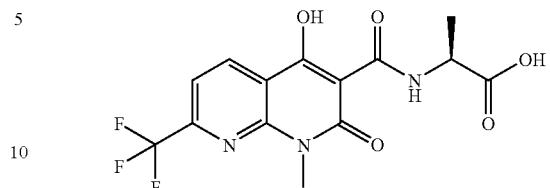

(b) (S)-2-(4-Hydroxy-1-methyl-2-oxo-7-(trifluoromethyl)-1,2-dihydro-1,8-naphthyridine-3-carboxamido)propanoic acid. The title compound was prepared similarly to the procedure described for Example 1 (g) by treatment of (S)-tert-butyl 2-(4-hydroxy-1-methyl-2-oxo-7-(trifluoromethyl)-1,2-dihydro-1,8-naphthyridine-3-carboxamido)propanoate with TFA. MS (ESI, pos. ion) m/z: 360 (M+1). ¹H NMR (300 MHz, DMSO-d₆) δ ppm: 10.54 (d, J=6.7 Hz, 1 H), 8.72 (d, J=7.9 Hz, 1 H), 7.87 (d, J=8.0 Hz, 1 H), 4.46-4.63 (m, 1 H), 3.67 (s, 3 H), 1.47 (d, J=7.2 Hz, 3 H).

Example 90

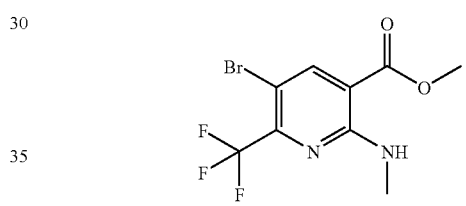

(a) Methyl 5-bromo-2-(methylamino)-6-(trifluoromethyl)nicotinate. To a solution of methyl 2-(methylamino)-6-(trifluoromethyl)nicotinate (1.5 g, 6 mmol, Example 86 (b)) in acetic acid (5 mL, 87 mmol) was added dropwise a solution of bromine (0.7 mL, 13 mmol) in acetic acid (5 mL, 87 mmol) with stirring at room temperature. After the addition, the reaction mixture was stirred for 10 minutes and concentrated under reduced pressure (bath temp 50° C. and pressure 30 Torr). The residue was azeotroped to dryness with toluene (1×) and MeOH (2×) and dried in vacuo to give the title compound as a yellow solid. MS (ESI, pos. ion) m/z: 314 (M+1).

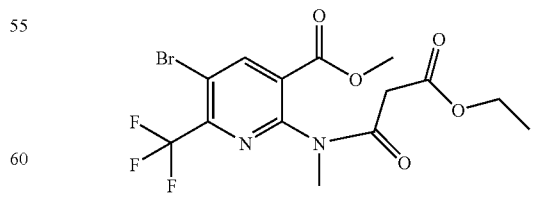

(b) Methyl 5-bromo-2-(3-ethoxy-N-methyl-3-oxopropanamido)-6-(trifluoromethyl)nicotinate. The title compound was prepared similarly to the procedure described for Example 77 (c) by treatment of methyl 5-bromo-2-(methy lamino)-6-(trifluoromethyl)nicotinate with ethyl malonoyl chloride. MS (ESI, pos. ion) m/z: 428 (M+1).

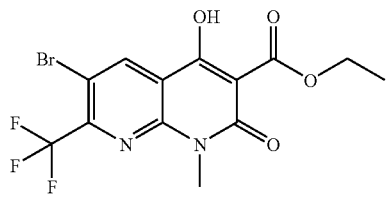

(c) Ethyl 6-bromo-4-hydroxy-1-methyl-2-oxo-7-(trifluoromethyl)-1,2-dihydro-1,8-naphthyridine-3-carboxylate. The title compound was prepared similarly to the procedure described for Example 77 (d) by treatment of methyl 5-bromo-2-(3-ethoxy-N-methyl-3-oxopropanamido)-6-(trifluoromethyl)nicotinate with EtONa. MS (ESI, pos. ion) m/z: 396 (M+1).

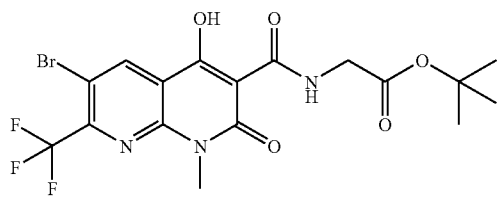

(d) tert-Butyl 2-(6-bromo-4-hydroxy-1-methyl-2-oxo-7-(trifluoromethyl)-1,2-dihydro-1,8-naphthyridine-3-carboxamido)acetate. The title compound was prepared from ethyl 6-bromo-4-hydroxy-1-methyl-2-oxo-7-(trifluoromethyl)-1,2-dihydro-1,8-naphthyridine-3-carboxylate and tert-butyl 2-aminoacetate hydrochloride analogously to the conditions described in Example 1 (f). MS (ESI, pos. ion) m/z: 426 (-tert-Bu) (M+1).

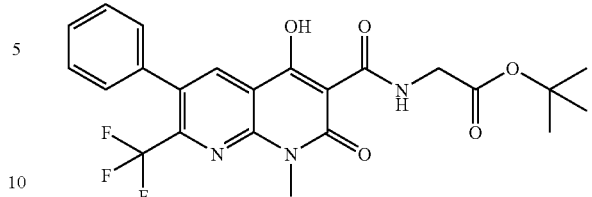

(e) tert-Butyl 2-(4-hydroxy-1-methyl-2-oxo-6-phenyl-7-(trifluoromethyl)-1,2-dihydro-1,8-naphthyridine-3-carboxamido)acetate. The title compound was prepared from tert-butyl 2-(6-bromo-4-hydroxy-1-methyl-2-oxo-7-(trifluoromethyl)-1,2-dihydro-1,8-naphthyridine-3-carboxamido)acetate and phenylboronic acid, similarly to the procedure described for Example 2 (a). MS (ESI, pos. ion) m/z: 422 (-tert-Bu) (M+1).

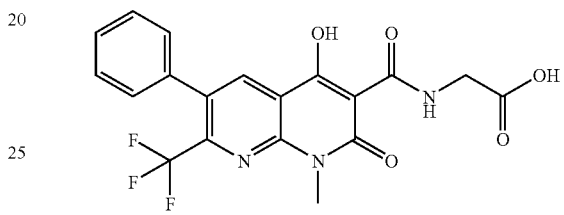

(f) 2-(4-Hydroxy-1-methyl-2-oxo-6-phenyl-7-(trifluoromethyl)-1,2-dihydro-1,8-naphthyridine-3-carboxamido) acetic acid. The title compound was prepared similarly to the procedure described for Example 1 (g) by treatment of tert-butyl 2-(4-hydroxy-1-methyl-2-oxo-6-phenyl-7-(trifluoromethyl)-1,2-dihydro-1,8-naphthyridine-3-carboxamido)acetate with TFA. MS (ESI, pos. ion) m/z: 422 (M+1). $^1$H NMR (300 MHz, DMSO-$d_6$) δ ppm: 13.01 (s, 1 H), 10.26-10.51 (m, 1 H), 8.38 (s, 1 H), 7.34-7.61 (m, 5H), 4.17 (d, J=5.6 Hz, 2 H), 3.73 (s, 3 H).

Additional Examples

TABLE 6

The following examples were prepared from tert-butyl 2-(6-bromo-4-hydroxy-1-methyl-2-oxo-7-(trifluoromethyl)-1,2-dihydro-1,8-naphthyridine-3-carboxamido)acetate (Example 90 (d)) and commercially available boronic acids or boronic acid esters analogously to the procedures described for the preparation of Example 32 (a, b) and 21 (b).

| Ex. | Structure | Name | MS (ESI) m/z | $^1$H NMR |
|---|---|---|---|---|
| 91 | (structure shown) | 2-(4-Hydroxy-1-methyl-2-oxo-6-(pyridin-3-yl)-7-(trifluoromethyl)-1,2-dihydro-1,8-naphthyridine-3-carboxamido) acetic acid | 423 (M + 1) | $^1$H NMR (300 MHz, DMSO-$d_6$) δ ppm: 13.00 (br. s, 1 H), 10.03-10.67 (m, 1 H), 8.71 (d, J = 5.7 Hz, 1 H), 8.64 (s, 1 H), 8.51 (s, 1 H), 7.91 (d, J = 7.9 Hz, 1 H), 7.57 (dd, J = 7.6, 5.0 Hz, 1 H), 4.17 (d, J = 5.6 Hz, 2 H), 3.73 (s, 3 H). |

TABLE 6-continued

The following examples were prepared from tert-butyl 2-(6-bromo-4-hydroxy-1-methyl-2-oxo-7-(trifluoromethyl)-1,2-dihydro-1,8-naphthyridine-3-carboxamido)acetate (Example 90 (d)) and commercially available boronic acids or boronic acid esters analogously to the procedures described for the preparation of Example 32 (a, b) and 21 (b).

| Ex. | Structure | Name | MS (ESI) m/z | $^1$H NMR |
|---|---|---|---|---|
| 92 | 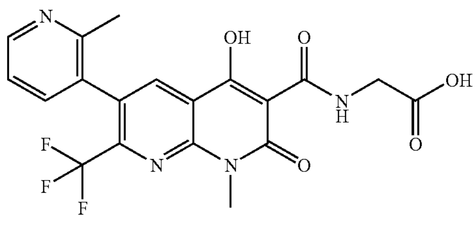 | 2-(4-Hydroxy-1-methyl-6-(2-methylpyridin-3-yl)-2-oxo-7-(trifluoromethyl)-1,2-dihydro-1,8-naphthyridine-3-carboxamido) acetic acid | 437 (M + 1) | $^1$H NMR (400 MHz, DMSO-d$_6$) δ ppm: 12.95 (br. s, 1 H), 10.38 (s, 1 H), 8.69 (d, J = 4.7 Hz, 1 H), 8.55 (s, 1 H), 7.90 (d, J = 7.2 Hz, 1 H), 7.51-7.62 (m, 1 H), 4.17 (d, J = 5.3 Hz, 2 H), 3.74 (s, 3 H), 2.31 (s, 3 H). |
| 93 | 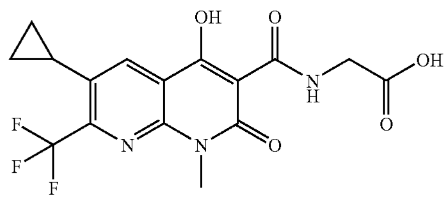 | 2-(6-cyclopropyl-4-hydroxy-1-methyl-2-oxo-7-(trifluoromethyl)-1,2-dihydro-1,8-naphthyridine-3-carboxamido) acetic acid | 386 (M + 1) | $^1$H NMR (300 MHz, DMSO-d$_6$) δ ppm: 13.06 (br. s, 1 H), 10.40 (t, J = 5.3 Hz, 1 H), 8.12 (s, 1 H), 4.15 (d, J = 5.6 Hz, 2 H), 3.65 (s, 3 H), 2.05-2.34 (m, 1 H), 1.01-1.25 (m, 2 H), 0.72-0.96 (m, 2 H). |

Example 94

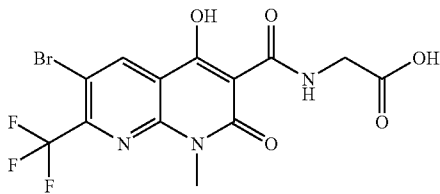

2-(6-Bromo-4-hydroxy-1-methyl-2-oxo-7-(trifluoromethyl)-1,2-dihydro-1,8-naphthyridine-3-carboxamido)acetic acid. The title compound was prepared similarly to the procedure described for Example 1 (g) by treatment of tert-butyl 2-(6-bromo-4-hydroxy-1-methyl-2-oxo-7-(trifluoromethyl)-1,2-dihydro-1,8-naphthyridine-3-carboxamido)acetate (Example 90 (d)) with TFA. MS (ESI, pos. ion) m/z: 425 (M+1). $^1$H NMR (300 MHz, DMSO-d$_6$) δ ppm: 13.02 (br. s, 1 H), 10.34 (s, 1 H), 8.81 (s, 1 H), 4.16 (d, J=5.7 Hz, 2 H), 3.65 (s, 3 H).

Example 95

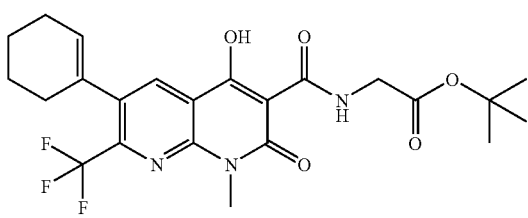

(a) tert-Butyl 2-(6-cyclohexenyl-4-hydroxy-1-methyl-2-oxo-7-(trifluoromethyl)-1,2-dihydro-1,8-naphthyridine-3-carboxamido)acetate. The title compound was prepared from tert-butyl 2-(6-bromo-4-hydroxy-1-methyl-2-oxo-7-(trifluoromethyl)-1,2-dihydro-1,8-naphthyridine-3-carboxamido)acetate (Example 90 (d)) and 2-cyclohexenyl-4,4,5,5-tetramethyl-1,3,2-dioxaborolane, similarly to the procedure described for Example 2 (a). MS (ESI, pos. ion) m/z: 424 (-tert-Bu) (M+1).

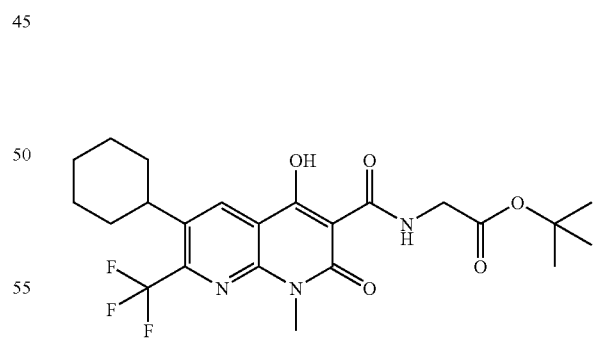

(b) tert-Butyl 2-(6-cyclohexyl-4-hydroxy-1-methyl-2-oxo-7-(trifluoromethyl)-1,2-dihydro-1,8-naphthyridine-3-carboxamido)acetate. The title compound was prepared by hydrogenation of tert-butyl 2-(6-cyclohexenyl-4-hydroxy-1-methyl-2-oxo-7-(trifluoromethyl)-1,2-dihydro-1,8-naphthyridine-3-carboxamido)acetate, similarly to the procedure described for Example 5(a). MS (ESI, pos. ion) m/z: 428 (-tert-Bu) (M+1).

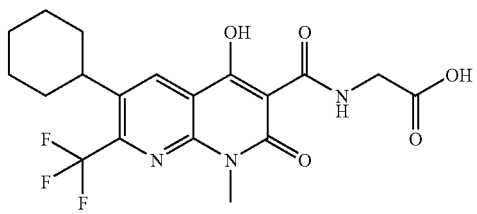

(c) 2-(6-Cyclohexyl-4-hydroxy-1-methyl-2-oxo-7-(trifluoromethyl)-1,2-dihydro-1,8-naphthyridine-3-carboxamido)acetic acid. The title compound was prepared similarly to the procedure described for Example 1 (g) by treatment of tert-butyl 2-(6-cyclohexyl-4-hydroxy-1-methyl-2-oxo-7-(trifluoromethyl)-1,2-dihydro-1,8-naphthyridine-3-carboxamido)acetate with TFA. MS (ESI, pos. ion) m/z: 428 (M+1). $^1$H NMR (300 MHz, DMSO-$d_6$) δ ppm: 12.99 (s, 1 H), 10.41 (t, J=5.4 Hz, 1 H), 8.60 (s, 1 H), 4.16 (d, J=5.6 Hz, 2 H), 3.66 (s, 3 H), 2.80-2.98 (m, 1 H), 1.54-1.91 (m, 7 H), 1.26-1.49 (m, 3 H).

Example 96

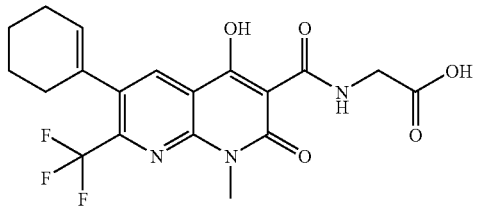

2-(6-Cyclohexenyl-4-hydroxy-1-methyl-2-oxo-7-(trifluoromethyl)-1,2-dihydro-1,8-naphthyridine-3-carboxamido) acetic acid. The title compound was prepared similarly to the procedure described for Example 1 (g) by treatment of tert-butyl 2-(6-cyclohexenyl-4-hydroxy-1-methyl-2-oxo-7-(trifluoromethyl)-1,2-dihydro-1,8-naphthyridine-3-carboxamido)acetate (Example 95 (a)) with TFA. MS (ESI, pos. ion) m/z: 426 (M+1). $^1$H NMR (300 MHz, DMSO-$d_6$) δ ppm: 13.02 (s, 1 H), 10.39 (t, J=5.6 Hz, 1 H), 8.35 (s, 1 H), 5.52-5.79 (m, 1 H), 4.15 (d, J=5.6 Hz, 2 H), 3.66 (s, 3 H), 2.04-2.37 (m, 4 H), 1.57-1.89 (m, 4 H).

Example 97

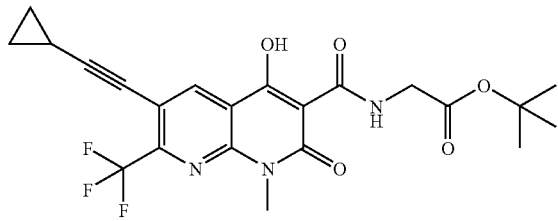

(a) tert-Butyl 2-(6-(2-cyclopropylethynyl)-4-hydroxy-1-methyl-2-oxo-7-(trifluoromethyl)-1,2-dihydro-1,8-naphthyridine-3-carboxamido)acetate. The title compound was prepared from tert-butyl 2-(6-bromo-4-hydroxy-1-methyl-2-oxo-7-(trifluoromethyl)-1,2-dihydro-1,8-naphthyridine-3-carboxamido)acetate (Example 90 (d)) and ethynylcyclopropane analogously to the procedure described for the preparation of Example 78 (a). MS (ESI, pos. ion) m/z: 409 (-tert-Bu) (M+1).

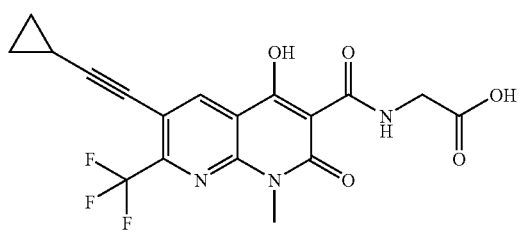

(b) 2-(6-(2-Cyclopropylethynyl)-4-hydroxy-1-methyl-2-oxo-7-(trifluoromethyl)-1,2-dihydro-1,8-naphthyridine-3-carboxamido)acetic acid. The title compound was prepared similarly to the procedure described for Example 1 (g) by treatment of tert-butyl 2-(6-(2-cyclopropylethynyl)-4-hydroxy-1-methyl-2-oxo-7-(trifluoromethyl)-1,2-dihydro-1,8-naphthyridine-3-carboxamido)acetate with TFA. MS (ESI, pos. ion) m/z: 410 (M+1). $^1$H NMR (300 MHz, DMSO-$d_6$) δ ppm: 13.01 (br. s, 1 H), 10.34 (s, 1 H), 8.53 (s, 1 H), 4.15 (d, J=5.6 Hz, 2 H), 3.65 (s, 3 H), 1.48-1.85 (m, 1 H), 0.91-1.05 (m, 2 H), 0.76-0.87 (m, 2 H).

Example 98

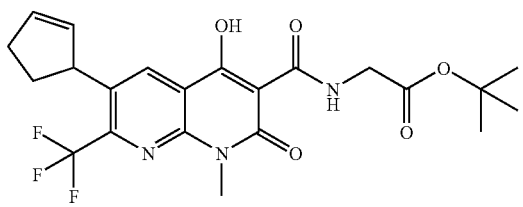

(a) tert-Butyl 2-(6-(cyclopent-2-enyl)-4-hydroxy-1-methyl-2-oxo-7-(trifluoromethyl)-1,2-dihydro-1,8-naphthyridine-3-carboxamido)acetate. A mixture of tert-butyl 2-(6-bromo-4-hydroxy-1-methyl-2-oxo-7-(trifluoromethyl)-1,2-dihydro-1,8-naphthyridine-3-carboxamido)acetate (1.00 g, 2082 μmol, Example 90 (d)), palladium acetate (0.023 g, 104 μmol), sodium acetate (0.205 g, 2499 μmol), and cyclopentene (0.9 mL, 10412 μmol) was flushed with argon and treated with tri-tert-butylphosphine (0.04 mL, 208 μmol). The reaction vessel was sealed and the mixture was heated at 120° C. for 2.5 hours. The reaction mixture was left to reach room temperature, diluted with EtOAc, and washed with 5% aqueous HCl (3×), saturated NaHCO$_3$, and brine. The organic layer was dried over MgSO$_4$, and filtered. The filtrate was evaporated under reduced pressure, and the residue was washed with hexane, and dried in vacuo to give the crude title compound, which was used in the next step without additional purification.

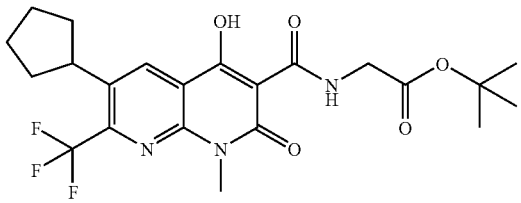

(b) tert-Butyl 2-(6-cyclopentyl-4-hydroxy-1-methyl-2-oxo-7-(trifluoromethyl)-1,2-dihydro-1,8-naphthyridine-3-carboxamido)acetate. A solution of tert-butyl 2-(6-(cyclopent-2-enyl)-4-hydroxy-1-methyl-2-oxo-7-(trifluoromethyl)-1,2-dihydro-1,8-naphthyridine-3-carboxamido)acetate (200 mg, 428 μmol) in EtOAc (20 mL) was hydrogenated over palladium black (20 mg) under 1 atm hydrogen at room temperature for 16 hours. The reaction mixture was filtered through a plug of Celite®, and the filtrate was evaporated under reduced pressure. The residue was purified by silica gel column chromatography (gradient: 0-30% EtOAc/hexanes) to give the title compound. MS (ESI, pos. ion) m/z: 414 (-tert-Bu) (M+1).

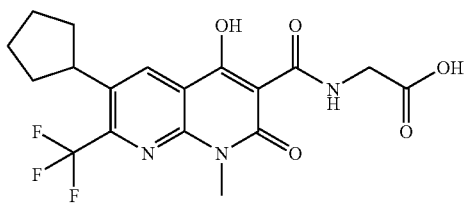

(c) 2-(6-Cyclopentyl-4-hydroxy-1-methyl-2-oxo-7-(trifluoromethyl)-1,2-dihydro-1,8-naphthyridine-3-carboxamido)acetic acid. The title compound was prepared similarly to the procedure described for Example 1 (g) by treatment of tert-butyl 2-(6-cyclopentyl-4-hydroxy-1-methyl-2-oxo-7-(trifluoromethyl)-1,2-dihydro-1,8-naphthyridine-3-carboxamido)acetate with TFA. MS (ESI, pos. ion) m/z: 414 (M+1). $^1$H NMR (300 MHz, DMSO-d$_6$) δ ppm: 13.04 (br. s, 1 H), 10.40 (t, J=5.0 Hz, 1 H), 8.56 (s, 1 H), 4.15 (d, J=5.4 Hz, 2 H), 3.66 (s, 3 H), 3.24-3.41 (m, 1 H), 1.99-2.16 (m, 2 H), 1.88 (s, 2 H), 1.57-1.80 (m, 4 H).

Example 99

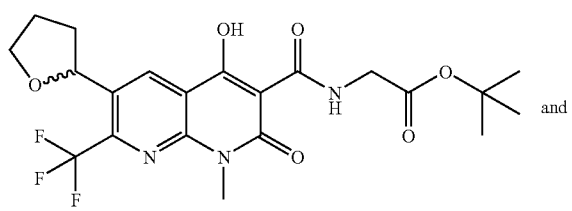

and

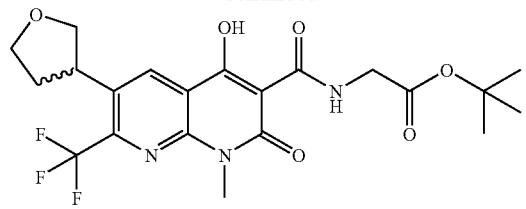

(a) (R,S) tert-Butyl 2-(4-hydroxy-1-methyl-2-oxo-6-(tetrahydrofuran-2-yl)-7-(trifluoromethyl)-1,2-dihydro-1,8-naphthyridine-3-carboxamido)acetate and (R,S) tert-Butyl 2-(4-hydroxy-1-methyl-2-oxo-6-(tetrahydrofuran-3-yl)-7-(trifluoromethyl)-1,2-dihydro-1,8-naphthyridine-3-carboxamido)acetate. The title compounds were prepared as a 1:1 mixture from tert-butyl 2-(6-bromo-4-hydroxy-1-methyl-2-oxo-7-(trifluoromethyl)-1,2-dihydro-1,8-naphthyridine-3-carboxamido)acetate (Example 90 (d)) and 2,5-dihydrofuran similarly to the procedure described for Example 98 (a).

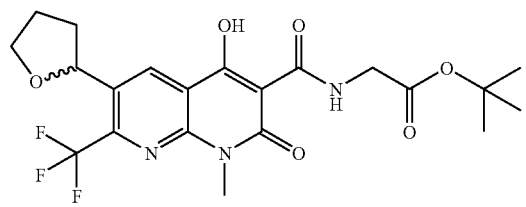

(b) (R,S) tert-Butyl 2-(4-hydroxy-1-methyl-2-oxo-6-(tetrahydrofuran-2-yl)-7-(trifluoromethyl)-1,2-dihydro-1,8-naphthyridine-3-carboxamido)acetate. The title compound was isolated after separation of the 1:1 mixture of products in step (a) by silica gel column chromatography (gradient: 0-20% EtOAc/hexanes). MS (ESI, pos. ion) m/z: 416 (-tert-Bu) (M+1). $^1$H NMR (300 MHz, CDCl$_3$) δ ppm: 10.38-10.86 (m, 1 H), 8.80 (s, 1 H), 5.29 (t, 1 H), 4.20-4.34 (m, 1 H), 4.14 (d, J=5.4 Hz, 2 H), 3.92-4.07 (m, 1 H), 3.81 (s, 3 H), 2.35-2.60 (m, 1 H), 1.99-2.18 (m, 2 H), 1.61-1.81 (m, 1 H), 1.51 (s, 9 H).

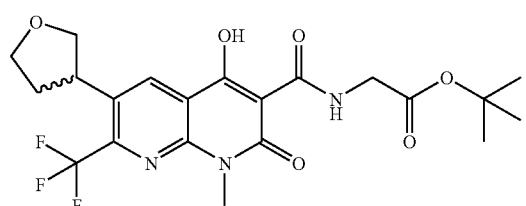

(c) (R,S) tert-Butyl 2-(4-hydroxy-1-methyl-2-oxo-6-(tetrahydrofuran-3-yl)-7-(trifluoromethyl)-1,2-dihydro-1,8-naphthyridine-3-carboxamido)acetate. The title compound was isolated as the second component of the 1:1 mixture of products in step (a). MS (ESI, pos. ion) m/z: 416 (-tert-Bu) (M+1). $^1$H NMR (300 MHz, CDCl$_3$) δ ppm: 10.62 (t, J=4.0 Hz, 1 H), 8.60 (s, 1 H), 4.16-4.24 (m, 1 H), 4.07-4.16 (m, 3 H), 3.83-4.01 (m, 3 H), 3.81 (s, 3 H), 2.40-2.60 (m, 1 H), 1.92-2.13 (m, 1 H), 1.51 (s, 9 H).

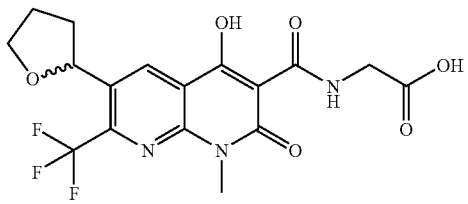

(d) (R,S) 2-(4-Hydroxy-1-methyl-2-oxo-6-(tetrahydrofuran-2-yl)-7-(trifluoromethyl)-1,2-dihydro-1,8-naphthyridine-3-carboxamido)acetic acid. The title compound was prepared similarly to the procedure described for Example 1 (g) by treatment of tert-butyl 2-(6-cyclopentyl-4-hydroxy-1-methyl-2-oxo-7-(trifluoromethyl)-1,2-dihydro-1,8-naphthyridine-3-carboxamido)acetate with TFA. MS (ESI, pos. ion) m/z: 416 (M+1). $^1$H NMR (300 MHz, DMSO-$d_6$) δ ppm: 12.97 (br. s, 1 H), 10.38 (t, J=5.3 Hz, 1 H), 8.65 (s, 1 H), 5.18 (t, J=8.0 Hz, 1 H), 4.05-4.30 (m, 3 H), 3.80-4.00 (m, 1 H), 3.66 (s, 3 H), 2.29-2.47 (m, 1 H), 1.89-2.17 (m, 2 H), 1.55-1.84 (m, 1 H).

Example 100

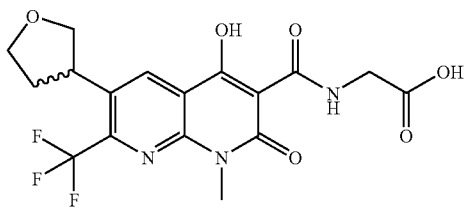

(R,S) 2-(4-Hydroxy-1-methyl-2-oxo-6-(tetrahydrofuran-3-yl)-7-(trifluoromethyl)-1,2-dihydro-1,8-naphthyridine-3-carboxamido)acetic acid. The title compound was prepared similarly to the procedure described for Example 1 (g) by treatment of (R,S) tert-butyl 2-(4-hydroxy-1-methyl-2-oxo-6-(tetrahydrofuran-3-yl)-7-(trifluoromethyl)-1,2-dihydro-1,8-naphthyridine-3-carboxamido)acetate (Example 99 (c)) with TFA. MS (ESI, pos. ion) m/z: 416 (M+1). $^1$H NMR (300 MHz, DMSO-$d_6$) δ ppm: 13.00 (br. s, 1 H), 10.39 (t, J=5.3 Hz, 1 H), 8.55 (s, 1 H), 4.15 (d, J=5.6 Hz, 2 H), 4.01-4.11 (m, 1 H), 3.92-4.01 (m, 1 H), 3.70-3.88 (m, 3 H), 3.66 (s, 3 H), 2.38-2.47 (m, 1 H), 1.89-2.06 (m, 1 H).

Examples 101 and 102

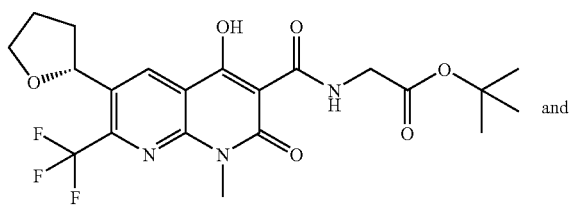

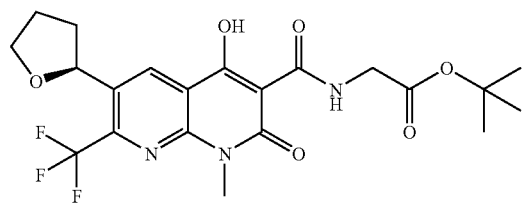

(a) (R)-tert-Butyl 2-(4-hydroxy-1-methyl-2-oxo-6-(tetrahydrofuran-2-yl)-7-(trifluoromethyl)-1,2-dihydro-1,8-naphthyridine-3-carboxamido)acetate and (S)-tert-Butyl 2-(4-hydroxy-1-methyl-2-oxo-6-(tetrahydrofuran-2-yl)-7-(trifluoromethyl)-1,2-dihydro-1,8-naphthyridine-3-carboxamido)acetate. The title compounds were prepared by separation of the racemic mixture (R,S) tert-butyl 2-(4-hydroxy-1-methyl-2-oxo-6-(tetrahydrofuran-2-yl)-7-(trifluoromethyl)-1,2-dihydro-1,8-naphthyridine-3-carboxamido)acetate (Example 99 (b)) by preparative SFC on a chiral column (Chiralpak AD-H, 150×4.6 mm, 5 μm) with mobile phase (85:15 liquid $CO_2$/MeOH (0.2% diethylamine) and flow rate (65 mL/min) at 40° C.

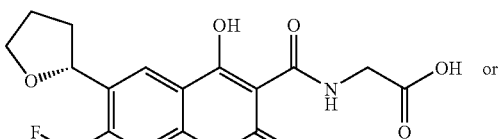
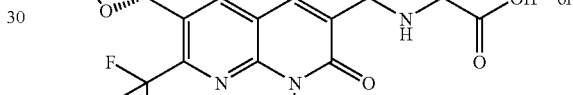

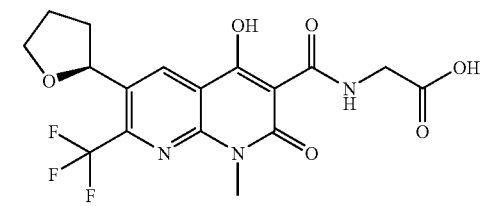

(b) (R)-2-(4-Hydroxy-1-methyl-2-oxo-6-(tetrahydrofuran-2-yl)-7-(trifluoromethyl)-1,2-dihydro-1,8-naphthyridine-3-carboxamido)acetic acid or (S)-2-(4-Hydroxy-1-methyl-2-oxo-6-(tetrahydrofuran-2-yl)-7-(trifluoromethyl)-1,2-dihydro-1,8-naphthyridine-3-carboxamido)acetic acid (Example 101). The title compound was prepared similarly to the procedure described for Example 1 (g) by treatment of (R)-tert-butyl 2-(4-hydroxy-1-methyl-2-oxo-6-(tetrahydrofuran-2-yl)-7-(trifluoromethyl)-1,2-dihydro-1,8-naphthyridine-3-carboxamido)acetate or (S)-tert-butyl 2-(4-hydroxy-1-methyl-2-oxo-6-(tetrahydrofuran-2-yl)-7-(trifluoromethyl)-1,2-dihydro-1,8-naphthyridine-3-carboxamido)acetate with TFA. MS (ESI, pos. ion) m/z: 416 (M+1). $^1$H NMR (300 MHz, DMSO-$d_6$) δ ppm: 10.39 (t, J=5.5 Hz, 1 H), 8.66 (s, 1 H), 5.00-5.29 (m, 1 H), 4.10-4.24 (m, 3 H), 3.80-3.97 (m, 1 H), 3.67 (s, 3 H), 2.34-2.45 (m, 1 H), 1.95-2.09 (m, 2 H), 1.60-1.77 (m, 1 H).

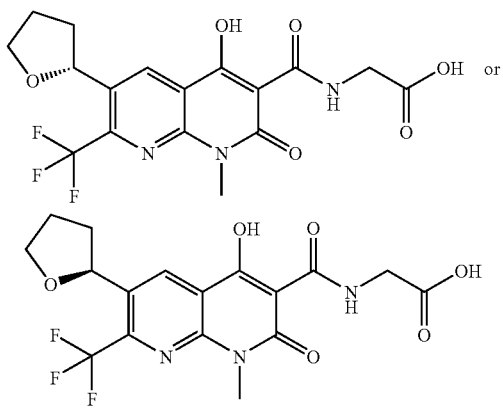

(c) (R)-2-(4-Hydroxy-1-methyl-2-oxo-6-(tetrahydrofuran-2-yl)-7-(trifluoromethyl)-1,2-dihydro-1,8-naphthyridine-3-carboxamido)acetic acid or (S)-2-(4-Hydroxy-1-methyl-2-oxo-6-(tetrahydrofuran-2-yl)-7-(trifluoromethyl)-1,2-dihydro-1,8-naphthyridine-3-carboxamido)acetic acid (Example 102). The title compound was prepared similarly to the procedure described for Example 1 (g) by treatment of the other enantiomer of (R)-tert-butyl 2-(4-hydroxy-1-methyl-2-oxo-6-(tetrahydrofuran-2-yl)-7-(trifluoromethyl)-1,2-dihydro-1,8-naphthyridine-3-carboxamido)acetate or (S)-tert-butyl 2-(4-hydroxy-1-methyl-2-oxo-6-(tetrahydrofuran-2-yl)-7-(trifluoromethyl)-1,2-dihydro-1,8-naphthyridine-3-carboxamido)acetate with TFA. MS (ESI, pos. ion) m/z: 416 (M+1). $^1$H NMR (300 MHz, DMSO-d$_6$) δ ppm: 10.38 (t, J=5.5 Hz, 1 H), 8.66 (s, 1 H), 5.11-5.23 (m, 1 H), 4.11-4.23 (m, 3 H), 3.83-3.93 (m, 1 H), 3.67 (s, 3 H), 1.95-2.06 (m, 3 H), 1.63-1.77 (m, 1 H).

Examples 103 and 104

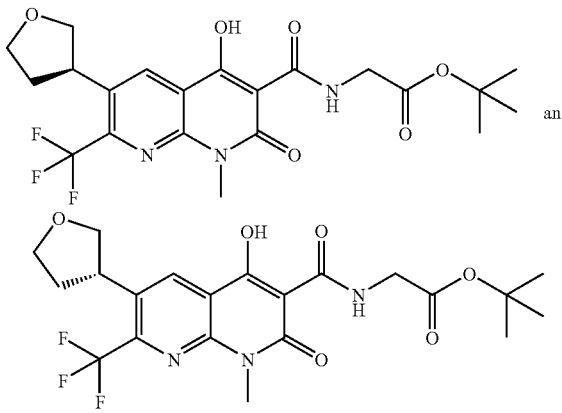

(a) (R)-tert-Butyl 2-(4-hydroxy-1-methyl-2-oxo-6-(tetrahydrofuran-3-yl)-7-(trifluoromethyl)-1,2-dihydro-1,8-naphthyridine-3-carboxamido)acetate and (S)-tert-Butyl 2-(4-hydroxy-1-methyl-2-oxo-6-(tetrahydrofuran-3-yl)-7-(trifluoromethyl)-1,2-dihydro-1,8-naphthyridine-3-carboxamido)acetate. The title compounds were isolated by separation of the racemic mixture (R,S) tert-butyl 2-(4-hydroxy-1-methyl-2-oxo-6-(tetrahydrofuran-3-yl)-7-(trifluoromethyl)-1,2-dihydro-1,8-naphthyridine-3-carboxamido)acetate (Example 99 (c)) as described in Example 101 (a).

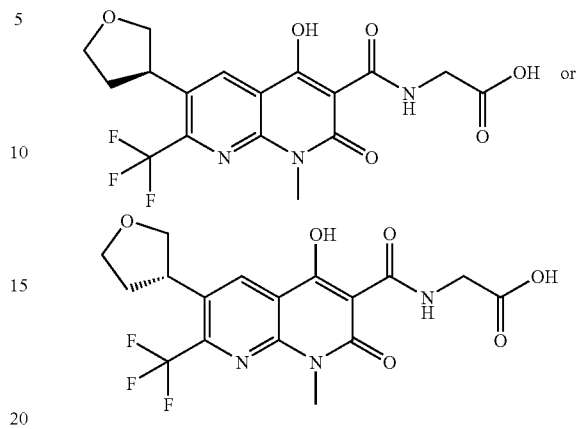

(b) (R)-2-(4-Hydroxy-1-methyl-2-oxo-6-(tetrahydrofuran-3-yl)-7-(trifluoromethyl)-1,2-dihydro-1,8-naphthyridine-3-carboxamido)acetic acid or (S)-2-(4-Hydroxy-1-methyl-2-oxo-6-(tetrahydrofuran-3-yl)-7-(trifluoromethyl)-1,2-dihydro-1,8-naphthyridine-3-carboxamido)acetic acid (Example 103). The title compound was prepared similarly to the procedure described for Example 1 (g) by treatment of one of the enantiomers of (R)-tert-butyl 2-(4-hydroxy-1-methyl-2-oxo-6-(tetrahydrofuran-3-yl)-7-(trifluoromethyl)-1,2-dihydro-1,8-naphthyridine-3-carboxamido)acetate or (S)-tert-butyl 2-(4-hydroxy-1-methyl-2-oxo-6-(tetrahydrofuran-3-yl)-7-(trifluoromethyl)-1,2-dihydro-1,8-naphthyridine-3-carboxamido)acetate with TFA. MS (ESI, pos. ion) m/z: 416 (M+1). $^1$H NMR (300 MHz, CDCl$_3$) δ ppm: 10.62 (t, J=5.3 Hz, 1 H), 8.61 (s, 1 H), 4.32 (d, J=5.6 Hz, 2 H), 4.05-4.26 (m, 2 H), 3.82-4.02 (m, 3 H), 3.81 (s, 3 H), 2.38-2.69 (m, 1 H), 1.79-2.17 (m, 1 H).

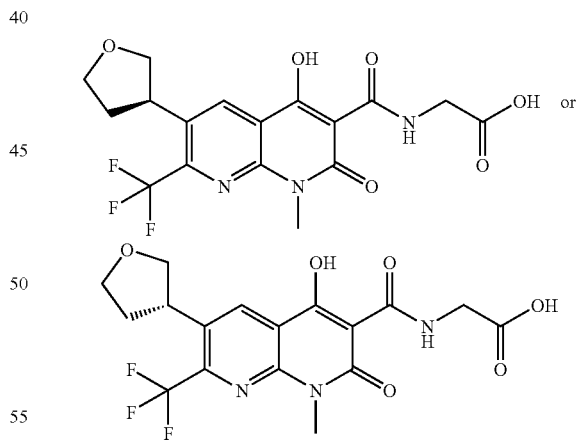

(c) (R)-2-(4-Hydroxy-1-methyl-2-oxo-6-(tetrahydrofuran-3-yl)-7-(trifluoromethyl)-1,2-dihydro-1,8-naphthyridine-3-carboxamido)acetic acid or (S)-2-(4-Hydroxy-1-methyl-2-oxo-6-(tetrahydrofuran-3-yl)-7-(trifluoromethyl)-1,2-dihydro-1,8-naphthyridine-3-carboxamido)acetic acid (Example 104). The title compound was prepared similarly to the procedure described for Example 1 (g) by treatment of the other enantiomer of (R)-tert-butyl 2-(4-hydroxy-1-methyl-2-oxo-6-(tetrahydrofuran-3-yl)-7-(trifluoromethyl)-1,2-dihydro-1,8-naphthyridine-3-carboxamido)acetate or (S)-tert-butyl 2-(4-hydroxy-1-methyl-2-oxo-6-(tetrahydrofuran-3-yl)-7-(trifluoromethyl)-1,2-dihydro-1,8-naphthyridine-3-carboxamido)acetate with TFA. MS (ESI, pos. ion) m/z: 416 (M+1). $^1$H NMR (300 MHz, CDCl$_3$) δ ppm: 10.62 (t, J=5.3 Hz, 1 H), 8.61 (s, 1 H), 4.32 (d, J=5.6 Hz, 2 H), 3.83-4.26 (m, 5 H), 3.81 (s, 3 H), 2.42-2.63 (m, 1 H), 1.92-2.11 (m, 1 H).

Example 105

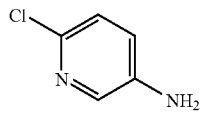

(a) 6-Chloropyridin-3-amine. A mixture of 2-chloro-5-nitropyridine (100 g, 0.63 mol) and Raney Ni (60 g) in MeOH (500 mL) was stirred under 45 psi H$_2$ atmosphere at room temperature for 5 hours. The reaction mixture was filtered, and the filtrate was evaporated under reduced pressure to afford the crude title compound, which was used in the next step without additional purification.

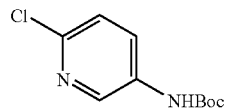

(b) tert-Butyl 6-chloropyridin-3-ylcarbamate. To a solution of the crude 6-chloropyridin-3-amine from the step above in dioxane (800 mL) was added (Boc)$_2$O at room temperature, and the resulting solution was heated at reflux overnight. The reaction mixture was left to reach room temperature, and evaporated under reduced pressure. The residue was purified by column chromatography to give the title compound.

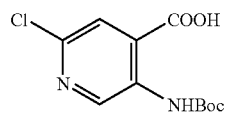

(c) 5-(tert-Butoxycarbonyl)-2-chloroisonicotinic acid. To a solution of tert-butyl 6-chloropyridin-3-ylcarbamate (10 g, 0.045 mol) and N,N,N',N'-tetramethyleethylenediamine (20 mL) in dry Et$_2$O (200 mL) was added n-BuLi (2.5 M solution in hexanes, 84 mL) dropwise with stirring at −78° C. After the addition, the reaction mixture was warmed to −15° C. and stirred at the same temperature for 2 hours. The mixture was cooled to −78° C. and CO$_2$ gas was bubbled into the reaction solution at −78° C. for 1 hour. The reaction mixture was then stirred at room temperature overnight, cooled to 0° C. and quenched with water. The pH of the aqueous phase was adjusted to pH=3 with 1N hydrochloric acid. The organic layer was separated, and the aqueous layer was extracted twice with EtOAc. The combined organic layers were dried over anhydrous MgSO$_4$, and filtered. The filtrate was evaporated under reduced pressure, and the residue was dried in vacuo to give the title compound.

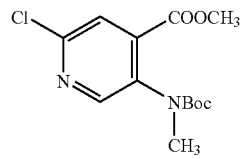

(d) Methyl 5-(tert-butoxycarbonyl)-2-chloroisonicotinate. To a solution of 5-(tert-butoxycarbonyl)-2-chloroisonicotinic acid (1 g, 3.7 mmol) in dry DMF (10 mL), was added NaH (60% suspension in mineral oil, 0.37 g, 9.24 mmol) in small portions with stirring and cooling with an ice-bath. After the addition, the reaction mixture was treated with MeI (0.524 mL, 9.24 mmol) dropwise, and then stirred at room temperature for 1 hour. The reaction mixture was poured into water and stirred at room temperature for 3 hours. The precipitate was filtered and dried in vacuo to afford the title compound as a solid.

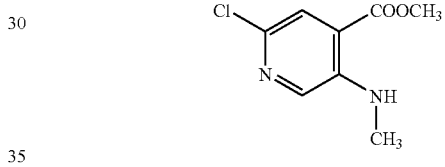

(e) Methyl 2-chloro-5-(methylamino)isonicotinate. To a solution of methyl 5-(tert-butoxycarbonyl)-2-chloroisonicotinate (0.5 g, 1.7 mmol) in dry DCM (10 mL) was added TFA (4.4 mL) with stirring and cooling with an ice-bath. The mixture was stirred at room temperature for 2 hours and evaporated under reduced pressure. The residue was dissolved in water, and the solution was adjusted to pH=8 by treatment with saturated NaHCO$_3$. The mixture was extracted twice with EtOAc. The combined organic layers were dried over anhydrous MgSO$_4$, and filtered. The filtrate was evaporated under reduced pressure, and the residue was dried in vacuo to give the title compound.

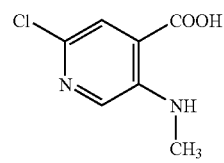

(f) 2-Chloro-5-(methylamino)isonicotinic acid. A mixture of methyl 2-chloro-5-(methylamino)isonicotinate (10 g, 0.05 mol) and 2 N NaOH (50 mL) in EtOH (50 mL) was heated at 55° C. for 2 hours. The reaction mixture was cooled to room temperature and most of the EtOH was evaporated under reduced pressure. The pH of the aqueous residue was adjusted to pH=3 with 1 N HCl, and the solid precipitate was filtered and dried in vacuo to give the title compound.

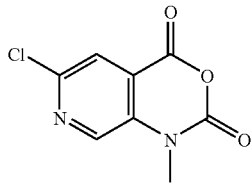

(g) 6-Chloro-1-methyl-1H-pyrido[3,4-d][1,3]oxazine-2,4-dione. The title compound was prepared analogously to Example 1 (c) from 2-chloro-5-(methylamino)isonicotinic acid and phosgene.

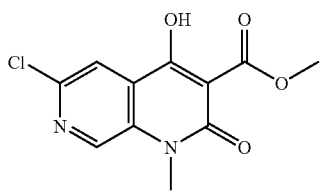

(h) Methyl 6-chloro-4-hydroxy-1-methyl-2-oxo-1,2-dihydro-1,7-naphthyridine-3-carboxylate. The title compound was prepared analogously to Example 1 (e) from 6-chloro-1-methyl-1H-pyrido[3,4-d][1,3]oxazine-2,4-dione and methyl malonate.

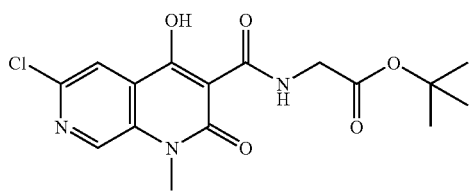

(i) tert-Butyl 2-(6-chloro-4-hydroxy-1-methyl-2-oxo-1,2-dihydro-1,7-naphthyridine-3-carboxamido)acetate. The title compound was prepared similarly to the procedure described for Example 1 (f) from methyl 6-chloro-4-hydroxy-1-methyl-2-oxo-1,2-dihydro-1,7-naphthyridine-3-carboxylate. MS (ESI, pos. ion) m/z: 368 (M+1).

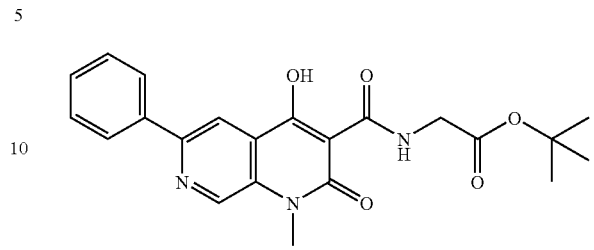

(j) tert-Butyl 2-(4-hydroxy-1-methyl-2-oxo-6-phenyl-1,2-dihydro-1,7-naphthyridine-3-carboxamido)acetate. The title compound was prepared similarly to the procedure described for Example 12 (a) from tert-butyl 2-(6-chloro-4-hydroxy-1-methyl-2-oxo-1,2-dihydro-1,7-naphthyridine-3-carboxamido)acetate and phenylboronic acid. MS (ESI, pos. ion) m/z: 410 (M+1).

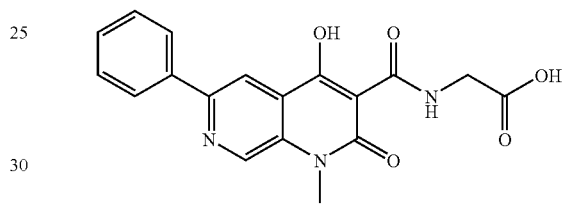

(k) N-((4-Hydroxy-1-methyl-2-oxo-6-phenyl-1,2-dihydro-1,7-naphthyridin-3-yl)carbonyl)glycine. The title compound was prepared as an off-white solid, similarly to the procedure described for Example 1 (g), by treatment of tert-butyl 2-(4-hydroxy-1-methyl-2-oxo-6-phenyl-1,2-dihydro-1,7-naphthyridine-3-carboxamido)acetate with TFA. MS (ESI, pos. ion) m/z: 354 (M+1). $^1$H NMR (400 MHz, DMSO-$d_6$) δ ppm: 12.99 (s, 1 H), 10.52-10.56 (m, 1 H), 9.17 (s, 1 H), 8.36 (s, 1 H), 8.15 (d, J=7.4 Hz, 2 H), 7.43-7.55 (m, 3 H), 4.17 (d, J=5.5 Hz, 2 H), 3.76 (s, 3 H).

Additional Examples

TABLE 7

The following examples were prepared from tert-butyl 2-(6-chloro-4-hydroxy-1-methyl-2-oxo-1,2-dihydro-1,7-naphthyridine-3-carboxamido)acetate (Example 105 (i)) and commercially available boronic acids or boronic acid esters as described for the preparation of Example 105 (j) and 105 (k).

| Ex. | Structure | Name | MS (ESI) m/z | $^1$H NMR |
|---|---|---|---|---|
| 106 | 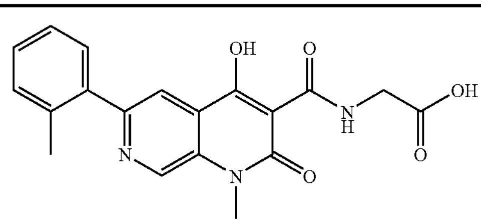 | N-((4-Hydroxy-1-methyl-6-(2-methylphenyl)-2-oxo-1,2-dihydro-1,7-naphthyridin-3-yl)carbonyl)glycine | 368 (M + 1) | $^1$H NMR (400 MHz, DMSO-$d_6$) δ ppm: 10.55 (s, 1 H), 9.17 (s, 1 H), 7.96 (s, 1 H), 7.47 (d, J = 6.9 Hz, 1 H), 7.30-7.38 (m, 3 H), 4.16 (d, J = 5.5 Hz, 2 H), 3.76 (s, 3 H), 2.37 (s, 3 H) |

TABLE 7-continued

The following examples were prepared from tert-butyl 2-(6-chloro-4-hydroxy-1-methyl-2-oxo-1,2-dihydro-1,7-naphthyridine-3-carboxamido)acetate (Example 105 (i)) and commercially available boronic acids or boronic acid esters as described for the preparation of Example 105 (j) and 105 (k).

| Ex. | Structure | Name | MS (ESI) m/z | $^1$H NMR |
|---|---|---|---|---|
| 107 | 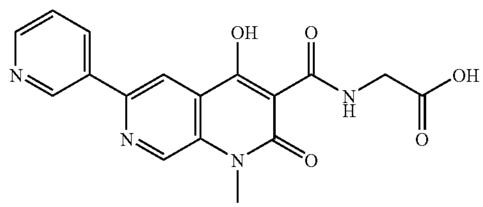 | N-((4-Hydroxy-1-methyl-2-oxo-6-(3-pyridinyl)-1,2-dihydro-1,7-naphthyridin-3-yl)carbonyl) glycine | 355 (M + 1) | $^1$H NMR (400 MHz, DMSO-d$_6$) δ ppm: 10.52 (s, 1 H), 9.29-9.49 (s, 1 H), 9.14-9.32 (s, 1 H), 8.59-8.83 (m, 1 H), 8.46-8.59 (s, 1 H), 7.58-7.78 (m, 1 H), 4.17 (d, J = 5.5 Hz, 1 H), 3.78 (s, 3 H). |
| 108 | 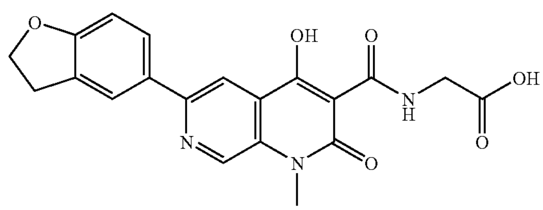 | N-((6-(2,3-Dihydro-1-benzofuran-5-yl)-4-hydroxy-1-methyl-2-oxo-1,2-dihydro-1,7-naphthyridin-3-yl)carbonyl) glycine | 396 (M + 1) | $^1$H NMR (400 MHz, DMSO-d$_6$) δ ppm: 10.55 (s, 1 H), 9.09 (s, 1 H), 8.24 (s, 1 H), 8.02 (s, 1 H), 7.90 (m, 1 H), 6.88 (d, J = 8.2 Hz, 1 H), 4.60 (t, J = 8.6 Hz, 2 H), 4.16 (d, J = 5.3 Hz, 2 H), 3.74 (s, 3 H), 3.27 (m, 2 H). |
| 109 | 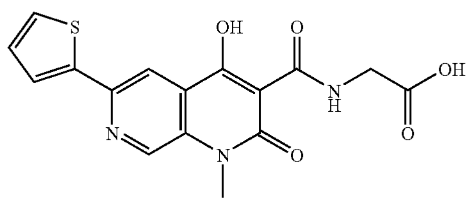 | N-((4-Hydroxy-1-methyl-2-oxo-6-(2-thienyl)-1,2-dihydro-1,7-naphthyridin-3-yl)carbonyl) glycine | 360 (M + 1) | $^1$H NMR (400 MHz, DMSO-d$_6$) δ ppm: 10.53 (t, J = 5.7 Hz, 1 H), 8.25-8.36 (s, 1 H), 7.85-7.96 (m, 1 H), 7.58-7.70 (m, 1 H), 7.12-7.25 (m, 1 H), 4.17 (d, J = 5.3 Hz, 2 H), 3.73 (s, 3 H). |
| 110 | 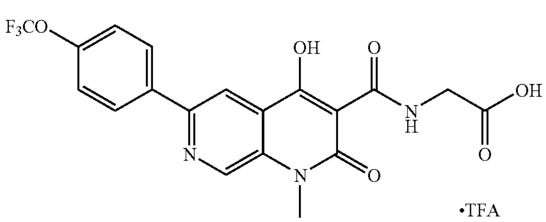 | 2-(4-Hydroxy-1-methyl-2-oxo-6-(4-(trifluoromethoxy) phenyl)-1,2-dihydro-1,7-naphthyridine-3-carboxamido) acetic acid, Trifluoroacetic acid salt. | 438 (M + 1) | $^1$H NMR (400 MHz, DMSO-d$_6$) δ ppm: 9.18 (s, 1 H), 8.40 (s, 1 H), 8.28 (d, J = 8.8 Hz, 3 H), 7.50 (s, 3 H), 4.17 (d, J = 5.5 Hz, 2 H), 3.76 (s, 4 H), 3.38 (s, 3 H). |

Example 111

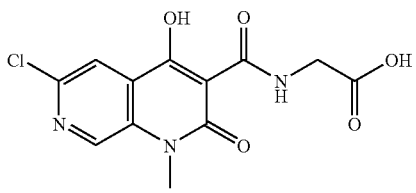

2-(6-Chloro-4-hydroxy-1-methyl-2-oxo-1,2-dihydro-1,7-naphthyridine-3-carboxamido)acetic acid. The title compound was prepared similarly to the procedure described for Example 1 (g), by treatment of tert-butyl 2-(6-chloro-4-hydroxy-1-methyl-2-oxo-1,2-dihydro-1,7-naphthyridine-3-carboxamido)acetate (Example 105 (i)) with TFA. MS (ESI, pos. ion) m/z: 310 (M+1). $^1$H NMR (400 MHz, DMSO-$d_6$) δ ppm: 10.46 (s, 1 H), 8.91 (s, 1 H), 7.94 (s, 1 H), 4.15 (d, J=5.5 Hz, 2 H), 3.69 (s, 3 H).

Example 112

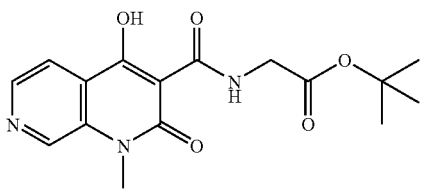

(a) tert-Butyl 2-(4-hydroxy-1-methyl-2-oxo-1,2-dihydro-1,7-naphthyridine-3-carboxamido)acetate. To a mixture of tert-butyl 2-(6-chloro-4-hydroxy-1-methyl-2-oxo-1,2-dihydro-1,7-naphthyridine-3-carboxamido)acetate (100 mg, 0.272 mmol, Example 105 (i)) and ammonium formate (429 mg, 6.8 mmol) in EtOH (2.7 mL) was added 10% Pd/C (29 mg) under nitrogen atmosphere. The reaction mixture was heated at 65° C. for 30 minutes and left to reach room temperature. The mixture was filtered, the filter cake was washed with EtOAc, and the combined filtrate was evaporated under reduced pressure. The residue was purified by prep. HPLC (gradient: 0% MeCN/water+0.1% TFA-90% MeCN/water+1% TFA) to give the title compound.

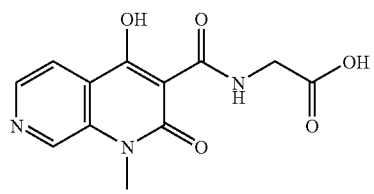

(b) N-((4-Hydroxy-1-methyl-2-oxo-1,2-dihydro-1,7-naphthyridin-3-yl)carbonyl)glycine. The title compound was prepared as a white solid, similarly to the procedure described for Example 1 (g), by treatment of tert-butyl 2-(4-hydroxy-1-methyl-2-oxo-1,2-dihydro-1,7-naphthyridine-3-carboxamido)acetate with TFA. MS (ESI, pos. ion) m/z: 278 (M+1). $^1$H NMR (400 MHz, DMSO-$d_6$) δ ppm: 10.52 (s, 1 H), 9.09 (s, 1 H), 8.56 (d, J=5.1 Hz, 1 H), 7.93 (d, J=5.1 Hz, 1 H), 4.15 (d, J=5.7 Hz, 2 H), 3.72 (s, 3 H).

Example 113

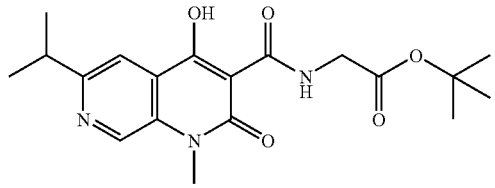

(a) tert-Butyl 2-(4-hydroxy-6-isopropyl-1-methyl-2-oxo-1,2-dihydro-1,7-naphthyridine-3-carboxamido)acetate. A mixture of tert-butyl 2-(6-chloro-4-hydroxy-1-methyl-2-oxo-1,2-dihydro-1,7-naphthyridine-3-carboxamido)acetate (96 mg, 0.261 mmol, Example 105 (i)), Fe(III)(acac)$_3$ (5 mg, 13 μmol), THF (0.87 mL), toluene (0.87 mL), and 1-methylpyrrolidone (0.174 mL) was stirred at room temperature for 5 minutes. Isopropylmagnesium chloride (2 M solution in THF, 0.522 mL, 1.044 mmol) was added dropwise, and the mixture was stirred for 20 minutes at room temperature. The reaction mixture was diluted with EtOAc (75 mL), washed with 3 N HCl, dried over Na$_2$SO$_4$, and filtered. The filtrate was evaporated under reduced pressure and the residue was purified by preparative HPLC (gradient: 0% MeCN/water+0.1% TFA-90% MeCN/water+1% TFA) to give the title compound as a light-yellow solid. MS (ESI, pos. ion) m/z: 376 (M+1).

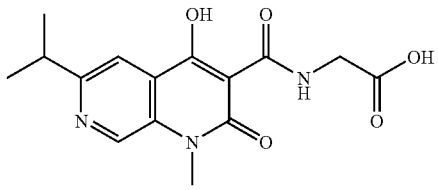

(b) N-((4-Hydroxy-1-methyl-6-(1-methylethyl)-2-oxo-1,2-dihydro-1,7-naphthyridin-3-yl)carbonyl)glycine. The title compound was prepared similarly to the procedure described for Example 1 (g), by treatment of tert-butyl 2-(4-hydroxy-6-isopropyl-1-methyl-2-oxo-1,2-dihydro-1,7-naphthyridine-3-carboxamido)acetate with TFA. MS (ESI, pos. ion) m/z: 320 (M+1). $^1$H NMR (400 MHz, DMSO-$d_6$) δ ppm: 10.55 (t, J=5.5 Hz, 1 H), 9.02 (s, 1 H), 7.77 (s, 1 H), 4.15 (d, J=5.5 Hz, 2 H), 3.19 (m, 1 H), 1.29 (d, J=6.9 Hz, 6 H).

Example 114

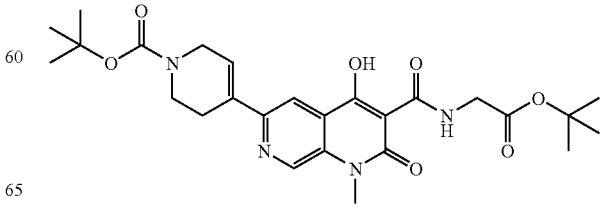

(a) tert-Butyl 4-(3-((2-tert-butoxy-2-oxoethyl)carbamoyl)-4-hydroxy-1-methyl-2-oxo-1,2-dihydro-1,7-naphthyridin-6-yl)-5,6-dihydropyridine-1(2H)-carboxylate. The title compound was prepared similarly to the procedure described for Example 105 (O), by treatment of tert-butyl 2-(6-chloro-4-hydroxy-1-methyl-2-oxo-1,2-dihydro-1,7-naphthyridine-3-carboxamido)acetate (Example 105 (i)) with tert-butyl 4-(4,4,5,5-tetramethyl-1,3,2-dioxaborolan-2-yl)-5,6-dihydropyridine-1(2H)-carboxylate.

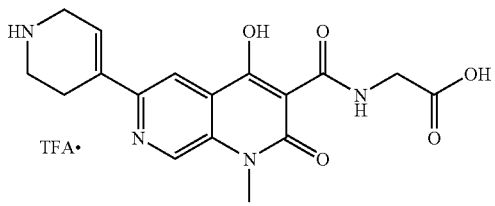

(b) 2-(4-Hydroxy-1-methyl-2-oxo-6-(1,2,3,6-tetrahydropyridin-4-yl)-1,2-dihydro-1,7-naphthyridine-3-carboxamido)acetic acid, Trifluoroacetic acid salt. The title compound was prepared similarly to the procedure described for Example 1 (g), by treatment of tert-butyl 4-(3-((2-tert-butoxy-2-oxoethyl)carbamoyl)-4-hydroxy-1-methyl-2-oxo-1,2-dihydro-1,7-naphthyridin-6-yl)-5,6-dihydropyridine-1(2H)-carboxylate with TFA. MS (ESI, pos. ion) m/z: 359 (M+1). $^1$H NMR (400 MHz, DMSO-$d_6$) δ ppm: 10.46-10.59 (m, 1 H), 9.08 (s, 1 H), 8.80-8.94 (m, 1 H), 7.99 (s, 1 H), 6.78-6.87 (m, 1 H), 4.16 (d, J=5.5 Hz, 2 H), 3.86 (m, 2 H), 3.73 (s, 3 H), 3.38 (m, 2 H), 2.83 (m, 2 H).

Example 115

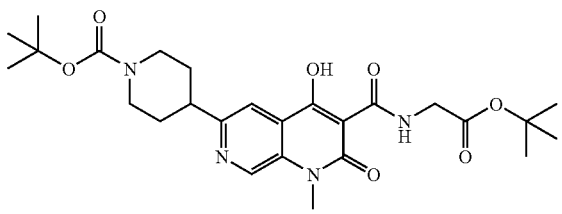

(a) tert-Butyl 4-(3-((2-tert-butoxy-2-oxoethyl)carbamoyl)-4-hydroxy-1-methyl-2-oxo-1,2-dihydro-1,7-naphthyridin-6-yl)-5,6-dihydropyridine-1(2H)-carboxylate. A solution of tert-butyl 4-(3-((2-tert-butoxy-2-oxoethyl)carbamoyl)-4-hydroxy-1-methyl-2-oxo-1,2-dihydro-1,7-naphthyridin-6-yl)-5,6-dihydropyridine-1(2H)-carboxylate (0.3 g, 0.6 mmol, Example 114 (a)) in a 9:1 mixture of MeOH/DCM (20 mL) was flushed with nitrogen gas and 10% Pd/C (0.1 g) was added. The mixture was then stirred in a Parr shaker under 50 psi hydrogen atmosphere for 4 hours at room temperature. The reaction mixture was filtered from the catalyst through a pad of Celite®, and the filter cake was washed with MeOH. The filtrate was evaporated under reduced pressure, and the residue purified by silica gel column chromatography (gradient: 5-10% 1 M NH$_3$ in MeOH/DCM to provide the title compound as a light-yellow solid. MS (ESI, pos. ion) m/z: 517 [M+1].

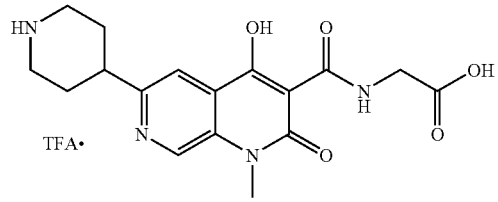

(b) 2-(4-Hydroxy-1-methyl-2-oxo-6-(piperidin-4-yl)-1,2-dihydro-1,7-naphthyridine-3-carboxamido)acetic acid, Trifluoroacetic acid salt. The title compound was prepared similarly to the procedure described for Example 1 (g), by treatment of tert-butyl 4-(3-((2-tert-butoxy-2-oxoethyl)carbamoyl)-4-hydroxy-1-methyl-2-oxo-1,2-dihydro-1,7-naphthyridin-6-yl)-5,6-dihydropyridine-1(2H)-carboxylate with TFA. MS (ESI, pos. ion) m/z: 361 (M+1). $^1$H NMR (400 MHz, DMSO-$d_6$) δ ppm: 10.44-10.68 (m, 1 H), 8.88-9.19 (s, 1 H), 7.61-7.92 (s, 1 H), 4.12-4.16 (m, 2 H), 3.71 (s, 3 H), 3.01-3.19 (m, 4 H), 1.96-2.06 (m, 4 H).

Example 116

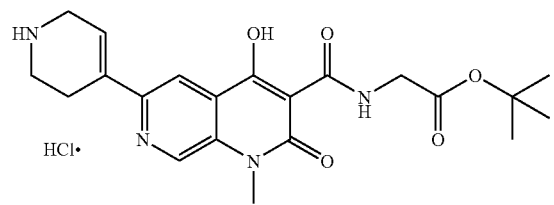

(a) tert-Butyl 2-(4-hydroxy-1-methyl-2-oxo-6-(1,2,3,6-tetrahydropyridin-4-yl)-1,2-dihydro-1,7-naphthyridine-3-carboxamido)acetate, Hydrochloric acid salt. A solution of tert-butyl 4-(3-((2-tert-butoxy-2-oxoethyl)carbamoyl)-4-hydroxy-1-methyl-2-oxo-1,2-dihydro-1,7-naphthyridin-6-yl)-5,6-dihydropyridine-1 (2H)-carboxylate (0.5 g, 1.0 mmol, Example 114 (a)) in DCM (2 mL) was treated with 4 M HCl in dioxane (2 mL) with stirring at room temperature. The mixture was stirred at room temperature for 2 h, and was diluted with Et$_2$O (10 mL). The precipitate was filtered, washed with Et$_2$O (10 mL), and dried in vacuo to give the title compound as a yellow solid. MS (ESI, pos. ion) m/z: 415 (M+1).

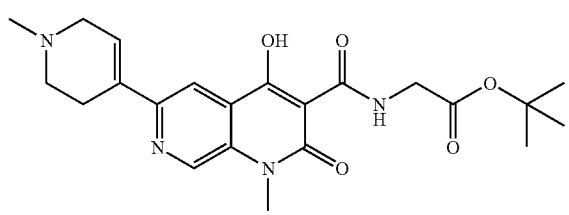

(b) tert-Butyl 2-(4-hydroxy-1-methyl-6-(1-methyl-1,2,3,6-tetrahydropyridin-4-yl)-2-oxo-1,2-dihydro-1,7-naphthyridine-3-carboxamido)acetate. To a solution of tert-butyl 2-(4-hydroxy-1-methyl-2-oxo-6-(1,2,3,6-tetrahydropyridin-4-yl)-1,2-dihydro-1,7-naphthyridine-3-carboxamido)acetate, hydrochloric acid salt (0.14 g, 0.31 mmol) in chloroform (5 mL) was added formaldehyde (37 wt. % in water, 0.5 mL, 6.2 mmol), sodium cyanoborohydride (0.081 g, 1.6 mmol) and MeOH (2 mL). The mixture was stirred at room temperature for 2 hours, and was evaporated under reduced pressure. The residue was purified by silica gel column chromatography (10% 2 M NH$_3$ in MeOH/DCM) to provide the title compound as a pale-yellow solid. MS (ESI, pos. ion) m/z: 429 [M+].

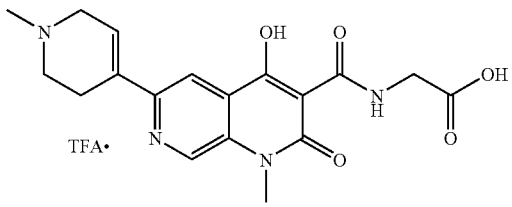

(c) 2-(4-Hydroxy-1-methyl-6-(1-methyl-1,2,3,6-tetrahydropyridin-4-yl)-2-oxo-1,2-dihydro-1,7-naphthyridine-3-carboxamido)acetic acid, Trifluoroacetic acid salt. The title compound was prepared similarly to the procedure described for Example 1 (g), by treatment of tert-butyl 2-(4-hydroxy-1-methyl-6-(1-methyl-1,2,3,6-tetrahydropyridin-4-yl)-2-oxo-1,2-dihydro-1,7-naphthyridine-3-carboxamido)acetate with TFA. MS (ESI, pos. ion) m/z: 373 [M+1]. $^1$H NMR (400 MHz, DMSO-d$_6$) δ ppm: 10.35-10.66 (m, 1 H), 9.08 (s, 1 H), 8.01 (m, 1 H), 6.59-6.97 (m, 1 H), 4.10-4.20 (m, 2 H), 3.90-3.99 (m, 2 H), 3.73 (s, 3 H), 3.46 (m, 2 H), 2.92-2.80 (m, 5 H).

Example 117

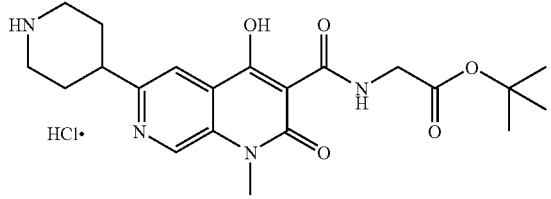

(a) tert-Butyl 2-(4-hydroxy-1-methyl-2-oxo-6-(piperidin-4-yl)-1,2-dihydro-1,7-naphthyridine-3-carboxamido)acetate, Hydrochloric acid salt. The title compound was prepared by treatment of tert-butyl 4-(3-(((2-tert-butoxy-2-oxoethyl)carbamoyl)-4-hydroxy-1-methyl-2-oxo-1,2-dihydro-1,7-naphthyridin-6-yl)piperidine-1-carboxylate (Example 115 (a)) with 4 M HCl in dioxane under the conditions of Example 116 (a). MS (ESI, pos. ion) m/z: 517 [M+1].

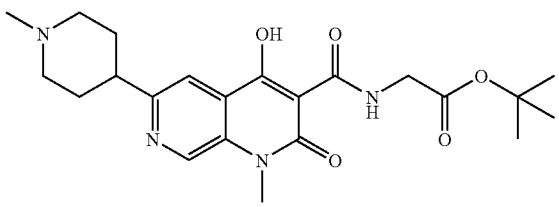

(b) tert-Butyl 2-(4-hydroxy-1-methyl-6-(1-methylpiperidin-4-yl)-2-oxo-1,2-dihydro-1,7-naphthyridine-3-carboxamido)acetate. The title compound was prepared by treatment of tert-butyl 2-(4-hydroxy-1-methyl-2-oxo-6-(piperidin-4-yl)-1,2-dihydro-1,7-naphthyridine-3-carboxamido)acetate, hydrochloric acid salt with formaldehyde under the conditions of Example 116 (b). MS (ESI, pos. ion) m/z: 431 [M+1].

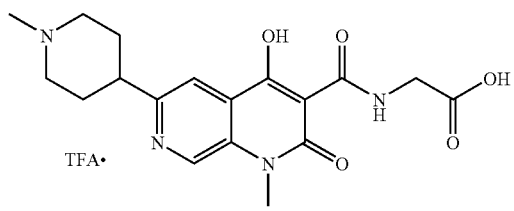

(c) 2-(4-Hydroxy-1-methyl-6-(1-methylpiperidin-4-yl)-2-oxo-1,2-dihydro-1,7-naphthyridine-3-carboxamido)acetic acid, Trifluoroacetic acid salt. The title compound was prepared similarly to the procedure described for Example 1 (g), by treatment of tert-butyl 2-(4-hydroxy-1-methyl-6-(1-methylpiperidin-4-yl)-2-oxo-1,2-dihydro-1,7-naphthyridine-3-carboxamido)acetate with TFA. MS (ESI, pos. ion) m/z: 375 [M+1]. $^1$H NMR (400 MHz, DMSO-d$_6$) δ ppm: 10.53 (s, 1 H), 9.04 (s, 1 H), 7.81 (s, 1 H), 4.15 (d, J=5.5 Hz, 2 H), 3.71 (s, 3 H), 3.54-3.67 (m, 2 H), 3.04-3.15 (m, 2 H), 2.84 (s, 3 H), 2.63-2.78 (m, 1 H), 1.86-2.23 (m, 3 H).

Example 118

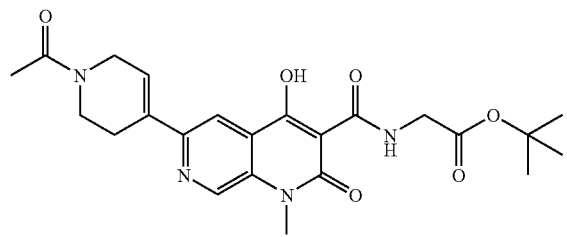

(a) tert-Butyl 2-(6-(1-acetyl-1,2,3,6-tetrahydropyridin-4-yl)-4-hydroxy-1-methyl-2-oxo-1,2-dihydro-1,7-naphthyridine-3-carboxamido)acetate. To a solution of tert-butyl 2-(4-hydroxy-1-methyl-2-oxo-6-(1,2,3,6-tetrahydropyridin-4-yl)-1,2-dihydro-1,7-naphthyridine-3-carboxamido)acetate, hydrochloric acid salt (100 mg, 222 μmol, Example 116 (a)) in EtOH (4 mL) was added triethylamine (62 μL, 444 lμmol) and 2-trifluoromethyl-N,N-diacetylaniline (218 mg, 887 μmol). After stirring at room temperature for 5 hours, the mixture was diluted with DCM (100 mL), washed with saturated NaHCO$_3$ (30 mL), dried over anhydrous Na$_2$SO$_4$, and filtered. The filtrate was evaporated under reduced pressure, and the residue was purified by silica gel column chromatography (gradient: 2-5% 2 M NH$_3$ in MeOH/DCM) to provide the title compound as a pale-yellow solid. MS (ESI, pos. ion) m/z: 457 [M+1].

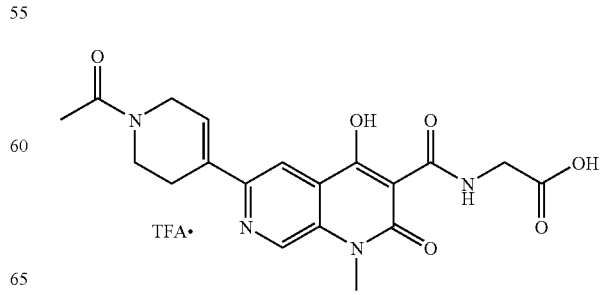

(b) 2-(6-(1-Acetyl-1,2,3,6-tetrahydropyridin-4-yl)-4-hydroxy-1-methyl-2-oxo-1,2-dihydro-1,7-naphthyridine-3-carboxamido)acetic acid, Trifluoroacetic acid salt. The title compound was prepared similarly to the procedure described for Example 1 (g), by treatment of tert-butyl 2-(6-(1-acetyl-1,2,3,6-tetrahydropyridin-4-yl)-4-hydroxy-1-methyl-2-oxo-1,2-dihydro-1,7-naphthyridine-3-carboxamido)acetate with TFA. MS (ESI, pos. ion) m/z: 401 [M+1]. $^1$H NMR (400 MHz, DMSO-$d_6$) δ ppm: 10.46-10.62 (s, 1 H), 9.06 (s, 1 H), 7.94 (s, 1 H), 6.77-6.89 (m, 1 H), 4.20-4.26 (m, 1 H), 4.10-4.20 (m, 4 H), 3.62-3.76 (m, 5 H), 2.55-2.76 (m, 2 H), 2.01-2.14 (s, 3 H).

Example 119

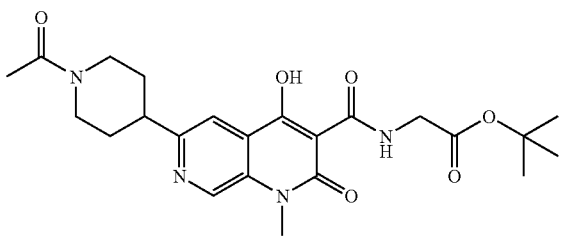

(a) tert-Butyl 2-(6-(1-acetylpiperidin-4-yl)-4-hydroxy-1-methyl-2-oxo-1,2-dihydro-1,7-naphthyridine-3-carboxamido)acetate. To a mixture of tert-butyl 2-(4-hydroxy-1-methyl-2-oxo-6-(piperidin-4-yl)-1,2-dihydro-1,7-naphthyridine-3-carboxamido)acetate, hydrochloric acid salt (0.16 g, 0.35 mmol, Example 117 (a)) and acetic anhydride (3.3 mL, 35 mmol) was added 4-dimethylaminopyridine (0.043 g, 0.35 mmol). After stirring at room temperature for 4 hours, the mixture was evaporated under reduced pressure. The residue was purified by silica gel column chromatography (gradient: 1-5% 2 M NH$_3$ in MeOH/DCM to give the title compound. MS (ESI, pos. ion) m/z: 459 [M+1].

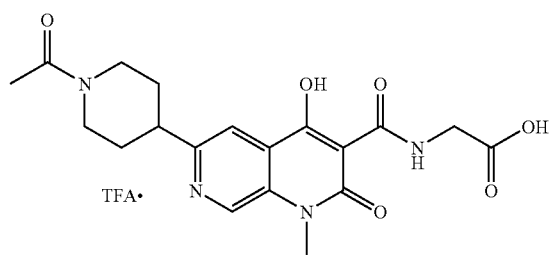

(b) 2-(6-(1-Acetylpiperidin-4-yl)-4-hydroxy-1-methyl-2-oxo-1,2-dihydro-1,7-naphthyridine-3-carboxamido)acetic acid, Trifluoroacetic acid salt. The title compound was prepared similarly to the procedure described for Example 1 (g), by treatment of tert-butyl 2-(6-(1-acetylpiperidin-4-yl)-4-hydroxy-1-methyl-2-oxo-1,2-dihydro-1,7-naphthyridine-3-carboxamido)acetate with TFA. MS (ESI, pos. ion) m/z: 403 [M+1]. $^1$H NMR (400 MHz, DMSO-$d_6$) δ ppm: 10.56-10.62 (s, 1 H), 9.01 (s, 1 H), 7.78 (s, 1 H), 4.45-4.63 (m, 1 H), 4.08-4.18 (m, 2 H), 3.84-4.00 (m, 1 H), 3.70 (s, 3 H), 3.01-3.21 (m, 1 H), 2.57-2.75 (m, 1 H), 2.04 (s, 3 H), 1.47-1.98 (m, 4 H).

Example 120

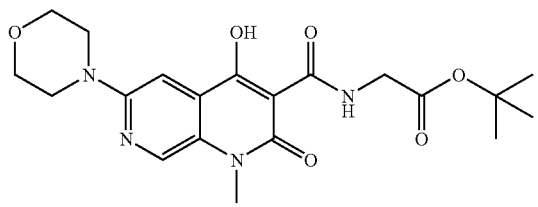

(a) tert-Butyl 2-(4-hydroxy-1-methyl-6-morpholino-2-oxo-1,2-dihydro-1,7-naphthyridine-3-carboxamido)acetate. A mixture of tert-butyl 2-(6-chloro-4-hydroxy-1-methyl-2-oxo-1,2-dihydro-1,7-naphthyridine-3-carboxamido)acetate (0.1 g, 272 μmol, Example 105 (i)), Pd(OAc)$_2$ (6 mg, 27 μmol) and BINAP (17 mg, 27 μmol) in dioxane (2 mL) was treated with morpholine (71 mg, 816 μmol) and butyllithium (2.5 M solution in hexanes, 326 μL, 816 μmol) with stirring at room temperature under nitrogen atmosphere. The mixture was stirred at 80° C. for 3 hours, left to reach room temperature, and filtered through a Celite® plug. The filter cake was washed with 10% MeOH/DCM. The combined filtrate was evaporated under reduced pressure, and the residue purified by silica gel column chromatography (gradient: 2-5% 2 M NH$_3$ in MeOH/DCM) to give the title compound.

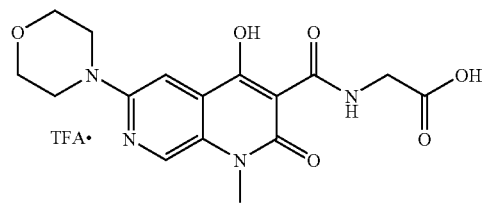

(b) 2-(4-Hydroxy-1-methyl-6-morpholino-2-oxo-1,2-dihydro-1,7-naphthyridine-3-carboxamido)acetic acid, Trifluoroacetic acid salt. The title compound was prepared similarly to the procedure described for Example 1 (g), by treatment of tert-butyl 2-(4-hydroxy-1-methyl-6-morpholino-2-oxo-1,2-dihydro-1,7-naphthyridine-3-carboxamido)acetate with TFA. MS (ESI, pos. ion) m/z: 363 [M+1]. $^1$H NMR (400 MHz, DMSO-$d_6$) ppm: 10.57-10.78 (m, 1 H), 8.63-8.74 (s, 1 H), 7.12-7.32 (s, 1 H), 4.06-4.27 (m, 1 H), 3.70-3.79 (m, 4 H), 3.65 (s, 3 H), 3.45 (m, 4 H).

Example 121

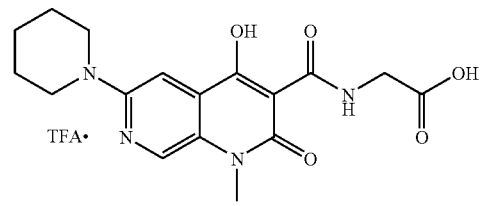

2-(4-Hydroxy-1-methyl-2-oxo-6-(piperidin-1-yl)-1,2-dihydro-1,7-naphthyridine-3-carboxamido)acetic acid, Trifluoroacetic acid salt. The title compound was prepared from tert-butyl 2-(6-chloro-4-hydroxy-1-methyl-2-oxo-1,2-dihydro-1,7-naphthyridine-3-carboxamido)acetate (Example 105 (i)) and piperidine analogously to the procedures described for the preparation of Example 120. MS (ESI, pos. ion) m/z: 360 [M+1]. $^1$H NMR (400 MHz, DMSO-$d_6$) δ ppm: 10.67 (s, 1 H), 8.65 (s, 1 H), 7.14 (s, 1 H), 4.14 (d, J=5.5 Hz, 2 H), 3.53 (s, 3 H), 1.60 (m, 10 H).

Example 122

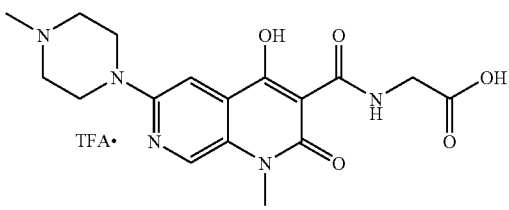

2-(4-Hydroxy-1-methyl-6-(4-methylpiperazin-1-yl)-2-oxo-1,2-dihydro-1,7-naphthyridine-3-carboxamido)acetic acid, Trifluoroacetic acid salt. The title compound was prepared from tert-butyl 2-(6-chloro-4-hydroxy-1-methyl-2-oxo-1,2-dihydro-1,7-naphthyridine-3-carboxamido)acetate (Example 105 (i)) and 1-methylpiperazine analogously to the procedures described for the preparation of Example 120. MS (ESI, pos. ion) m/z: 376 [M+1]. $^1$H NMR (400 MHz, CDCl$_3$) δ ppm: 8.52 (s, 1 H), 7.35 (s, 1 H), 4.20-4.23 (m, 2 H), 3.71 (s, 3 H), 3.38-3.41 (m, 8 H), 2.89 (s, 3 H).

Example 123

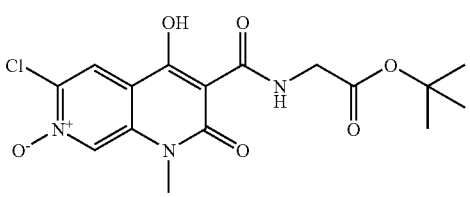

(a) tert-Butyl 2-(6-chloro-4-hydroxy-1-methyl-2-oxo-1,2-dihydro-1,7-naphthyridine-3-carboxamido)acetate, N-oxide. A mixture of tert-butyl 2-(6-chloro-4-hydroxy-1-methyl-2-oxo-1,2-dihydro-1,7-naphthyridine-3-carboxamido)acetate (0.68 g, 1.8 mmol, Example 105 (i)) and m-chloroperoxybenzoic acid (0.64 g, 3.7 mmol) in dichloroethane (80 mL) was refluxed for 2 hours. The reaction mixture was left to reach room temperature, diluted with DCM (100 mL), washed with saturated NaHCO$_3$ (20 mL), dried over anhydrous Na$_2$SO$_4$, and filtered. The filtrate was evaporated under reduced pressure, and the residue purified by silica gel column chromatography (gradient: 2-5% 2 M NH$_3$ in MeOH/DCM to give the title compound as a yellow solid. MS (ESI, pos. ion) m/z: 384 [M+1].

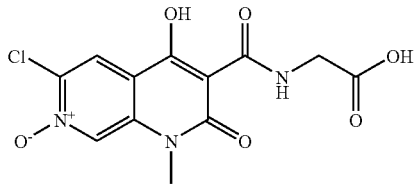

(b) 2-(6-Chloro-4-hydroxy-1-methyl-2-oxo-1,2-dihydro-1,7-naphthyridine-3-carboxamido)acetic acid, N-oxide. The title compound was prepared similarly to the procedure described for Example 1 (g), by treatment of tert-butyl 2-(6-chloro-4-hydroxy-1-methyl-2-oxo-1,2-dihydro-1,7-naphthyridine-3-carboxamido)acetate, N-oxide with TFA. MS (ESI, pos. ion) m/z: 363 [M+1]. $^1$H NMR (400 MHz, DMSO-$d_6$) δ ppm: 10.30 (s, 1 H), 8.96 (s, 1 H), 8.24 (s, 1 H), 4.14 (d, J=5.5 Hz, 2 H), 3.55 (s, 3 H).

Example 124

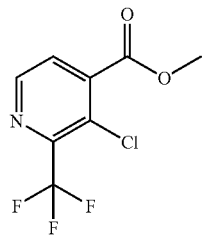

(a) Methyl 3-chloro-2-(trifluoromethyl)isonicotinate. To a solution of 3-chloro-2-(trifluoromethyl)isonicotinic acid (53.5 g, 238 mmol, prepared as described in Cottet, F.; Marull, M.; Mongin, F.; Espinosa, D.; Schlosser, M. *Synthesis,* 2004, 10, 1619-1624) in toluene (600 mL) and MeOH (400 mL) was added (trimethylsilyl)diazomethane (2 M solution in hexanes, 178 mL, 357 mmol) dropwise with stirring at room temperature. After the addition, the reaction mixture was stirred for 1 hour at room temperature, and was evaporated under reduced pressure. The oily residue was purified by silica gel column chromatography (50% EtOAc/hexanes) to afford the title compound as a pale-yellow oil. MS (ESI, pos. ion) m/z: 240 (M+1).

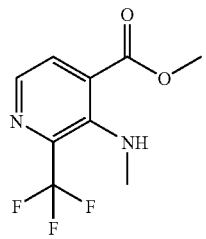

(b) Methyl 3-(methylamino)-2-(trifluoromethyl)isonicotinate. To a solution of methyl 3-chloro-2-(trifluoromethyl) isonicotinate (20 g, 83.7 mmol) in THF (116 mL) was added K$_2$CO$_3$ (34.7 g, 251 mmol). The mixture was stirred at room temperature for 10 minutes, and treated with 2 M solution of methylamine in THF (83.7 mL, 167 mmol). The vessel was sealed and heated at 60° C. overnight. The reaction mixture was left to reach room temperature and was filtered. The filtrate was evaporated under reduced pressure, and the residue was suspended in DCM (50 mL). The suspension was filtered, and the filtrate was evaporated under reduced pressure. The residue was purified by silica gel column chromatography (DCM) to give the title compound. MS (ESI, pos. ion) m/z: 235 (M+1).

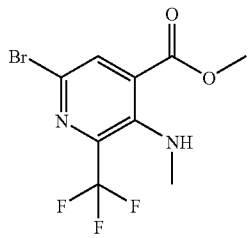

(c) Methyl 6-bromo-3-(methylamino)-2-(trifluoromethyl) isonicotinate. To a solution of methyl 3-(methylamino)-2-(trifluoromethyl)isonicotinate (3.48 g, 14.9 mmol) in MeCN (20 mL) was added N-bromosuccinimide (3.97 g, 22.3 mmol) and glacial acetic acid (0.08 mL, 1.5 mmol). The mixture was stirred at 50° C. for 24 hours, left to reach room temperature, diluted with EtOAc (150 mL), and washed with water (3×50 mL). The combined water phase was extracted with EtOAc (3×50 mL). The combined organic extracts were dried over MgSO$_4$, and filtered. The filtrate was evaporated under reduced pressure, and the residue dried in vacuo to give the title compound as a yellow/orange solid. MS (ESI, pos. ion) m/z: 313 (M+1).

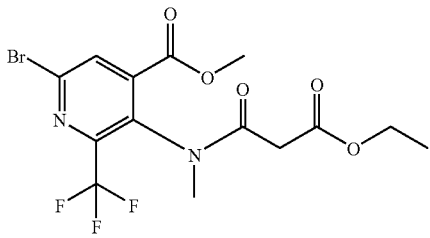

(d) Methyl 6-bromo-3-(3-ethoxy-N-methyl-3-oxopropanamido)-2-(trifluoromethyl)isonicotinate. To a mixture of methyl 6-bromo-3-(methylamino)-2-(trifluoromethyl)isonicotinate (4.52 g, 14.4 mmol) and K$_2$CO$_3$ (6.0 g, 43.2 mmol) in DCM (100 mL) was added ethyl malonyl chloride (5.6 mL, 43.2 mmol) dropwise with stirring at 80° C. The reaction mixture was stirred at 80° C. for 4 hours, and was cooled to room temperature. Additional ethyl malonyl chloride (5.6 mL, 43.2 mmol) was added to the reaction mixture and the stirring was continued for 20 minutes. The reaction mixture was washed with water (2×200 mL), and the combined aqueous phase was extracted with dichloroethane (2×100 mL). The combined dichloroethane extract was dried over MgSO$_4$, and filtered. The filtrate was evaporated under reduced pressure to give the crude title compound as an orange oil, which was used in the next step without further purification. MS (ESI, pos. ion) m/z: 427 (M+1).

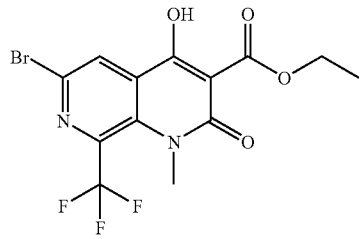

(e) Ethyl 6-bromo-4-hydroxy-1-methyl-2-oxo-8-(trifluoromethyl)-1,2-dihydro-1,7-naphthyridine-3-carboxylate. A 1 M solution of NaOEt was prepared by adding sodium metal (667 mg, 29 mmol) to EtOH (29.0 mL). A solution of the crude methyl 6-bromo-3-(3-ethoxy-N-methyl-3-oxopropanamido)-2-(trifluoromethyl)isonicotinate (assumed 14.4 mmol) in EtOH (10.0 mL) was added slowly to the 1 M sodium ethoxide solution with stirring at room temperature. After the addition, the reaction mixture was stirred for 1 hour, neutralized to pH=7 with 4 M HCl in dioxane, and concentrated to an orange gum. The gum was dissolved in aqueous sodium carbonate with heating, and the solution was acidified to pH=5 with 2 M HCl. The solution was stirred until white crystals appeared, and was acidified to pH=3 with 2 M HCl. The reaction mixture was filtered, and the filter cake was dried in vacuo for 72 hours to give the title compound as an off-white solid. MS (ESI, pos. ion) m/z: 395 (M+1). $^1$H-NMR (400 MHz, DMSO-d$_6$) δ ppm: 8.27 (s, 1 H); 4.28 (q, J=7.1 Hz, 2 H); 3.45 (d, J=2.2 Hz, 3 H); 1.27 (t, J=7.1 Hz, 3 H).

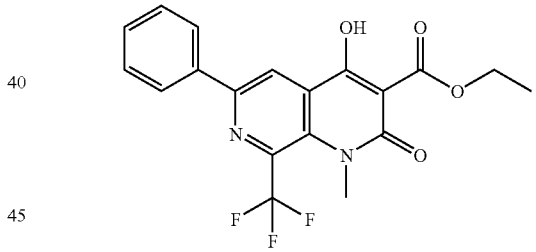

(f) Ethyl 4-hydroxy-1-methyl-2-oxo-6-phenyl-8-(trifluoromethyl)-1,2-dihydro-1,7-naphthyridine-3-carboxylate. A suspension of ethyl 6-bromo-4-hydroxy-1-methyl-2-oxo-8-(trifluoromethyl)-1,2-dihydro-1,7-naphthyridine-3-carboxylate (230 mg, 582 μmol), phenylboronic acid (106 mg, 873 μmol) and potassium carbonate (241 mg, 1746 μmol) in EtOH (5.8 mL) was treated with Pd$_2$(dba)$_3$ (53 mg, 58 μmol), and 2-dicyclohexylphosphino-2',4',6'-triisopropylbiphenyl (55 mg, 116 μmol) at room temperature under nitrogen atmosphere. The reaction mixture was heated to 80° C. for 3 hours, left to reach room temperature, and diluted with EtOAc (100 mL). The mixture was washed with saturated aqueous solution of NaHCO$_3$ (3×50 mL), dried over Na$_2$SO$_4$, and filtered. The filtrate was evaporated under reduced pressure and the residue purified by silica gel column chromatography (gradient: 0-30% EtOAc/hexanes) to give the title compound as a yellow solid. MS (ESI, pos. ion) m/z: 393 (M+1).

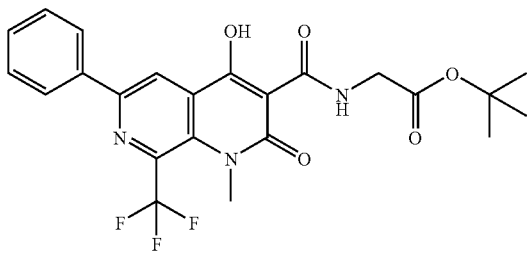

(g) tert-Butyl 2-(4-hydroxy-1-methyl-2-oxo-6-phenyl-8-(trifluoromethyl)-1,2-dihydro-1,7-naphthyridine-3-carboxamido)acetate. The title compound was prepared similarly to the procedure described for Example 1 (f) from ethyl 4-hydroxy-1-methyl-2-oxo-6-phenyl-8-(trifluoromethyl)-1,2-dihydro-1,7-naphthyridine-3-carboxylate. MS (ESI, pos. ion) m/z: 478 (M+1).

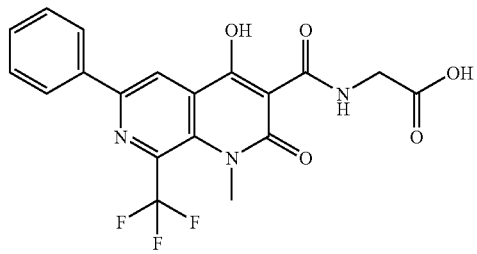

(h) 2-(4-Hydroxy-1-methyl-2-oxo-6-phenyl-8-(trifluoromethyl)-1,2-dihydro-1,7-naphthyridine-3-carboxamido) acetic acid. The title compound was prepared as an off-white solid, similarly to the procedure described for Example 1 (g), by treatment of tert-butyl 2-(4-hydroxy-1-methyl-2-oxo-6-phenyl-8-(trifluoromethyl)-1,2-dihydro-1,7-naphthyridine-3-carboxamido)acetate with TFA. MS (ESI, pos. ion) m/z: 422 (M+1). $^1$H NMR (400 MHz, DMSO-$d_6$) δ ppm: 8.57-8.69 (s, 1 H), 8.09-8.25 (m, 2 H), 7.43-7.64 (m, 3 H), 4.10-4.28 (m, 2 H), 3.61 (s, 3 H).

Example 125

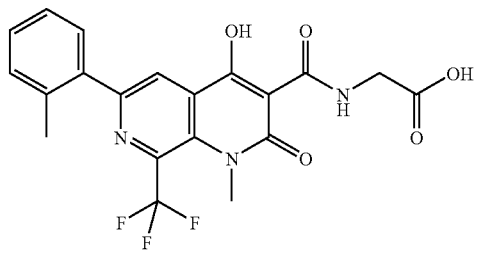

N-((4-Hydroxy-1-methyl-6-(2-methylphenyl)-2-oxo-8-(trifluoromethyl)-1,2-dihydro-1,7-naphthyridin-3-yl)carbonyl)glycine. The title compound was prepared similarly to the procedures described for Example 124 (f-h) from ethyl 6-bromo-4-hydroxy-1-methyl-2-oxo-8-(trifluoromethyl)-1,2-dihydro-1,7-naphthyridine-3-carboxylate (Example 124 (e)). MS (ESI, pos. ion) m/z: 436 (M+1). $^1$H NMR (400 MHz, DMSO-$d_6$) δ ppm: 8.28 (s, 1 H), 7.58 (d, J=7.2 Hz, 1 H), 7.38 (s, 3 H), 4.17 (d, J=5.5 Hz, 2 H), 2.43 (s, 3 H) 3.61 (s, 3 H).

Example 126

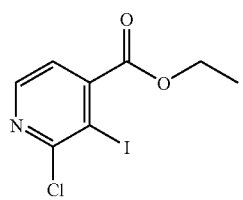

(a) Ethyl 2-chloro-3-iodoisonicotinate. To a solution of diisopropylamine (3 g, 28 mmol) in THF (50 mL) was added butyllithium (2.5 M solution in hexanes, 11.2 mL, 28 mmol) dropwise with stirring at 0° C. After the addition, the mixture was stirred for 30 minutes at 0° C., and was cooled to −78° C. A solution of ethyl 2-chloroisonicotinate (5.2 g, 28 mmol) in THF (20 mL) was added dropwise, and the mixture was stirred at −78° C. for 1.5 hours. To the reaction mixture was added dropwise a solution of iodine (7 g, 28 mmol) in THF (20 mL) in 10 minutes, and the stirring was continued for 1 hour at −78° C. The reaction mixture was quenched with saturated $Na_2S_2O_3$ (20 mL), left to reach room temperature, and extracted with EtOAc (3×50 mL). The combined extract was washed with brine (20 mL), dried over anhydrous $Na_2SO_4$, and filtered. The filtrate was evaporated under reduced pressure, and the residue was purified by silica gel column chromatography (gradient: 10-20% EtOAc/hexanes) to give the title compound as a yellow oil. MS (ESI, pos. ion) m/z: 312 (M+1).

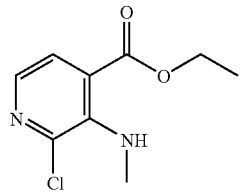

(b) Ethyl 2-chloro-3-(methylamino)isonicotinate. A mixture of ethyl 2-chloro-3-iodoisonicotinate (0.3 g, 1.0 mmol), $K_2CO_3$ (0.1 g, 10.0 mmol) and methylamine (2 M solution in THF, 1.5 mL, 3 mmol) in MeCN (5 mL) was heated at 100° C. in a microwave synthesizer for 20 minutes. The reaction mixture was diluted with EtOAc (100 mL), washed with saturated $NaHCO_3$ (20 mL), dried over anhydrous $Na_2SO_4$, and filtered. The filtrate was evaporated under reduced pressure and the residue purified by silica gel column chromatography (gradient: 10-20% EtOAc/hexanes) to give the title compound as yellow oil. MS (ESI, pos. ion) m/z: 215 (M+1).

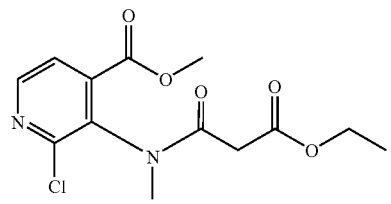

(c) Ethyl 2-chloro-3-(3-ethoxy-N-methyl-3-oxopropanamido)isonicotinate. To a mixture of 2-chloro-3-(methylamino)isonicotinate (0.1 g, 466 μmol), and K$_2$CO$_3$ (129 mg, 932 μmol) in THF (10 mL) was added ethyl 3-chloro-3-oxopropanoate (140 mg, 932 μmol) dropwise with stirring at room temperature. After the addition, the reaction mixture was stirred for 2 hours at room temperature and was filtered. The filter cake was washed with DCM (20 mL), and the combined filtrate was evaporated under reduced pressure, and dried in vacuo to give the title compound which was used in the next step without additional purification.

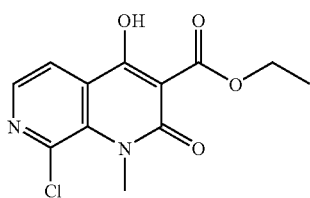

(d) Ethyl 8-chloro-4-hydroxy-1-methyl-2-oxo-1,2-dihydro-1,7-naphthyridine-3-carboxylate. The crude product from step (c) above was treated with NaOEt (prepared by dissolving 0.1 g Na in EtOH (5 mL)) and stirred at room temperature for 15 hours. The reaction mixture was diluted with H$_2$O (10 mL), neutralized to pH=7 with 1N HCl, and extracted with DCM (3×30 mL). The combined extract was washed with saturated NH$_4$Cl (20 mL), dried over anhydrous Na$_2$SO$_4$, and filtered. The filtrate was evaporated under reduced pressure and the residue purified by silica gel column chromatography (gradient: 10-50% EtOAc/hexanes) to give the title compound as a pale-yellow solid. MS (ESI, pos. ion) m/z: 283 (M+1).

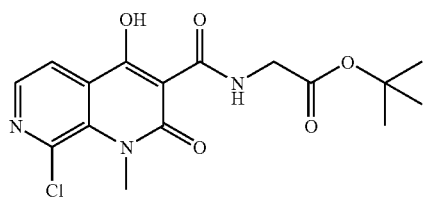

(e) tert-Butyl 2-(8-chloro-4-hydroxy-1-methyl-2-oxo-1,2-dihydro-1,7-naphthyridine-3-carboxamido)acetate. The title compound was prepared as a pale-yellow solid, similarly to the procedure described for Example 1 (f), by treatment of ethyl 8-chloro-4-hydroxy-1-methyl-2-oxo-1,2-dihydro-1,7-naphthyridine-3-carboxylate with tert-butyl 2-aminoacetate hydrochloride. MS (ESI, pos. ion) m/z: 368 (M+1).

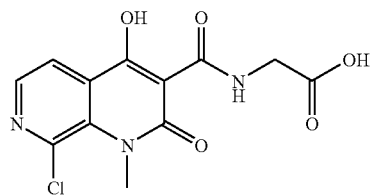

(f) 2-(8-Chloro-4-hydroxy-1-methyl-2-oxo-1,2-dihydro-1,7-naphthyridine-3-carboxamido)acetic acid. The title compound was prepared as an off-white solid, similarly to the procedure described for Example 1 (g), by treatment of tert-butyl 2-(8-chloro-4-hydroxy-1-methyl-2-oxo-1,2-dihydro-1,7-naphthyridine-3-carboxamido)acetate with TFA. MS (ESI, pos. ion) m/z: 312 (M+1). $^1$H NMR (400 MHz, DMSO-d$_6$) δ ppm: 8.35 (d, J=5.1 Hz, 1 H), 7.97 (d, J=4.9 Hz, 1 H), 4.12-4.18 (m, 2 H), 3.82 (s, 3 H).

Example 127

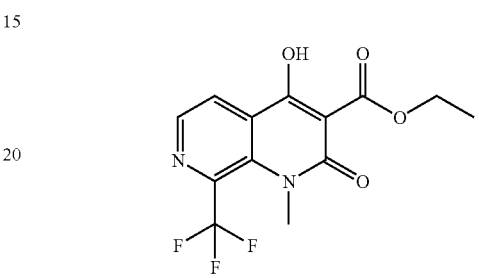

(a) Ethyl 4-hydroxy-1-methyl-2-oxo-8-(trifluoromethyl)-1,2-dihydro-1,7-naphthyridine-3-carboxylate. A mixture of ethyl 6-bromo-4-hydroxy-1-methyl-2-oxo-8-(trifluoromethyl)-1,2-dihydro-1,7-naphthyridine-3-carboxylate (0.30 g, 0.76 mmol, Example 124 (e)) and NaOAc (0.093 g, 1.1 mmol) in MeOH (20 mL) was treated with 10% Pd/C (0.24 g) under nitrogen atmosphere. The reaction vessel was degassed and backfilled with hydrogen (3×), and the mixture was stirred at 23° C. for 2 hours under hydrogen atmosphere. The reaction mixture was filtered from the catalyst through a pad of Celite®, and the filter cake was washed with MeOH (20 mL). The combined filtrate was evaporated under reduced pressure, and the residue purified by silica gel column chromatography (gradient: 10-30% 2 M NH$_3$ in MeOH/DCM) to give the title compound as yellow solid. MS (ESI, pos. ion) m/z: 317 [M+1].

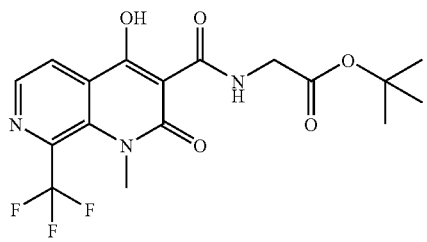

(b) tert-Butyl 2-(4-hydroxy-1-methyl-2-oxo-8-(trifluoromethyl)-1,2-dihydro-1,7-naphthyridine-3-carboxamido)acetate. The title compound was prepared as a pale-yellow solid, similarly to the procedure described for Example 1 (f), by treatment of ethyl 4-hydroxy-1-methyl-2-oxo-8-(trifluo romethyl)-1,2-dihydro-1,7-naphthyridine-3-carboxylate with tert-butyl 2-aminoacetate hydrochloride.

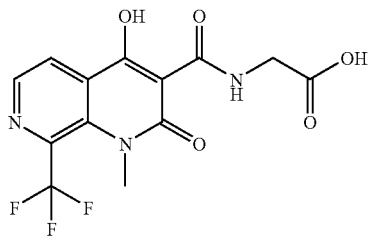

(c) 2-(4-Hydroxy-1-methyl-2-oxo-8-(trifluoromethyl)-1,2-dihydro-1,7-naphthyridine-3-carboxamido)acetic acid. The title compound was prepared similarly to the procedure described for Example 1 (g) by treatment of tert-butyl 2-(4-hydroxy-1-methyl-2-oxo-8-(trifluoromethyl)-1,2-dihydro-1,7-naphthyridine-3-carboxamido)acetate with TFA. MS (ESI, pos. ion) m/z: 346 (M+1). $^1$H NMR (400 MHz, DMSO-$d_6$) δ ppm: 10.29 (s, 1 H), 8.67 (d, J=4.9 Hz, 1 H), 8.24 (d, J=4.7 Hz, 1 H), 4.16 (d, J=5.7 Hz, 2 H), 3.57 (s, 3 H).

Example 128

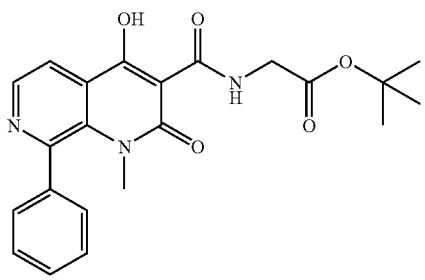

(a) tert-Butyl 2-(4-hydroxy-1-methyl-2-oxo-8-phenyl-1,2-dihydro-1,7-naphthyridine-3-carboxamido)acetate. The title compound was prepared similarly to the procedure described for Example 12 (a) from tert-butyl 2-(8-chloro-4-hydroxy-1-methyl-2-oxo-1,2-dihydro-1,7-naphthyridine-3-carboxamido)acetate (Example 126 (e)) and phenylboronic acid.

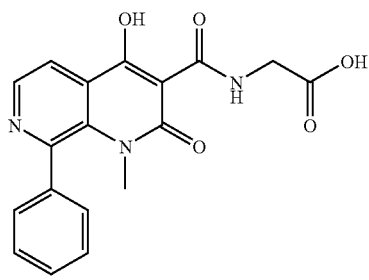

(b) 2-(4-Hydroxy-1-methyl-2-oxo-8-phenyl-1,2-dihydro-1,7-naphthyridine-3-carboxamido)acetic acid. The title compound was prepared similarly to the procedure described for Example 1 (g) by treatment of tert-butyl 2-(4-hydroxy-1-methyl-2-oxo-8-phenyl-1,2-dihydro-1,7-naphthyridine-3-carboxamido)acetate with TFA. MS (ESI, pos. ion) m/z: 354 (M+1). $^1$H NMR (400 MHz, DMSO-$d_6$) δ ppm: 10.37-10.54 (m, 1 H), 8.51-8.69 (m, 1 H), 7.82-8.02 (m, 1 H), 7.40-7.64 (m, 5 H), 4.09-4.23 (m, 1 H), 2.96 (s, 3 H).

Example 129

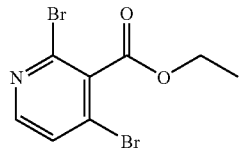

(a) Ethyl 2,4-dibromonicotinate. The regioselectivity of this transformation is similar to the known ortho-lithiation reactions of 2-halo-3-bromopyridines with BuLi or LDA, with subsequent halogen migration to the 4-position (see Rocca, C., et al. *J. Org. Chem.* 1993, 58, 7832-7838, and the references cited therein). To a solution of diisopropylamine (2 g, 22 mmol) in THF (50 mL) was added butyllithium (2.5 M solution in hexanes, 9 mL, 22 mmol) dropwise with stirring at 0° C. After the addition, the mixture was stirred for 30 minutes at 0° C. then was cooled to −78° C. A solution of 2,3-dibromopyridine (5 g, 21 mmol) in THF (20 mL) was added dropwise over 20 minutes, and the mixture was stirred at −78° C. for another 20 minutes. The reaction mixture was then treated with ethyl cyanoformate (3 g, 25 mmol), stirred at −78° C. for 2 hours, and was left to warm up to 0° C. The mixture was quenched with saturated NH$_4$Cl (20 mL), stirred for 10 minutes, and extracted with EtOAc (3×50 mL). The combined extract was washed with brine (20 mL), dried over anhydrous Na$_2$SO$_4$, and filtered. The filtrate was evaporated under reduced pressure, and the residue purified by silica gel column chromatography (20% EtOAc/hexanes) to give the title compound as colorless oil. (ESI, pos. ion) m/z: 309 (M+1). The structure of the title compound was confirmed by 2D-NOESY $^1$H-NMR analysis of the aminomethyl derivative described in step (b).

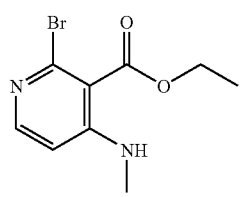

(b) Ethyl 2-bromo-4-(methylamino)nicotinate. A solution of ethyl 2,4-dibromonicotinate (0.25 g, 809 µmol) in THF (5 mL) was treated with methylamine (2 M solution in THF, 607 µl, 1214 µmol), and stirred at room temperature for 4 hours. The reaction mixture was diluted with DCM (100 mL), washed with saturated NaHCO$_3$ (20 mL), dried over anhydrous Na$_2$SO$_4$, and filtered. The filtrate was evaporated under reduced pressure and the residue purified by silica gel column chromatography (gradient: 10-20% EtOAc/hexanes) to give the title compound. MS (ESI, pos. ion) m/z: 259; 261 (M+1).

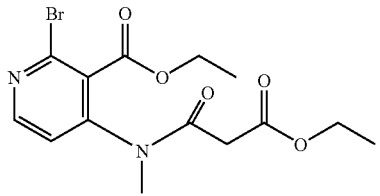

(c) Ethyl 2-bromo-4-(3-ethoxy-N-methyl-3-oxopropanamido)nicotinate. The title compound was prepared similarly to the procedures described for Example 126 (c) from ethyl 2-bromo-4-(methylamino)nicotinate (100 mg, 386 μmol) and ethyl malonoyl chloride. MS (ESI, pos. ion) m/z: 373; 375 (M+1).

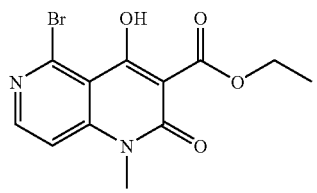

(d) Ethyl 5-bromo-4-hydroxy-1-methyl-2-oxo-1,2-dihydro-1,6-naphthyridine-3-carboxylate. The title compound was prepared similarly to the procedure described for Example 126 (d) by treatment of ethyl 2-bromo-4-(3-ethoxy-N-methyl-3-oxopropanamido)nicotinate with NaOEt, and was isolated as white solid. MS (ESI, pos. ion) m/z: 327; 329 (M+1).

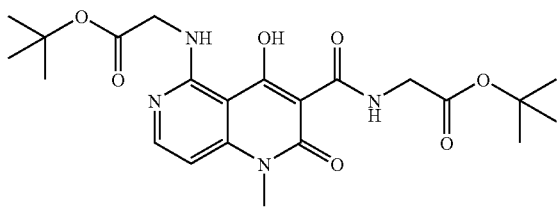

(e) tert-Butyl 2-(4-hydroxy-1-methyl-2-oxo-3-((tert-butyloxycarbonylmethyl)carbamoyl)-1,2-dihydro-1,6-naphthyridin-5-ylamino)acetate. A mixture of ethyl 5-bromo-4-hydroxy-1-methyl-2-oxo-1,2-dihydro-1,6-naphthyridine-3-carboxylate (45 mg, 138 μmol), and glycine tert-butyl ester hydrochloride (70 mg, 412 μmol) in dioxane (5 mL) was treated with N,N'-diisopropylethylamine (99 μL, 550 μmol), and heated at 80° C. with stirring for 15 hours. The reaction mixture was cooled to room temperature, diluted with H$_2$O (100 mL), neutralized with 10% HCl to pH=7, and extracted with DCM (3×50 mL). The combined extract was washed with H$_2$O (20 mL) and brine (20 mL), dried over anhydrous Na$_2$SO$_4$, and filtered. The filtrate was evaporated under reduced pressure and the residue purified by silica gel column chromatography (gradient: 10-15% EtOAc/hexanes) to give the title compound as a pale-yellow solid. MS (ESI, pos. ion) m/z: 463 (M+1).

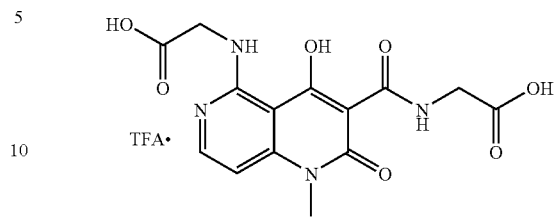

(f) 2-{4-Hydroxy-1-methyl-2-oxo-3-[(carboxymethyl)carbamoyl]-1,2-dihydro-1,6-naphthyridin-5-ylamino}acetic acid, Trifluoroacetic acid salt. The title compound was prepared similarly to the procedure described for Example 1 (g) by treatment of tert-butyl 2-(4-hydroxy-1-methyl-2-oxo-3-((tert-butyloxycarbonylmethyl)carbamoyl)-1,2-dihydro-1,6-naphthyridin-5-ylamino)acetate with TFA. MS (ESI, pos. ion) m/z: 351 (M+1). $^1$H NMR (400 MHz, DMSO-d$_6$) δ ppm: 10.49-10.62 (m, 1 H), 8.44-8.59 (m, 1 H), 8.15 (d, J=6.1 Hz, 1 H), 6.68 (d, J=5.9 Hz, 1 H), 4.16 (d, J=11.0 Hz, 4 H), 3.51 (s, 3 H).

Example 130

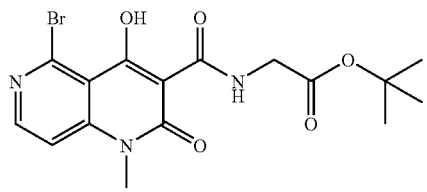

(a) tert-Butyl 2-(5-bromo-4-hydroxy-1-methyl-2-oxo-1,2-dihydro-1,6-naphthyridine-3-carboxamido)acetate. The title compound was prepared similarly to the procedure described for Example 1 (f), by treatment of ethyl 5-bromo-4-hydroxy-1-methyl-2-oxo-1,2-dihydro-1,6-naphthyridine-3-carboxylate (Example 129 (d)) with tert-butyl 2-aminoacetate, hydrochloride.

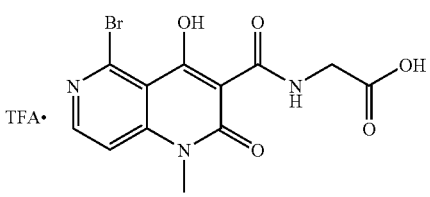

(b) 2-(5-Bromo-4-hydroxy-1-methyl-2-oxo-1,2-dihydro-1,6-naphthyridine-3-carboxamido)acetic acid, Trifluoroacetic acid salt. The title compound was prepared similarly to the procedure described for Example 1 (g) by treatment of tert-butyl 2-(5-bromo-4-hydroxy-1-methyl-2-oxo-1,2-dihydro-1,6-naphthyridine-3-carboxamido)acetate with TFA. MS (ESI, pos. ion) m/z: 356, 358 (M+1). $^1$H NMR (400 MHz, DMSO- $d_6$) δ ppm: 10.59 (m, 1 H), 8.41 (d, J=4.0 Hz, 1 H), 7.27 (d, J=8.0 Hz, 1 H), 4.25 (m, 2 H), 3.7 (s, 3 H).

Example 131

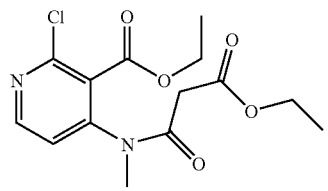

(a) Ethyl 2-chloro-4-(3-ethoxy-N-methyl-3-oxopropanamido)nicotinate. The title compound was obtained as a by-product in the reaction described in Example 128 (c). MS (ESI, pos. ion) m/z: 329 (M+1).

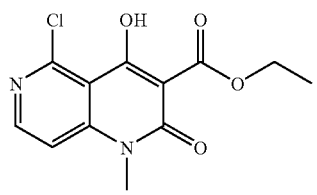

(b) Ethyl 5-chloro-4-hydroxy-1-methyl-2-oxo-1,2-dihydro-1,6-naphthyridine-3-carboxylate. The title compound was prepared similarly to the procedure described for Example 126 (d) by treatment of ethyl 2-chloro-4-(3-ethoxy-N-methyl-3-oxopropanamido)nicotinate with NaOEt. MS (ESI, pos. ion) m/z: 283 (M+1).

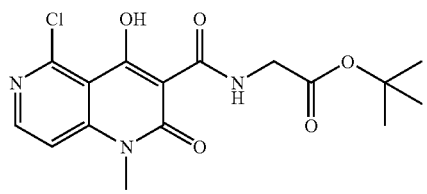

(c) tert-Butyl 2-(5-chloro-4-hydroxy-1-methyl-2-oxo-1,2-dihydro-1,6-naphthyridine-3-carboxamido)acetate. The title compound was prepared similarly to the procedure described for Example 1 (f), by treatment of ethyl 5-chloro-4-hydroxy-1-methyl-2-oxo-1,2-dihydro-1,6-naphthyridine-3-carboxylate with tert-butyl 2-aminoacetate, hydrochloride. MS (ESI, pos. ion) m/z: 368 (M+1).

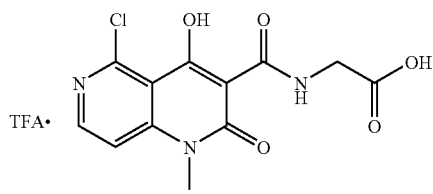

(d) 2-(5-Chloro-4-hydroxy-1-methyl-2-oxo-1,2-dihydro-1,6-naphthyridine-3-carboxamido)acetic acid. The title compound was prepared similarly to the procedure described for Example 1 (g) by treatment of tert-butyl 2-(5-chloro-4-hydroxy-1-methyl-2-oxo-1,2-dihydro-1,6-naphthyridine-3-carboxamido)acetate with TFA. MS (ESI, pos. ion) m/z: 312 (M+1). $^1$H NMR (400 MHz, DMSO-$d_6$) δ ppm: 10.59 (m, 1 H), 8.46 (d, J=8.0 Hz, 1 H), 7.27 (d, J=8.0 Hz, 1 H), 4.25 (m, 2 H), 3.71 (s, 3 H).

Example 132

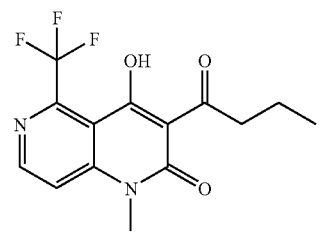

(a) Ethyl 4-hydroxy-1-methyl-2-oxo-5-(trifluoromethyl)-1,2-dihydro-1,6-naphthyridine-3-carboxylate. A mixture of KF (57 mg, 978 μmol) and copper(I) iodide (186 mg, 978 μmol) was heated by open flame in vacuo until a greenish homogenous liquid was obtained. The reaction mixture was cooled to room temperature and then treated with ethyl 5-bromo-4-hydroxy-1-methyl-2-oxo-1,2-dihydro-1,6-naphthyridine-3-carboxylate (80 mg, 245 μmol, Example 129 (d)) and (trifluoromethyl)trimethylsilane (139 μL, 978 μmol), and stirred at room temperature for 3 hours. The mixture was filtered through a plug of Celite®, and the filter cake was washed with 10% MeOH/DCM (50 mL). The combined filtrate was evaporated under reduced pressure, and the residue was purified by silica gel column chromatography (50% EtOAc/hexanes) to give the title compound as a yellow solid. MS (ESI, pos. ion) m/z: 317 (M+1).

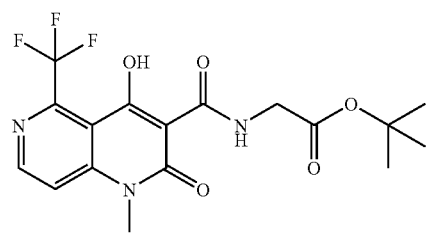

(b) tert-Butyl 2-(4-hydroxy-1-methyl-2-oxo-5-(trifluoromethyl)-1,2-dihydro-1,6-naphthyridine-3-carboxamido)acetate. The title compound was prepared similarly to the procedure described for Example 1 (f), by treatment of ethyl 4-hydroxy-1-methyl-2-oxo-5-(trifluoromethyl)-1,2-dihydro-1,6-naphthyridine-3-carboxylate with tert-butyl 2-aminoacetate hydrochloride. MS (ESI, pos. ion) m/z: 346 (M+1).

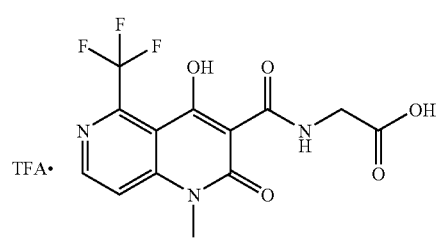

(c) 2-(4-Hydroxy-1-methyl-2-oxo-5-(trifluoromethyl)-1,2-dihydro-1,6-naphthyridine-3-carboxamido)acetic acid, Trifluoroacetic acid salt. The title compound was prepared similarly to the procedure described for Example 1 (g) by treatment of tert-butyl 2-(4-hydroxy-1-methyl-2-oxo-5-(trifluoromethyl)-1,2-dihydro-1,6-naphthyridine-3-carboxamido)acetate with TFA. MS (ESI, pos. ion) m/z: 402 (M+1). $^1$H NMR (400 MHz, DMSO-$d_6$) δ ppm: 10.59 (m, 1 H), 8.81 (d, J=8.0 Hz, 1 H), 7.93 (d, J=8.0 Hz, 1 H), 4.16 (m, 2 H), 3.79 (s, 3 H).

Example 133

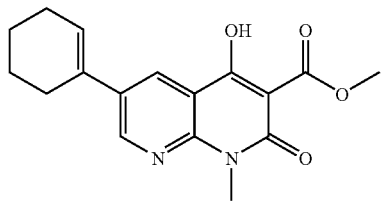

(a) Methyl 6-cyclohexenyl-4-hydroxy-1-methyl-2-oxo-1,2-dihydro-1,8-naphthyridine-3-carboxylate. Methyl 4-hydroxy-6-iodo-1-methyl-2-oxo-1,2-dihydro-1,8-naphthyridine-3-carboxylate (0.200 g, 0.555 mmol, Example 26 (f)), 2-cyclohexenyl-4,4,5,5-tetramethyl-1,3,2-dioxaborolane (0.231 g, 1.11 mmol), sodium carbonate (0.833 mL, 1.67 mmol) and Pd(0)(PPh$_3$)$_4$ (0.128 g, 0.111 mmol) were combined in DMF (15 mL) and water (2 mL). The tube was flushed with argon and sealed. The reaction was heated at 140° C. for 15 minutes in a microwave (Personal Chemistry 300 W). The mixture was cooled to room temperature, diluted with EtOAc (100 mL) and washed with water (2×50 mL). The aqueous layer was acidified to pH 3 with concentrated HCl and extracted with DCM (2×50 mL). The DCM solution was washed with brine, dried over Magnesium sulfate, concentrated and dried in vacuo. The product was purified by silica flash column chromatography (0-100% DCM in hexane), concentrated, and dried in vacuo to give methyl 6-cyclohexenyl-4-hydroxy-1-methyl-2-oxo-1,2-dihydro-1,8-naphthyridine-3-carboxylate (0.103 g, 59.0% yield). LC/MS: M+H=315.2. C$_{17}$H$_{18}$N$_2$O$_4$. MW=314.34. $^1$H NMR (300 MHz, DMSO-$d_6$) δ ppm 8.84 (1 H, d, J=2.3 Hz), 8.30 (1 H, d, J=2.3 Hz), 7.53-7.70 (1 H, m), 6.35 (1 H, t, J=3.4 Hz), 3.83 (3 H, s), 3.60 (3 H, s), 2.39-2.46 (2 H, m), 2.16-2.26 (2 H, m), 1.71-1.81 (2 H, m), 1.64 (2 H, d, J=3.7 Hz).

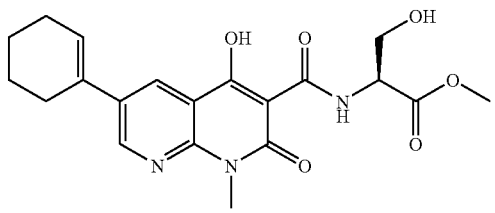

(b) (S)-methyl 2-(6-cyclohexenyl-4-hydroxy-1-methyl-2-oxo-1,2-dihydro-1,8-naphthyridine-3-carboxamido)-3-hydroxypropanoate. A mixture of 1-serine methyl ester hydrochloride (0.619 g, 3.98 mmol), methyl 6-cyclohexenyl-4-hydroxy-1-methyl-2-oxo-1,2-dihydro-1,8-naphthyridine-3-carboxylate (0.250 g, 0.795 mmol) and triethylamine (g, mmol) in 1,4-dioxane (7 mL) was heated at 120° C. for 14 hours. The mixture was concentrated in vacuo, treated with DCM (50 mL) and filtered. The residue washed with MeOH (2×25 mL), and the combined filtrate was concentrated in vacuo. The product was purified by silica flash column chromatography (0-100% EtOAc in hexane), concentrated and dried in vacuo to give (S)-methyl 2-(6-cyclohexenyl-4-hydroxy-1-methyl-2-oxo-1,2-dihydro-1,8-naphthyridine-3-carboxamido)-3-hydroxypropanoate (0.0995 g, 31.2% yield). LC/MS: M+H=402.2. C$_{20}$H$_{23}$N$_3$O$_6$. MW=401.41. $^1$H NMR (400 MHz, DMSO-$d_6$) δ ppm 10.80 (1 H, d, J=7.4 Hz), 8.94 (1 H, d, J=2.3 Hz), 8.29 (1 H, d, J=2.3 Hz), 6.40 (1 H, br. s.), 5.40 (1 H, t, J=5.1 Hz), 4.64-4.71 (1 H, m), 3.88-3.96 (1 H, m), 3.73-3.80 (1 H, m), 3.71 (3 H, s), 3.70 (3 H, s), 2.41-2.48 (2 H, m), 2.19-2.27 (2 H, m), 1.72-1.82 (2 H, m), 1.59-1.68 (2 H, m).

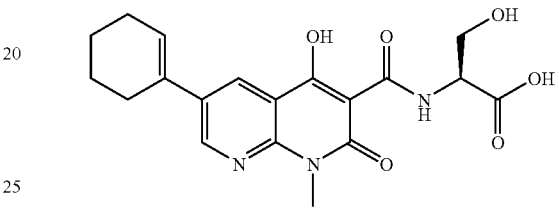

(c) (S)-2-(6-cyclohexenyl-4-hydroxy-1-methyl-2-oxo-1,2-dihydro-1,8-naphthyridine-3-carboxamido)-3-hydroxypropanoic acid. (S)-methyl 2-(6-cyclohexenyl-4-hydroxy-1-methyl-2-oxo-1,2-dihydro-1,8-naphthyridine-3-carboxamido)-3-hydroxypropanoate (0.0995 g, 0.248 mmol) was dissolved in THF (5 mL) in a 100 mL round bottom flask. 1 N aqueous sodium hydroxide (2.50 mL, 2.50 mmol) was added, and the mixture was stirred at 25° C. for 14 hours. The mixture was then diluted with water (30 mL) and extracted with EtOAc (2×25 mL). The aqueous solution was made acidic with 5 N HCl(aq) and a precipitate formed. The precipitate was collected by filtration and washed with Et$_2$O. The collected product was dissolved in MeOH, concentrated and dried in vacuo to give (S)-2-(6-cyclohexenyl-4-hydroxy-1-methyl-2-oxo-1,2-dihydro-1,8-naphthyridine-3-carboxamido)-3-hydroxypropanoic acid (0.065 g, 67.7% yield). LC/MS: M+H=388.1. C$_{19}$H$_{21}$N$_3$O$_6$. MW=387.39. $^1$H NMR (300 MHz, DMSO-$d_6$) δ ppm 13.07 (1 H, s), 10.75 (1 H, d, J=7.7 Hz), 8.94 (1 H, d, J=2.3 Hz), 8.29 (1 H, d, J=2.3 Hz), 6.40 (1 H, t, J=3.7 Hz), 5.33 (1 H, s), 4.52-4.61 (1 H, m), 3.87-3.97 (1 H, m), 3.73-3.84 (1 H, m), 3.64-3.73 (3 H, m), 2.39-2.47 (2 H, m), 2.16-2.30 (2 H, m), 1.56-1.84 (4 H, m).

The following are examples of methods that may be used to quantitate HIF PHD activity and the inhibition of HIF PHD activity by compounds of the present invention.

Expression, Purification and Europium Labeling of VCB and Design of an Eu-VCB based TR-FRET Assay for the Detection of Hydroxyprolyl HIF1α Peptides The VCB complex is defined as the Von Hippel-Lindau protein (pVHL), elongin B and elongin C heterotrimeric complex. VCB specifically binds to hydroxyproline residues of HIF1α, initiating polyubiquitinylation of HIF1α and its subsequent proteolytic destruction. In the absence of prolyl hydroxylase activity, VCB does not bind unmodified HIF1α. The VCB complex was expressed in *E. coli* and purified from the soluble fraction. The amino acid sequences of the three protein components are as follows:

VHL (Amino Acids 54-213)
(SEQ ID NO: 1)
MHHHHHHEAGRPRPVLRSVNSREPSQVIFCNRSPRVVLPVWLNFDGEPQP

YPTLPPGTGRRIHSYRGHLWLFRDAGTHDGLLVNQTELFVPSLNVDGQPI

FANITLPVYTLKERCLQVVRSLVKPENYRRLDIVRSLYEDLEDHPNVQKD

LERLTQERIAHQRMGD

ElonginB
(SEQ ID NO: 2)
MDVFLMIRRHKTTIFTDAKESSTVFELKRIVEGILKRPPDEQRLYKDDQL

LDDGKTLGECGFTSQTARPQAPATVGLAFRADDTFEALCIEPFSSPPELP

DVMKPQDSGSSANEQAVQ*

ElonginC (Amino Acids 17-112)
(SEQ ID NO: 3)
MYVKLISSDGHEFIVKREHALTSGTIKAMLSGPGQFAENETNEVNFREIP

SHVLSKVCMYFTYKVRYTNSSTEIPEFPIAPEIALELLMAANFLDC

The N-terminus of VHL contains a six histidine affinity tag for purification purposes.

A VCB-based assay allows a highly sensitive and direct measurement of enzymatic product formation (HIF1α protein or fragments thereof containing a hydroxylated proline residue) and is suitable for high throughput screening.

For expression in *E. coli*, VHL 54-213 was cloned into pAMG21 (Plux promoter) between the NdeI-XhoI site. Immediately downstream of this is the ElonginC gene cloned into the XhoI site to SacII. There is a 13 bp spacer between the stop codon of VHL and the initiating codon of ElonginC. The expression plasmid pAMG21 is a 6118 base pair plasmid that was derived from the expression vector pCFM1656 (ATCC #69576), which in turn can be derived from the expression vector system described in U.S. Pat. No. 4,710,473. This design allows for chemical rather than thermal induction of protein expression by substitution of the promoter region, replacing a synthetic bacteriophage lambda pl promoter with a DNA segment containing the LuxR gene and the LuxPR promoter, and affords regulation of expression by the plasmid-encoded LuxR protein, thereby allowing any *E. coli* strain to serve as host.

ElonginB was cloned into pTA2 (pACYC184.1 based vector) under the control of a Lac promoter. Competent *E. coli* cells were transformed with the pAMG21-VHL-ElonginC construct. These *E. coli* cells were rendered competent again prior to transformation with the pTA2-elonginB construct to produce the final *E. coli* strain containing both plasmid constructs. Induction of protein expression was initiated by the addition of IPTG and N-(3-oxo-hexanoyl)-homoserine lactone (HSL) at 30° C.

Bacterial cells were lysed by a microfluidizer in aqueous buffer of pH 8.0 and the soluble fraction was separated by centrifugation. The soluble *E. coli* fraction was subjected to Nickel-NTA chelating chromatography to utilize the six histidine affinity tag located on the pVHL construct. The pooled fractions from the nickel column were applied to a Superdex 200 size exclusion chromatography (SEC) column. The protein eluted as a monomer on SEC, indicating that the three protein components formed a complex in solution. The fractions from the SEC column were pooled and applied to a Q Sepharose anion exchange column for final purification. The purified complex was visualized by SDS-PAGE and the identities of the three protein components were confirmed by N-terminal amino acid sequencing.

Purified VCB was exchanged into 50 mM sodium carbonate buffer pH 9.2 and labeled with a europium chelate overnight. LANCE™ europium chelate (PerkinElmer, Inc; Eu-W1024ITC chelate; catalog number is AD0013) was used to label the lysine residues of the VCB complex. The chelate contains an isothiocyanate reactive group that specifically labels proteins on lysine residues (there are fifteen lysine residues in the VCB protein complex). The resulting europylated VCB was purified by desalting columns and quantitated by standard means. The labeling yield was determined to be 6.6 europium groups per one VCB complex.

Two peptides were produced by SynPep, Inc.: a hydroxyproline modified peptide and an unmodified control peptide. VCB was expected to specifically bind to the hydroxyproline modified peptide (a mimic of enzymatic hydroxylation by prolyl hydroxylase). VCB was not expected to bind to the unmodified peptide. Both peptides were produced with a biotin group at the N-terminus to allow for binding by the streptavidin-labeled fluorescent acceptor allophycocyanin (streptavidin APC; Prozyme, Inc.).

The sequence of the custom synthesized HIF1α peptides (amino acids 556-575, with methionine residues replaced with alanine residues to prevent oxidation) were as follows:

(unmodified)
(SEQ ID NO: 4)
Biotin-DLDLEALAPYIPADDDFQLR-CONH₂

(modified)
(SEQ ID NO: 5)
Biotin-DLDLEALA[hyP]YIPADDDFQLR-CONH₂

The peptides were purchased from SynPep as lyophilized solids and were suspended in DMSO for experimental use. The peptides were quantitated according to their absorbance at 280 nm.

Experiments were conducted in 96 well Costar polystyrene plates. Biotinylated peptides and europylated VCB were suspended in the following buffer: 100 mM HEPES 7.5, 0.1 M NaCl, 0.1% BSA and 0.05% Tween 20. The reagents were allowed to reach equilibrium by shaking for 1 hour before the plates were read on the Discovery Instrument (Packard). The data output is the ratio of the 665 nm and 620 nm emission signal resulting from the 320 nm excitation.

As shown in FIG. 1, the specific interaction of europylated VCB with the hydroxyproline modified HIF1α peptide coupled to streptavidin APC generated a fluorescence signal detectable over the background signal. These results demonstrate a fluorescence signal generated by the specific interaction of Eu-VCB with hyp-HIF1α peptide. Each bar represents the data from a single well of a 96 well assay plate. The signal to background ratio was calculated from data from a control plate (unmodified peptide). Eu-VCB concentration was titrated across rows (nM) and streptavidin APC concentrations were titrated down columns. The peptide concentration was fixed at 100 nM.

Detection of Enzymatically Converted Hydroxyprolyl HIF-1α by HIF PHD2 and Inhibition of HIF PHD2 Activity Binding of the P564-HIF1α peptide to VCB was validated utilizing the homogeneous time-resolved FRET (TR-FRET) technology. A 17 amino acid (17aa) peptide with an N-terminally labeled biotin molecule corresponding to amino acid sequences 558 to 574 of the HIF1α protein was synthesized in-house (DLEMLAPYIPMDDDFQL (SEQ ID NO: 6)). A second 17aa peptide containing a hydroxylated proline at position 564 was chemically generated to mimic the PHD enzyme converted product form of the protein that is recognized by VCB. The assay was performed in a final volume of 100 μL in buffer containing 50 mM Tris-HCl (pH 8), 100 mM NaCl, 0.05% heat inactivated FBS, 0.05% Tween-20, and 0.5% $NaN_3$. The optimal signal over background and the linear range of detection was determined by titrating the hydroxylated or unhydroxylated peptide at varied concentrations between 0 and 1 μM with a titration of VCB-Eu at varying concentrations between 0 and 50 nM with 50 nM of streptavidin APC. The binding reagents were allowed to reach equilibrium by shaking for 1 hour before it was read on the Discovery Instrument (Packard). The data output is the ratio of the 665 nm and 620 nm emission signal resulting from the 320 nm excitation.

HIF PHD2 activity was detected by P564-HIF1α peptide and VCB binding in the TR-FRET format. HIF PHD2 was assayed at various concentrations between 0 and 400 nM with 3 μM HIF1α peptide in buffer containing 50 mM Tris-HCl (pH 7.5), 100 mM NaCl, 0.05% Tween 20, 2 mM 2-oxoglutarate (2-OG), 2 mM ascorbic acid and 100 μM $FeCl_2$ in a final volume of 100 μL. The time-course was determined by periodically transferring 2.5 μL of the reaction into 250 μL of 10× TR-FRET buffer containing 500 mM HEPES (pH 7.5), 1 M NaCl, 1% BSA, and 0.5% Tween-20 to terminate the enzyme reaction. 15 nM HIF-1α peptide from the terminated reaction was added to 35 nM streptavidin-APC and 10 nM VCB-Eu to a final volume of 100 μL in 10× TR-FRET buffer. The TR-FRET reagents were placed on a shaker for 1 hour before detection on the Discovery platform.

Figure 2A:
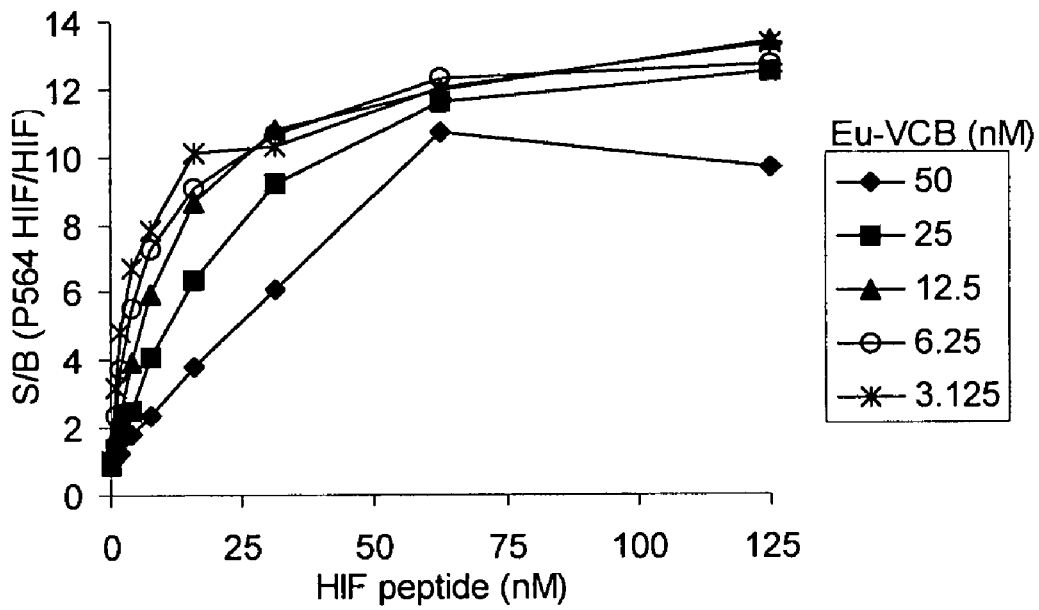
FIGS. 2A and 2B are graphs illustrating the ratio of TR-FRET signal generated by the interaction of Eu-VCB with streptavidin-APC-hydroxyprolyl HIF1α peptide over background signal generated by the interaction of Eu-VCB with streptavidin-APC-HIF1α peptide (nonhydroxylated).
Figure 2B:
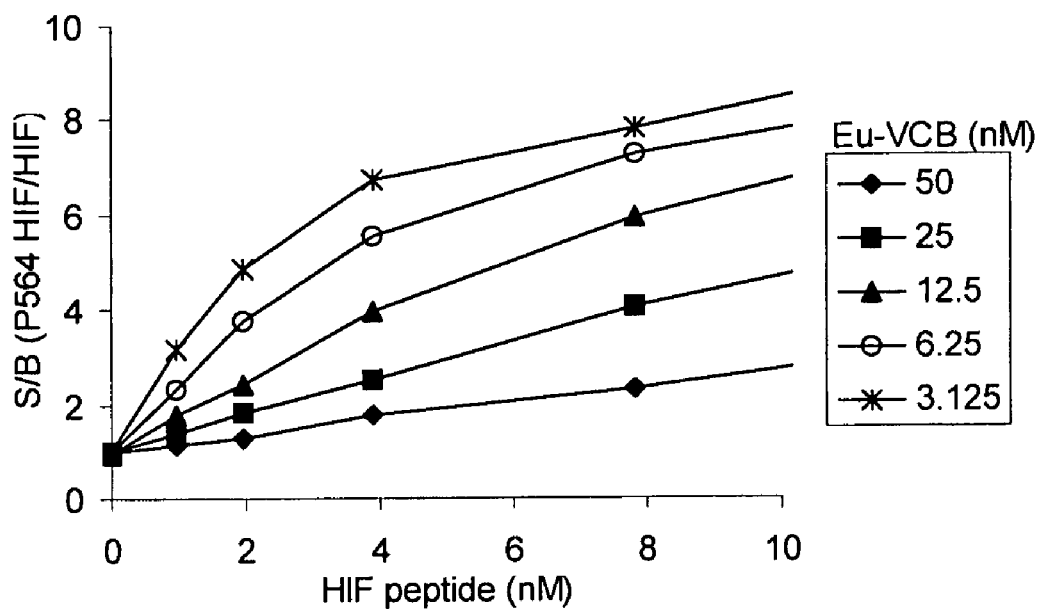

As demonstrated in FIGS. 2A and 2B, there was a dose dependent increase in TR-FRET signal resulting from binding of the hydroxylated-P564-HIF1α peptide to VCB-Eu compared to the unhydroxylated form of the peptide resulting in a 14 fold signal over noise ratio at 125 nM HIF1α peptide. VCB binding to the APC bound peptide permits a FRET transfer between the Eu and APC. The signal was linear to 2 nM peptide with 3.125 nM VCB, but increases to 62.5 nM peptide with 50 nM VCB resulting in a larger linear range.

Figure 3A:
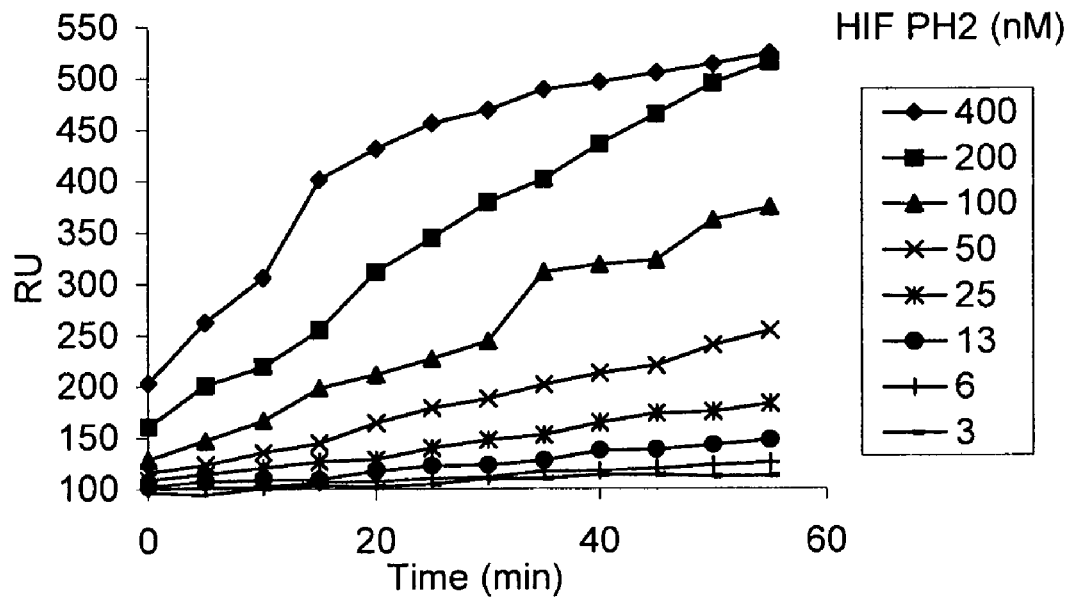
FIGS. 3A and 3B are graphs illustrating VCB binding and TR-FRET detection for determining HIF PHD2 hydroxylation of a HIF1α peptide.
Figure 3B:
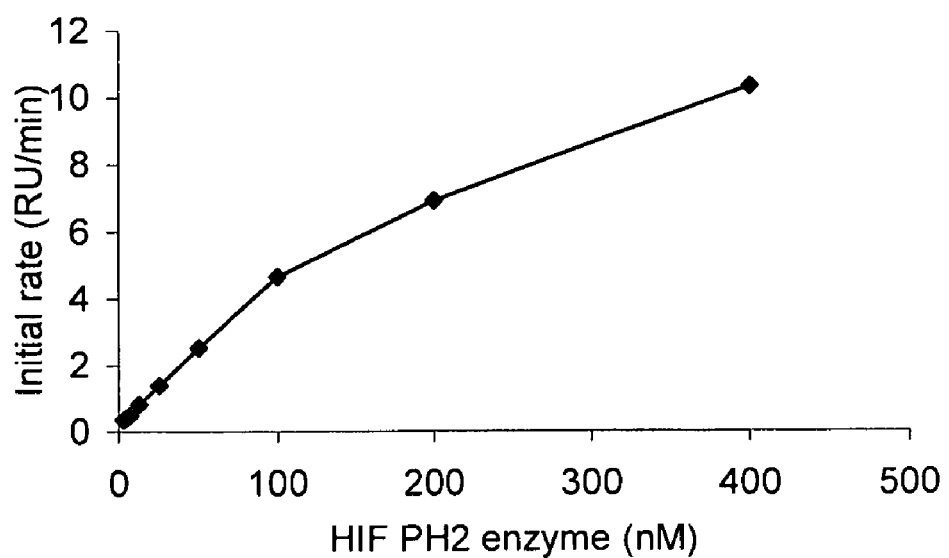

TR-FRET detection utilizing Eu-labeled VCB is a practical system for determining HIF PHD2 catalytic activity. HIF PHD2 hydroxylation of the HIF1α peptide results in the increase affinity of VCB to the peptide and hence and increased FRET signal. As shown in FIGS. 3A and 3B, activity was verified with a fairly linear and an increasing TR-FRET signal over time. There was a dose dependant increase in initial rates with increasing HIF PHD2 enzyme concentration up to 400 nM. The initial rates were linear to 100 nM enzyme.

Inhibition of HIF PHD2 activity was quantified utilizing the TR-FRET technology. HIF PHD2 catalyzes a hydroxyl modification on the proline residue of the P564-HIF1α peptide substrate (Biotin-DLEMLAPYIPMDDDFQL (SEQ ID NO: 7)) resulting in recognition and binding of the europylated Von Hippel-Lindau protein (pVHL), elongin B and elongin C heterotrimeric (VCB-Eu) complex.

The PHD2 inhibition assay was executed by addition of freshly dissolved $FeCl_2$ to 178.57 μM (100 μM final concentration) in PHD2 Reaction Buffer containing 30 mM MES, pH 6, 10 mM NaCl, 0.25% Brij-35, 0.01% BSA, and 1% DMSO. 28 μL of the iron solution and 2 μL of inhibitor compounds serially diluted in 100% DMSO (5% DMSO final) were added to black polypropylene 96-well microtiter plates. To that, 10 μL of 10 nM PHD2 (2 nM final) was added to all wells of the plate except for the 8 wells of column 12 (LO control), and allowed to incubate at room temperature on the shaker for one hour. Column 6 was the HI control containing PHD2 enzyme and 5% DMSO vehicle, but no inhibitor compound. To initiate the PHD2 enzymatic reaction, 10 μL of a solution containing 500 nM P564-HIF1α peptide (100 nM final), 10 mM ascorbic acid (2 mM final), and 1.25 μM 2-oxoglutarate (α-ketoglutarate; 0.25 μM final) in PHD2 Reaction Buffer was added to all wells of the plate and allowed to incubate on the shaker at room temperature for one hour.

The reaction was terminated by addition of 25 μL TR-FRET Buffer (50 mM TRIS-HCl, pH 9, 100 mM NaCl, 0.05% BSA, and 0.5% Tween-20) containing 150 mM succinate (product inhibitor; 50 mM final), 75 nM streptavidin-APC (25 nM final), and 7.5 nM VCB-Eu (2.5 nM final). The TR-FRET detection reagents were placed on a shaker for 1 hour to reach binding equilibrium before reading on the Discovery platform (PerkinElmer). Europium is excited at 315 nm and phosphoresces at 615 nm with a large Stoke's shift. APC, in turn, emits at 655 nm upon excitation at 615 nm. The TR-FRET signal is measured as the ratio of the APC 655 nm signal divided by the internal europium reference 615 nm emission signal.

The POC (percentage of control) was determined by comparing the signal from hydroxylated peptide substrate in the enzyme reaction containing inhibitor compound with that from PHD2 enzyme with DMSO vehicle alone (HI control), and no enzyme (LO control). POC was calculated using the formula: % control (POC)=(cpd−average LO)/(average HI−average LO)*100. Data (consisting of POC and inhibitor concentration in μM) was fitted to a 4-parameter equation $(y=A+((B-A)/(1+((x/C)^D))))$, where A is the minimum y (POC) value, B is the maximum y (POC), C is the x (cpd concentration) at the point of inflection and D is the slope factor) using a Levenburg-Marquardt non-linear regression algorithm.

In certain embodiments, compounds of the present invention exhibit a HIF PHD inhibitory activity $IC_{50}$ value of 40 μM or less. In additional embodiments, compounds of the present invention exhibit a HIF PHD inhibitory activity $IC_{50}$ value of 10 μM or less and in further embodiments, compounds of the present invention exhibit a HIP PHD inhibitory activity $IC_{50}$ value of 5 μM or less.

The following table includes PHD2 $IC_{50}$ values obtained using the procedures set forth herein for various Examples compounds described herein.

| Table of PHD2 $IC_{50}$ values of Example Compounds | |
|---|---|
| Example | [a]PHD2 $IC_{50}$ (nM) |
| 1 | +++++ |
| 2 | +++++ |
| 3 | ++++ |
| 4 | +++++ |
| 5 | +++++ |
| 6 | +++++ |
| 7 | +++++ |
| 8 | ++++ |
| 9 | +++++ |
| 10 | +++++ |
| 11 | +++++ |
| 12 | +++++ |
| 13 | +++++ |
| 14 | +++++ |

Table of PHD2 $IC_{50}$ values of Example Compounds

| Example | $PHD2\ IC_{50}$ (nM)[a] |
|---|---|
| 15 | +++ |
| 16 | ++++ |
| 17 | +++++ |
| 18 | +++ |
| 19 | ++++ |
| 20 | +++++ |
| 21 | +++++ |
| 22 | ++++ |
| 23 | +++ |
| 24 | ++ |
| 25 | +++++ |
| 26 | ++++ |
| 27 | +++++ |
| 28 | +++++ |
| 29 | +++++ |
| 30 | ++++ |
| 31 | +++++ |
| 32 | ++++ |
| 33 | ++++ |
| 34 | +++++ |
| 35 | ++++ |
| 36 | +++ |
| 37 | +++ |
| 38 | +++ |
| 39 | ++++ |
| 40 | +++ |
| 41 | ++++ |
| 42 | ++++ |
| 43 | +++ |
| 44 | +++++ |
| 45 | +++++ |
| 46 | +++ |
| 47 | +++++ |
| 48 | +++++ |
| 49 | +++ |
| 50 | +++++ |
| 51 | +++++ |
| 52 | +++ |
| 53 | +++++ |
| 54 | ++++ |
| 55 | ++++ |
| 56 | ++++ |
| 57 | +++++ |
| 58 | ++++ |
| 59 | ++++ |
| 60 | +++ |
| 61 | +++++ |
| 62 | +++++ |
| 63 | +++++ |
| 64 | ++++ |
| 65 | +++++ |
| 66 | +++++ |
| 67 | +++++ |
| 68 | +++++ |
| 69 | ++++ |
| 70 | ++++ |
| 71 | ++++ |
| 72 | ++++ |
| 73 | +++++ |
| 74 | +++ |
| 75 | +++++ |
| 76 | ++++ |
| 77 | ++++ |
| 78 | +++++ |
| 79 | +++++ |
| 80 | +++ |
| 81 | +++++ |
| 82 | +++++ |
| 83 | ++++ |
| 84 | +++ |
| 85 | +++++ |
| 86 | +++++ |
| 87 | +++++ |
| 88 | +++ |
| 89 | ++++ |
| 90 | +++++ |
| 91 | +++++ |
| 92 | +++++ |
| 93 | ++++ |
| 94 | +++++ |
| 95 | +++ |
| 96 | +++++ |
| 97 | +++++ |
| 98 | +++ |
| 99 | +++++ |
| 100 | +++++ |
| 101 | +++++ |
| 102 | ++++ |
| 103 | +++++ |
| 104 | ++++ |
| 105 | +++++ |
| 106 | +++++ |
| 107 | ++++ |
| 108 | +++++ |
| 109 | +++++ |
| 110 | +++++ |
| 111 | +++++ |
| 112 | ++++ |
| 113 | +++++ |
| 114 | ++++ |
| 115 | ++++ |
| 116 | +++++ |
| 117 | +++++ |
| 118 | +++++ |
| 119 | +++++ |
| 120 | +++++ |
| 121 | ++++ |
| 122 | +++ |
| 123 | +++++ |
| 124 | +++ |
| 125 | +++++ |
| 126 | ++++ |
| 127 | +++++ |
| 128 | +++++ |
| 129 | +++++ |
| 130 | +++++ |
| 131 | +++++ |
| 132 | ++++ |
| 133 | ++ |

[a] $IC_{50}$ value ranges
+ $IC_{50} > 1{,}000$ nM
++ $500\ \text{nM} \leq IC_{50} \leq 1{,}000$ nM
+++ $100\ \text{nM} \leq IC_{50} \leq 500$ nM
++++ $50\ \text{nM} \leq IC_{50} \leq 100$ nM
+++++ $IC_{50} < 50$ nM All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of Formula I:

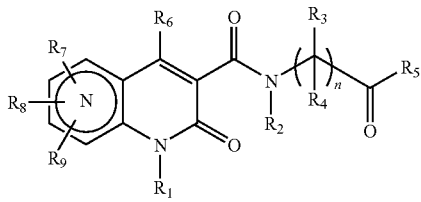

I a pharmaceutically acceptable salt thereof, and mixtures of any of the foregoing, wherein:

n is 1;

each $R_1$ is independently chosen from H, lower alkyl or substituted lower alkyl;

$R_2$ is chosen from H, lower alkyl and substituted lower alkyl;

$R_3$ and $R_4$ are independently chosen from H, lower alkyl, substituted lower alkyl, lower haloalkyl, or substituted lower haloalkyl, or $R_3$ and $R_4$ can join together to form a 3 to 6 membered ring or a substituted 3 to 6 membered ring;

$R_5$ is chosen from OH, SH, $NH_2$, lower alkyl, substituted lower alkyl, lower alkoxy, substituted lower alkoxy or sulfanyl;

$R_6$ is OH;

each of $R_7$, $R_8$, and $R_9$ is independently chosen from H, alkyl, substituted alkyl, alkenyl, substituted alkenyl, alkynyl, substituted alkynyl, alkoxy, substituted alkoxy, $NR_{3a}R_{4a}$, C(O)OH, $OR_{12a}$, $SR_{12a}$, $SO_2R_{12}$, CN, $NO_2$, halo, aryl, substituted aryl, heteroaryl, substituted heteroaryl, heteroarylalkyl, substituted heteroarylalkyl, heterocyclo, substituted heterocyclo, heterocycloalkyl, substituted heterocycloalkyl, alkoxycarbonyl, substituted alkoxycarbonyl, or —X—$R_{11}$, wherein:

$R_{3a}$ and $R_{4a}$ are independently chosen from H, lower alkyl, substituted lower alkyl, lower haloalkyl, or substituted lower haloalkyl, or $R_{3a}$ and $R_{4a}$ can join together to form a 3 to 6 membered ring or a substituted 3 to 6 membered ring;

X is chosen from —N($R_{10}$)—Y— and —Y—N($R_{10}$)—;

Y is chosen from C(O), $SO_2$, alkylene, substituted alkylene, alkenylene, substituted alkenylene, alkynylene, and substituted alkynylene;

$R_{10}$ is chosen from H, lower alkyl, and substituted lower alkyl, $R_{11}$ is chosen from H, heterocyclo, substituted heterocyclo, aryl, substituted aryl, heteroaryl and substituted heteroaryl;

$R_{12}$ is chosen from H, alkyl, substituted alkyl, alkenyl, substituted alkenyl, alkynyl, substituted alkynyl or $NR_{3a}R_{4a}$; and $R_{12a}$ is chosen from H, alkyl, substituted alkyl, alkenyl, substituted alkenyl, alkynyl, or substituted alkynyl;

wherein optionally at least one of adjacent pairs $R_6$ and $R_7$, $R_7$ and $R_8$, $R_8$ and $R_9$, and $R_9$ and $R_1$, join together to form a 4 to 7 membered ring or a substituted 4 to 7 membered ring;

and further wherein $R_3$ and $R_4$ are not both H.

2. The compound according to claim 1, wherein the compound of Formula I has the Formula II

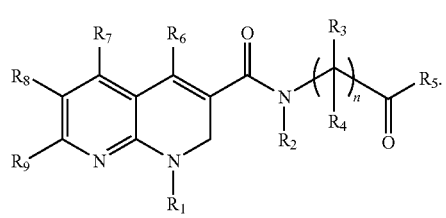

II

3. The compound according to claim 1, wherein the compound of Formula I has the Formula III $$\text{III}$$

4. The compound according to claim 1, wherein the compound of Formula I has the Formula IV $$\text{IV}$$

5. The compound according to claim 1, wherein the compound of Formula I has the Formula V $$\text{V}$$

6. The compound according to claim 1, wherein $R_5$ is OH.
7. The compound according to claim 1, wherein at least one of $R_7$, $R_8$, and $R_9$ is H.
8. The compound according to claim 1, wherein at least one of $R_7$, $R_8$, and $R_9$ is a substituted or unsubstituted aryl, substituted or unsubstituted heteroaryl, substituted or unsubstituted cycloalkyl, or a substituted or unsubstituted heterocyclo group.
9. The compound according to claim 8, wherein at least one of $R_7$, $R_8$, and $R_9$ is a heterocyclo group.
10. The compound according to claim 8, wherein at least one of $R_7$, $R_8$, and $R_9$ is a heteroaryl group.
11. The compound according to claim 8, wherein at least one of $R_7$, $R_8$, and $R_9$ is a phenyl or substituted phenyl group.
12. The compound according to claim 1, wherein at least one of $R_7$, $R_8$, and $R_9$ is independently chosen from halo or a moiety substituted with at least one halo.
13. The compound according to claim 12, wherein at least one of $R_7$, $R_8$, and $R_9$ is trifluoromethyl.
14. The compound according to claim 1, wherein at least one of $R_7$, $R_8$, and $R_9$ is independently chosen from H, alkyl, substituted alkyl, alkenyl, substituted alkenyl, alkynyl, and substituted alkynyl.
15. A pharmaceutical composition, comprising at least one pharmaceutically acceptable excipient, and a therapeutically effective amount of the compound according to claim 1.

16. The pharmaceutical composition of claim 15, wherein the compound is present in an amount effective for the treatment of ischemia or anemia.
17. A method of increasing HIF levels or activity in a subject, comprising administering to the subject compound according to claim 1.
18. A method of modulating the amount of HIF in a cell, comprising contacting the cell with the compound according to claim 1.
19. A method of treating at least one disease in a patient in need of such treatment, comprising administering to the patient a therapeutically effective amount of the compound according to claim 1, wherein the at least one disease is ischemia or anemia.
20. The method according to claim 19, wherein the at least one disease is ischemia.
21. The method according to claim 19, wherein the at least one disease is anemia.
22. A method of inhibiting HIF hydroxylation in a subject, comprising administering to the subject the compound according to claim 1.
23. A compound of Formula I:

$$\text{I}$$

a pharmaceutically acceptable salt thereof, and mixtures of any of the foregoing, wherein:

n is 1;

each $R_1$ is independently chosen from H, lower alkyl or substituted lower alkyl;

$R_2$ is chosen from H, lower alkyl and substituted lower alkyl;

$R_3$ and $R_4$ are both H;

$R_5$ is chosen from OH, SH, $NH_2$, lower alkyl, substituted lower alkyl, lower alkoxy, substituted lower alkoxy or sulfanyl;

$R_6$ is OH;

each of $R_7$, $R_8$, and $R_9$ is independently chosen from H, alkyl, substituted alkyl, alkenyl, substituted alkenyl, alkynyl, substituted alkynyl, alkoxy, substituted alkoxy, $NR_{3a}R_{4a}$, C(O)OH, $OR_{12a}$, $SR_{12a}$, $SO_2R_{12}$, CN, $NO_2$, halo, aryl, substituted aryl, heteroaryl, substituted heteroaryl, heteroarylalkyl, substituted heteroarylalkyl, heterocyclo, substituted heterocyclo, heterocycloalkyl, substituted heterocycloalkyl, alkoxycarbonyl, substituted alkoxycarbonyl, or —X—$R_{11}$, wherein:

$R_{3a}$ and $R_{4a}$ are independently chosen from H, lower alkyl, substituted lower alkyl, lower haloalkyl, or substituted lower haloalkyl, or $R_{3a}$ and $R_{4a}$ can join together to form a 3 to 6 membered ring or a substituted 3 o 6 membered ring;

X is chosen from —N($R_{10}$)—Y— and —Y—N($R_{10}$)—;

Y is chosen from C(O), $SO_2$, alkylene, substituted alkylene, alkenylene, substituted alkenylene, alkynylene, and substituted alkynylene;

$R_{10}$ is chosen from H, lower alkyl, and substituted lower alkyl, $R_{11}$ is chosen from H, heterocyclo, substituted heterocyclo, aryl, substituted aryl, heteroaryl and substituted heteroaryl;

$R_{12}$ is chosen from H, alkyl, substituted alkyl, alkenyl, substituted alkenyl, alkynyl, substituted alkynyl or $NR_{3a}R_{4a}$; and $R_{12a}$ is chosen from H, alkyl, substituted alkyl, alkenyl, substituted alkenyl, alkynyl, or substituted alkynyl;

wherein optionally at least one of adjacent pairs $R_6$ and $R_7$, $R_7$ and $R_8$, $R_8$ and $R_9$, and $R_9$ and $R_1$, join together to form a 4 to 7 membered ring or a substituted 4 to 7 membered ring, wherein at least one of the following is true:

a) the compound of Formula I has the Formula IV

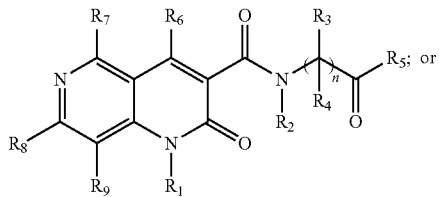

IV b) the compound of Formula I has the Formula V

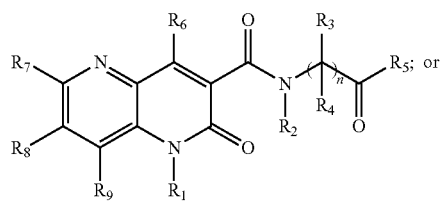

V c) at least one of $R_7$ $R_8$ and $R_9$ is a substituted or unsubstituted aryl, substituted or unsubstituted heteroaryl, substituted or unsubstituted cycloalkyl, or a substituted or unsubstituted heterocyclo group; or d) at least one of $R_7$ $R_8$ and $R_9$ is independently chosen from halo or a moiety substituted with at least one halo.

24. The compound according to claim 23, wherein the compound of Formula I has the Formula II

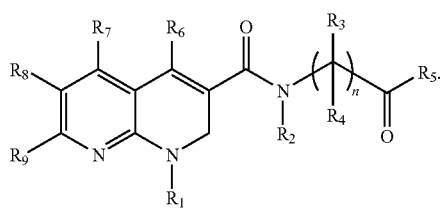

II

25. The compound according to claim 23, wherein the compound of Formula I has the Formula III

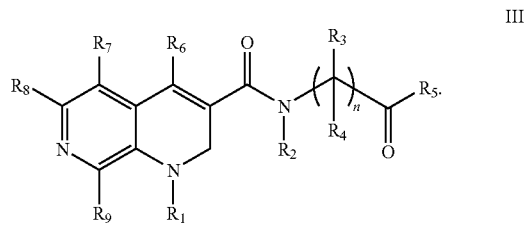

III

26. The compound according to claim 23, wherein the compound of Formula I has the Formula IV

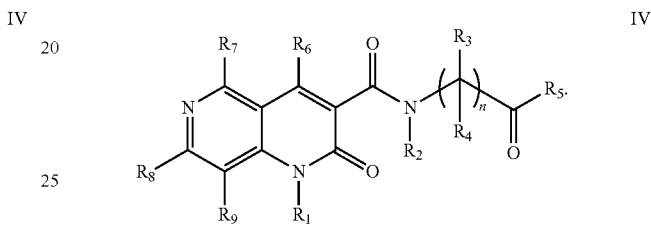

IV

27. The compound according to claim 23, wherein the compound of Formula I has the Formula V

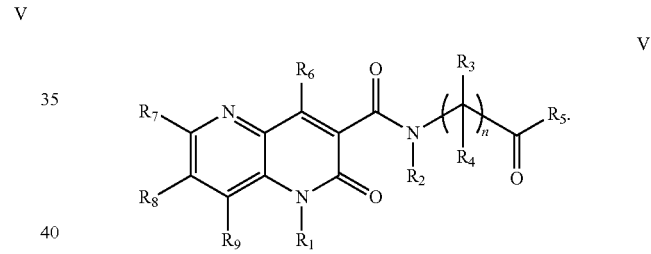

V

28. The compound according to claim 23, wherein $R_5$ is OH.

29. The compound according to claim 23, wherein at least one of $R_7$, $R_8$, and $R_9$ is H.

30. The compound according to claim 23, wherein at least one of $R_7$, $R_8$, and $R_9$ is a substituted or unsubstituted aryl, substituted or unsubstituted heteroaryl, substituted or unsubstituted cycloalkyl, or a substituted or unsubstituted heterocyclo group.

31. The compound according to claim 30, wherein at least one of $R_7$, $R_8$, and $R_9$ is a heterocyclo group.

32. The compound according to claim 30, wherein at least one of $R_7$, $R_8$, and $R_9$ is a heteroaryl group.

33. The compound according to claim 30, wherein at least one of $R_7$, $R_8$, and $R_9$ is a phenyl or substituted phenyl group.

34. The compound according to claim 23, wherein at least one of $R_7$, $R_8$, and $R_9$ is independently chosen from halo or a moiety substituted with at least one halo.

35. The compound according to claim 34, wherein at least one of $R_7$, $R_8$, and $R_9$ is trifluoromethyl.

36. The compound according to claim 23, wherein at least one of $R_7$, $R_8$, and $R_9$ is independently chosen from H, alkyl, substituted alkyl, alkenyl, substituted alkenyl, alkynyl, and substituted alkynyl.

37. A pharmaceutical composition, comprising at least one pharmaceutically acceptable excipient, and a therapeutically effective amount of the compound according to claim 23.

38. The pharmaceutical composition of claim 37, wherein the compound is present in an amount effective for the treatment of ischemia or anemia.

39. A method of increasing HIF levels or activity in a subject, comprising administering to the subject the compound according to claim 23.

40. A method of modulating the amount of HIF in a cell, comprising contacting the cell with the compound according to claim 23.

41. A method of treating at least one disease in a patient in need of such treatment, comprising administering to the patient a therapeutically effective amount of the compound according to claim 23, wherein the at least one disease is ischemia or anemia.

42. The method according to claim 41, wherein the at least one disease is ischemia.

43. The method according to claim 41, wherein the at least one disease is anemia.

44. A method of inhibiting HIF hydroxylation in a subject, comprising administering to the subject the compound according to claim 23.

45. The compound of claim 1, wherein the compound is selected from
(S)-2-(4-hydroxy-6-iodo-1-methyl-2-oxo-1,2-dihydro-1, 8-naphthyridine-3-carboxamido)propanoic acid;
(S)-2-(4-hydroxy-1-methyl-2-oxo-6-phenyl-1,2-dihydro-1,8-naphthyridine-3-carboxamido)propanoic acid;
(S)-2-(4-hydroxy-2-oxo-7-(trifluoromethyl)-1,2-dihydro-1,8-naphthyridine-3-carboxamido)propanoic acid;
(S)-2-(4-hydroxy-1-methyl-2-oxo-7-(trifluoromethyl)-1, 2-dihydro-1,8-naphthyridine-3-carboxamido)propanoic acid; or
(S)-2-(6-cyclohexenyl-4-hydroxy-1-methyl-2-oxo-1,2-dihydro-1,8-naphthyridine-3-carboxamido)-3-hydroxypropanoic acid; or
a pharmaceutically acceptable salt thereof.

46. A pharmaceutical composition, comprising at least one pharmaceutically acceptable excipient, and a therapeutically effective amount of the compound or salt according to claim 45.

47. A method of treating at least one disease in a patient in need of such treatment, comprising administering to the patient a therapeutically effective amount the compound or salt according to claim 45, wherein the at least one disease is ischemia or anemia.

48. The compound of claim 23, wherein the compound is selected from
N-((7-bromo-4-hydroxy-1-methyl-2-oxo-1,2-dihydro-1, 5-naphthyridin-3-yl)carbonyl)glycine;
2-(4-hydroxy-1-methyl-2-oxo-7-(thiophen-2-yl)-1,2-dihydro-1,5-naphthyridine-3-carboxamido)acetic acid;
2-(4-hydroxy-1-methyl-2-oxo-7-phenyl-1,2-dihydro-1,5-naphthyridine-3-carboxamido)acetic acid;
2-(7-cyclopentenyl-4-hydroxy-1-methyl-2-oxo-1,2-dihydro-1,5-naphthyridine-3-carboxamido)acetic acid;
2-(7-cyclopentyl-4-hydroxy-1-methyl-2-oxo-1,2-dihydro-1,5-naphthyridine-3-carboxamido)acetic acid;
2-(7-cyano-4-hydroxy-1-methyl-2-oxo-1,2-dihydro-1,5-naphthyridine-3-carboxamido)acetic acid;
2-(7-ethynyl-4-hydroxy-1-methyl-2-oxo-1,2-dihydro-1, 5-naphthyridine-3-carboxamido)acetic acid;
2-(4-hydroxy-1-methyl-2-oxo-7-(prop-1-ynyl)-1,2-dihydro-1,5-naphthyridine-3-carboxamido)acetic acid;
2-(4-hydroxy-1-methyl-7-(3-methylbut-1-ynyl)-2-oxo-1, 2-dihydro-1,5-naphthyridine-3-carboxamido)acetic acid;
2-(4-hydroxy-7-(3-methoxyprop-1-ynyl)-1-methyl-2-oxo-1,2-dihydro-1,5-naphthyridine-3-carboxamido) acetic acid;
2-(7-bromo-4-hydroxy-1-methyl-2-oxo-1,2-dihydro-1,8-naphthyridine-3-carboxamido)acetic acid;
2-(4-hydroxy-1-methyl-2-oxo-7-phenyl-1,2-dihydro-1,8-naphthyridine-3-carboxamido)acetic acid;
N-((4-hydroxy-1-methyl-2-oxo-7-(2-thienyl)-1,2-dihydro-1,8-naphthyridin-3-yl)carbonyl)glycine;
N((4-hydroxy-1-methyl-7-(4-methylphenyl)-2-oxo-1,2-dihydro-1,8-naphthyridin-3-yl)carbonyl)glycine;
N((4-hydroxy-1-methyl-2-oxo-7-(3-pyridinyl)-1,2-dihydro-1,8-naphthyridin-3-yl)carbonyl)glycine;
2-(7-cyclohexyl-4-hydroxy-1-methyl-2-oxo-1,2-dihydro-1,8-naphthyridine-3-carboxamido)acetic acid;
2-(4-hydroxy-1-methyl-2-oxo-7-(piperidin-1-yl)-1,2-dihydro-1,8-naphthyridine-3-carboxamido)acetic acid;
2-(4-hydroxy-1-methyl-7-morpholino-2-oxo-1,2-dihydro-1,8-naphthyridine-3-carboxamido)acetic acid;
2-(4-hydroxy-1-methyl-2-oxo-7-(4-(trifluoromethyl)piperidin-1-yl)-1,2-dihydro-1,8-naphthyridine-3-carboxamido)acetic acid;
2-(6-(3,6-dihydro-2H-pyran-4-yl)-4-hydroxy-1-methyl-2-oxo-1,2-dihydro-1,8-naphthyridine-3-carboxamido) acetic acid;
2-(4-hydroxy-1-methyl-6-(4-methylpyrimidin-2-yl)-2-oxo-1,2-dihydro-1,8-naphthyridine-3-carboxamido) acetic acid;
2-(4-hydroxy-1-methyl-2-oxo-6-(4-(trifluoromethyl)pyrimidin-2-yl)-1,2-dihydro-1,8-naphthyridine-3-carboxamido)acetic acid;
2-(4-hydroxy-6-(4-methoxypyrimidin-2-yl)-1-methyl-2-oxo-1,2-dihydro-1,8-naphthyridine-3-carboxamido) acetic acid;
2-(6-(4,6-dimethylpyrimidin-2-yl)-4-hydroxy-1-methyl-2-oxo-1,2-dihydro-1,8-naphthyridine-3-carboxamido) acetic acid;
2-(6-(6-chloropyrimidin-4-yl)-4-hydroxy-1-methyl-2-oxo-1,2-dihydro-1,8-naphthyridine-3-carboxamido) acetic acid;
N-((4-hydroxy-1-methyl-2-oxo-6-(6-(trifluoromethyl)-2-pyridinyl)-1,2-dihydro-1,8-naphthyridin-3-yl)carbonyl)glycine;
2-(6-(2-(dimethylamino)phenyl)-4-hydroxy-1-methyl-2-oxo-1,2-dihydro-1,8-naphthyridine-3-carboxamido) acetic acid;
2-(4-hydroxy-1-methyl-2-oxo-6-(tetrahydro-2H-pyran-4-yl)-1,2-dihydro-1,8-naphthyridine-3-carboxamido)acetic acid;
N-((4-hydroxy-1-methyl-6-(2-methylphenyl)-2-oxo-1,2-dihydro-1,8-naphthyridin-3-yl)carbonyl)glycine;
N-((6-(2,3-dihydro-1-benzofuran-5-yl)-4-hydroxy-1-methyl-2-oxo-1,2-dihydro-1,8-naphthyridin-3-yl)carbonyl)glycine;
N-((6-(2,6-dimethylphenyl)-4-hydroxy-1-methyl-2-oxo-1,2-dihydro-1,8-naphthyridin-3-yl)carbonyl)glycine;
N-((6-(2-(aminocarbonyl)phenyl)-4-hydroxy-1-methyl-2-oxo-1,2-dihydro-1,8-naphthyridin-3-yl)carbonyl) glycine;
N-((4-hydroxy-1-methyl-2-oxo-6-(2-(trifluoromethyl) phenyl)-1,2-dihydro-1,8-naphthyridin-3-yl)carbonyl) glycine;
2-(4-hydroxy-1-methyl-2-oxo-6-(pyridin-4-yl)-1,2-dihydro-1,8-naphthyridine-3-carboxamido)acetic acid;

2-(4-hydroxy-1-methyl-2-oxo-6-(pyridin-3-yl)-1,2-dihydro-1,8-naphthyridine-3-carboxamido)acetic acid;
2-(4-hydroxy-1-methyl-6-(2-methylpyridin-3-yl)-2-oxo-1,2-dihydro-1,8-naphthyridine-3-carboxamido)acetic acid;
2-(4-hydroxy-1-methyl-2-oxo-6-phenyl-1,2-dihydro-1,8-naphthyridine-3-carboxamido)acetic acid;
2-(6-(6-fluoro-2-methylpyridin-3-yl)-4-hydroxy-1-methyl-2-oxo-1,2-dihydro-1,8-naphthyridine-3-carboxamido)acetic acid;
N-((6-(2-fluoro-6-methyl-3-pyridinyl)-4-hydroxy-1-methyl-2-oxo-1,2-dihydro-1,8-naphthyridin-3-yl)carbonyl)glycine;
N-((6-(4-(dimethylamino)phenyl)-4-hydroxy-1-methyl-2-oxo-1,2-dihydro-1,8-naphthyridin-3-yl)carbonyl)glycine;
N-((6-(3-(dimethylamino)phenyl)-4-hydroxy-1-methyl-2-oxo-1,2-dihydro-1,8-naphthyridin-3-yl)carbonyl)glycine;
N-((6-(6-fluoro-3-pyridinyl)-4-hydroxy-1-methyl-2-oxo-1,2-dihydro-1,8-naphthyridin-3-yl)carbonyl)glycine;
N-((4-hydroxy-1-methyl-6-(6-(methyloxy)-3-pyridinyl)-2-oxo-1,2-dihydro-1,8-naphthyridin-3-yl)carbonyl)glycine;
N-((4-hydroxy-1-methyl-6-(2-(methyloxy)-3-pyridinyl)-2-oxo-1,2-dihydro-1,8-naphthyridin-3-yl)carbonyl)glycine;
N-((4-hydroxy-1-methyl-6-(3-(4-morpholinyl)phenyl)-2-oxo-1,2-dihydro-1,8-naphthyridin-3-yl)carbonyl)glycine;
N-((4-hydroxy-1-methyl-6-(5-(methyloxy)-3-pyridinyl)-2-oxo-1,2-dihydro-1,8-naphthyridin-3-yl)carbonyl)glycine;
N-((4-hydroxy-1-methyl-6-(4-methyl-3,4-dihydro-2H-1,4-benzoxazin-7-yl)-2-oxo-1,2-dihydro-1,8-naphthyridin-3-yl)carbonyl)glycine;
N-((4-hydroxy-1-methyl-6-(2-(4-morpholinyl)phenyl)-2-oxo-1,2-dihydro-1,8-naphthyridin-3-yl)carbonyl)glycine;
N-((4-hydroxy-1-methyl-2-oxo-6-(2-(1-piperidinyl)phenyl)-1,2-dihydro-1,8-naphthyridin-3-yl)carbonyl)glycine;
N-((4-hydroxy-1methyl-2-oxo-6-(3-(1-piperidinyl)phenyl)-1,2-dihydro-1,8-naphthyridin-3-yl)carbonyl)glycine;
N-((4-hydroxy-1-methyl-2-oxo-6-(3-(1-pyrrolidinyl)phenyl)-1,2-dihydro-1,8-naphthyridin-3-yl)carbonyl)glycine;
N-((4-hydroxy-1-methyl-2-oxo-6-(5-pyrimidinyl)-1,2-dihydro-1,8-naphthyridin-3-yl)carbonyl)glycine;
N-((6-(6-(dimethylamino)-3-pyridinyl)-4-hydroxy-1-methyl-2-oxo-1,2-dihydro-1,8-naphthyridin-3-yl)carbonyl)glycine;
N-((4-hydroxy-1-methyl-6-(4-(4-morpholinyl)phenyl)-2-oxo-1,2-dihydro-1,8-naphthyridin-3-yl)carbonyl)glycine;
2-(4-hydroxy-6-(2-methoxypyrimidin-5-yl)-1-methyl-2-oxo-1,2-dihydro-1,8-naphthyridine-3-carboxamido)acetic acid;
2-(6-(2-fluoropyridin-4-yl)-4-hydroxy-1-methyl-2-oxo-1,2-dihydro-1,8-naphthyridine-3-carboxamido)acetic acid;
2-(6-cyclohexyl-4-hydroxy-1-methyl-2-oxo-1,2-dihydro-1,8-naphthyridine-3-carboxamido)acetic acid;
(R)-tert-butyl 2-(4-hydroxy-1-methyl-2-oxo-6-(tetrahydro-2H-pyran-2-yl)-1,2-dihydro-1,8-naphthyridine-3-carboxamido)acetate;
(S)-tert-butyl 2-(4-hydroxy-1-methyl-2-oxo-6-(tetrahydro-2H-pyran-2-yl)-1,2-dihydro-1,8-naphthyridine-3-carboxamido)acetate;
2-(4-hydroxy-1-methyl-2-oxo-6-(tetrahydrofuran-2-yl)-1,2-dihydro-1,8-naphthyridine-3-carboxamido)acetic acid;
2-(4-hydroxy-6-iodo-1-methyl-2-oxo-1,2-dihydro-1,8-naphthyridine-3-carboxamido)acetic acid;
2-(6-fluoro-4-hydroxy-1-methyl-2-oxo-1,2-dihydro-1,8-naphthyridine-3-carboxamido)acetic acid;
2-(4-hydroxy-1-methyl-2-oxo-7-(trifluoromethyl)-1,2-dihydro-1,8-naphthyridine-3-carboxamido)acetic acid;
2-(4-hydroxy-2-oxo-7-(trifluoromethyl)-1,2-dihydro-1,8-naphthyridine-3-carboxamido)acetic acid;
2-(4-hydroxy-1-methyl-2-oxo-6-phenyl-7-(trifluoromethyl)-1,2-dihydro-1,8-naphthyridine-3-carboxamido)acetic acid;
2-(4-hydroxy-1-methyl-2-oxo-6-(pyridin-3-yl)-7-(trifluoromethyl)-1,2-dihydro-1,8-naphthyridine-3-carboxamido)acetic acid;
2-(4-hydroxy-1-methyl-6-(2-methylpyridin-3-yl)-2-oxo-7-(trifluoromethyl)-1,2-dihydro-1,8-naphthyridine-3-carboxamido)acetic acid;
2-(6-cyclopropyl-4-hydroxy-1-methyl-2-oxo-7-(trifluoromethyl)-1,2-dihydro-1,8-naphthyridine-3-carboxamido)acetic acid;
2-(6-bromo-4-hydroxy-1-methyl-2-oxo-7-(trifluoromethyl)-1,2-dihydro-1,8-naphthyridine-3-carboxamido)acetic acid;
2-(6-cyclohexyl-4-hydroxy-1-methyl-2-oxo-7-(trifluoromethyl)-1,2-dihydro-1,8-naphthyridine-3-carboxamido)acetic acid
2-(6-cyclohexenyl-4-hydroxy-1-methyl-2-oxo-7-(trifluoromethyl)-1,2-dihydro-1,8-naphthyridine-3-carboxamido)acetic acid;
2-(6-(2-cyclopropylethynyl)-4-hydroxy-1-methyl-2-oxo-7-(trifluoromethyl)-1,2-dihydro-1,8-naphthyridine-3-carboxamido)acetic acid;
2-(6-cyclopentyl-4-hydroxy-1-methyl-2-oxo-7-(trifluoromethyl)-1,2-dihydro-1,8-naphthyridine-3-carboxamido)acetic acid;
(R)-2-(4-hydroxy-1-methyl-2-oxo-6-(tetrahydrofuran-2-yl)-7-(trifluoromethyl)-1,2-dihydro-1,8-naphthyridine-3-carboxamido)acetic acid;
(S)-2-(4-hydroxy-1-methyl-2-oxo-6-(tetrahydrofuran-2-yl)-7-(trifluoromethyl)-1,2-dihydro-1,8-naphthyridine-3-carboxamido)acetic acid;
(R)-2-(4-hydroxy-1-methyl-2-oxo-6-(tetrahydrofuran-3-yl)-7-(trifluoromethyl)-1,2-dihydro-1,8-naphthyridine-3-carboxamido)acetic acid;
(S)-2-(4-hydroxy-1-methyl-2-oxo-6-(tetrahydrofuran-3-yl)-7-(trifluoromethyl)-1,2-dihydro-1,8-naphthyridine-3-carboxamido)acetic acid;
N-((4-hydroxy-1-methyl-2-oxo-6-phenyl-1,2-dihydro-1,7-naphthyridin-3-yl)carbonyl)glycine;
N-((4-hydroxy-1-methyl-6-(2-methylphenyl)-2-oxo-1,2-dihydro-1,7-naphthyridin-3-yl)carbonyl)glycine;
N-((4-hydroxy-1-methyl-2-oxo-6-(3-pyridinyl)-1,2-dihydro-1,7-naphthyridin-3-yl)carbonyl)glycine;
N-((6-(2,3-dihydro-1-benzofuran-5-yl)-4-hydroxy-1-methyl-2-oxo-1,2-dihydro-1,7-naphthyridin-3-yl)carbonyl)glycine;
N-((4-hydroxy-1-methyl-2-oxo-6-(2-thienyl)-1,2-dihydro-1,7-naphthyridin-3-yl)carbonyl)glycine;
2-(4-hydroxy-1-methyl-2-oxo-6-(4-(trifluoromethoxy)phenyl)-1,2-dihydro-1,7-naphthyridine-3-carboxamido)acetic acid;

2-(6-chloro-4-hydroxy-1-methyl-2-oxo-1,2-dihydro-1,7-naphthyridine-3-carboxamido)acetic acid;
2-(4-hydroxy-1-methyl-2-oxo-6-(1,2,3,6-tetrahydropyridin-4-yl)-1,2-dihydro-1,7-naphthyridine-3-carboxamido)acetic acid;
2-(4-hydroxy-1-methyl-2-oxo-6-(piperidin-4-yl)-1,2-dihydro-1,7-naphthyridine-3-carboxamido)acetic acid;
2-(4-hydroxy-1-methyl-6-(1-methyl-1,2,3,6-tetrahydropyridin-4-yl)-2-oxo-1,2-dihydro-1,7-naphthyridine-3-carboxamido)acetic acid;
2-(4-hydroxy-1-methyl-6-(1-methylpiperidin-4-yl)-2-oxo-1,2-dihydro-1,7-naphthyridine-3-carboxamido)acetic acid;
2-(6-(1-acetyl-1,2,3,6-tetrahydropyridin-4-yl)-4-hydroxy-1-methyl-2-oxo-1,2-dihydro-1,7-naphthyridine-3-carboxamido)acetic acid;
2-(6-(1-acetylpiperidin-4-yl)-4-hydroxy-1-methyl-2-oxo-1,2-dihydro-1,7-naphthyridine-3-carboxamido)acetic acid;
2-(4-hydroxy-1-methyl-6-morpholino-2-oxo-1,2-dihydro-1,7-naphthyridine-3-carboxamido)acetic acid;
2-(4-hydroxy-1-methyl-2-oxo-6-(piperidin-1-yl)-1,2-dihydro-1,7-naphthyridine-3-carboxamido)acetic acid;
2-(4-hydroxy-1-methyl-6-(4-methylpiperazin-1-yl)-2-oxo-1,2-dihydro-1,7-naphthyridine-3-carboxamido)acetic acid;
2-(4-hydroxy-1-methyl-2-oxo-6-phenyl-8-(trifluoromethyl)-1,2-dihydro-1,7-naphthyridine-3-carboxamido)acetic acid;
N-((4-hydroxy-1-methyl-6-(2-methylphenyl)-2-oxo-8-(trifluoromethyl)-,2-dihydro-1,7-naphthyridin-3-yl)carbonyl)glycine;
2-(8-chloro-4-hydroxy-1-methyl-2-oxo-1,2-dihydro-1,7-naphthyridine-3-carboxamido)acetic acid;
2-(4-hydroxy-1-methyl-2-oxo-8-(trifluoromethyl)-1,2-dihydro-1,7-naphthyridine-3-carboxamido)acetic acid;
2-(4-hydroxy-1-methyl-2-oxo-8-phenyl-1,2-dihydro-1,7-naphthyridine-3-carboxamido)acetic acid;
2-{4-hydroxy-1-methyl-2-oxo-3-[(carboxymethyl)carbamoyl]-1,2-dihydro-1,6-naphthyridin-5-ylamino}acetic acid;
2-(5-bromo-4-hydroxy-1-methyl-2-oxo-1,2-dihydro-1,6-naphthyridine-3-carboxamido)acetic ac;
2-(5-chloro-4-hydroxy-1-methyl-2-oxo-1,2-dihydro-1,6-naphthyridine-3-carboxamido)acetic acid;
2-(4-hydroxy-1-methyl-2-oxo-5-(trifluoromethyl)-1,2-dihydro-1,6-naphthyridine-3-carboxamido)acetic acid; or
a pharmaceutically acceptable salt thereof.

49. A pharmaceutical composition, comprising at least one pharmaceutically acceptable excipient, and a therapeutically effective amount of the compound or salt according to claim 48.

50. A method of treating at least one disease in a patient in need of such treatment, comprising administering to the patient a therapeutically effective amount the compound or salt according to claim 48, wherein the at least one disease is ischemia or anemia.

* * * * *